US008343927B2

(12) United States Patent
Mickle et al.

(10) Patent No.: US 8,343,927 B2
(45) Date of Patent: *Jan. 1, 2013

(54) PHARMACEUTICAL COMPOSITIONS FOR PREVENTION OF OVERDOSE OR ABUSE

(75) Inventors: Travis Mickle, Charlottesville, VA (US);
Suma Krishnan, Blacksburg, VA (US);
James Scott Moncrief, Christiansburg, VA (US); Christopher Lauderback, Blacksburg, VA (US)

(73) Assignee: Shire LLC, Florence, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/881,008

(22) Filed: Sep. 13, 2010

(65) Prior Publication Data
US 2011/0046226 A1    Feb. 24, 2011

Related U.S. Application Data

(63) Continuation of application No. 11/089,056, filed on Mar. 25, 2005, which is a continuation-in-part of application No. 09/933,708, filed on Aug. 22, 2001, now abandoned, and a continuation-in-part of application No. 10/156,527, filed on May 29, 2002, now Pat. No. 7,060,708, and a continuation-in-part of application No. 10/953,119, filed on Sep. 30, 2004, now Pat. No. 7,375,083, and a continuation-in-part of application No. 10/953,110, filed on Sep. 30, 2004, now Pat. No. 7,338,939, and a continuation-in-part of application No. 10/923,257, filed on Aug. 23, 2004, now Pat. No. 7,622,441, and a continuation-in-part of application No. 10/923,088, filed on Aug. 23, 2004, now Pat. No. 7,427,600, which is a continuation-in-part of application No. PCT/US03/05525, filed on Feb. 24, 2003, said application No. 11/089,056 is a continuation-in-part of application No. 10/955,006, filed on Sep. 30, 2004, now Pat. No. 7,169,752, and a continuation-in-part of application No. 10/953,116, filed on Sep. 30, 2004, now Pat. No. 7,375,082, and a continuation-in-part of application No. 10/953,111, filed on Sep. 30, 2004, now abandoned, and a continuation-in-part of application No. PCT/US2004/032131, filed on Sep. 30, 2004.

(60) Provisional application No. 60/358,368, filed on Feb. 22, 2002, provisional application No. 60/366,258, filed on Mar. 22, 2002, provisional application No. 60/358,381, filed on Feb. 22, 2002, provisional application No. 60/567,800, filed on May 5, 2004, provisional application No. 60/507,012, filed on Sep. 30, 2003, provisional application No. 60/567,802, filed on May 5, 2004, provisional application No. 60/568,011, filed on May 5, 2004, provisional application No. 60/362,082, filed on Mar. 7, 2002.

(51) Int. Cl.
*A61K 38/00* (2006.01)
*A61K 51/00* (2006.01)
*A61K 38/04* (2006.01)
*A61K 38/06* (2006.01)
*A61K 31/785* (2006.01)
*A61P 3/04* (2006.01)
*A61P 25/00* (2006.01)

(52) U.S. Cl. ........ 514/18.1; 514/17.7; 514/1.3; 514/1.1; 530/330; 530/331; 424/1.69

(58) Field of Classification Search .................. None
See application file for complete search history.

(56) References Cited

U.S. PATENT DOCUMENTS

| | | | |
|---|---|---|---|
| 3,331,814 A | 7/1967 | Randall et al. |
| 3,676,492 A | 7/1972 | Biel et al. |
| 3,843,696 A | 10/1974 | Wagner et al. |
| 3,846,399 A | 11/1974 | Hirschmann et al. |
| 3,875,137 A | 4/1975 | Jones et al. |
| 3,878,187 A | 4/1975 | Schneider et al. |
| 3,884,898 A | 5/1975 | Schneider |
| 3,975,342 A | 8/1976 | Gross |
| 3,998,799 A | 12/1976 | Bodor et al. |
| 4,025,501 A | 5/1977 | Leute |
| 4,040,907 A | 8/1977 | Ullman et al. |
| 4,043,989 A | 8/1977 | Schneider et al. |
| 4,064,235 A | 12/1977 | Yanaihara et al. |
| 4,064,236 A | 12/1977 | Dorn et al. |
| 4,221,778 A | 9/1980 | Raghunathan |
| 4,224,316 A | 9/1980 | Momany |
| 4,242,256 A | 12/1980 | Sharpe et al. |
| 4,297,346 A | 10/1981 | Rips et al. |

(Continued)

FOREIGN PATENT DOCUMENTS
AU            54168165            1/1965
(Continued)

OTHER PUBLICATIONS

U.S. Appl. No. 12/698,323, entitled Amphetamine Prodrugs and Uses Thereof, filed Feb. 2, 2010.
Aggarwal, et al. Synthesis and Biological Evlauation of Produgs of Zidovudine, J. Med. Chem., 33(5):1505-1511 (1990).
Amidon G. et al. 5-Amino Acid Esters of Antiviral Nuclosides, Acyclovir, and AZT Are Absorbed by the Intestinal PEPT1 Peptide Transporter, Pharm Res, 16(2):175 (1999), Abstract.
Amidon, G. et al., A Theoretical Basis for a Biophamaceutic Drug Classification: The Corrleation of In Vitro Drug Product Dissolution and In Vivo Bioavailability, Pharmaceutical Research, vol. 12, No. 3 (1995).

(Continued)

*Primary Examiner* — Maury Audet
(74) *Attorney, Agent, or Firm* — Blank Rome LLP

(57) ABSTRACT

The invention relates to pharmaceutical compositions comprised of a chemical moiety attached to an active agent in a manner that substantially decreases the potential of the active agent to cause overdose or to be abused. When delivered at the proper dosage the pharmaceutical composition provides therapeutic activity similar to that of the parent active agent.

11 Claims, 86 Drawing Sheets

U.S. PATENT DOCUMENTS

| | | | |
|---|---|---|---|
| 4,346,166 A | 8/1982 | Montag et al. |
| 4,358,604 A | 11/1982 | Albarella et al. |
| 4,399,121 A | 8/1983 | Albarella et al. |
| 4,426,453 A | 1/1984 | Cree et al. |
| 4,427,660 A | 1/1984 | Schiffman et al. |
| 4,457,907 A | 7/1984 | Porter |
| 4,483,807 A | 11/1984 | Asano et al. |
| 4,489,080 A | 12/1984 | Lomen |
| 4,489,165 A | 12/1984 | Wagner et al. |
| 4,490,221 A | 12/1984 | Collange et al. |
| 4,552,864 A | 11/1985 | Antoni et al. |
| 4,569,844 A | 2/1986 | Jones |
| 4,584,398 A | 4/1986 | Kuroiwa et al. |
| 4,587,046 A | 5/1986 | Goodman et al. |
| 4,650,675 A | 3/1987 | Borel et al. |
| 4,650,750 A | 3/1987 | Giese |
| 4,657,873 A | 4/1987 | Gadow et al. |
| 4,730,048 A | 3/1988 | Portoghese |
| 4,753,804 A | 6/1988 | Iaccheri et al. |
| 4,776,121 A | 10/1988 | Vicino |
| 4,801,575 A | 1/1989 | Pardridge |
| 4,829,070 A | 5/1989 | Bodor |
| 4,863,735 A | 9/1989 | Kohn et al. |
| 4,902,505 A | 2/1990 | Pardridge et al. |
| 4,925,673 A | 5/1990 | Steiner et al. |
| 4,960,790 A | 10/1990 | Stella et al. |
| 4,976,962 A | 12/1990 | Bichon et al. |
| 5,026,827 A | 6/1991 | Miyazaki et al. |
| 5,057,317 A | 10/1991 | Iida |
| 5,073,641 A | 12/1991 | Bundgaard et al. |
| 5,087,616 A | 2/1992 | Myers et al. |
| 5,120,859 A | 6/1992 | Webb |
| 5,169,933 A | 12/1992 | Anderson et al. |
| 5,183,883 A | 2/1993 | Tanaka et al. |
| 5,196,107 A | 3/1993 | Nakaoka et al. |
| 5,196,406 A | 3/1993 | Kamei et al. |
| 5,219,564 A | 6/1993 | Zalipsky et al. |
| 5,225,204 A | 7/1993 | Chen et al. |
| 5,233,025 A | 8/1993 | Miyazaki et al. |
| 5,238,714 A | 8/1993 | Wallace et al. |
| 5,298,491 A | 3/1994 | Chauveau et al. |
| 5,324,522 A | 6/1994 | Krenning et al. |
| 5,362,831 A | 11/1994 | Mongelli et al. |
| 5,378,712 A | 1/1995 | Alig et al. |
| 5,424,292 A | 6/1995 | Pellicciari et al. |
| 5,451,410 A | 9/1995 | Milstein et al. |
| 5,463,022 A | 10/1995 | Inoue et al. |
| 5,470,997 A | 11/1995 | Buechler et al. |
| 5,501,987 A | 3/1996 | Ordonez et al. |
| 5,529,915 A | 6/1996 | Phillips et al. |
| 5,534,496 A | 7/1996 | Lee et al. |
| 5,594,110 A | 1/1997 | Fiume et al. |
| 5,610,283 A | 3/1997 | Buechler |
| 5,618,926 A | 4/1997 | Salamone et al. |
| 5,643,957 A | 7/1997 | Leone-Bay et al. |
| 5,670,477 A | 9/1997 | Poduslo et al. |
| 5,681,811 A | 10/1997 | Ekwuribe |
| 5,700,549 A | 12/1997 | Garant et al. |
| 5,707,979 A | 1/1998 | Peyman et al. |
| 5,741,705 A | 4/1998 | Blom et al. |
| 5,756,291 A | 5/1998 | Griffin et al. |
| 5,762,909 A | 6/1998 | Uzgiris |
| 5,767,227 A | 6/1998 | Latham et al. |
| 5,776,885 A | 7/1998 | Orsolini et al. |
| 5,792,451 A | 8/1998 | Sarubbi et al. |
| 5,792,786 A | 8/1998 | Whittaker et al. |
| 5,811,127 A | 9/1998 | Milstein et al. |
| 5,820,881 A | 10/1998 | Milstein |
| 5,843,634 A | 12/1998 | Brate et al. |
| 5,846,743 A | 12/1998 | Janmey et al. |
| 5,851,536 A | 12/1998 | Yager et al. |
| 5,861,387 A | 1/1999 | Labrie et al. |
| 5,863,899 A | 1/1999 | Cheronis et al. |
| 5,882,645 A | 3/1999 | Toth et al. |
| 5,891,459 A | 4/1999 | Cooke et al. |
| 5,891,478 A | 4/1999 | Johnson et al. |
| 5,898,033 A | 4/1999 | Swadesh et al. |
| 5,910,569 A | 6/1999 | Latham et al. |
| 5,935,988 A | 8/1999 | Matzke et al. |
| 5,935,995 A | 8/1999 | Bosslet et al. |
| 5,948,750 A | 9/1999 | Garsky et al. |
| 5,952,294 A | 9/1999 | Lazo et al. |
| 5,955,105 A | 9/1999 | Mitra et al. |
| 5,965,519 A | 10/1999 | Yatvin et al. |
| 5,965,695 A | 10/1999 | Simon et al. |
| 5,977,163 A | 11/1999 | Li et al. |
| 5,981,507 A | 11/1999 | Josephson et al. |
| 6,005,004 A | 12/1999 | Katz et al. |
| 6,030,941 A | 2/2000 | Summerton et al. |
| 6,043,230 A | 3/2000 | Arimilli et al. |
| 6,048,736 A | 4/2000 | Kosak |
| 6,051,685 A | 4/2000 | Sakurada et al. |
| 6,074,659 A | 6/2000 | Kunz et al. |
| 6,075,120 A | 6/2000 | Cheronis et al. |
| 6,093,391 A | 7/2000 | Kabanov et al. |
| 6,146,658 A | 11/2000 | Bosslet et al. |
| 6,235,718 B1 | 5/2001 | Balasubramanium et al. |
| 6,255,285 B1 | 7/2001 | Kotake et al. |
| 6,258,836 B1 | 7/2001 | Shashoua |
| 6,262,107 B1 | 7/2001 | Li et al. |
| 6,267,968 B1 | 7/2001 | Bahr et al. |
| 6,306,993 B1 | 10/2001 | Rothbard et al. |
| 6,309,633 B1 | 10/2001 | Ekwuribe et al. |
| 6,340,696 B1 | 1/2002 | Camden |
| 6,355,666 B1 | 3/2002 | Lai et al. |
| 6,407,137 B2 | 6/2002 | Shashoua |
| 6,429,223 B1 | 8/2002 | Lai et al. |
| 6,458,842 B1 | 10/2002 | Dickinson et al. |
| 6,632,922 B1 | 10/2003 | Deming et al. |
| 6,680,365 B1 | 1/2004 | Deming |
| 6,686,446 B2 | 2/2004 | Deming et al. |
| 6,713,452 B2 | 3/2004 | Ekwuribe et al. |
| 6,716,452 B1 | 4/2004 | Piccariello et al. |
| 6,740,641 B2 | 5/2004 | Gao et al. |
| 6,784,186 B1 | 8/2004 | Jackson et al. |
| 6,818,659 B2 | 11/2004 | Rajopadhye |
| 6,846,831 B2 | 1/2005 | Clemens |
| 6,913,768 B2 | 7/2005 | Couch et al. |
| 7,060,708 B2 * | 6/2006 | Piccariello et al. ........... 514/282 |
| 7,089,140 B1 | 8/2006 | McKenzie et al. |
| 7,163,918 B2 | 1/2007 | Piccariello et al. |
| 7,169,752 B2 * | 1/2007 | Mickle et al. ................. 514/1.3 |
| 7,338,939 B2 * | 3/2008 | Mickle et al. ................. 514/1.3 |
| 7,375,082 B2 * | 5/2008 | Mickle et al. ................. 514/1.3 |
| 7,375,083 B2 * | 5/2008 | Mickle et al. ................. 514/1.3 |
| 7,427,600 B2 * | 9/2008 | Mickle et al. ................. 514/1.1 |
| 7,438,900 B2 | 10/2008 | Piccariello et al. |
| 7,622,441 B2 * | 11/2009 | Mickle et al. ................. 514/1.1 |
| 7,772,222 B2 * | 8/2010 | Mickle ........................ 514/183 |
| 7,776,917 B2 * | 8/2010 | Mickle ........................ 514/561 |
| 2001/0026624 A1 | 10/2001 | Kon et al. |
| 2001/0031873 A1 | 10/2001 | Greenwald et al. |
| 2002/0031236 A1 | 3/2002 | Shimizu et al. |
| 2002/0059013 A1 | 5/2002 | Rajala et al. |
| 2002/0095134 A1 | 7/2002 | Pettis et al. |
| 2002/0097947 A1 | 7/2002 | Lim et al. |
| 2002/0098999 A1 | 7/2002 | Gallop et al. |
| 2002/0099013 A1 | 7/2002 | Piccariello et al. |
| 2002/0151526 A1 | 10/2002 | Gallop et al. |
| 2002/0151529 A1 | 10/2002 | Cundy et al. |
| 2002/0164373 A1 | 11/2002 | Maloney |
| 2002/0173468 A1 | 11/2002 | Lerchen et al. |
| 2002/0183390 A1 | 12/2002 | Javitt |
| 2003/0004177 A1 | 1/2003 | Kao et al. |
| 2003/0077297 A1 | 4/2003 | Chen et al. |
| 2003/0091593 A1 | 5/2003 | Bachmann et al. |
| 2003/0130205 A1 | 7/2003 | Christian |
| 2004/0052731 A1 | 3/2004 | Hirsh et al. |
| 2004/0058946 A1 | 3/2004 | Buchwald et al. |
| 2004/0063628 A1 | 4/2004 | Piccariello et al. |
| 2004/0106636 A1 | 6/2004 | Kream |
| 2004/0131680 A1 | 7/2004 | Goldenheim et al. |
| 2004/0132968 A1 | 7/2004 | Reed et al. |
| 2004/0161382 A1 | 8/2004 | Yum et al. |
| 2004/0180036 A1 | 9/2004 | Ashton et al. |
| 2004/0204434 A1 | 10/2004 | Shafer et al. |
| 2005/0038121 A1 | 2/2005 | Mickle et al. |

| | | | |
|---|---|---|---|
| 2005/0054561 A1 | 3/2005 | Mickle et al. | |
| 2005/0065086 A1 | 3/2005 | Kirk et al. | |
| 2005/0069550 A1 | 3/2005 | Piccariello et al. | |
| 2005/0074424 A1 | 4/2005 | Salnikov | |
| 2005/0074425 A1 | 4/2005 | Waugh et al. | |
| 2005/0080012 A1 | 4/2005 | Mickle et al. | |
| 2005/0112088 A1 | 5/2005 | Zhao et al. | |
| 2005/0176644 A1 | 8/2005 | Mickle et al. | |
| 2005/0176645 A1 | 8/2005 | Mickle et al. | |
| 2005/0176646 A1 | 8/2005 | Mickle et al. | |
| 2005/0266070 A1 | 12/2005 | Mickle et al. | |
| 2006/0014697 A1 | 1/2006 | Mickle et al. | |
| 2007/0042955 A1 | 2/2007 | Mickle et al. | |
| 2007/0060500 A1 | 3/2007 | Mickle et al. | |
| 2007/0066537 A1 | 3/2007 | Mickle et al. | |
| 2007/0197451 A1 | 8/2007 | Mickle et al. | |
| 2007/0203055 A1 | 8/2007 | Mickle et al. | |
| 2008/0090771 A1 | 4/2008 | Moncrief | |
| 2009/0234018 A1* | 9/2009 | Mickle | 514/626 |
| 2009/0239949 A1* | 9/2009 | Mickle | 514/561 |
| 2010/0292336 A1* | 11/2010 | Mickle | 514/626 |
| 2010/0292337 A1* | 11/2010 | Mickle | 514/626 |
| 2011/0213034 A1* | 9/2011 | Mickle | 514/565 |

FOREIGN PATENT DOCUMENTS

| | | |
|---|---|---|
| EP | 0187547 A2 | 7/1986 |
| FR | 1421130 A | 12/1965 |
| GB | 1092089 A | 11/1967 |
| GB | 1112347 A | 5/1968 |
| WO | WO-9411021 A1 | 5/1994 |
| WO | WO-9512605 A1 | 5/1995 |
| WO | WO-9514033 A1 | 5/1995 |
| WO | WO-9736616 A2 | 10/1997 |
| WO | WO-9804277 A1 | 2/1998 |
| WO | WO-9939691 A2 | 8/1999 |
| WO | WO-9949901 A1 | 10/1999 |
| WO | WO-0037103 A2 | 6/2000 |
| WO | WO-0052078 A1 | 9/2000 |
| WO | WO-0053233 A1 | 9/2000 |
| WO | WO-0234237 A1 | 5/2002 |
| WO | WO-03034980 A2 | 5/2003 |
| WO | WO-2004/064839 A1 | 8/2004 |
| WO | WO-2004082620 A2 | 9/2004 |
| WO | WO-2005118642 A2 | 12/2005 |
| WO | WO-2006059106 A2 | 6/2006 |

OTHER PUBLICATIONS

Apr. 7, 2000, Letter to Astrzeneca LP.
Apr. 7, 2000, Letter to Banc of America Securities, LLC.
Apr. 7, 2000, Letter to Chase, Hambrecht and Quist.
Apr. 7, 2000, Letter to Credit Suisse First Boston Corporation.
Apr. 7, 2000, Letter to Johnson & Johnson.
Apr. 7, 2000, Letters to Bear, Stearns & Company, Inc.
Aug. 31, 1999 Presentation to SCIOS, Inc.
Bai et al., Structural Specificity of Mucosal-Cell Transport and Metabolism of Peptide Drugs; Implication for Oral Peptide Drug Delivery:, Pharmaceutical Research, Kluwer Academic Publishers, NY NY, vol. 9, No. 8, Jan. 1, 1992, pp. 969-978, XP008069566.
Balimane P.V., et al., Direct Evidence for Peptide Transporter (PEPT1)-Mediated Uptake of a Nonpeptide Prodrug, Valacyclovir, Biochem Biophys Res Commun, 250(2):246-251 (1998), Abstract.
Balimane, P, et al., Effect of Ionization of the Variable Uptake of Valacyclovir via the Human Intestinal Peptide Transporter (HEPT1) In CHP Cells, Biopharm Drug Dispos, 2195):165-174 (2000), Abstract.
Bankers Presentation, Mar. 27-31, 2000.
Bunevicius, R., Effects of Thyroxine As Compared With Thyroxine Plus Triodothyronine in Patients With Hypothyrodisim, The New England Journal of Medicine, vol. 340, No. 6 (1999).
Burnette, Thimysta C., et al., Metabolic Disposition of the Acyclovir Produg Valacicolovir in the Rat, Drug Metabolism and Disposition, 22(1):60-64 (1994).
Canaris G., The Colorado Thyroid Disease Prevalence Study, Archives Internal Medicine Articles and Abstracts, vol. 160, No. 4 (2000).

De Vrueh, Remco, L.A., et al., Transport of L-Valine-Acyclovir via the Oligopeptide Transporter in the Human Intestinal Cell Line, CACO-2, Journal of Pharmacology and Experimental Therapeutics, 286(2):1166-1170 (1988).
Deutsche Banc Alex Bornw 2000 Health Care Conference Presentation, May 10, 2000, Baltimore, MD.
Deutsche Banc Alex Brown 2000.
Deutsche Banc Alex Brown 2000 Health Care Conference Presentation, May 10, 2000, Baltimore, MD.
Feb. 10, 2000, Lotus Presentation.
Feb. 2000 Presentation to Andrx.
Final Report, Study Completion Date Jun. 25, 1998.
Friedrichsen, G.M., et al., Model Prodrugs Designed for the Intestinal Peptide Transporter a Synthetic Approach for Coupling of Hydroxy-Containing Compounds to Dipeptides Eur J Pharm Sci, 1491):13-19 (2001), Abstract.
Guo, A. et al., Interactions of a Nonpeptidic Drug Valacyclovir, With the Human Intestinal Peptide Transporter (HPEPT1) Expressed in a Mammalinan Cell Line, Pharmacol Exp Ther, 289(1):448-454 (1999) Abstract.
Han H.K. et al., Cellular Uptake Mechanism of Amino Acid Ester Prodrugs in CACO-2HPEPT1 Cells Overexpressing a Human Peptide Transporter, Pharm Res, 15(9):1382-1386 (1998) Abstract.
Han, H. et al., 5-Amino Acid Esters of Antiviral Nuclosides, Acyclovir and AZT and Absorbed by the Intestinal PEPT1 Peotide Transporter, Pharm Res. 15(8):1154-1159 (1998) Abstract.
Han, Hyo-Kyung, et al., Targeted Prodrug Design to Optimize Drug Delivery, AAPS Pharmsci, 2(1):Article 6 (2000).
Havranova, Marie et al., A High-Molecular Mass Derivative of Trypsin-Kallikrein Inhibitor for Potential Medical Use, II, Hoppe-Seyler's Z. Physiol. Chem., 363:295-303 (1982).
Herrera-Ruiz, D., et al., Spatial Expression Patterns of Peptide Transporters in the Human and Rate Gastrointestinal Tracts, CACO-2 In Vitro Cell Culture Model, and Multiple Human Tissues, AAPS Pharmsci. 3(1):E9 (2001), Abstract.
Hosztafi, S. et al., Synthesis and Analgetic Activity of Nicotine Esters of Morphine Derivatives, Arzneim.-Forsch/Drug Res. 43(II), NR. 11 (1993).
Hughes, et al., Lipidic Peptides, III: Lipidic Amino Acid and Oligomer Conjugates of Morphine, Journal of Pharmaceutical Sciences, vol. 80, No. 12, Dec. 1991.
International Search Report for PCT/US03/05524 Dated Feb. 24, 2003.
International Search Report for PCT/US03/05525 Dated Oct. 9, 2003.
International Search Report for PCT/US04/17204 Dated Oct. 15, 2004.
International Search Report, Dated Sep. 3, 2003.
Introducing Polythryoid, Presentation, Mar. 2000.
Investment Banking (Long) Presentation, Apr. 27, 2000.
Investment Banking (Short) Presentation, Apr. 27, 2000.
Investment Banking Presentation, Mar. 27-31, 2000.
Kim et al., B.M. Journal of Pharmaceutical Sciences, vol. 90 (11), p. 1767-1775, Nov. 2001.
Knutter, I, et al., A Novel Inhibitor of the Mammalian Peptide Transporter PEPT1, Biochemistry, 40(14):4454-4458 (2001), Abstract.
Kovacs, J. et al., Glutamic and Aspartic Anhydrides, Rearrangement of N-Carboxyglutamic, 1,5-Anhydride to the Leuchs' Anhydride and Conversion of the Latter to Pyroglutamic Acid, 85:1839-1844 (Jun. 20, 1963).
KPMG Auditors' Report, Mar. 12, 1999.
Kramer, Werner et al., Intestinal Absorption of Peptides by Coupling to Bile Acids, The Journal of Biochemistry, 269(14)10621-1627 (1994).
Kumar, et al., Safety and Pharmacokinetics of Abacavir Following Oral Administration of Escalating Single Doses in Human Immunodeficiency Virus Type 1-Infected Adults, Antimicrobial Agents and Chemotherapy, vol. 43, No. 3, Mar. 1999, pp. 603-608, XP002530985 ISSN: 0066-4804.
Leibach, F.H. et al., Peptide Transporters in the Intestine and the Kidney, Annu Rev Nutri, 16:99-119 (1996) Abstract.
Leopold, Caludia S. et al., in Vivo Pharmacokinetic Study for the Assessment of Poly(L-Aspartic Acid) As a Drug Carrier for Colon- Specific Drug Delivery, Journal of Pharmacokinetics and Biopharmaceutics, Vol. 23, No. 4, 1995, p. 397-406, XP002530986.

Li, Chun, et al., Complete Regression of Well-Established Tumors Using a Novel Water-Soluble Poly(L-Gluatmic Acid)-Paclitaxel Conjugate, Cancer Res, 58:2404-2409 (1998).

Ma, Y. et al., Enzymatic Mechanism of Thyroxine Biosynthesis, Identification of the Lost Three-Carbon Fragment, J. Am. Chem. Soc. 1999, vol. 121, No. 38, p. 8697-8698.

Mar. 15, 2000 Presentation to BASF.

Marriq, Caludine, et al., Amino Acid Sequence of the Unique 3,5,3'-Trilodothyronine-Containing Sequence From Porcine Thyroglobulin, Biochemical and Biophysical Research-Communications, 112(1):206-213 (1983).

Negishi, Naoki, et al., Coupling of Naltrexone to Biodegrable Poly (?-Amino Acids), Pharmaceutical Research, 4(4):305-310 (1987).

Negishi, Naoki, et al., Coupling of Naltrexone to Biodegrable Poly (α-Amino Acids), Pharmaceutical Research, 4(4):305-310 (1987).

Oh, D., et al., Estimating the Fraction Dose Absorbed From Suspensions of Poorly Soluble Compounds in Humans: A Mathematical Model, Pharmaceutical Research, vol. 10, No. 2 (1993).

Oh, DM, et al., Drug Transport and Targeting. Intestinal Transport, Pharma Biotechnol, 12:59-88 (1999) Abstract.

Okada, Masahiko, et al., Synthesis of Glycopeptide-Conjugates via Ring-Opening Polymerization of Sugar-Substituted α-Amino Acid N-Carboxyanyhydrides (Glyconcas), Proc. Japan Acad., 73:205-209 (1997).

Orten, James M et al., Thyroxine, Human Biochemistry, 9th Ed. C.V. Mosby Company St. Louis, pp. 401-405 (1975).

Pade, V., et al., Link Between Drug Absorption Solubility and Permeability Measurements in CACO-2 Cells, Journal of Pharmceutical Sciences, vol. 87, No. 12 (1998).

Pharma Presentation, Apr. 2000.

Pharma Presentation, Mar. 27-31, 2000, New York, NY.

Pharmaceutical Presentation, Mar. 27-31, 2000.

Presentation to Knoll Pharmaceutical, Apr. 10, 2000.

Promise of Polythroid, Presentation, Mar. 2000.

Rawitch, Allen B., et al., The Isolation of Indentical Thyroxine Containing Amino Acid Sequences From Bovine, Ovine and Porcine Thyroglobulins, Biochemical and Biophysical Research Communications, 118(2): 423-429 (1984).

Ryser, Hugues J.P., et al., Conjugation of Methotrexate to Poly (L-Lysine) Increases Drug Transport and Overcomes Drug Resistance in Cultured Cells, Proc. Natl. Acad Sci USA, 75(8):3867-3870 (1978).

Sawada, Kyoko, et al. Recognition of L-Amino Acid Ester Compounds by Rat Peptide Transporters PEPT1 and PEPT2, Journal of Pharmacology and Experimental Therapeutics, 291(2):705-709 (1999).

Schmidt, Brigitte F., et al., Peptide-Linked 1,30Dialkyl-3-Acyltriazenes: Gastrin Receptor Directed Antinoeplastic Alkylating Agents, Journal of Medicinal Chemistry, 37(22):3812-3817 91994), 1994.

Shen, H. et al., Developmental Expression of PEPT1 or PEPT2 in Rat Small Intestine, Colon, and Kidney, Pediatr Res, 49(6):789-795 (2001) Abstract.

Shiraga T., et al., Cellular and Moelcular Mechanisms of Dietary Regulation of Rat Intestinal H+/Peptide Transporter PEPT1, Gastroenterology, 116(2):354-362 (1999) Abstract.

Supplementary European Search Report for EP 01273387 Dated Sep. 28, 2004.

Supplementary Partial European Search Report for EP 01966056, Dated Apr. 7, 2005.

Tamai, I., et al., Improvement of L-Dopa Absorption by Dipeptidyl-Derivation, Utilizing Peptide Transporter PEPT1, J Pharma Sci, 87(12):1542-1546 (1998) Abstract.

Toft, A. Thyroid Hormone Replacement—One Hormone or Two?, The New England Journal of Medicine, vol. 340, No. 6 (1999).

Toth, Isivan, A Novel Chemical Approach to Drug Delivery: Lipidic Amino Acid Conjugates, Journal of Drug Targeting, 2:217-239 (1994).

U.S. Appl. No. 10/923,088, Entitled Active Agent Delivery Systems and Methods for Protecting and Administering Active Agents, Mickle, et al., filed Aug. 23, 2004.

U.S. Appl. No. 10/953,111, Entitled Compounds and Compositions for the Prevention of Overdose of Oxycodone, Mickle et al., filed Aug. 23, 2004.

U.S. Appl. No. 11/179,801, Entitled Carbohydrate Conjugates to Prevent Abuse of Controlled Substances, Mickle, et al., filed Jul. 13, 2005.

U.S. Appl. No. 11/392,878, Entitled Pharmaceutical Compositions for Prevention of Overdose or Abuse, Mickle et al., filed Apr. 4, 2006.

U.S. Appl. No. 11/400,304, Entitled Abuse Resistant Amphetamine Prodrugs, Mickle et al., filed Apr. 10, 2006.

U.S. Appl. No. 11/933,846: Non-Final Office Action Dated Jun. 11, 2010, Including Form PTO-892 (11 Pages).

Zunino, Franco, et al., Anti-Tumor Activity of Daunorubicin Linked to Poly-L-Aspartic Acid, International Journal of Cancer, 30:465-470 (1994).

Zunino, Franco, et al., Comparison of Antitumor Effects of Daunorubicin Covalently Linked to Poly-L-Amino Acid Carriers, European Journal of Cancer & Clinical Oncology, 20(3):121-125 (1984).

Answer and Counterclaim (Feb. 28, 2011) in *Shire LLC v. Kempharm (W.D. Va.)*, Civil Action No. 7:10-CV-00434.

Bai, J.P.F. et al., Gastrointestinal Transport of Peptide and Protein Drugs and Prodrugs: In Welling PG, Balant LP, eds. Handbook of Experimental Pharmacology Heidelberg: Springer-Verlag; 1994:110:189-206.

Bennett, D.B., et al.; Drug-coupled Poly (amino Acids) as Polymeric Prodrugs Journal of Bioactive and Compatible Polymers. vol. 3, pp. 44-52 (1988).

Bennett, R., et al., "O-Phosphoric Acid Esters of 3,5-Diiodotyrosine and Thyroxine," Journal of Medicinal and Pharmaceutical Chemistry, 2(5): 493-498 (1960).

Bennett, Raymond, et al., "O-Phosporic Acid Esters of 3,5-Diiodoyrosine and Thyroxine," Chemical Abstracts, 55(9):8303 (1961).

Cohen B.M. Journal of Asthma, 1984; V. 21(5) pp. 305-309.

Franssen et al., "Low Molecular Weight Proteins as Carriers for Renal Drug Targeting. Preparation of Drug-Protein Conjugates and Drug-spacer Derivatives and Their Catabolism in Renal Cortex Homogenates and Lysosomal Lystates," J. Med. Chem. 1992; 35: 1246-1259.

Furukawa, et al., "Effects of Glu-His-pro-amphetamine (TRH-amphetamine) guinea-pig: Antagonistic effect of amphetamine on TRH response", European Journal of Pharmacology, Elsevier BV., NL, vol. 112, No. 2, Jun. 7, 1985, pp. 237-241, XP025547293.

Giammona et al., Coupling of antiviral agent zidovudine to polyapartamide and in vitro drug release studies, Journal of Controlled Release 1998 vol. 54, pp. 321-331.

Greene, Theodora et al., "Protection for Phenols," Protective Groups in Organic Synthesis, $2^{nd}$ Ed., John Wiley & Sones, Inc. (1991).

Hussain et al. Synthesis and Structural Eludication of Lipophilic Azidothymidine Conjugates. Liebigs Ann. Chem. 1992, pp. 169-171.

Jung et al., Synthesis and In Vitro/In Vivo Evaluation of 5-Aminosalicyl-Glycine. Journal of Pharmaceutical Sciences May 2000 vol. 89, No. 5, pp. 594-602.

Kawai, Tohru, et al., "Direct Polymerization of N-Carboxyl Anhydride of L-Glutamic Acid," Makromol. Chem., 182:2127-2137 (1981).

Kinoshita et al., Serum Leucine Aminopeptidase Assay . . . Japanese Journal of Clinical Chemistry 1993, vol. 22, pp. 143-146.

Kuchimanchi KR, et al., "Intestinal absorption and biodistribution of cosalane and its amino acid conjugates: novel anti-HIV agents" International Journal of Pharacuetics 231(2002) 197-221.

Matsumoto et al. 'Double-Drugs'—A New Class or Prodrug .. Bioorganic & Medicinal Chemistry Letters, 2000, vol. 10, pp. 1227-1231.

Nariyoshi, Ebihara, et al., "Polyamino Acid Block Copolymer and Preparation Thereof," (Abstract of JP55145736) (Nov. 13, 1980).

Nishida, Koyo, et al., "Pharmacokinetic Analysis of in Vivo Metabolism of Amino Acid or Dipetide Conjugates of Salicyclic Acid in Rabbit Intestinal Microorganisms," Pharmaceutical Research, 11(1): 160-164 (1994).

Perisico, F.J., et al., "Effect of Tolmetin Glycine Amide (McN-4366), a Prodrug of Tolmetin Sodium, on Adjuvant Arthritis in the Rate," The Journal of Pharmacology and Experimental Therapeutics, 247(3): 889-896 (1986).

Physician's Desk Reference, "Acuprin 18 Adult Low Dose Aspirin Contaqins 81 Mg of Enteric Coated Aspirin," Jan. 1, 1996, XP002932207,2 pages.

Portoghese, P.S. et al., J. Med Chem (1997(30(11) pp. 1991-1994.

Schenk, J., The functioning neuronal transporter for dopamine: kinretic mechanisms and effects of amphetamines, cocaine and methyphenidata, Progress in Drug Research, vol. 59, 2002.

Schmidt, Briggitte F., et al., "Peptide-Linked 1,3-Dialkyl-3-acyltriazenes: Gastrin Receptor Directed Antineoplastic Alkylating Agents," Journal of Medicinal Chemistry, 37(22): 3812-3817 (1994).

Shimizu, NS et al., "Inhibition of Infection of T-cell with Human Immunodefficiency virus type 1 by dideoxynuclosides conjugates with oligopeptides" Antiviral Chemistry and Chemotherapy (1995) 6(1), 17-24.

Smith CB et al., "Dihydromorphine-peptide hybrids have mu receptor antagonistic and delta receptor agonistic activity on the mouse was deferens and bind with high affinity to opioid receptors in rat brain." NIDA Res Monogr. 75:189-92 (1986).

Smith Richard H., et al., "1,3-Dimethyl-3-acyltriazenes: Synthesis and Chemistry of a Novel Class of Biological Methylating Agents," J. Org. Chem. 51(20):3751-3757 (1986).

U.S. Appl. No. 12/169,389: Non-Final Office Action dated Dec. 10, 2010, Including Form PTO-892 (23 pages).

Ueki, Masaki, et al., Methylphosphinyl (Omp): A New Protecting Group of Tyrosine Suitable for Peptide Synthesis by Use of Boc-Amino Acids, I Tetrahedron Letters, 27(35):4181-4184 (1996).

Weber, et al., "Synthesis, In Vitro Skin Permaeation Studies, and PLS-Analysis of New Naproxen Derivatives," Pharmaceutical Research, 2001: 18(5):600-607.

U.S. Appl. No. 13/267,585, filed Oct. 6, 2011.

* cited by examiner

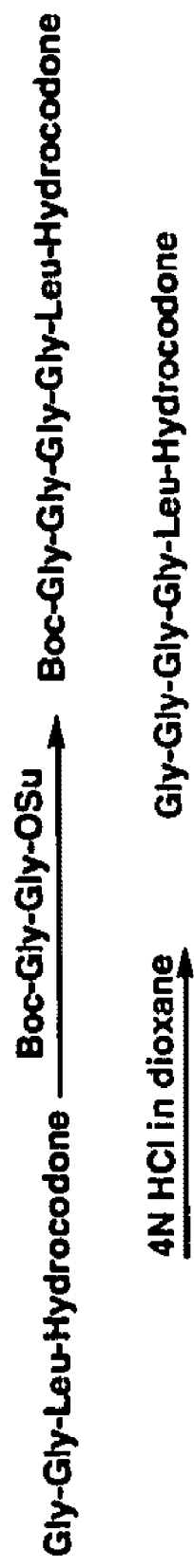
FIGURE 7
FIGURE 8

FIGURE 38
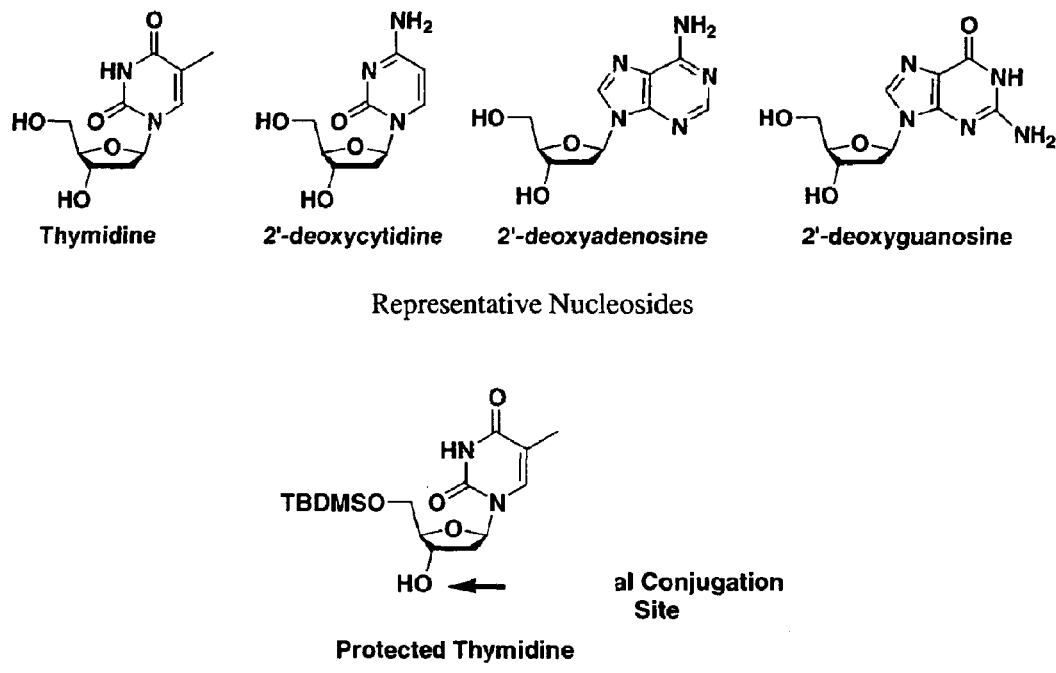
Representative Nucleosides
Site of Conjugation for Hydrocodone
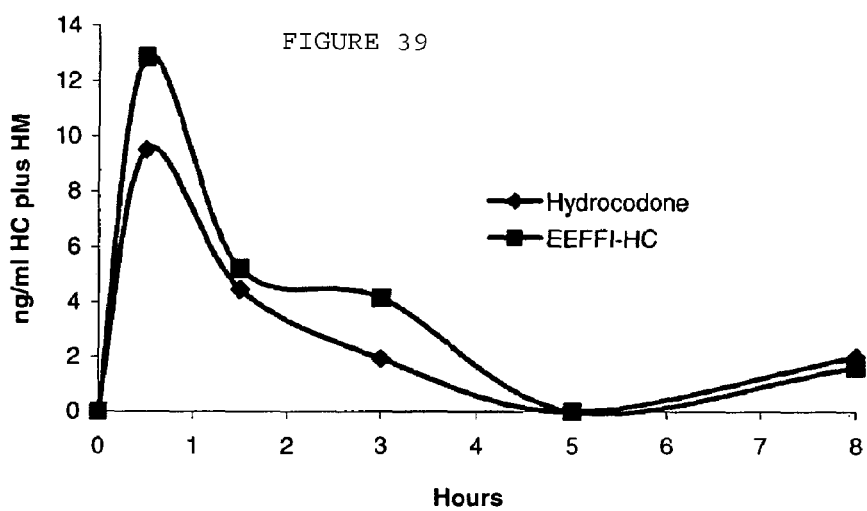
FIGURE 39

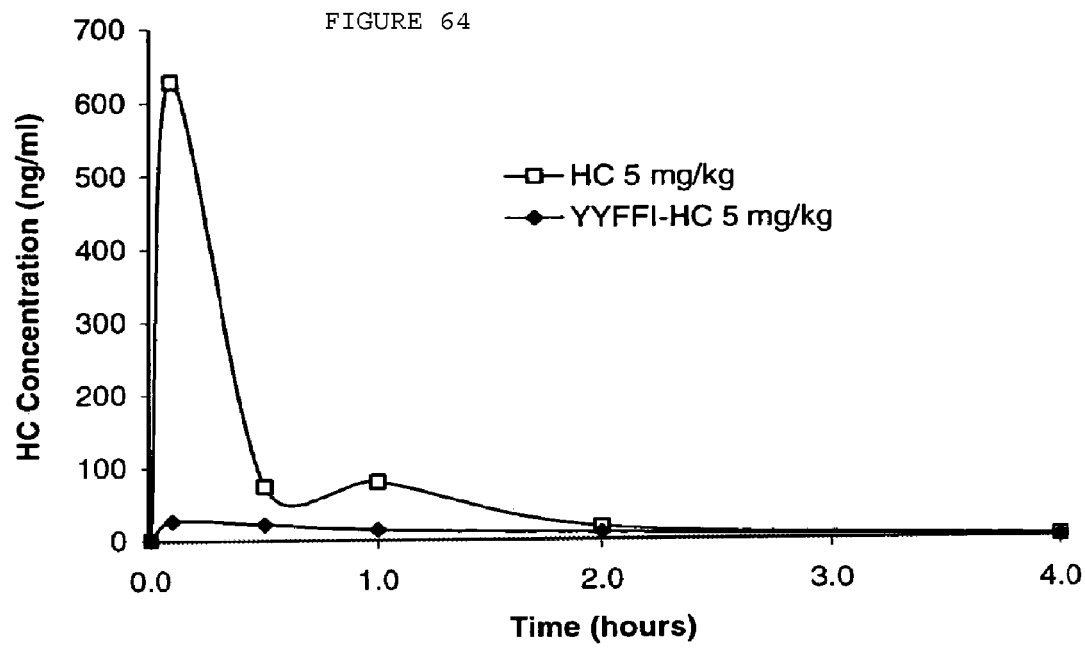
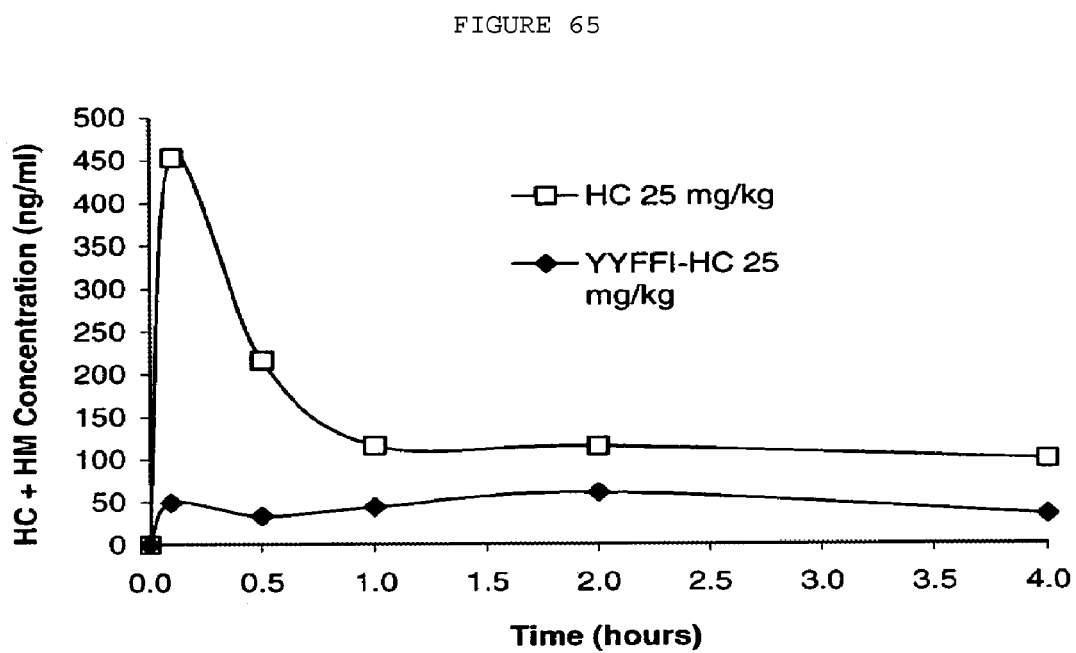

SEQUENCE LISTING

```
<160> NUMBER OF SEQ ID NOS: 25

<210> SEQ ID NO 1
<211> LENGTH: 5
<212> TYPE: PRT
<213> ORGANISM: Artificial Sequence
<220> FEATURE:
<223> OTHER INFORMATION: synthetic carrier

<400> SEQUENCE: 1

Gly Gly Gly Gly Leu
1               5

<210> SEQ ID NO 2
<211> LENGTH: 6
<212> TYPE: PRT
<213> ORGANISM: Artificial Sequence
<220> FEATURE:
<223> OTHER INFORMATION: synthetic carrier

<400> SEQUENCE: 2

Glu Glu Phe Phe Phe Ile
1               5

<210> SEQ ID NO 3
<211> LENGTH: 5
<212> TYPE: PRT
<213> ORGANISM: Artificial Sequence
<220> FEATURE:
<223> OTHER INFORMATION: synthetic carrier

<400> SEQUENCE: 3

Glu Glu Phe Phe Phe
1               5

<210> SEQ ID NO 4
<211> LENGTH: 5
<212> TYPE: PRT
<213> ORGANISM: Artificial Sequence
<220> FEATURE:
<223> OTHER INFORMATION: synthetic carrier
```

```
<400> SEQUENCE: 4

Tyr Tyr Phe Phe Ile
1               5

<210> SEQ ID NO 5
<211> LENGTH: 5
<212> TYPE: PRT
<213> ORGANISM: Artificial Sequence
<220> FEATURE:
<223> OTHER INFORMATION: synthetic carrier

<400> SEQUENCE: 5

Glu Glu Phe Phe Ile
1               5

<210> SEQ ID NO 6
<211> LENGTH: 5
<212> TYPE: PRT
<213> ORGANISM: Artificial Sequence
<220> FEATURE:
<223> OTHER INFORMATION: synthetic carrier

<400> SEQUENCE: 6

Tyr Tyr Lys Tyr Tyr
1               5

<210> SEQ ID NO 7
<211> LENGTH: 5
<212> TYPE: PRT
<213> ORGANISM: Artificial Sequence
<220> FEATURE:
<223> OTHER INFORMATION: synthetic carrier

<400> SEQUENCE: 7

Phe Phe Lys Phe Phe
1               5

<210> SEQ ID NO 8
<211> LENGTH: 4
<212> TYPE: PRT
<213> ORGANISM: Artificial Sequence
<220> FEATURE:
<223> OTHER INFORMATION: synthetic carrier

<400> SEQUENCE: 8

Lys Lys Gly Gly
1

<210> SEQ ID NO 9
<211> LENGTH: 5
<212> TYPE: PRT
<213> ORGANISM: Artificial Sequence
<220> FEATURE:
<223> OTHER INFORMATION: synthetic carrier

<400> SEQUENCE: 9

Glu Glu Glu Glu Glu
1               5

<210> SEQ ID NO 10
<211> LENGTH: 5
<212> TYPE: PRT
<213> ORGANISM: Artificial Sequence
<220> FEATURE:
<223> OTHER INFORMATION: synthetic carrier

<400> SEQUENCE: 10
```

```
Glu Glu Gly Gly Ile
1               5

<210> SEQ ID NO 11
<211> LENGTH: 5
<212> TYPE: PRT
<213> ORGANISM: Artificial Sequence
<220> FEATURE:
<223> OTHER INFORMATION: synthetic carrier

<400> SEQUENCE: 11

Glu Glu Gly Gly Leu
1               5

<210> SEQ ID NO 12
<211> LENGTH: 5
<212> TYPE: PRT
<213> ORGANISM: Artificial Sequence
<220> FEATURE:
<223> OTHER INFORMATION: synthetic carrier

<400> SEQUENCE: 12

Gly Gly Gly Gly Ile
1               5

<210> SEQ ID NO 13
<211> LENGTH: 5
<212> TYPE: PRT
<213> ORGANISM: Artificial Sequence
<220> FEATURE:
<223> OTHER INFORMATION: synthetic carrier

<400> SEQUENCE: 13

Lys Lys Gly Gly Ile
1               5

<210> SEQ ID NO 14
<211> LENGTH: 5
<212> TYPE: PRT
<213> ORGANISM: Artificial Sequence
<220> FEATURE:
<223> OTHER INFORMATION: synthetic carrier

<400> SEQUENCE: 14

Lys Lys Pro Pro Ile
1               5

<210> SEQ ID NO 15
<211> LENGTH: 5
<212> TYPE: PRT
<213> ORGANISM: Artificial Sequence
<220> FEATURE:
<223> OTHER INFORMATION: synthetic carrier

<400> SEQUENCE: 15

Tyr Tyr Gly Gly Ile
1               5

<210> SEQ ID NO 16
<211> LENGTH: 5
<212> TYPE: PRT
<213> ORGANISM: Artificial Sequence
<220> FEATURE:
<223> OTHER INFORMATION: synthetic carrier

<400> SEQUENCE: 16

Gly Gly Pro Pro Ile
```

```
<210> SEQ ID NO 17
<211> LENGTH: 5
<212> TYPE: PRT
<213> ORGANISM: Artificial Sequence
<220> FEATURE:
<223> OTHER INFORMATION: synthetic carrier

<400> SEQUENCE: 17

Asp Asp Phe Phe Ile
1               5

<210> SEQ ID NO 18
<211> LENGTH: 5
<212> TYPE: PRT
<213> ORGANISM: Artificial Sequence
<220> FEATURE:
<223> OTHER INFORMATION: synthetic carrier

<400> SEQUENCE: 18

Glu Glu Asp Asp Ile
1               5

<210> SEQ ID NO 19
<211> LENGTH: 5
<212> TYPE: PRT
<213> ORGANISM: Artificial Sequence
<220> FEATURE:
<223> OTHER INFORMATION: synthetic carrier

<400> SEQUENCE: 19

Lys Lys Asp Asp Ile
1               5

<210> SEQ ID NO 20
<211> LENGTH: 5
<212> TYPE: PRT
<213> ORGANISM: Artificial Sequence
<220> FEATURE:
<223> OTHER INFORMATION: synthetic carrier

<400> SEQUENCE: 20

Tyr Tyr Glu Glu Ile
1               5

<210> SEQ ID NO 21
<211> LENGTH: 5
<212> TYPE: PRT
<213> ORGANISM: Artificial Sequence
<220> FEATURE:
<223> OTHER INFORMATION: synthetic carrier

<400> SEQUENCE: 21

Asp Asp Asp Asp Ile
1               5

<210> SEQ ID NO 22
<211> LENGTH: 5
<212> TYPE: PRT
<213> ORGANISM: Artificial Sequence
<220> FEATURE:
<223> OTHER INFORMATION: synthetic carrier

<400> SEQUENCE: 22

Lys Lys Glu Glu Ile
1               5
```

```
<210> SEQ ID NO 23
<211> LENGTH: 5
<212> TYPE: PRT
<213> ORGANISM: Artificial Sequence
<220> FEATURE:
<223> OTHER INFORMATION: synthetic carrier

<400> SEQUENCE: 23

Tyr Tyr Phe Pro Ile
1               5

<210> SEQ ID NO 24
<211> LENGTH: 5
<212> TYPE: PRT
<213> ORGANISM: Artificial Sequence
<220> FEATURE:
<223> OTHER INFORMATION: synthetic carrier

<400> SEQUENCE: 24

Gly Gly Lys Gly Gly
1               5

<210> SEQ ID NO 25
<211> LENGTH: 5
<212> TYPE: PRT
<213> ORGANISM: Artificial Sequence
<220> FEATURE:
<223> OTHER INFORMATION: synthetic carrier

<400> SEQUENCE: 25

Pro Pro Lys Pro Pro
1               5
```

PHARMACEUTICAL COMPOSITIONS FOR PREVENTION OF OVERDOSE OR ABUSE

CROSS REFERENCE TO RELATED APPLICATIONS

This application is a continuation of U.S. patent application Ser. No. 11/089,056, filed Mar. 25, 2005, which is a continuation-in-part application and claims priority to 35 U.S.C. §120 to U.S. application Ser. No. 09/933,708 filed Aug. 22, 2001; U.S. patent application Ser. No. 11/089,056 is also a continuation-in-part and claims benefit under 35 U.S.C. 120 to U.S. application Ser. No. 10/156,527 filed May 29, 2002, which claims the benefit under 35 U.S.C. 119(e) to U.S. Provisional application No. 60/358,368 filed Feb. 22, 2002, and U.S. Provisional application No. 60/366,258 filed Mar. 22, 2002 and U.S. Provisional No. 60/358,381 filed Feb. 22, 2002; U.S. patent application Ser. No. 11/089,056 is also a continuation-in-part and claims benefit under 35 U.S.C. 120 to U.S. application Ser. 10/953,119 filed Sep. 30, 2004, which claims benefit under 35 U.S.C. 119(e) to U.S. Provisional application No. 60/567,800 filed May 5, 2004; U.S. Provisional application No. 60/507,012 filed Sep. 30, 2003; U.S. Provisional application No. 60/567,802 filed May 5, 2004; and U.S. Provisional application No. 60/568,011 filed on May 5, 2004; U.S. patent application Ser. No. 11/089,056 is also a continuation-in-part and claims benefit under 35 U.S.C. §120 to U.S. application Ser. No. 10/953,110 filed Sep. 30, 2004; U.S. patent application Ser. No. 11/089,056 is also a continuation-in-part and claims benefit under 35 U.S.C. §120 to Ser. No. 10/923,257 filed Aug. 23, 2004; U.S. patent application Ser. No. 11/089,056 is also a continuation-in-part and claims benefit under 35 U.S.C. §120 to Ser. No. 10/923,088 filed Aug. 23, 2004 which claims benefit under 35 U.S.C. §120 to and is a continuation-in-part application of PCT application No. US03/05525 filed Feb. 24, 2003 which claims benefit under 35 U.S.C. §119(e) to U.S. Provisional Application No. 60/362,082 filed Mar. 7, 2002; U.S. patent application Ser. No. 11/089,056 is also a continuation-in-part and claims benefit under 35 U.S.C. §120 to U.S. application Ser. No. 10/955,006 filed Sep. 30, 2004; U.S. patent application Ser. No. 11/089,056 is also a continuation-in-part and claims benefit under 35 U.S.C. §120 to U.S. application Ser. No. 10/953,116 filed Sep. 30, 2004; U.S. patent application Ser. No. 11/089,056 is also a continuation-in-part and claims benefit under 35 U.S.C. 120 to U.S. application Ser. No. 10/953,111 filed Sep. 30, 2004; U.S. patent application Ser. No. 11/089,056 is a continuation-in-part and claims benefit under 35 U.S.C. §119 to PCT/US04/32131 filed Sep. 30, 2004. Each of the above applications are hereby incorporated by reference in their entirety.

BACKGROUND

Accidental and intentional overdose with prescription and over the counter drugs is a serious health problem with thousands of fatalities occurring each year as a result. The present invention relates to pharmaceutical compositions comprised of a chemical moiety attached to an active agent in a manner that substantially decreases the potential of the active agent to cause overdose or to be abused. When delivered at the proper dosage the pharmaceutical composition provides therapeutic activity similar to that of the parent active agent. However, when the composition is delivered at higher doses the potential for overdose or abuse is reduced due to the limited bioavailability of the active agent as compared to the active agent delivered as free drug.

BRIEF DESCRIPTION OF THE FIGURES

FIG. 7. illustrates the preparation of Gly-Gly-Leu-Hydrocodone.

FIG. 8. illustrates preparation of Gly-Gly-Gly-Gly-Leu-Hydrocodone.

FIG. 38. illustrates nucleosides and conjugation sites.

FIG. 39. Oral bioavailability in rats for hydrocodone vs. EEFFFI-HC at a dose (1 mg/kg) approximating a therapeutic human dose equivalent measured as free hydrocodone.

FIG. 64. Oral bioavailability of hydromorphone (concentration vs. time) following administration of hydrocodone bitratrate or YYFFI-HC at 5 mg/kg (equimolar doses with equivalent content of hydrocodone base) in rats, measured as free hydrocodone.

FIG. 65. Oral bioavailability of hydrocodone plus hydromorphone (concentration vs. time) following administration of hydrocodone bitratrate or YYFFI-HC at 25 mg/kg (equimolar doses with equivalent content of hydrocodone base) in rats, measured as free hydrocodone.

Figure 120:
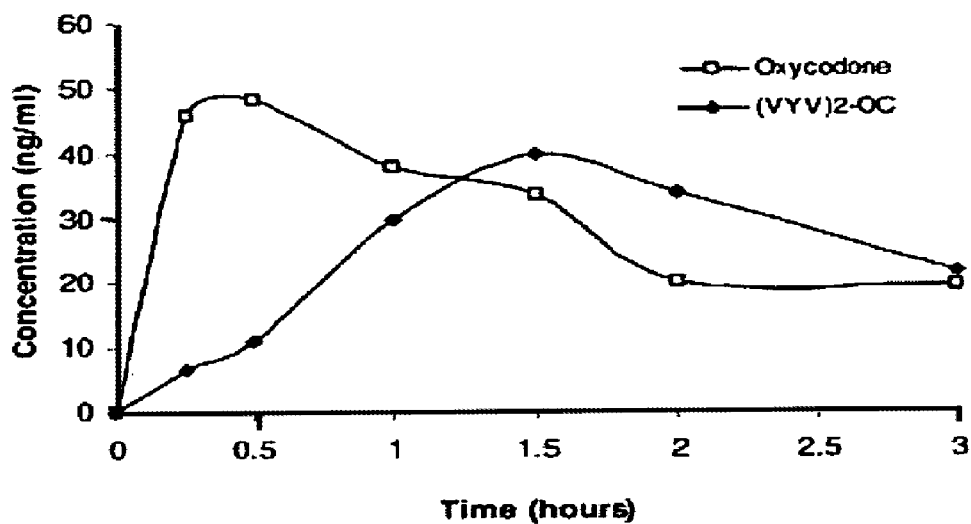

FIG. 120. Oral bioavailability of abuse-resistant oxycodone disubstituted tripeptide conjugates, measured as free oxycodone.

Figure 121:
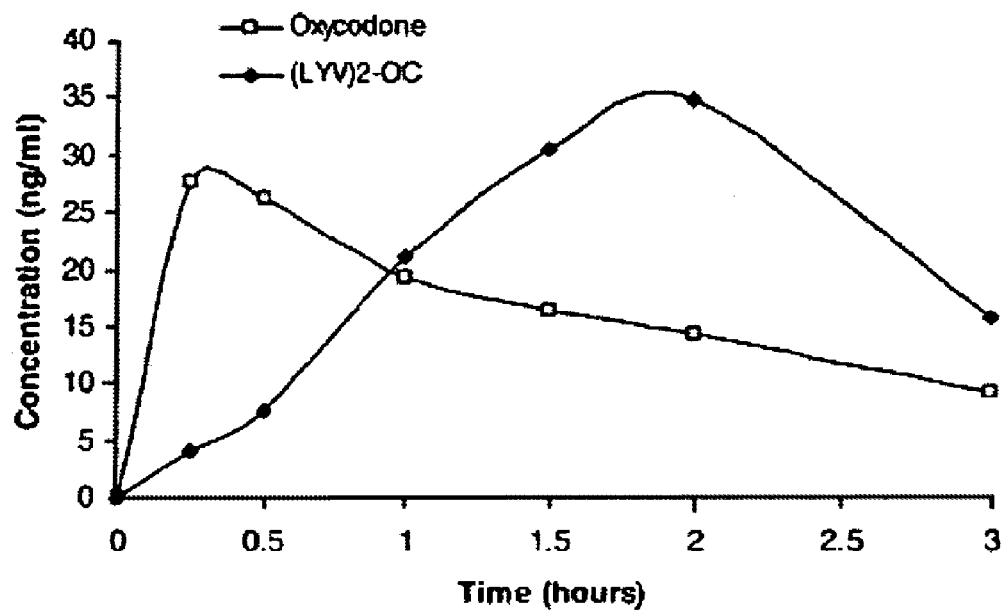

FIG. 121. Oral bioavailability of abuse-resistant oxycodone disubstituted tripeptide conjugates, measured as free oxycodone.

Figure 122:
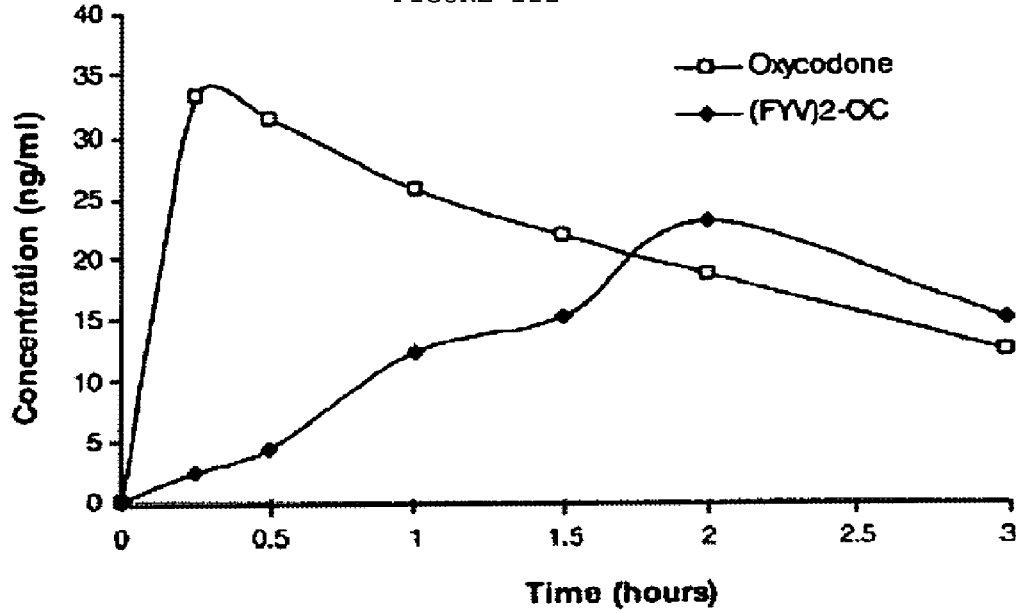

FIG. 122. Oral bioavailability of abuse-resistant oxycodone disubstituted tripeptide conjugates, measured as free oxycodone.

Figure 123:
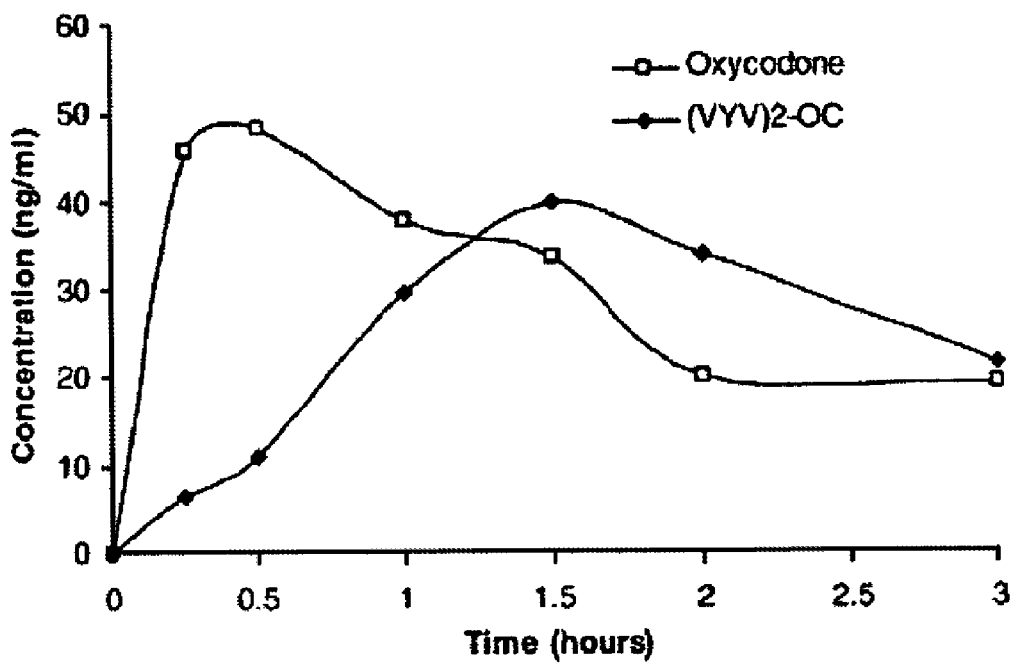

FIG. 123. Oral bioavailability of abuse-resistant oxycodone disubstituted tripeptide conjugates, measured as free oxycodone.

Figure 124:
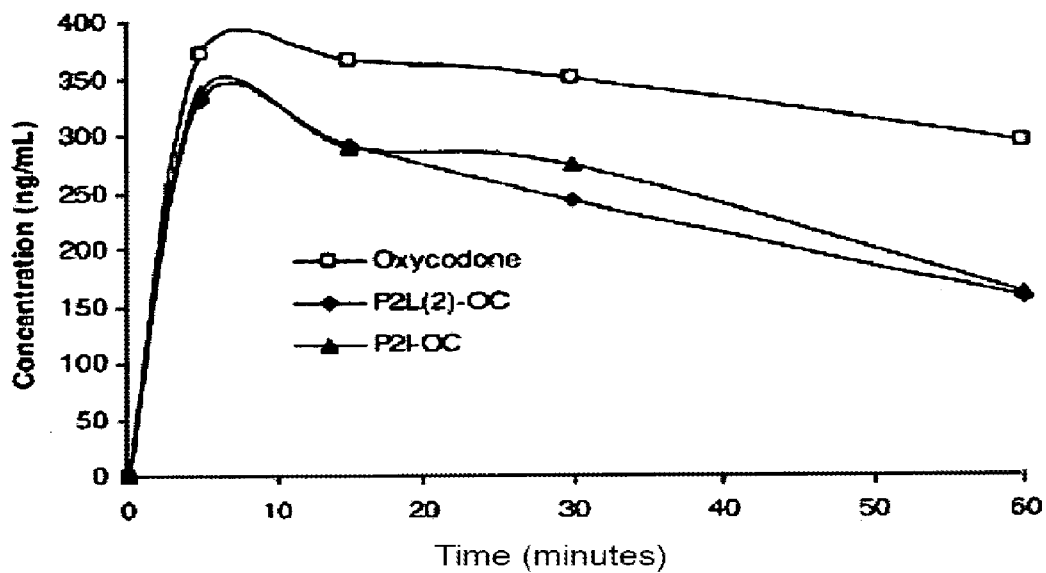

FIG. 124. Intranasal bioavailability of abuse-resistant oxycodone disubstituted tripeptide conjugates, measured as free oxycodone.

Figure 125:
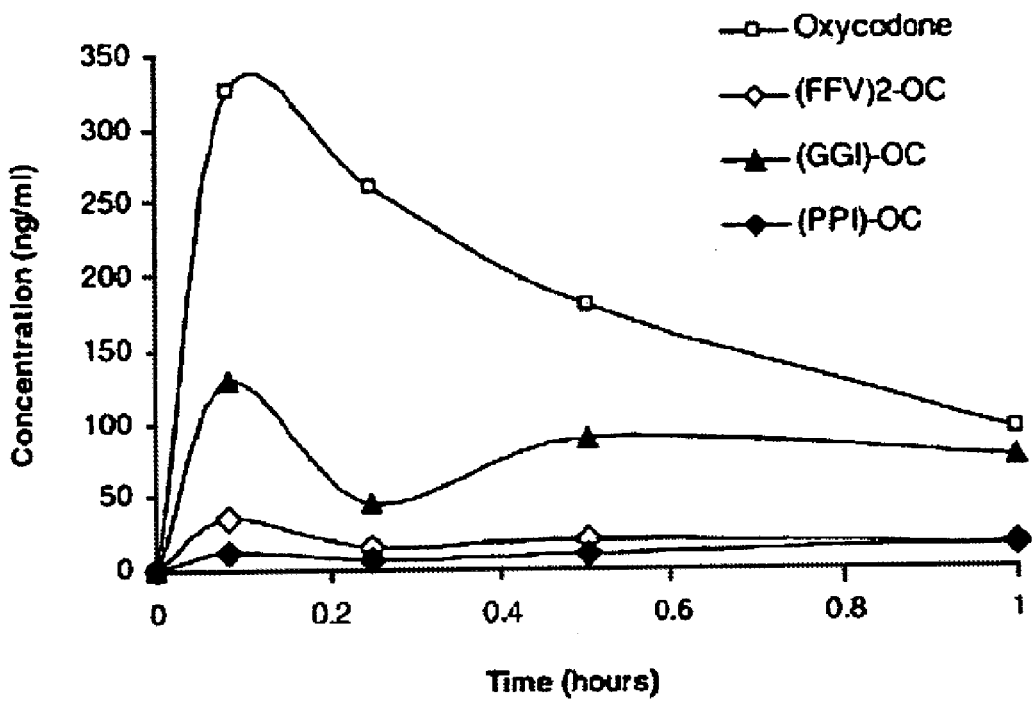

FIG. 125. Intranasal bioavailability of abuse-resistant oxycodone disubstituted tripeptide conjugates, measured as free oxycodone.

Figure 126:
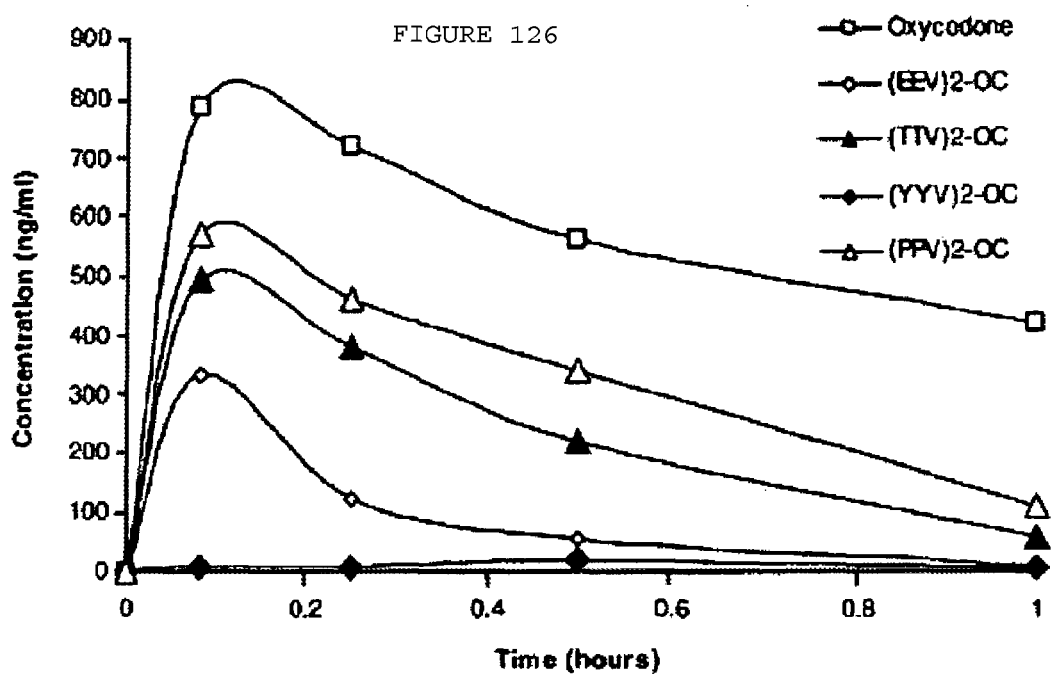

FIG. 126. Intranasal bioavailability of abuse-resistant oxycodone disubstituted tripeptide conjugates, measured as free oxycodone.

Figure 127:
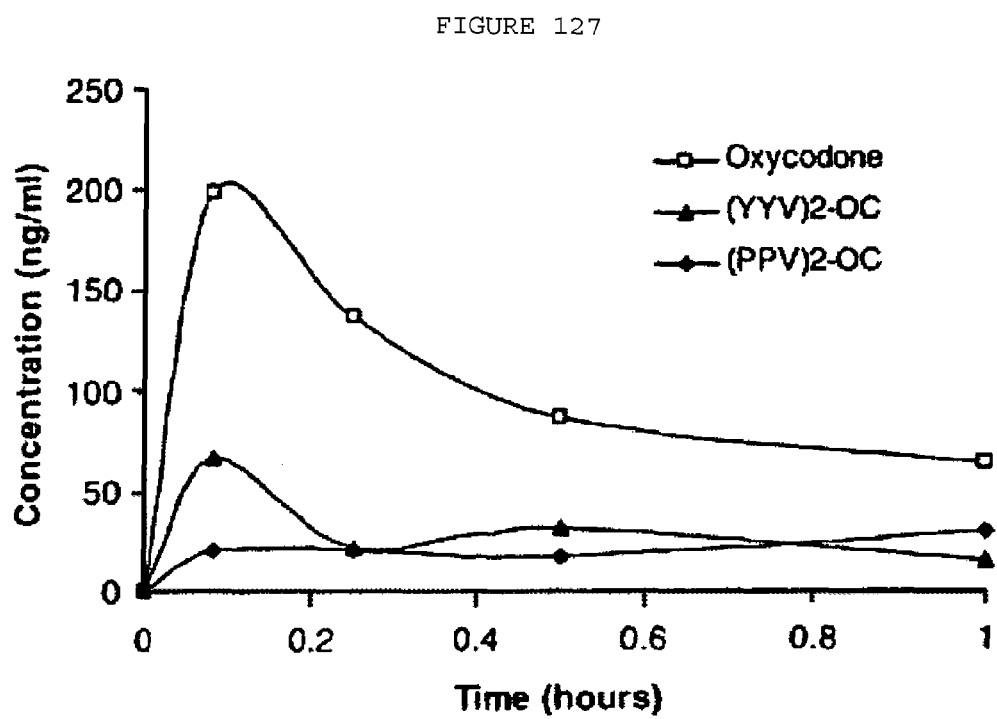

FIG. 127. Intravenous bioavailability of abuse-resistant oxycodone disubstituted tripeptide conjugates, measured as free oxycodone.

Figure 128:
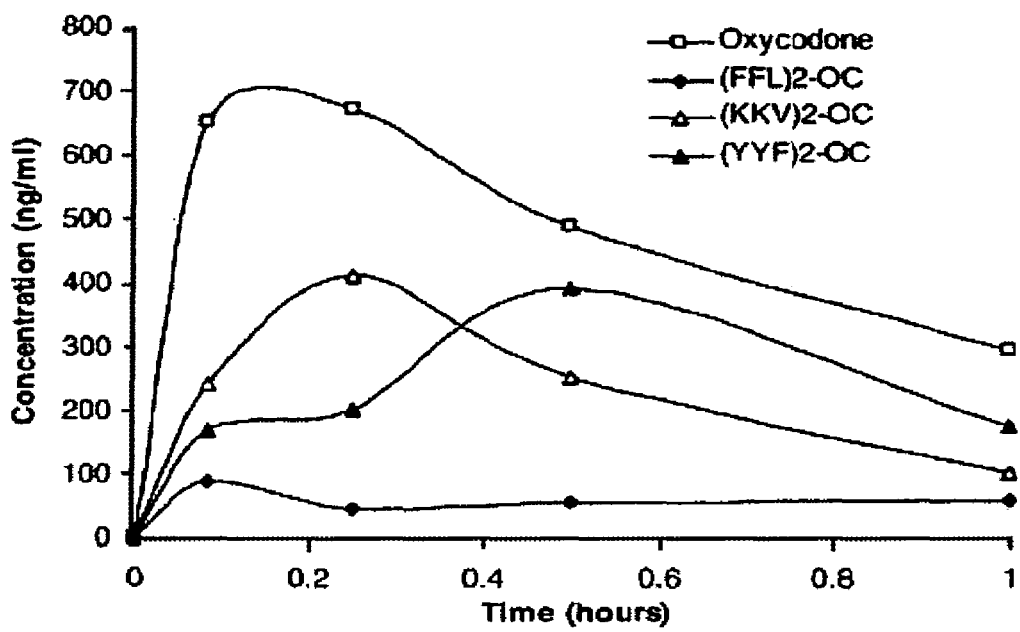

FIG. 128. Intranasal bioavailability of abuse-resistant oxycodone disubstituted tripeptide conjugates, measured as free oxycodone.

Figure 129:
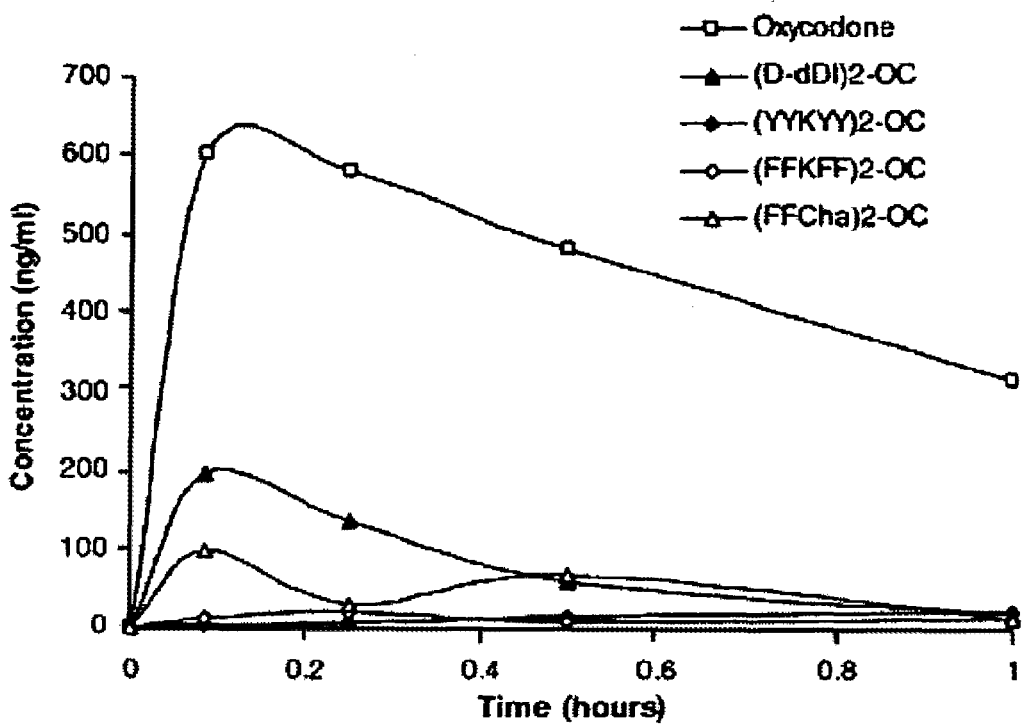

FIG. 129. Intranasal bioavailability of abuse-resistant oxycodone disubstituted tripeptide conjugates, measured as free oxycodone.

Figure 130:
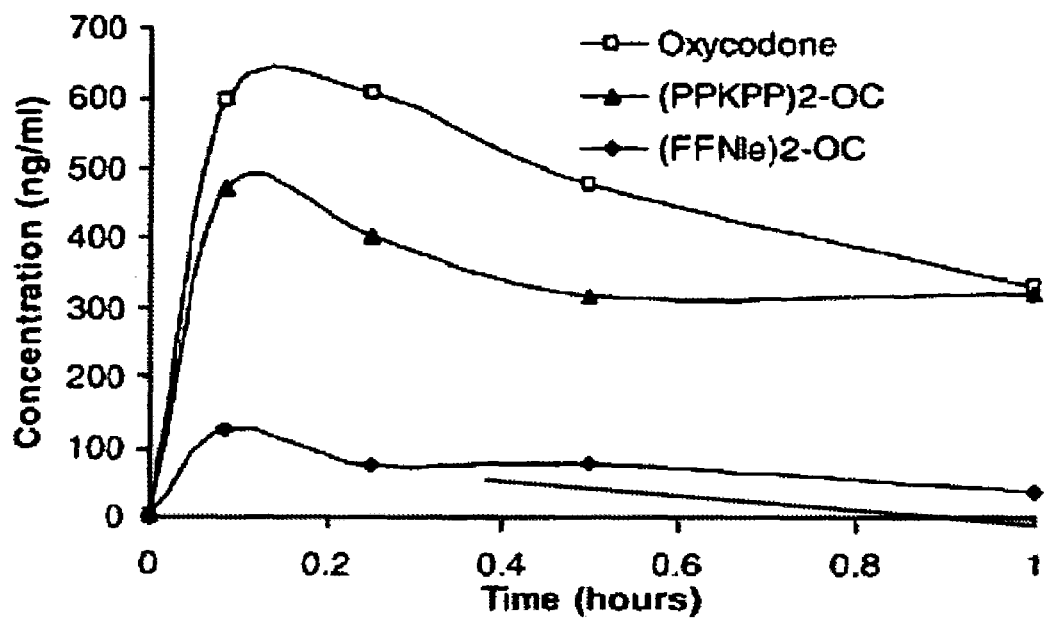

FIG. 130. Intranasal bioavailability of abuse-resistant oxycodone disubstituted tripeptide conjugates, measured as free oxycodone.

Figure 131:
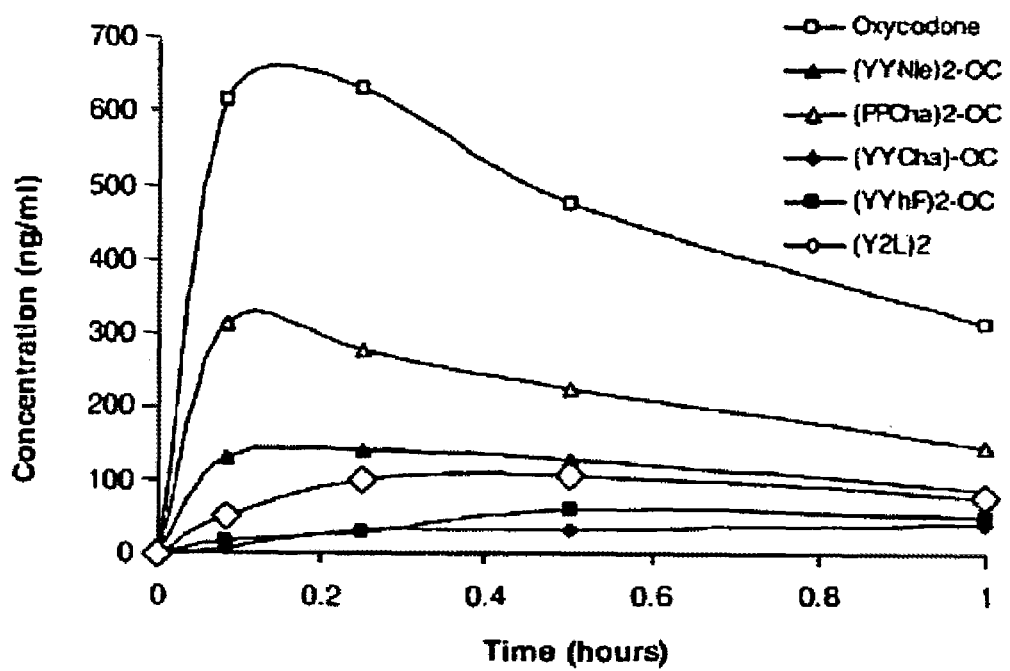

FIG. 131. Intranasal bioavailability of abuse-resistant oxycodone disubstituted tripeptide conjugates, measured as free oxycodone.

Figure 132:
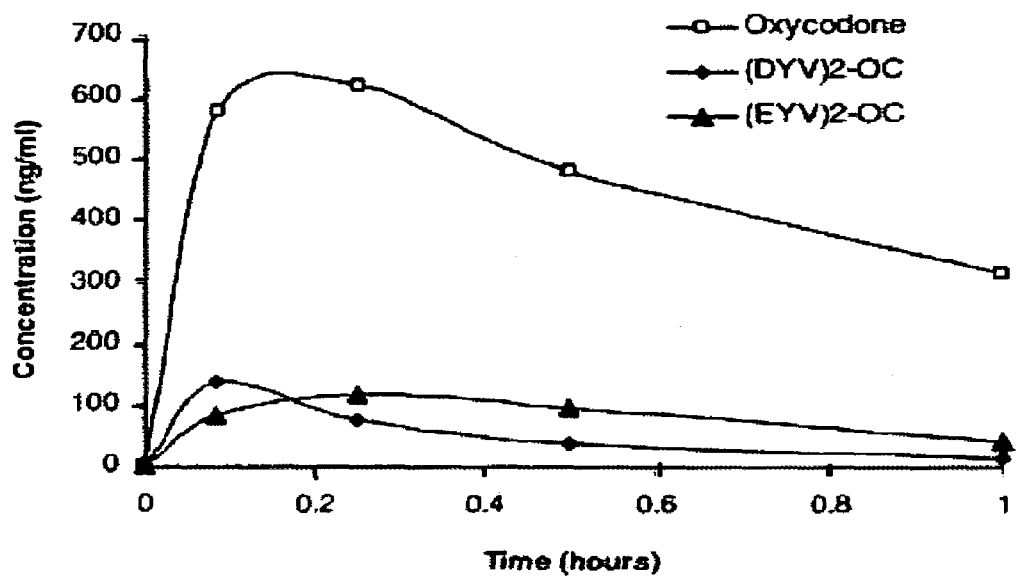

FIG. 132. Intranasal bioavailability of abuse-resistant oxycodone disubstituted tripeptide conjugates, measured as free oxycodone.

Figure 133:
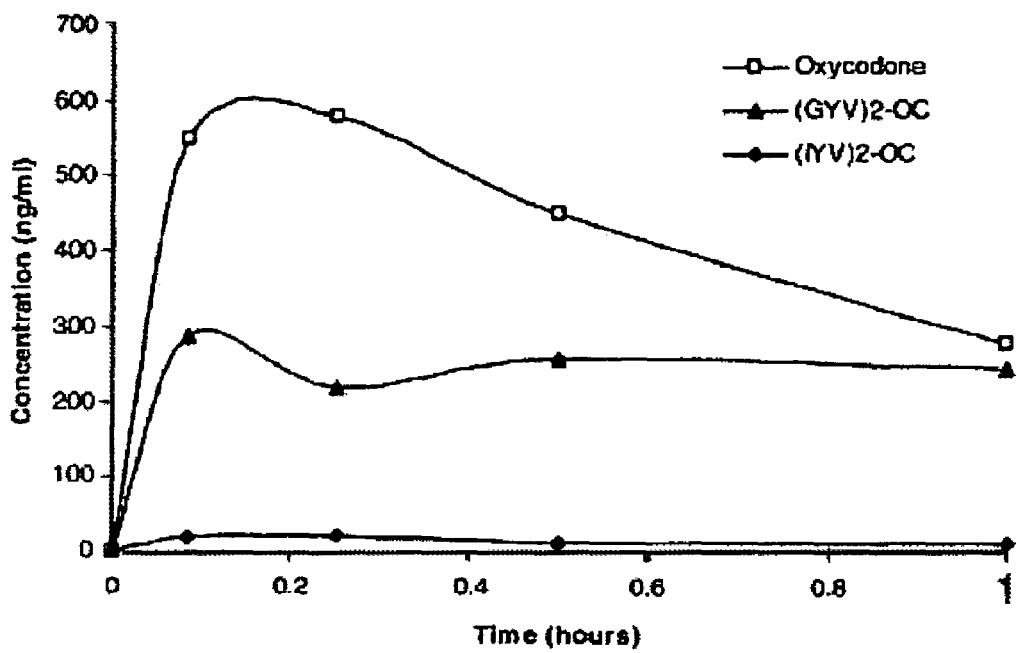

FIG. 133. Intranasal bioavailability of abuse-resistant oxycodone disubstituted tripeptide conjugates, measured as free oxycodone.

Figure 134:
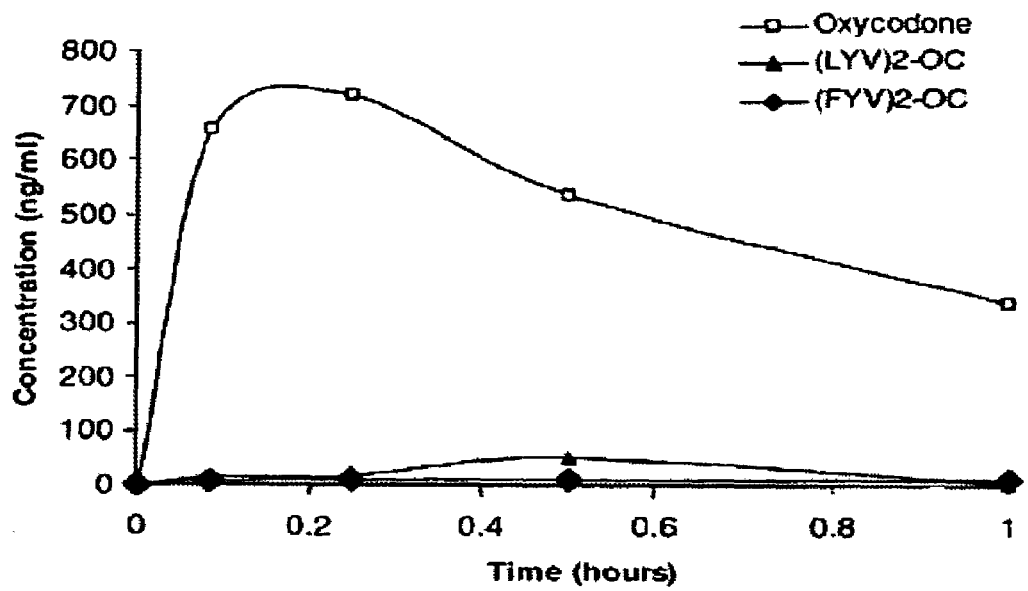

FIG. 134. Intranasal bioavailability of abuse-resistant oxycodone disubstituted tripeptide conjugates, measured as free oxycodone.

Figure 135:
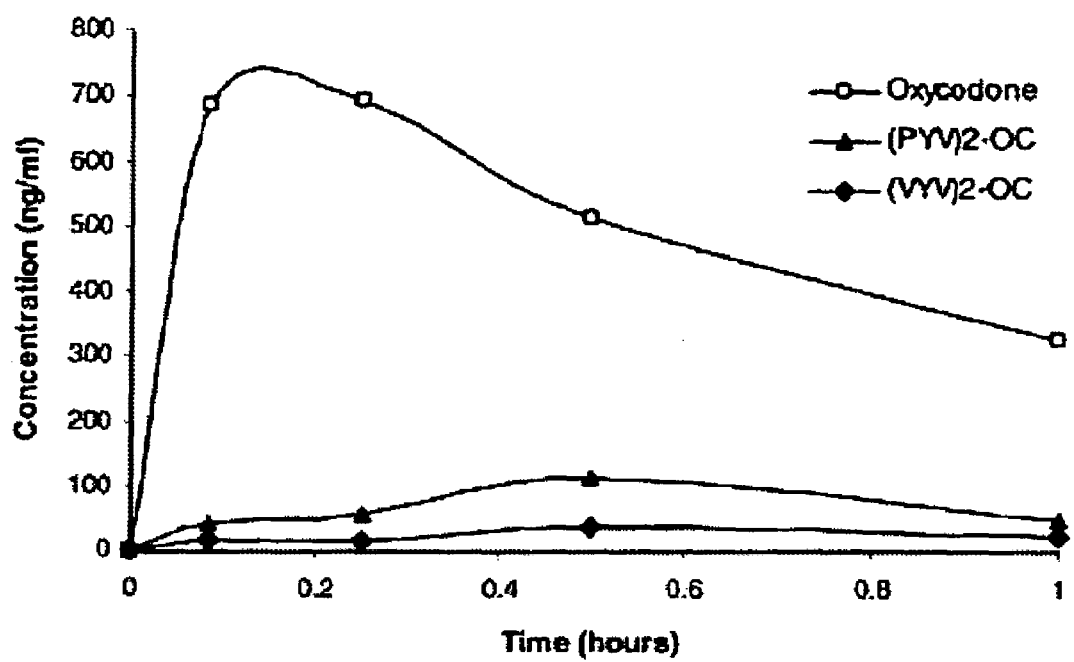

FIG. 135. Intranasal bioavailability of abuse-resistant oxycodone disubstituted tripeptide conjugates, measured as free oxycodone.

Figure 136:
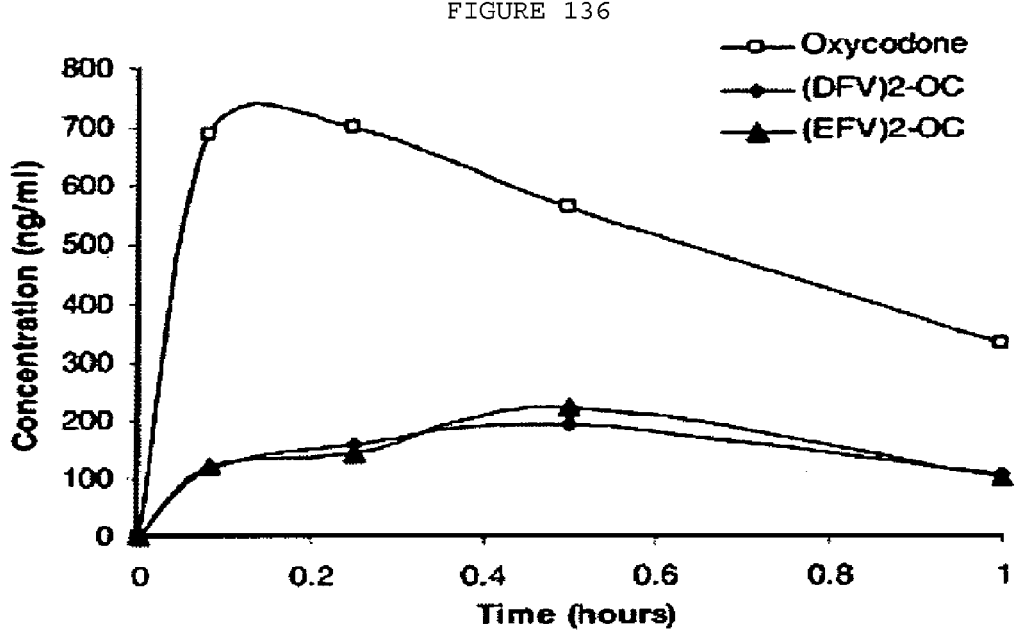

FIG. 136. Intranasal bioavailability of abuse-resistant oxycodone disubstituted tripeptide conjugates, measured as free oxycodone.

Figure 137:
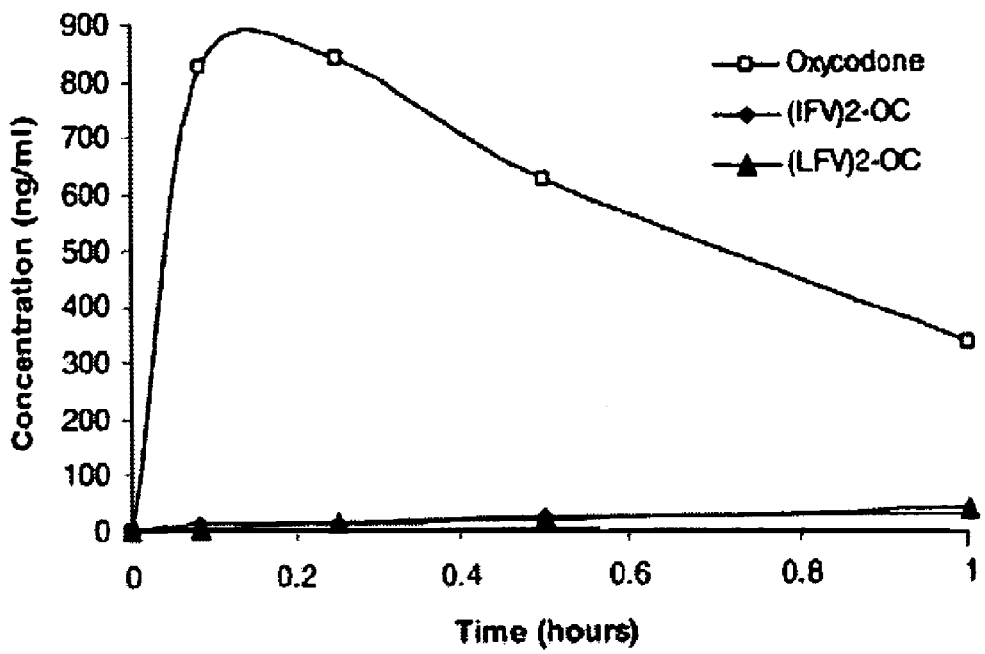

FIG. 137. Intranasal bioavailability of abuse-resistant oxycodone disubstituted tripeptide conjugates, measured as free oxycodone.

Figure 138:
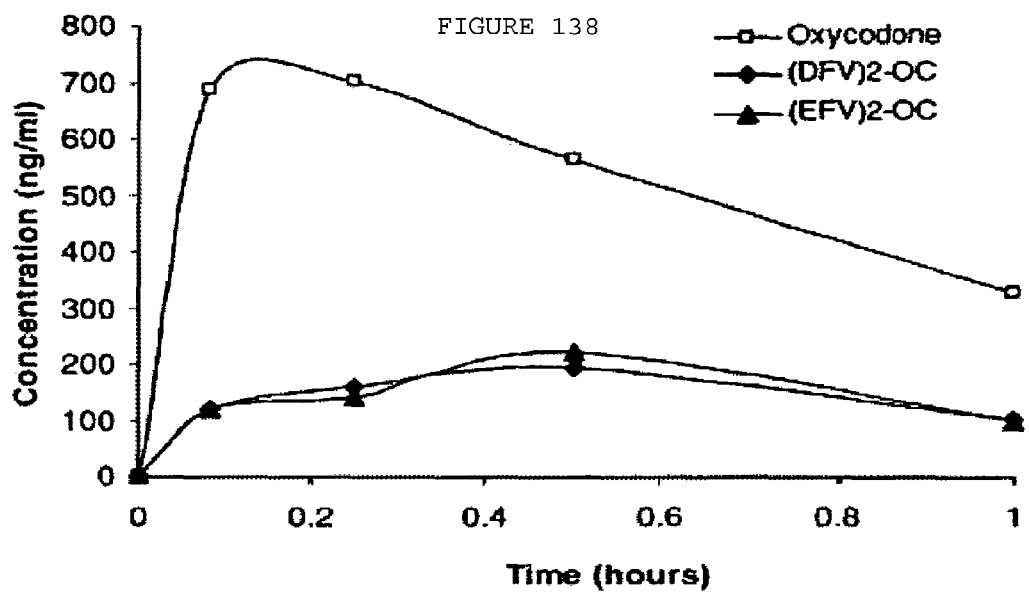

FIG. 138. Intranasal bioavailability of abuse-resistant oxycodone disubstituted tripeptide conjugates, measured as free oxycodone.

Figure 139:
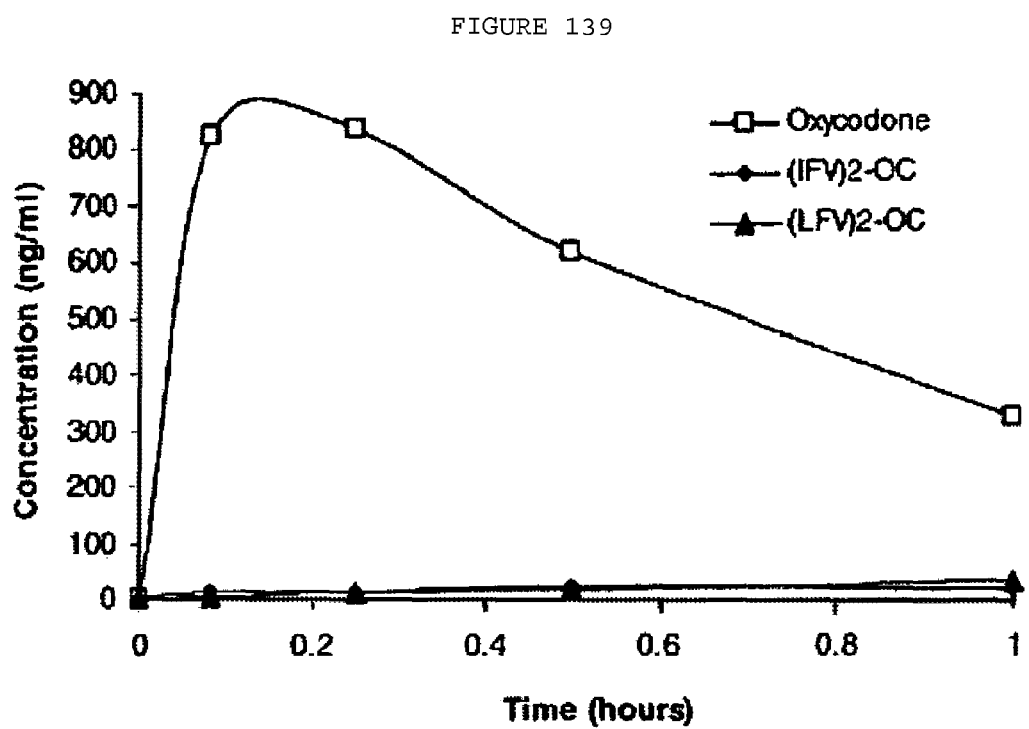

FIG. 139. Intranasal bioavailability of abuse-resistant oxycodone disubstituted tripeptide conjugates, measured as free oxycodone.

Figure 140:
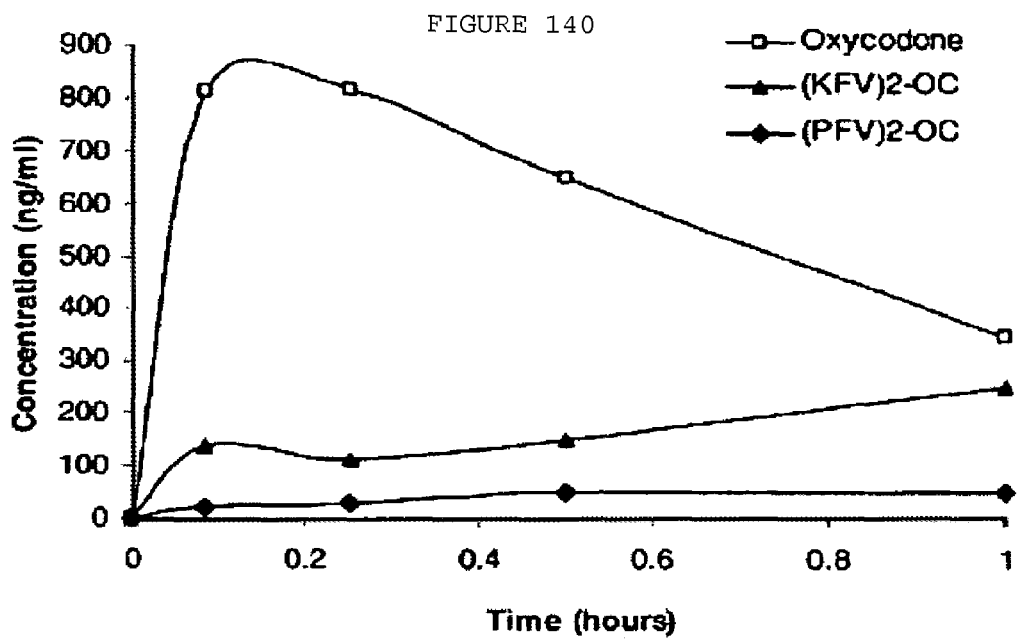

FIG. 140. Intranasal bioavailability of abuse-resistant oxycodone disubstituted tripeptide conjugates, measured as free oxycodone.

Figure 141:
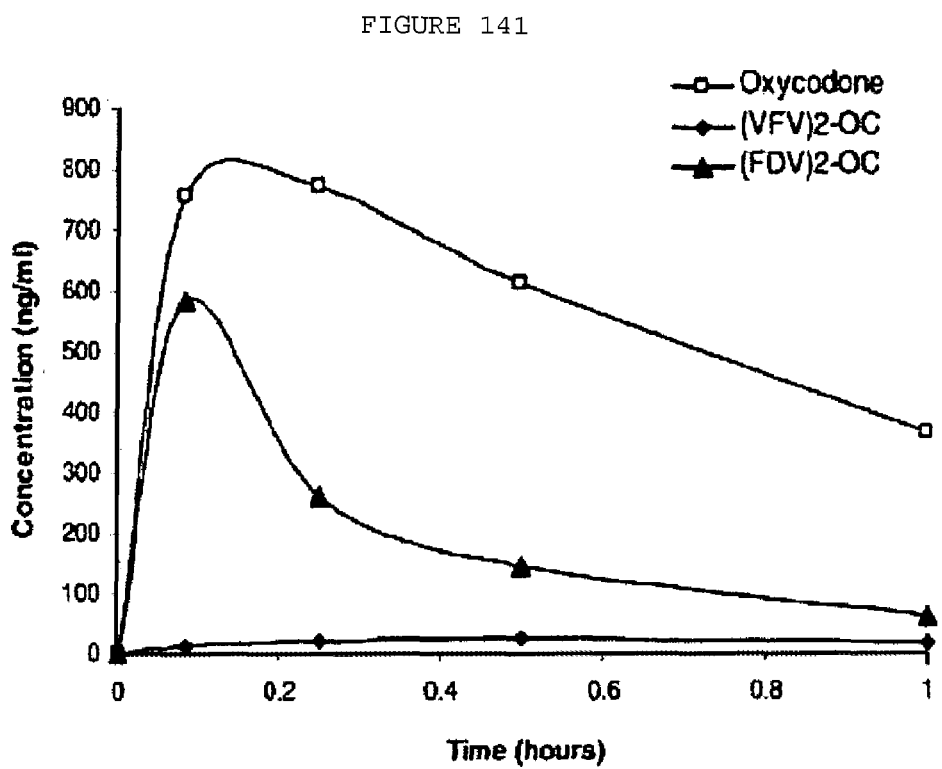

FIG. 141. Intranasal bioavailability of abuse-resistant oxycodone disubstituted tripeptide conjugates, measured as free oxycodone.

Figure 142:
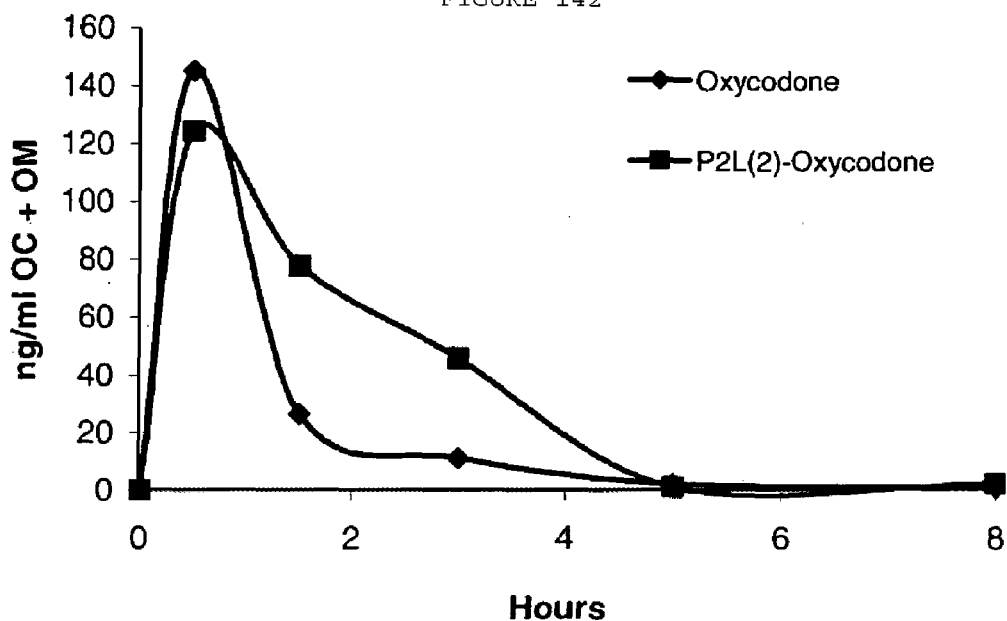

FIG. 142. Oral bioavailability in rats of oxycodone vs. $P2L_{(2)}$-Oxycodone at a dose (2.5 mg/kg) approximating a therapeutic human dose equivalent measured as free oxycodone.

Figure 143:
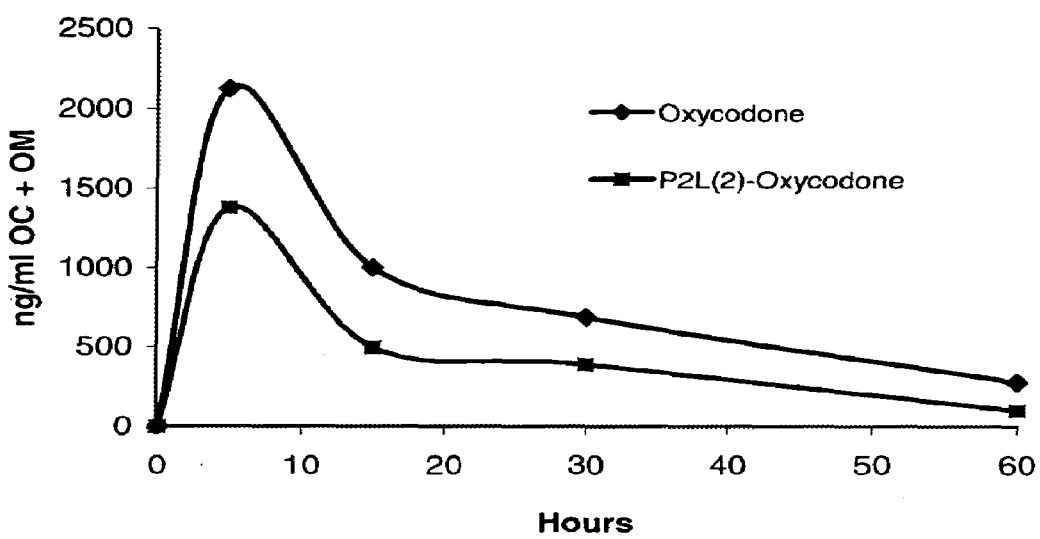

FIG. 143. Decrease in bioavailability of $P2L_{(2)}$-Oxycodone as compared to oxycodone by the intranasal route of administration-dose 2.5 mg/kg measured as free oxycodone.

Figure 144:
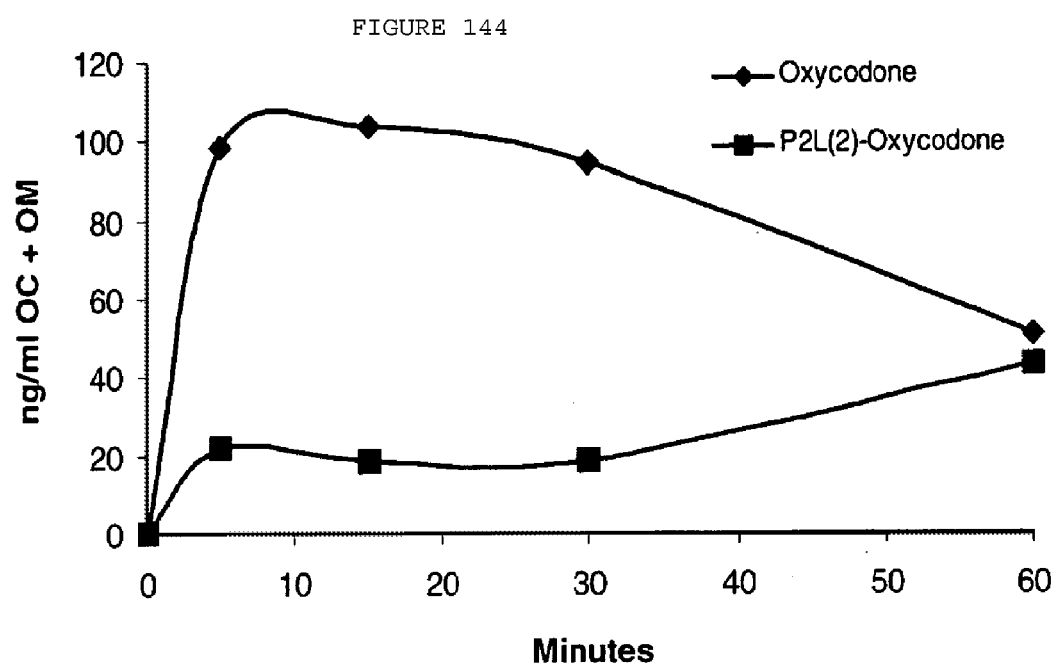

FIG. 144. Decrease in bioavailability of $P2L_{(2)}$-Oxycodone as compared to oxycodone by the intravenous route of administration-dose 0.5 mg/kg measured as free oxycodone.

DETAILED DESCRIPTION OF THE INVENTION

The present invention relates to changing the pharmacokinetic and pharmacological properties of active agents through covalent modification. Covalent attachment of a chemical moiety to an active agent can change the rate and extent of absorption, metabolism, distribution, and elimination of the active agent. When administered at a normal therapeutic dose the bioavailability (area under the time-versus-concentration curve; AUC) of the active agent is similar to that of the parent active agent compound. As the oral dose is increased, however, the bioavailability of the covalently modified active agent relative to the parent active agent begins to decline. At suprapharmacological doses the bioavailability of the active agent conjugate is substantially decreased as compared to the parent active agent. The relative decrease in bioavailability at higher doses abates the euphoria obtained when doses of the active agent conjugate are taken above those of the intended prescription. This in turn diminishes the abuse potential, whether unintended or intentionally sought.

Persons that abuse prescription drugs commonly seek to increase their euphoria by snorting or injecting the drugs. These routes of administration increase the rate and extent of drug absorption and provide a faster, nearly instantaneous, effect. This increases the amount of drug that reaches the central nervous system where it has its effect. In a particular embodiment of the invention the bioavailability of the covalently modified active agent is substantially decreased by the intranasal and intravenous routes as compared to the parent active agent. Thus the illicit practice of snorting and shooting the drug loses its advantage.

In accordance with the present invention and as used herein, the following terms are defined with the following meanings, unless explicitly stated otherwise. For additional methods of attaching active agents to carriers, see U.S. application Ser. No. 10/156,527, and/or PCT/US03/05524, and/or PCT/US03/05525 and/or PCT/US04/17204 each of which is hereby incorporated by reference in its entirety. In the present invention, dextroamphetamine is covalently attached to the peptide via the amino group.

The invention utilizes covalent modification of an active agent to decrease its potential for causing overdose or being abused. The active agent is covalently modified in a manner that decreases its pharmacological activity, as compared to the unmodified active agent, at doses above those considered therapeutic, e.g., at doses inconsistent with the manufacturer's instructions. When given at lower doses, such as those intended for therapy, the covalently modified active agent retains pharmacological activity similar to that of the unmodified active agent. The covalent modification of the active agent may comprise the attachment of any chemical moiety through conventional chemistry.

Compounds, compositions and methods of the invention provide reduced potential for overdose, reduced potential for abuse or addiction and/or improve the active agent's characteristics with regard to high toxicities or suboptimal release profiles.

The following is a non-exclusive list of compounds that may be used in connection with the invention: alphacetylmethadol hydrochloride, anileridine, apomorphine, bemidone, betacetylmethadol hydrochloride, buprenorphine hydrochloride, butorphanol tartrate, codeine, dezocine, dihydrocodeine, dihydromorphine, dipanone hydrochloride, eptazocine hydrobromide, ethylmorphine, etorphine hydrochloride, hydromorphone, ketobemidone, levorphanol tartrate, loperamide, meptazinol hydrochloride, methyldihydromorphinone, nalbuphine hydrochloride, nalbuphine hydrochloride, normorphine, oxycodone, oxymorphone, pentazocine, piminodine, tramadol, allobarbitone, alprazolan, amylobarbitone, barbitone sodium, butobarbitone, captodiame hydrochloride, chloral betaine, chloral hydrate, chloralose, chlorhexadol, chlormethiazole edisylate, cinolazepam, potassium clorazepate, cyclobarbitone calcium, delorzepam, difebarbamate, enciprazine hydrochloride, flunitrazepam, hexobarbitone sodium, ibomal, lorazepam, lormetazepam, meprobamate, methylpentynol, midazolam maleate, oxazepam, pentabarbitone calcium, phenprobamate, proxibarbal, quinalbaritone, quinalbarbitone sodium, secbutobarbitone sodium, temazepam, triclofos sodium, zalepan, and zolazepam hydrochloride.

Throughout this application the use of "opioid" is meant to include any drug that activates the opioid receptors found in the brain, spinal cord and gut. There are three broad classes of opioids: naturally occurring opium alkaloids, such as morphine (the prototypical opioid) and codeine; semi-synthetics such as heroine, oxycodone and hydrocodone that are produced by modifying natural opium alkaloids and have similar chemical structures; and pure synthetics such as fentanyl and methadone that are not produced from opium and may have very different chemical structures than the opium alkaloids. Other opioids include hydroxymorphone, oxymorphone, methadone, levorphanol, dihydrocodeine, meperidine, diphenoxylate, sufentanil, alfentanil, propoxyphene, pentazocine, nalbuphine, butorphanol, buprenorphine, meptazinol, dezocine, and pharmaceutically acceptable salts thereof.

Throughout this application the use of "oxycodone" is meant to include a narcotic alkaloid (chemical formula $C_{18}H_{21}NO_4$) and its derivatives such as the hydrochloride salt of oxycodone. Oxycodone is related to codeine and is used as an analgesic and/or a sedative. Oxycodone is a powerful and potentially addictive opioid analgesic synthesized from thebaine. It is similar to codeine, but is more potent and has a higher dependence potential. It is effective orally and is often marketed in combination with aspirin (Percodan®) or acetaminophen (Percocet®) for the relief of pain. It is also sold in a sustained-release form under the trade name Oxycontin®. All of these deriviatives or combinations of oxycodone are encompassed by the present invention.

Throughout this application the use of "hydrocodone" is meant to include a semisynthetic narcotic analgesic and antitussive prepared from codeine with multiple actions qualitatively similar to those of codeine. It is commonly used for the relief of moderate to moderately severe pain. Trade names include Anexsia®, Hycodan®, Hycomine®, Lorcet®, Lortab®, Norco®, Tussionex®, Tylox®, and Vicodin®. Derivatives of hydrocodone, such as hydrocodone bitartrate and hydrocodone polistirex, are encompassed by the present invention.

Throughout this application the use of "peptide" is meant to include a single amino acid, a dipeptide, a tripeptide, an oligopeptide, a polypeptide, or the carrier peptide. Oligopeptide is meant to include from 2 amino acids to 70 amino acids. Further, at times the invention is described as being an active agent attached to an amino acid, a dipeptide, a tripeptide, an oligopeptide, or polypeptide to illustrate specific embodiments for the active agent conjugate. Preferred lengths of the conjugates and other preferred embodiments are described herein.

Throughout this application the use of "chemical moiety" is meant to include at least amino acids, peptides, glycopeptides, carbohydrates, lipids, nucleosides, or vitamins.

"Carbohydrates" includes sugars, starches, cellulose, and related compounds. e.g., $(CH_2O)_n$, wherein n is an integer larger than 2 or $C_n(H_2O)_{n-1}$, with n larger than 5. More specific examples include for instance, fructose, glucose, lactose, maltose, sucrose, glyceraldehyde, dihydroxyacetone, erythrose, ribose, ribulose, xylulose, galactose, mannose, sedoheptulose, neuraminic acid, dextrin, and glycogen.

A "glycoprotein" is a compound containing carbohydrate (or glycan) covalently linked to protein. The carbohydrate may be in the form of a monosaccharide, disaccharide(s), oligosaccharide(s), polysaccharide(s), or their derivatives (e.g. sulfo- or phospho-substituted).

A "glycopeptide" is a compound consisting of carbohydrate linked to an oligopeptide composed of L- and/or D-amino acids. A glyco-amino-acid is a saccharide attached to a single amino acid by any kind of covalent bond. A glycosyl-amino-acid is a compound consisting of saccharide linked through a glycosyl linkage (O—, N— or S—) to an amino acid.

A "composition" as used herein, refers broadly to any composition containing a described molecule conjugates. The composition may comprise a dry formulation, an aqueous solution, or a sterile composition. Compositions comprising the molecules described herein may be stored in freeze-dried form and may be associated with a stabilizing agent such as a carbohydrate. In use, the composition may be deployed in an aqueous solution containing salts, e.g., NaCl, detergents, e.g., sodium dodecyl sulfate (SDS), and other components.

A "controlled substance" is a substance subject to federal regulation of its manufacture, sale, or distribution because of the potential for, or proved evidence of, abuse; because of its potential for psychic or physiological dependence; because it constitutes a public health risk; because of the scientific evidence of its pharmacologic effect; or because of its role as a precursor of other controlled substances.

Important note regarding stereochemistry: This patent is meant to cover all compounds discussed regardless of absolute configurations. Thus, natural, L-amino acids are discussed but the use of D-amino acids are also included.

The following abbreviations may be in this application:
BOC=t-butyloxycarbonyl
CMC=carboxymethylcellulose
DIPEA=di-isopropyl ethyl amine
mp=melting point
NMR=nuclear magnetic resonance
OSu=hydroxysuccinimido ester
Nia=Niacin
Bio=Biotin The attached chemical moiety may be any chemical substance that decreases the pharmacological activity until the active agent is released. Preferably the chemical moiety is a single amino acid, dipeptide or tripeptide, tetrapeptide, pentapeptide, or hexapeptide. The active agent binds to specific sites to produce various effects (Hoebel, et al., 1989). The attachment of certain chemical moieties can therefore diminish or prevent binding to these biological target sites. Preferably, absorption of the composition into the brain is prevented or substantially diminished and/or delayed when delivered by routes other than oral administration.

The attached chemical moiety may further comprise naturally occurring or synthetic substances. This would include but is not limited to the attachment of an active agent to one or more amino acids, peptides, lipids, carbohydrates, glycopeptides, nucleic acids or vitamins. These chemical moieties could be expected to affect delayed release in the gastrointestinal tract and prevent rapid onset of the desired activity, particularly when delivered by parenteral routes. (Hoebel, B. G., L. Hernandez, et al. (1989). "Microdialysis studies of brain norepinephrine, serotonin, and dopamine release during ingestive behavior. Theoretical and clinical implications." *Ann N Y Acad Sci* 575: 171-91).

For each of the embodiments recited herein, the amino acid or peptide may comprise of one or more of the naturally occurring (L-) amino acids: alanine, arginine, asparagine, aspartic acid, cysteine, glycine, glutamic acid, glutamine, histidine, isoleucine, leucine, lysine, methionine, proline, phenylalanine, serine, tryptophan, threonine, tyrosine, and valine. In another embodiment the amino acid or peptide is comprised of one or more of the naturally occurring (D) amino acids: alanine, arginine, asparagine, aspartic acid, cysteine, glycine, glutamic acid, glutamine, histidine, isoleucine, leucine, lysine, methionine, proline, phenylalanine, serine, tryptophan, threonine, tyrosine, and valine. In another embodiment the amino acid or peptide is comprised of one or more unnatural, non-standard or synthetic amino acids such as, aminohexanoic acid, biphenylalanine, cyclohexylalanine, cyclohexylglycine, diethylglycine, dipropylglycine, 2,3-diaminoproprionic acid, homophenylalanine, homoserine, homotyrosine, naphthylalanine, norleucine, ornithine, pheylalanine(4-fluoro), phenylalanine(2,3,4,5,6 pentafluoro), phenylalanine(4-nitro), phenylglycine, pipecolic acid, sarcosine, tetrahydroisoquinoline-3-carboxylic acid, and tert-leucine. In another embodiment the amino acid or peptide comprises of one or more amino acid alcohols. In another embodiment the amino acid or peptide comprises of one or more N-methyl amino acids.

In another embodiment, the specific carriers are utilized as a base short chain amino acid sequence and additional amino acids are added to the terminus or side chain. In another embodiment, the above amino acid sequence may have one more of the amino acids substituted with one of the 20 naturally occurring amino acids. It is preferred that the substitution be with an amino acid which is similar in structure or charge compared to the amino acid in the sequence. For instance, isoleucine (Ile)[I] is structurally very similar to leucine (Leu)[L], whereas, tyrosine (Tyr)[Y] is similar to phenylalanine (Phe)[F], whereas serine (Ser)[S] is similar to threonine (Thr)[T], whereas cysteine (Cys)[C] is similar to methionine (Met)[M], whereas alanine (Ala)[A] is similar to valine (Val)[V], whereas lysine (Lys)[K] is similar to arginine (Arg)[R], whereas asparagine (Asn)[N] is similar to glutamine (Gln)[Q], whereas aspartic acid (Asp)[D] is similar to glutamic acid (Glu)[E], whereas histidine (His)[H] is similar to proline (Pro)[P], and glycine (Gly)[G] is similar to tryptophan (Trp)[W]. In the alternative the preferred amino acid substitutions may be selected according to hydrophilic properties (i.e. polarity) or other common characteristics associated with the 20 essential amino acids. While preferred embodiments utilize the 20 natural amino acids for their GRAS characteristics, it is recognized that minor substitutions along the amino acid chain which do not effect the essential characteristics of the amino are also contemplated.

In one embodiment the carrier range is between one to 12 chemical moieties with one to 8 moieties being preferred. In another embodiment the number of chemical moieties attached is selected from 1, 2, 3, 4, 5, 6, or 7, etc. In another embodiment of the invention the molecular weight of the carrier portion of the conjugate is below about 2,500, more preferably below about 1,000 and most preferably below about 500.

The compositions and methods of the invention may be applied to various therapeutically valuable active agents (e.g., drugs) and include, for example, stimulants such as amphetamines, anticonvulsants, muscle relaxants, antidepressants, anxiolytics, benzodiazepines, sedatives, hypnotics, narcotics, steroids, respiratory agents, including antihistamines, antipsychotics including risperidone, and nonsteroidal anti-inflammatory agents.

Exemplary narcotics include opioids, hydrocodone, oxycodone, morphine, codeine, hydroxymorphone, oxymorphone, methadone, fentanyl, levorphanol, dihydrocodeine, meperidine, diphenoxylate, sufentanil, alfentanil, propoxyphene, pentazocine, nalbuphine, butorphanol, buprenorphine, meptazinol, dezocine or pharmaceutically acceptable salts thereof.

Exemplary benzodiazepines include alprazolam, chlordiazepoxide, clonazepam, clorazepate, diazepam, estazolam, flurazepam, halazepam, lorazepam, midazolam, oxazepam, quazepam, temazepam, or triazolam.

Exemplary nonsteroidal anti-inflammatory agents include ibuprofen, naproxen or indomethacin, aspirin or a salicylic acid derivative, or acetaminophen.

Exemplary anti-depressants include citalopram, fluoxetine, norfluoxetine, fluvoxamine, paroxetine, sertraline, amitriptyline, desipramine, doxepin, imipramine, nortryiptyline, bupropion, mirtazapine, nefazodone, trazodone, or venlafaxine.

Exemplary anti-psychotics include clozapine, haloperidol, olanzapine, quetiapine, or risperidone.

The compositions and methods of the invention provide active agents which when bound to the chemical moiety provide safer and/or more effective dosages for the above recited active agent classes through improved bioavailability curves and/or safer $C_{max}$ and/or reduce area under the curve for bioavailability, particularly for abused substances taken in doses above therapeutic levels. As a result, the compositions and methods of the invention may provide improved methods of treatment for attention deficit hyperactivity, attention deficit hyperactivity disorder (ADHD), attention deficit disorder (ADD), cognitive decline associated with acquired immunodeficiency syndrome (AIDS) or AIDS-related complex, depression, anxiety and anxiety related disorders, psychosis, nicotine addiction, narcotic addiction, alcoholism, narcolepsy, and/or analgesia.

In one embodiment the chemical moiety is comprised of an amino acid or a polypeptide. Preferred amino acid and peptide chemical moieties include, for example, Lys, Ser, Ala, Phe, Ile, Pro-Pro-Leu, Pro-Pro-Ile, Val-Val, Lys-Lys, Gly-Gly-Ile, Phe-Phe-Leu, Thr-Thr-Val, Tyr-Tyr-Val, Tyr-Tyr-Phe, Glu-Glu-Val, Asp-Asp-Val, Lys-Lys-Val, Glu-Glu-Phe-Phe-Ile, Glu-Glu-Phe-Phe-Phe, Tyr-Tyr-Ile, Asp-Asp-Ile, Tyr-Tyr-Phe-Phe-Ile, Tyr-Tyr-Lys-Tyr-Tyr, Phe-Phe-Lys-Phe-Phe, Glu-Glu-Phe-Phe-Ile, (Lys-Lys-Gly-Gly)$_2$, and [(l)-Lys-(d)-Lys-Leu]$_2$. In some embodiments, the active agent is disubstituted with one or more of the preceding chemical moieties.

Another embodiment of the invention is a composition for preventing overdose comprising an active agent which has been covalently bound to a chemical moiety.

Another embodiment of the invention is a composition for safely delivering an active agent comprising providing a therapeutically effective amount of said active agent which has been covalently bound to a chemical moiety wherein said chemical moiety reduces the rate of absorption of the active agent as compared to delivering the unbound active agent.

Another embodiment of the invention is a composition for reducing drug toxicity comprising providing a patient with an active agent which has been covalently bound to a chemical moiety wherein said chemical moiety increases the rate of clearance of an active agent when given at doses exceeding those within the therapeutic range of said active agent.

Another embodiment of the invention is a composition for reducing drug toxicity comprising providing a patient with an active agent which has been covalently bound to a chemical moiety wherein said chemical moiety provides a serum release curve which does not increase above said active agent toxicity level when given at doses exceeding those within the therapeutic range of said active agent.

Another embodiment of the invention is a composition for reducing bioavailability of active agent comprising active agent covalently bound to a chemical moiety wherein said bound active agent maintains a steady-state serum release curve which provides a therapeutically effective bioavailability but prevents spiking or increase blood serum concentrations compared to unbound active agent when given at doses exceeding those within the therapeutic range of said active agent.

Another embodiment of the invention is a composition for preventing a $C_{max}$ spike for active agent while still providing a therapeutically effective bioavailability curve comprising an active agent which has been covalently bound to a chemical moiety.

Another embodiment of the invention is a composition for preventing a toxic release profile in a patient comprising active agent covalently bound to a chemical moiety wherein said bound active agent maintains a steady-state serum release curve which provides a therapeutically effective bioavailability but prevents spiking or increase blood serum concentrations compared to unbound active agent.

Another embodiment of the invention is a compound of Formula I:

$$A\text{-}X_n\text{---}Z_m$$

wherein A is active agent as defined herein; X is a chemical moiety as defined herein and n is between 1 and 50 and increments therein; and Z is a further chemical moiety different from X which acts as an adjuvant and m is between 1 and 50 and increments therein. In another embodiment n is between 1 and 10 and m is 0. It should be recognized that the compounds of this formula may be used alone or in combination with any of the recited embodiments of the invention.

In one embodiment, a compound of the formula: $A\text{-}X_m\text{---}Z_n$ wherein A is an active agent; X is a linker covalently bound to A; and Z is an amino acid, peptide, or oligopeptide covalently bound to X, wherein m and n range from 1 to 50 is utilized in connection with the present invention. It should be recognized that the formula $A\text{-}X_m\text{---}Z_n$ generally describes the components making up the compound and does not imply any particular order in the attachment or type of bond between the elements A, X, or Z. In the above formula X may comprise a small linear or cyclic molecule containing 2-6 atoms with one or more heteroatoms and one or more functional groups. The functional groups may be selected from amines, amides, alcohols or acids. A may be oxycodone or hydrocodone. X may be an enolate or an amino acid. In one embodiment, Z is bonded to X through a side chain of the amino acid. In another embodiment, Z may be bonded to X through a peptide bond. The linker X may comprise the following amino acids: Ser, Lys, Glu, Asp, Ala, Leu, Phe, Val, Gly, Tyr, Pro, or Thr. In one embodiment, where X is lysine, Z is bonded to lysine through the side chain of the lysine. In another embodiment, where X is lysine, Z is bonded to lysine through a peptide bond.

In one embodiment, the —X—Z component of the formula $A\text{-}X_m\text{---}Z_n$ comprises Lys-Lys, Lys-Lys-Val, (Lys-Lys-Gly-Gly)$_2$, [(1)-Lys-(d)-Lys-Leu]$_2$, Glu-Glu, Glu-Glu-Phe-Phe-Phe-Ile, Glu-Glu-Phe-Phe-Phe, Glu-Glu-Phe-Phe-Ile, Glu-Glu-Val, Asp-Asp, Asp-Asp-Asp, Asp-Asp-Glu, Asp-Asp-Ser, Asp-Asp-Lys, Asp-Asp-Cys, Asp-Asp-Val, Ala-Ser, Ala-Cys, Leu-Glu, Leu-Ser, Leu-Asp, Leu-Asn, Leu-Thr, Leu-Arg, Leu-Cys, Leu-Gln, Leu-Tyr, Val-Glu, Val-Ser, Val-Asp, Val-Asn, Val-Thr, Val-Arg, Val-Cys, Val-Gln, Val-Tyr, Val-Val, Gly-Gly-Leu, Gly-Gly-Gly-Gly-Leu, Gly-Gly-Ile, Asp-Asp-Ile, Pro-Pro-Leu, Pro-Pro-Ile, or Thr-Thr-Val.

In one embodiment, the —X—Z component of the formula $A\text{-}X_m\text{---}Z_n$ comprises Ser-Ser, PolySer, Lys, Glu-Glu, Asp-Asp, Asp-Asp-Asp, Asp-Asp-Glu, Asp-Asp-Ser, Asp-Asp-Lys, Asp-Asp-Cys, Ala-Glu, Ala-Ser, Ala-Asp, Ala-Asn, Ala-Thr, Ala-Arg, Ala-Cys, Ala-Gln, Ala-Tyr, LeuGlu, Leu-Ser, Leu-Asp, Leu-Asn, Leu-Thr, Leu-Arg, Leu-Cys, Leu-Gln, Leu-Tyr, PheGlu, Phe-Ser, Phe-Asp, Phe-Asn, Phe-Thr, Phe-Arg, Phe-Cys, Phe-Gln, Phe-Tyr, Val-Glu, Val-Ser, Val-Asp, Val-Asn, Val-Thr, Val-Arg, Val-Cys, Val-Gln, or Val-Tyr.

In one embodiment, the —X—Z component of the formula $A\text{-}X_m\text{---}Z_n$ comprises Pro-Pro-Leu, Pro-Pro-He, Val-Val, Lys-Lys, Gly-Gly-Ile, Phe-Phe-Ile, Phe-Phe-Leu, Thr-Thr-Val, Tyr-Tyr-Val, Tyr-Tyr-Phe, Glu-Glu-Val, Asp-Asp-Val, Lys-Lys-Val, Glu-Glu-Phe-Phe-Ile, Glu-Glu-Phe-Phe-Phe, Tyr-Tyr-Ile, Asp-Asp-Ile, Tyr-Tyr-Phe-Phe-Ile, Tyr-Tyr-Lys-Tyr-Tyr, Phe-Phe-Lys-Phe-Phe, Glu-Glu-Phe-Phe-Ile, (Lys-Lys-Gly-Gly)$_2$, or [(1)-Lys-(d)-Lys-Leu]$_2$.

In one embodiment, the —X—Z component of the formula $A\text{-}X_m\text{---}Z_n$ comprises Ser-Ser, PolySer, Glu-Glu, Asp-Asp, Asp-Asp-Asp, Asp-Asp-Glu, Asp-Asp-Ser, Asp-Asp-Lys, Asp-Asp-Cys, Ala-Glu, Ala-Ser, Ala-Asp, Ala-Asn, Ala-Thr, Ala-Arg, Ala-Cys, Ala-Gln, Ala-Tyr, Leu-Glu, Leu-Ser, Leu-Asp, Leu-Asn, Leu-Thr, Leu-Arg, Leu-Cys, Leu-Gln, Leu-Tyr, Phe-Glu, Phe-Ser, Phe-Asp, Phe-Asn, Phe-Thr, Phe-Arg, Phe-Cys, Phe-Gln, Phe-Tyr, Val-Glu, Val-Ser, Val-Asp, Val-Asn, Val-Thr, Val-Arg, Val-Cys, Val-Gln, Val-Tyr, Ala-Pro, Gly-Gly-Leu, Gly-Gly-Gly-Gly-Leu, Glu-Glu-Phe-Phe-Ile, Glu-Glu-Phe-Phe-Phe, Tyr-Tyr-Ile, Asp-Asp-Ile, Tyr-Tyr-Phe-Phe-Ile, or Glu-Glu-Phe-Phe-Ile.

In one embodiment, the —X—Z component of the formula $A\text{-}X_m\text{---}Z_n$ comprises Ser-Ser, PolySer, Lys-Lys, Lys-Lys-Val, (Lys-Lys-Gly-Gly)$_2$, [(1)-Lys-(d)-Lys-Leu]$_2$, Glu-Glu, Glu-Glu-Phe-Phe-Phe-Ile, Glu-Glu-Phe-Phe-Phe, Glu-Glu-Phe-Phe-Ile, Glu-Glu-Val, Asp-Asp, Asp-Asp-Asp, Asp-Asp-Glu, Asp-Asp-Ser, Asp-Asp-Lys, Asp-Asp-Cys, Asp-Asp-Val, Ala-Glu, Ala-Pro, Ala-Ser, Ala-Asp, Ala-Asn, Ala-Thr, Ala-Arg, Ala-Cys, Ala-Gln, Ala-Tyr, Leu-Glu, Leu-Ser, Leu-Asp, Leu-Asn, Leu-Thr, Leu-Arg, Leu-Cys, Leu-Gln, Leu-Tyr, Phe-Glu, Phe-Ser, Phe-Asp, Phe-Asn, Phe-Thr, Phe-Arg, Phe-Cys, Phe-Gln, Phe-Tyr, Phe-Phe-Ile, Phe-Phe-Leu, Phe-Phe-Lys-Phe-Phe, Val-Glu, Val-Ser, Val-Asp, Val-Asn, Val-Thr, Val-Arg, Val-Cys, Val-Gln, Val-Tyr, Val-Val, Gly-Gly-Leu, Gly-Gly-Gly-Gly-Leu, Gly-Gly-Ile, Tyr-Tyr-Ile, Tyr-Tyr-Phe-Phe-Ile, Tyr-Tyr-Val, Tyr-Tyr-Phe, Tyr-Tyr-Lys-Tyr-Tyr, Asp-Asp-Ile, Pro-Pro-Leu, Pro-Pro-Ile, or Thr-Thr-Val.

In one embodiment, the component A of the formula $A\text{-}X_m\text{---}Z_n$ is a pain relief drug such as oxycodone or hydrocodone. The component A of the formula $A\text{-}X_m\text{---}Z_n$ may also be alphacetylmethadol hydrochloride, anileridine, apomorphine, bemidone, betacetylmethadol hydrochloride, buprenorphine hydrochloride, butorphanol tartrate, codeine, dezocine, dihydrocodeine, dihydromorphine, dipanone hydrochloride, eptazocine hydrobromide, ethylmorphine, etorphine hydrochloride, hydromorphone, ketobemidone, levorphanol tartrate, loperamide, meptazinol hydrochloride, methyldihydromorphinone, nalbuphine hydrochloride, nalbuphine hydrochloride, normorphine, oxycodone, oxymorphone, pentazocine, piminodine, tramadol, allobarbitone, alprazolan, amylobarbitone, barbitone sodium, butobarbitone, captodiame hydrochloride, chloral betaine, chloral hydrate, chloralose, chlorhexadol, chlormethiazole edisylate, cinolazepam, potassium clorazepate, cyclobarbitone calcium, delorzepam, difebarbamate, enciprazine hydrochloride, flunitrazepam, hexobarbitone sodium, ibomal, lorazepam, lormetazepam, meprobamate, methylpentynol, midazolam maleate, oxazepam, pentabarbitone calcium, phenprobamate, proxibarbal, quinalbaritone, quinalbarbitone sodium, secbutobarbitone sodium, temazepam, triclofos sodium, zalepan, or zolazepam hydrochloride.

In one embodiment, the compound $A\text{-}X_m\text{---}Z_n$ may be a component of a pharmaceutical composition including the compound and a pharmaceutically acceptable excipient. The compound $A\text{-}X_m\text{---}Z_n$ may be administered to a mammal in a therapeutically effective amount to treat pain. The mammal may be a human, primate, equine, canine, or feline.

In one embodiment, a compound of the formula: $A\text{-}X_m\text{-}Z_n$ wherein A is a drug radical; X is a small linear or cyclic molecule containing 2-6 atoms with one or more heteroatoms and one or more functional groups, wherein X is bonded to A through a carboxyl group; and Z is an amino acid, peptide, or oligopeptide covalently bound to X, wherein m and n range between 1 and 50 is utilized in connection with the present invention.

In one embodiment, a method of making a drug more difficult to abuse, comprising bonding to a nucleophile on the drug a radical of the formula —X—Z, wherein X is a linker; and Z is an amino acid or peptide covalently bound to X may be utilized.

In one embodiment, a compound comprising a drug radical covalently bonded to a first amino acid selected from the group consisting of Ser, Lys, Glu, Asp, Ala, Leu, Phe, Val, Gly, Tyr, Pro, and Thr, and a second amino acid or peptide covalently bonded to the first amino acid, wherein an optional linker attaches the first amino acid to the drug radical may be utilized in connection with the present invention.

In one embodiment, a compound comprising a drug radical covalently bonded to a peptide selected from the group consisting of Lys-Lys, Lys-Lys-Val, (Lys-Lys-Gly-Gly)$_2$, [(1)-Lys-(d)-Lys-Leu]$_2$, Glu-Glu, Glu-Glu-Phe-Phe-Phe-Ile, Glu-Glu-Phe-Phe-Phe, Glu-Glu-Phe-Phe-Ile, Glu-Glu-Val, Asp-Asp, Asp-Asp-Asp, Asp-Asp-Glu, Asp-Asp-Ser, Asp-Asp-Lys, Asp-Asp-Cys, Asp-Asp-Val, Ala-Ser, Ala-Cys, Leu-Glu, Leu-Ser, Leu-Asp, Leu-Asn, Leu-Thr, Leu-Arg, Leu-Cys, Leu-Gln, Leu-Tyr, Val-Glu, Val-Ser, Val-Asp, Val-Asn, Val-Thr, Val-Arg, Val-Cys, Val-Gln, Val-Tyr, Val-Val, Gly-Gly-Leu, Gly-Gly-Gly-Gly-Leu, Gly-Gly-Ile, Asp-Asp-Ile, Pro-Pro-Leu, Pro-Pro-Ile, and Thr-Thr-Val, wherein an optional linker attaches the first amino acid to the drug radical may be utilized in connection with the present invention.

In one embodiment, a compound comprising a drug radical covalently bonded to a peptide selected from the group consisting of Ser-Ser, PolySer, Lys, Glu-Glu, Asp-Asp, Asp-Asp-Asp, Asp-Asp-Glu, Asp-Asp-Ser, Asp-Asp-Lys, Asp-Asp-Cys, Ala-Glu, Ala-Ser, Ala-Asp, Ala-Asn, Ala-Thr, Ala-Arg, Ala-Cys, Ala-Gln, Ala-Tyr, LeuGlu, Leu-Ser, Leu-Asp, Leu-Asn, Leu-Thr, Leu-Arg, Leu-Cys, Leu-Gln, Leu-Tyr, Phe-Glu, Phe-Ser, Phe-Asp, Phe-Asn, Phe-Thr, Phe-Arg, Phe-Cys, Phe-Gln, Phe-Tyr, Val-Glu, Val-Ser, Val-Asp, Val-Asn, Val-Thr, Val-Arg, Val-Cys, Val-Gln, and Val-Tyr, wherein an optional linker attaches the first amino acid to the drug radical may be utilized in connection with the present invention.

In one embodiment, a compound comprising a drug radical covalently bonded to a peptide selected from the group consisting of Pro-Pro-Leu, Pro-Pro-He, Val-Val, Lys-Lys, Gly-Gly-Ile, Phe-Phe-He, Phe-Phe-Leu, Thr-Thr-Val, Tyr-Tyr-Val, Tyr-Tyr-Phe, Glu-Glu-Val, Asp-Asp-Val, Lys-Lys-Val, Glu-Glu-Phe-Phe-Ile, Glu-Glu-Phe-Phe-Phe, Tyr-Tyr-Ile, Asp-Asp-He, Tyr-Tyr-Phe-Phe-Ile, Tyr-Tyr-Lys-Tyr-Tyr, Phe-Phe-Lys-Phe-Phe, Glu-Glu-Phe-Phe-Ile, (Lys-Lys-Gly-Gly)$_2$, and [(1)-Lys-(d)-Lys-Leu]$_2$, wherein an optional linker attaches the first amino acid to the drug radical may be utilized in connection with the present invention.

In one embodiment, a compound comprising a drug radical covalently bonded to a peptide selected from the group consisting of Ser-Ser, PolySer, Glu-Glu, Asp-Asp, Asp-Asp-Asp, Asp-Asp-Glu, Asp-Asp-Ser, Asp-Asp-Lys, Asp-Asp-Cys, Ala-Glu, Ala-Ser, Ala-Asn, Ala-Thr, Ala-Arg, Ala-Cys, Ala-Gln, Ala-Tyr, Leu-Glu, Leu-Ser, Leu-Asp, Leu-Asn, Leu-Thr, Leu-Arg, Leu-Cys, Leu-Gln, Leu-Tyr, Phe-Glu, Phe-Ser, Phe-Asp, Phe-Asn, Phe-Thr, Phe-Arg, Phe-Cys, Phe-Gln, Phe-Tyr, Val-Glu, Val-Ser, Val-Asp, Val-Asn, Val-Thr, Val-Arg, Val-Cys, Val-Gln, Val-Tyr, Ala-Pro, Gly-Gly-Leu, Gly-Gly-Gly-Gly-Leu, Glu-Glu-Phe-Phe-Ile, Glu-Glu-Phe-Phe-Phe, Tyr-Tyr-Ile, Asp-Asp-Ile, Tyr-Tyr-Phe-Phe-Ile, and Glu-Glu-Phe-Phe-Ile, wherein an optional linker attaches the first amino acid to the drug radical may be utilized in connection with the present invention.

In one embodiment, a compound comprising a drug radical covalently bonded to a peptide selected from the group consisting of Ser-Ser, PolySer, Lys-Lys, Lys-Lys-Val, (Lys-Lys-Gly-Gly)$_2$, [(1)-Lys-(d)-Lys-Leu]$_2$, Glu-Glu, Glu-Glu-Phe-Phe-Phe-Ile, Glu-Glu-Phe-Phe-Phe, Glu-Glu-Phe-Phe-Ile, Glu-Glu-Val, Asp-Asp, Asp-Asp-Asp, Asp-Asp-Glu, Asp-Asp-Ser, Asp-Asp-Lys, Asp-Asp-Cys, Asp-Asp-Val, Ala-Glu, Ala-Pro, Ala-Ser, Ala-Asp, Ala-Asn, Ala-Thr, Ala-Arg, Ala-Cys, Ala-Gln, Ala-Tyr, Leu-Glu, Leu-Ser, Leu-Asp, Leu-Asn, Leu-Thr, Leu-Arg, Leu-Cys, Leu-Gln, Leu-Tyr, Phe-Glu, Phe-Ser, Phe-Asp, Phe-Asn, Phe-Thr, Phe-Arg, Phe-Cys, Phe-Gln, Phe-Tyr, Phe-Phe-Ile, Phe-Phe-Leu, Phe-Phe-Lys-Phe-Phe, Val-Glu, Val-Ser, Val-Asp, Val-Asn, Val-Thr, Val-Arg, Val-Cys, Val-Gln, Val-Tyr, Val-Val, Gly-Gly-Leu, Gly-Gly-Gly-Gly-Leu, Gly-Gly-Ile, Tyr-Tyr-Ile, Tyr-Tyr-Phe-Phe-Ile, Tyr-Tyr-Val, Tyr-Tyr-Phe, Tyr-Tyr-Lys-Tyr-Tyr, Asp-Asp-Ile, Pro-Pro-Leu, Pro-Pro-Ile, and Thr-Thr-Val, wherein an optional linker attaches the first amino acid to the drug radical may be utilized in connection with the present invention.

In one embodiment, a compound comprising a drug attached to a first amino acid via a carboxyl group of the first amino acid, which forms an ester linkage between the first amino acid and the drug, and a second amino acid or peptide attached to the first amino acid through the terminal carboxyl group of the second amino acid or peptide, wherein the drug is susceptible to release from the compound in therapeutically significant amounts through enzymatic cleavage, and not released from the compound in therapeutically significant amounts absent enzymatic action may be utilized in connection with the present invention.

In one embodiment, a compound comprising a drug attached to a first amino acid via a carboxyl group of the first amino acid, which forms an ester linkage between the first amino acid and the drug, and a second amino acid or peptide attached to the first amino acid through the terminal carboxyl group of the second amino acid or peptide, wherein the drug is susceptible to release from the compound through enzymatic cleavage may be utilized in connection with the present invention.

In one embodiment, a compound comprising a drug covalently bonded to a first amino acid via a carboxyl group of the first amino acid, which forms an ester linkage between the first amino acid and the drug, and a second amino acid or peptide attached to the first amino acid through the terminal carboxyl group of the second amino acid or peptide thereby forming a peptide bond with an —NH— group of the first amino acid, wherein the drug is susceptible to release from the compound through enzymatic cleavage may be utilized in connection with the present invention.

In one embodiment, a compound comprising an active agent covalently bonded to a natural or synthetic amino acid or peptide through a linker may be utilized in connection with the present invention. The linker may comprise a small linear or cyclic molecule containing 2-6 atoms with one or more heteroatoms and one or more functional groups. The functional groups may be selected from amines, amides, alcohols or acids.

Compositions of the invention comprise four essential types of attachment. These types of attachment are termed:

C-capped, N-capped, side-chain attached, and interspersed. C-capped comprises the covalent attachment of an active agent to the C-terminus of a peptide either directly or through a linker. N-capped comprises the covalent attachment of an active agent to the N-terminus of a peptide either directly or through a linker. Side-chain attachment comprises the covalent attachment of an active agent to the functional sidechain of a peptide either directly or through a linker. Interspersed comprises the attachment of active agents which themselves are amino acids. In this case the active agent would constitute a portion of the amino acid chain. Interspersed is herein meant to include the amino acid active agent (drug) being at the C-terminus, N-terminus, or interspersed throughout the peptide. When amino acid active agents are attached to the C-terminus or the N-terminus this results in the active agent being the end amino and is considered C-capped or N-capped respectively. Furthermore, amino acids with reactive side chains (e.g., glutamic acid, lysine, aspartic acid, serine, threonine and cysteine) can be incorporated for attaching multiple active agents or adjuvants to the same carrier peptide. This is particularly useful if a synergistic effect between two or more active agents is desired. The present invention also envisions the use of multiple active agents or multiple attachment sites of active agents along a peptide chain. Further embodiments of the invention will become clear from the following disclosure.

In another embodiment of the invention, the composition includes one or more adjuvants to enhance the bioavailability of the active agent. Addition of an adjuvant is particularly preferred when using an otherwise poorly absorbed active agent. Suitable adjuvants, for example, include: papain, which is a potent enzyme for releasing the catalytic domain of aminopeptidase-N into the lumen; glycorecognizers, which activate enzymes in the brush border membrane (BBM); and bile acids, which have been attached to peptides to enhance absorption of the peptides.

Absorption of the active agent in the intestinal tract can be enhanced either by virtue of being covalently attached to a peptide or through the synergistic effect of an added adjuvant. In a preferred embodiment of the invention the absorption of the active agent is increased due to its covalent attachment to a peptide, hereafter to be referred to as a transporter peptide, which is a specialized example of a carrier peptide. In a further embodiment, the transporter peptide activates a specific peptide transporter. In yet another embodiment the peptide transporter is either the PepT1 or the PepT2 transporters. In a preferred embodiment the transporter peptide contains two amino acids. In another preferred embodiment the transporter dipeptide is selected from the list of AlaSer, CysSer, AspSer, GluSer, PheSer, GlySer, HisSer, IleSer, LysSer, LeuSer, MetSer, AsnSer, ProSer, GlnSer, ArgSer, SerSer, ThrSer, ValSer, TrpSer, TyrSer.

In another embodiment, the present invention does not require the attachment of the active agent to an adjuvant that recognizes or is taken up by an active transporter. The invention also allows targeted delivery of active agents to specifics sites of action.

In another preferred embodiment the chain length of amino acid can be varied to suit different delivery criteria. In one embodiment, the present invention allows for the delivery of active agents with sustained release.

In another preferred embodiment the active agent is directly attached to the amino acid without the use of a linker.

Embodiments of the invention provide compositions which allow the active agent to be therapeutically effective when delivered at the proper dosage but reduces the rate of absorption or extent of bioavailability of the active agent when given at doses exceeding those within the therapeutic range of the active agent. Embodiments of the invention also provide compositions wherein the covalently bound chemical moiety increases the rate of clearance of active agent when given at doses exceeding those within the therapeutic range of the active agent.

In another embodiment the compositions have substantially lower toxicity compared to unbound active agent. In another embodiment the compositions reduce or eliminate the possibility of overdose by oral administration. In another embodiment the compositions reduce or eliminate the possibility of overdose by intranasal administration. In another embodiment the compositions reduce or eliminate the possibility of overdose by injection.

In another embodiment, the conjugates of the invention may further comprise a polymer blend which comprises at least one hydrophilic polymer and at least one water-insoluble polymer. The polymer may be used according to industry standard to further enhance the sustained release properties of the active agent conjugate without reducing the abuse resistance. Hydrophilic polymers suitable for use in the sustained release formulation include: one or more natural or partially or totally synthetic hydrophilic gums such as acacia, gum tragacanth, locust bean gum, guar gum, or karaya gum, modified cellulosic substances such as methylcellulose, hydroxomethylcellulose, hydroxypropyl methylcellulose, hydroxypropyl cellulose, hydroxyethylcellulose, carboxymethylcellulose; proteinaceous substances such as agar, pectin, carrageen, and alginates; and other hydrophilic polymers such as carboxypolymethylene, gelatin, casein, zein, bentonite, magnesium aluminum silicate, polysaccharides, modified starch derivatives, and other hydrophilic polymers known to those of skill in the art or a combination of such polymers.

Other formulations may further comprise pharmaceutical additives including, but not limited to: lubricants such as magnesium stearate, calcium stearate, zinc stearate, powdered stearic acid, hydrogenated vegetable oils, talc, polyethylene glycol, and mineral oil; colorants; binders such as sucrose, lactose, gelatin, starch paste, acacia, tragacanth, povidone polyethylene glycol, Pullulan and corn syrup; glidants such as colloidal silicon dioxide and talc; surface active agents such as sodium lauryl sulfate, dioctyl sodium sulfosuccinate, triethanolamine, polyoxyethylene sorbitan, poloxalkol, and quarternary ammonium salts; preservatives and stabilizers; excipients such as lactose, mannitol, glucose, fructose, xylose, galactose, sucrose, maltose, xylitol, sorbitol, chloride, sulfate and phosphate salts of potassium, sodium, and magnesium; and/or any other pharmaceutical additives known to those of skill in the art. Colorants include, but are not limited to, Emerald Green Lake, FD&C Red No. 40, FD&C Yellow No. 6, D&C Yellow No. 10, or FD&C Blue No. 1 and other various certified color additives (See 21 CFR, Part 74). In one preferred embodiment, a sustained release formulation further comprises magnesium stearate and Emerald Green Lake.

An active agent conjugate, which is further formulated with excipients may be manufactured according to any appropriate method known to those of skill in the art of pharmaceutical manufacture. For instance, the active agent conjugate and a hydrophilic polymer may be mixed in a mixer with an aliquot of water to form a wet granulation. The granulation may be dried to obtain hydrophilic polymer encapsulated granules of active agent-conjugate. The resulting granulation may be milled, screened, then blended with various pharmaceutical additives, water insoluble polymer, and additional hydrophilic polymer. The formulation may then tableted and may further be film coated with a protective coating which rapidly dissolves or disperses in gastric juices.

However, it should be noted that the active agent conjugate controls the release of active agent into the digestive tract over an extended period of time resulting in an improved profile when compared to immediate release combinations and reduces and/or prevents abuse without the addition of the above additives. In a preferred embodiment no further sustained release additives are required to achieve a blunted or reduced pharmacokinetic curve (e.g. reduced euphoric effect) while achieving therapeutically effective amounts of active agent release.

The compounds of the invention can be administered by a variety of dosage forms. Any biologically-acceptable dosage form known to persons of ordinary skill in the art, and combinations thereof, are contemplated. Examples of such dosage forms include, without limitation, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, granules, particles, microparticles, dispersible granules, cachets, douches, suppositories, creams, topicals, inhalants, aerosol inhalants, patches, particle inhalants, ingestibles, infusions, health bars, confections, animal feeds, cereals, yogurts, cereal coatings, foods, nutritive foods, functional foods and combinations thereof.

However, the most effective means for delivering the abuse-resistant compounds of the invention is orally, to permit maximum release of the active agent to provide therapeutic effectiveness and/or sustained release while maintaining abuse resistance. When delivered by the oral route the active agent is released into circulation, preferably over an extended period of time as compared to active agent alone.

Formulations of the invention suitable for oral administration can be presented as discrete units, such as capsules, caplets or tablets. These oral formulations also can comprise a solution or a suspension in an aqueous liquid or a non-aqueous liquid. The formulation can be an emulsion, such as an oil-in-water liquid emulsion or a water-in-oil liquid emulsion. The oils can be administered by adding the purified and sterilized liquids to a prepared enteral formula, which is then placed in the feeding tube of a patient who is unable to swallow.

Soft gel or soft gelatin capsules may be prepared, for example by dispersing the formulation in an appropriate vehicle (vegetable oils are commonly used) to form a high viscosity mixture. This mixture is then encapsulated with a gelatin based film using technology and machinery known to those in the soft gel industry. The industrial units so formed are then dried to constant weight.

Chewable tablets, for example may be prepared by mixing the formulations with excipients designed to form a relatively soft, flavored, tablet dosage form that is intended to be chewed rather than swallowed. Conventional tablet machinery and procedures, that is both direct compression and granulation, i.e., or slugging, before compression, can be utilized. Those individuals involved in pharmaceutical solid dosage form production are versed in the processes and the machinery used as the chewable dosage form is a very common dosage form in the pharmaceutical industry.

Film coated tablets, for example may be prepared by coating tablets using techniques such as rotating pan coating methods or air suspension methods to deposit a contiguous film layer on a tablet.

Compressed tablets, for example may be prepared by mixing the formulation with excipients intended to add binding qualities to disintegration qualities. The mixture is either directly compressed or granulated then compressed using methods and machinery known to those in the industry. The resultant compressed tablet dosage units are then packaged according to market need, i.e., unit dose, rolls, bulk bottles, blister packs, etc.

The invention also contemplates the use of biologically-acceptable carriers which may be prepared from a wide range of materials. Without being limited thereto, such materials include diluents, binders and adhesives, lubricants, plasticizers, disintegrants, colorants, bulking substances, flavorings, sweeteners and miscellaneous materials such as buffers and adsorbents in order to prepare a particular medicated composition.

Binders may be selected from a wide range of materials such as hydroxypropylmethylcellulose, ethylcellulose, or other suitable cellulose derivatives, povidone, acrylic and methacrylic acid co-polymers, pharmaceutical glaze, gums, milk derivatives, such as whey, starches, and derivatives, as well as other conventional binders known to persons skilled in the art. Exemplary non-limiting solvents are water, ethanol, isopropyl alcohol, methylene chloride or mixtures and combinations thereof. Exemplary non-limiting bulking substances include sugar, lactose, gelatin, starch, and silicon dioxide.

Preferred plasticizers may be selected from the group consisting of diethyl phthalate, diethyl sebacate, triethyl citrate, cronotic acid, propylene glycol, butyl phthalate, dibutyl sebacate, castor oil and mixtures thereof, without limitation. As is evident, the plasticizers may be hydrophobic as well as hydrophilic in nature. Water-insoluble hydrophobic substances, such as diethyl phthalate, diethyl sebacate and castor oil are used to delay the release of water-soluble vitamins, such as vitamin B6 and vitamin C. In contrast, hydrophilic plasticizers are used when water-insoluble vitamins are employed which aid in dissolving the encapsulated film, making channels in the surface, which aid in nutritional composition release.

It should be understood that in addition to the ingredients particularly mentioned above, the formulations of this invention can include other suitable agents such as flavoring agents, preservatives and antioxidants. Such antioxidants would be food acceptable and could include vitamin E, carotene, BHT or other antioxidants known to those of skill in the art.

Other compounds which may be included by admixture are, for example, medically inert ingredients, e.g. solid and liquid diluent, such as lactose, dextrose, saccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulphates; and other therapeutically acceptable accessory ingredients, such as humectants, preservatives, buffers and antioxidants, which are known additives for such formulations.

For oral administration, fine powders or granules containing diluting, dispersing and/or surface-active agents may be presented in a draught, in water or a syrup, in capsules or sachets in the dry state, in a non-aqueous suspension wherein suspending agents may be included, or in a suspension in water or a syrup. Where desirable or necessary, flavoring, preserving, suspending, thickening or emulsifying agents can be included.

Liquid dispersions for oral administration may be syrups, emulsions or suspensions. The syrups may contain as carrier, for example, saccharose or saccharose with glycerol and/or mannitol and/or sorbitol. In particular a syrup for diabetic patients can contain as carriers only products, for example sorbitol, which do not metabolize to glucose or which metabolize only a very small amount to glucose. The suspensions and the emulsions may contain a carrier, for example a natural gum, agar, sodium alginate, pectin, methylcellulose, carboxymethylcellulose or polyvinyl alcohol.

The dose range for adult human beings will depend on a number of factors including the age, weight and condition of the patient and the administration route. Tablets and other forms of presentation provided in discrete units conveniently contain a daily dose, or an appropriate fraction thereof, of one of the present compounds. For example, units may contain from 5 mg to 500 mg, but more usually from 10 mg to 250 mg, of one of the present compounds.

It is also possible for the dosage form to combine any forms of release known to persons of ordinary skill in the art. These include immediate release, extended release, pulse release, variable release, controlled release, timed release, sustained release, delayed release, long acting, and combinations thereof. The ability to obtain immediate release, extended release, pulse release, variable release, controlled release, timed release, sustained release, delayed release, long acting characteristics and combinations thereof is known in the art.

Compositions of the invention may be administered in a partial, i.e., fractional dose, one or more times during a 24 hour period, a single dose during a 24 hour period of time, a double dose during a 24 hour period of time, or more than a double dose during a 24 hour period of time. Fractional, double or other multiple doses may be taken simultaneously or at different times during the 24 hour period. The doses may be uneven doses with regard to one another or with regard to the individual components at different administration times.

Likewise, the compositions of the invention may be provided in a blister pack or other such pharmaceutical package. Further, the compositions of the present inventive subject matter may further include or be accompanied by indicia allowing individuals to identify the compositions as products for a prescribed treatment. The indicia may further additionally include an indication of the above specified time periods for administering the compositions. For example the indicia may be time indicia indicating a specific or general time of day for administration of the composition, or the indicia may be a day indicia indicating a day of the week for administration of the composition. The blister pack or other combination package may also include a second pharmaceutical product.

It will be appreciated that the pharmacological activity of the compositions of the invention can be demonstrated using standard pharmacological models that are known in the art. Furthermore, it will be appreciated that the inventive compositions can be incorporated or encapsulated in a suitable polymer matrix or membrane for site-specific delivery, or can be functionalized with specific targeting agents capable of effecting site specific delivery. These techniques, as well as other drug delivery techniques are well known in the art.

In another embodiment of the invention, the solubility and dissolution rate of the composition is substantially changed under physiological conditions encountered in the intestine, at mucosal surfaces, or in the bloodstream. In another embodiment the solubility and dissolution rate substantially decrease the bioavailability of the said pharmaceutical, particularly at doses above those intended for therapy. In another embodiment the decrease in bioavailability occurs upon oral administration. In another embodiment the decrease in bioavailability occurs upon intranasal administration. In another embodiment the decrease in bioavailability occurs upon intravenous administration.

Another particular embodiment of the invention provides that when the covalently modified active agent is provided for oral dosing in the form (e.g., a tablet or capsule) it is resistant to manipulation. Crushing of the tablet or disruption of the capsule does not substantially increase the rate and amount of active agent absorbed when compositions of the invention are ingested.

For each of the described embodiments one or more of the following characteristics may be realized. The toxicity of the compound is substantially lower than that of the unbound active agent. The covalently bound chemical moiety reduces or eliminates the possibility of overdose by oral administration. The covalently bound chemical moiety reduces or eliminates the possibility of overdose by intranasal administration. The covalently bound chemical moiety reduces or eliminates the possibility of overdose by injection.

The invention further provides methods for altering active agent in a manner that decreases their potential for abuse. Methods of the invention provide various ways to regulate pharmaceutical dosage through covalent attachment of active agent to different chemical moieties. One embodiment provides a method of preventing overdose comprising administering to an individual an active agent which has been covalently bound to a chemical moiety.

Another embodiment provides a method of safely delivering an active agent comprising providing a therapeutically effective amount of an active agent which has been covalently bound to a chemical moiety wherein the chemical moiety reduces the rate of absorption of active agent as compared to delivering the unbound active agent.

Another embodiment provides a method of reducing drug toxicity comprising providing a patient with an active agent which has been covalently bound to a chemical moiety wherein the chemical moiety increases the rate of clearance of a pharmacologically active agent when given at doses exceeding those within the therapeutic range of active agent.

Another embodiment provides a method of reducing drug toxicity comprising providing a patient with an active agent which has been covalently bound to a chemical moiety wherein the chemical moiety provides a serum release curve which does not increase above the active agent's toxicity level when given at doses exceeding those within the therapeutic range for the unbound active agent.

Another embodiment provides a method of reducing bioavailability of an active agent comprising providing active agent covalently bound to a chemical moiety wherein the bound active agent maintains a steady-state serum release curve which provides a therapeutically effective bioavailability but prevents spiking or increase blood serum concentrations compared to unbound active agent when given at doses exceeding those within the therapeutic range for the unbound active agent. Another embodiment provides a method of preventing a $C_{max}$ spike for active agent while still providing a therapeutically effective bioavailability curve comprising providing an active agent which has been covalently bound to a chemical moiety. In another embodiment, methods of the invention provide bioavailability curves similar to those found in FIGS. 1-144.

Another embodiment provides a method for preventing a toxic release profile in a patient comprising administering to a patient an active agent covalently bound to a chemical moiety wherein said bound active agent maintains a steady-state serum release curve which provides a therapeutically effective bioavailability but prevents spiking or increase blood serum concentrations compared to unbound active agent.

Another embodiment of the invention is a method for reducing or preventing abuse of a pharmaceutical composition, comprising providing, administering, or prescribing said composition to a human in need thereof, wherein said composition comprises a chemical moiety covalently attached to an active agent such that the pharmacological activity of active agent is substantially decreased when the composition is used in a manner inconsistent with the manufacturer's instructions. Another embodiment of the invention is a method for reducing or preventing abuse of a pharmaceutical composition, comprising consuming said composition, wherein said composition comprises a chemical moiety covalently attached to an active agent such that the pharmacological activity of the active agent is substantially decreased when the composition is used in a manner inconsistent with the manufacturer's instructions.

Another embodiment of the invention is a method of preventing overdose of a pharmaceutical composition, comprising providing, administering, or prescribing said pharmaceutical composition to a human in need thereof, wherein said composition comprises a chemical moiety covalently attached to an active agent in a manner that substantially decreases the potential of overdose from active agent. Another embodiment of the invention is a method of preventing overdose of a pharmaceutical composition, comprising consuming said pharmaceutical composition, wherein said composition comprises a chemical moiety covalently attached to active agent in a manner that substantially decreases the potential of overdose from the active agent.

Another embodiment of the invention is a method for reducing or preventing the euphoric effect of a pharmaceutical composition, comprising providing, administering, or prescribing said composition to a human in need thereof, wherein said composition comprises a chemical moiety covalently attached to an active agent such that the pharmacological activity of active agent is substantially decreased when the composition is used in a manner inconsistent with the manufacturer's instructions. Another embodiment of the invention is a method for reducing or preventing the euphoric effect of a pharmaceutical composition, comprising consuming said composition, wherein said composition comprises a chemical moiety covalently attached to an active agent such that the pharmacological activity of active agent is substantially decreased when the composition is used in a manner inconsistent with the manufacturer's instructions.

Another embodiment of the invention is any of the preceding methods wherein said pharmaceutical composition is adapted for oral administration, and wherein said active agent is resistant to release from said chemical moiety when the composition is administered parenterally, such as intranasally or intravenously. Preferably, said active agent may be released from said chemical moiety in the presence of acid and/or enzymes present in the stomach, intestinal tract, or blood serum. Optionally, said composition may be in the form of a tablet, capsule, oral solution, or oral suspension.

Another embodiment of the invention is any of the preceding methods wherein said chemical moiety is an amino acid, oligopeptide, polypeptide, carbohydrate, glycopeptide, nucleic acid, or vitamin. Preferably, said chemical moiety is an amino acid, oligopeptide, or polypeptide. Where the chemical moiety is a polypeptide, preferably said polypeptide comprises fewer than 70 amino acids, fewer than 50 amino acids, fewer than 10 amino acids, or fewer than 6 amino acids.

Another embodiment of the invention is any of the preceding methods wherein said covalent attachment comprises an ester or carbonate bond. Another embodiment of the invention is any of the preceding methods wherein said active agent covalently attaches to a chemical moiety through a ketone and/or hydroxyl in a pharmaceutically acceptable oral dosage form.

Another embodiment of the invention is any of the preceding methods wherein said composition yields a therapeutic effect without substantial euphoria. Preferably, said active agent provides a therapeutically bioequivalent AUC when compared to active agent alone but does provide a $C_{max}$ which results in euphoria.

Another embodiment of the invention is a method for reducing or preventing abuse of a pharmaceutical composition, comprising orally administering said composition to a human in need thereof, wherein said composition comprises an amino acid or peptide covalently attached to active agent such that the pharmacological activity of active agent is substantially decreased when the composition is used in a manner inconsistent with the manufacturer's instructions.

Another embodiment is a method of preventing overdose of a pharmaceutical composition, comprising orally administering said pharmaceutical composition to a human in need thereof, wherein said composition comprises an amino acid or peptide covalently attached to active agent in a manner that substantially decreases the potential of active agent to result in overdose.

Another embodiment is a method for reducing or preventing the euphoric effect of a pharmaceutical composition, comprising orally administering said composition to a human in need thereof, wherein said composition comprises an amino acid or peptide covalently attached to active agent such that the pharmacological activity of active agent is substantially decreased when the composition is used in a manner inconsistent with the manufacturer's instructions.

For each of the recited methods of the invention the following properties may be achieved through bonding active agent to the chemical moiety. In one embodiment, the toxicity of the compound may be substantially lower than that of the active agent when delivered in its unbound state or as a salt thereof. In another embodiment, the possibility of overdose by oral administration is reduced or eliminated. In another embodiment, the possibility of overdose by intranasal administration is reduced or eliminated. In another embodiment, the possibility of overdose by injection administration is reduced or eliminated.

Another embodiment of the invention provides methods of treating various diseases or conditions comprising administering compounds or compositions of the invention which further comprise commonly prescribed active agents for the respective illness or diseases wherein the amphetamine is covalently attached to a chemical moiety. For instance, one embodiment of the invention comprises a method of treating attention deficit hyperactivity comprising administering to a patient amphetamine covalently bound to a chemical moiety. Another embodiment provides a method of treating attention deficit hyperactivity disorder (ADHD) comprising administering to a patient compounds or compositions of the invention, such as amphetamine covalently bound to a chemical moiety. Another embodiment provides a method of treating attention deficit disorder (ADD) comprising administering to a patient compounds or compositions of the invention, amphetamine covalently bound to a chemical moiety.

Another embodiment of the invention provides a method of treating cognitive decline associated with acquired immunodeficiency syndrome (AIDS) or AIDS-related complex comprising administering to a patient compounds or compositions of the invention.

Another embodiment of the invention provides a method of treating depression comprising administering to a patient compounds or compositions of the invention. Another embodiment of the invention provides a method of treating anxiety and anxiety related disorders comprising administering to a patient compounds or compositions of the invention. Another embodiment of the invention provides a method of treating psychosis comprising administering to a patient compounds or compositions of the invention.

Another embodiment of the invention provides a method of treating nicotine addiction comprising administering to a patient compounds or compositions of the invention. Another embodiment of the invention provides a method of treating narcotic addiction comprising administering to a patient compounds or compositions of the invention. Another embodiment of the invention provides a method of treating alcoholism comprising administering to a patient compounds or compositions of the invention.

Another embodiment of the invention provides a method of treating narcolepsy comprising administering to a patient compounds or compositions of the invention. Another embodiment of the invention provides a method of providing analgesia comprising administering to a patient compounds or compositions of the invention.

In order to facilitate a more complete understanding of the invention, Examples are provided below. However, the scope of the invention is not limited to specific embodiments disclosed in these Examples, which are for purposes of illustration only.

EXAMPLES

The invention is illustrated by pharmacokinetic studies with amphetamine, hydrocodone, and oxycodone that have been covalently modified by attachment to various moieties such as an individual amino acid, specific short chained amino acid sequences such as di-, tri-, and pentapeptides, or carbohydrates such as ribose, etc. Studies include pharmacokinetic evaluations of the various drug conjugates administered by the oral, intranasal, and intravenous routes. Collectively the compounds demonstrate that active agents may be modified by covalent attachment to various moieties and retain their therapeutic value at normal doses while preventing potential overdose by oral administration and prevention of abuse through intranasal and intravenous administration.
Carrier Bound Narcotics Examples 33 through 83 Hydrocodone Applicability of Abuse Resistance for the Narcotic Analgesics Demonstrated Through the Use of Hydrocodone.

Examples 33 through 83 illustrate the applicability of a number of peptide-active agent compositions in reducing the potential for overdose while maintaining their therapeutic value wherein the peptides are conjugated to the active agent hydrocodone (HC). Exemplary compounds which were substituted at the 6 position of hydrocodone are termed EEFFI-HC, EEFFF-HC, YYI-HC, DDI-HC, and YYFFI-HC.

Oral, intranasal, and intravenous bioavailability studies of hydrocodone and hydrocodone conjugates were conducted in male Sprague-Dawley rats. Doses of hydrocodone bitartrate and hydrocodone conjugates containing equivalent amounts of hydrocodone were administered in deionized water. Oral administration was in 0.5 ml by gavage needle (with the exception of YYI-HC, which was delivered as a solid in gelatin capsules). Intranasal doses were administered by placing 20 microliters into the nasal flares of rats anesthetized with isoflurane. Intravenous administration was in 0.1 ml by tail vein injection. Plasma was collected by retroorbital sinus puncture under isoflurane anesthesia. Hydrocodone and hydromorphone (major active metabolite) concentrations were determined by LC/MS/MS.

The below examples are illustrative only and the below amino acid sequences attached to hydrocodone is not meant to be limiting. As such, synthesis and attachment of hydrocodone may be accomplished for instance view the following exemplary methods.

Hydrocodone Synthetic Examples Carbohydrates

Example 33

Galacto-Hydrocodone

Figure 1:
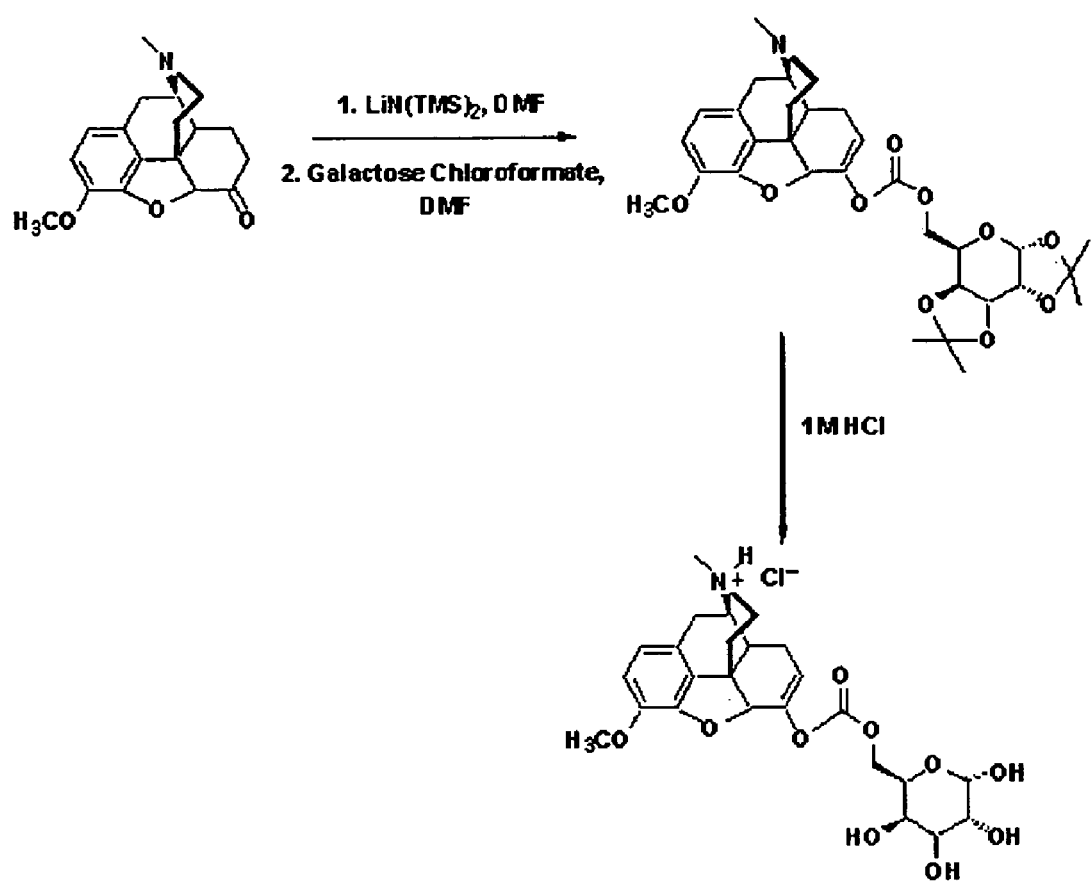
FIG. 1. illustrates preparation of Galacto-Hydrocodone.

FIG. 1 illustrates preparation of Galacto-Hydrocodone.

| Reagents | MW | Weight | mmoles | Molar Equivalents |
|---|---|---|---|---|
| 1. Hydrocodone | 299 | 0.223 g | 0.75 | 1.0 |
| 1. LiN(TMS)$_2$ in THF | 1M | 1.13 ml | 1.13 | 1.5 |
| 1. DMF | — | 5 ml | — | — |
| 2. Galactose Chloroformate | — | — | 1.49 | 2.0 |
| 2. DMF | — | 3 ml | — | — |
| 3. 1M HCl | 1M | 30 ml | — | — |
| 3. Acetone | — | 20 ml | — | — |

Galacto-Hydrocodone

To a solution of hydrocodone in DMF was added LiN(TMS)$_2$ in THF via syringe. The solution was stirred at ambient temperatures for 5 minutes then the chloroformate of galactose in DMF was added via syringe. The resulting solution was stirred at ambient temperatures for 2 hours. A TLC was taken (9:1 CHCl$_3$:MeOH; UV and 5% H$_2$SO$_4$ in MeOH; R$_{f(product)}$=~0.5). Reaction was neutralized to pH 7 with 6M HCl. Solvent was removed. Final product was purified using preparative TLC (0-10% MeOH in CHCl$_3$). Solid was collected as a white powder (0.180 g, 41% yield): $^1$H NMR (DMSO-d$_6$) δ 1.28 (2s, 6H), 1.37 (s, 3H), 1.44 (3, 3H), 1.49 (m, 2H), 1.88 (dt, 1H), 2.08 (m, 2H), 2.29 (s, 4H), 2.40 (m, 2H), 2.90 (d, 1H), 3.09 (s, 1H), 3.73 (s, 3H), 3.99 (dd, 1H), 4.14 (t, 1H), 4.26 (dt, 2H), 4.39 (d, 1H), 4.63 (d, 1H), 4.95 (s, 1H), 5.48 (d, 1H), 5.68 (d, 1H), 6.65 (d, 1H), 6.74 (d, 1H); MS Calculated mass=585.6 Found=586.4 (M+H).

To the protected galactose intermediate was added 30 ml of 1M HCl and 20 ml acetone. The resulting solution was stirred at ambient temperatures for 3 hours. Solvent was removed and final product dried under vacuum. Solid was collected as a white solid: MS Calculated mass=505.5 Found=506.4 (M+H).

Figure 2:
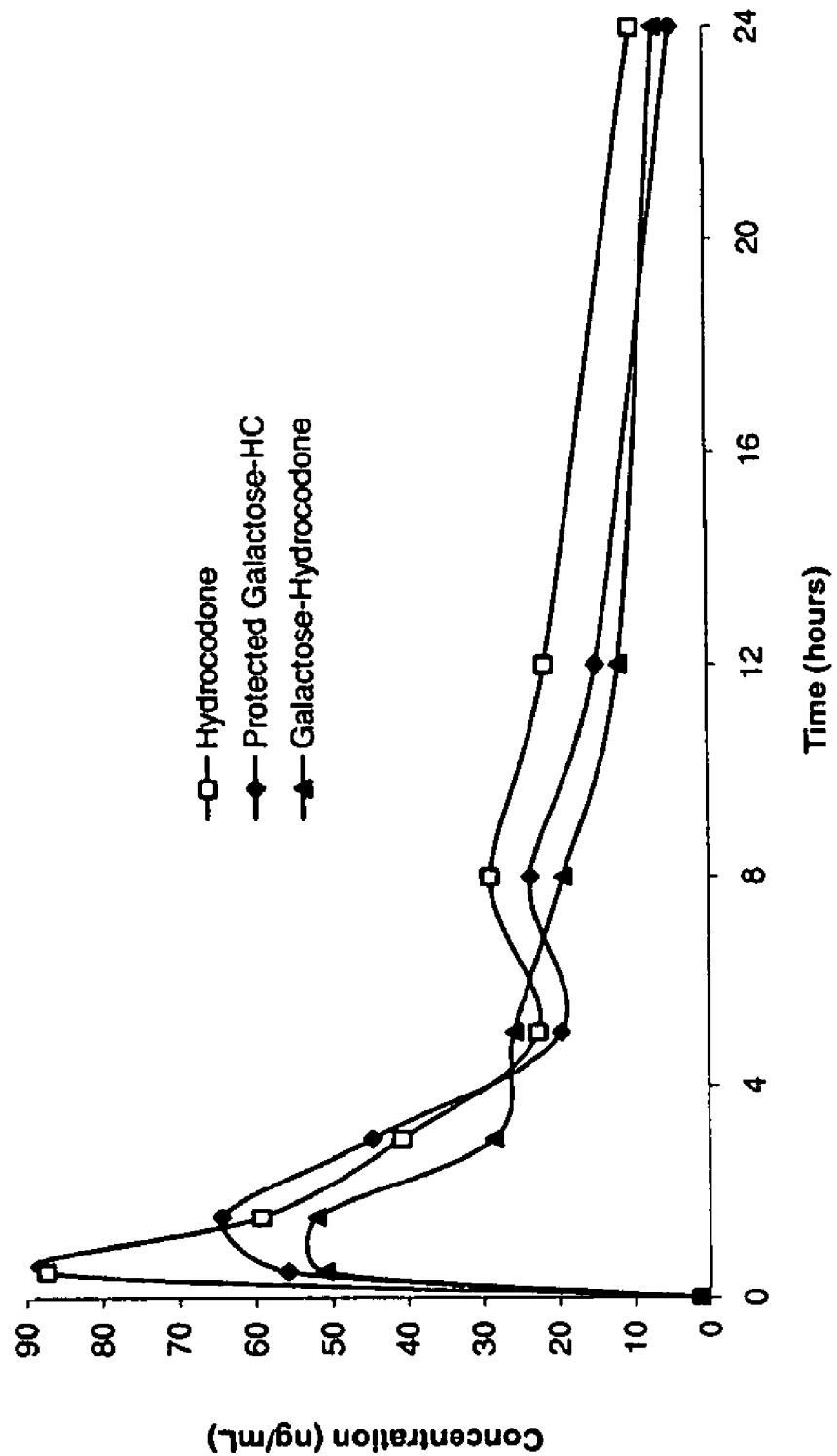
FIG. 2. Oral bioavailability of abuse-resistant hydrocodone carbohydrate conjugates, measured as free hydrocodone (with measured plasma levels by ELISA).

FIG. 2 depicts oral bioavailability of abuse-resistant hydrocodone carbohydrate conjugates, measured as free hydrocodone (with measured plasma levels by ELISA).

Example 34

Ribo-Hydrocodone

Figure 3:
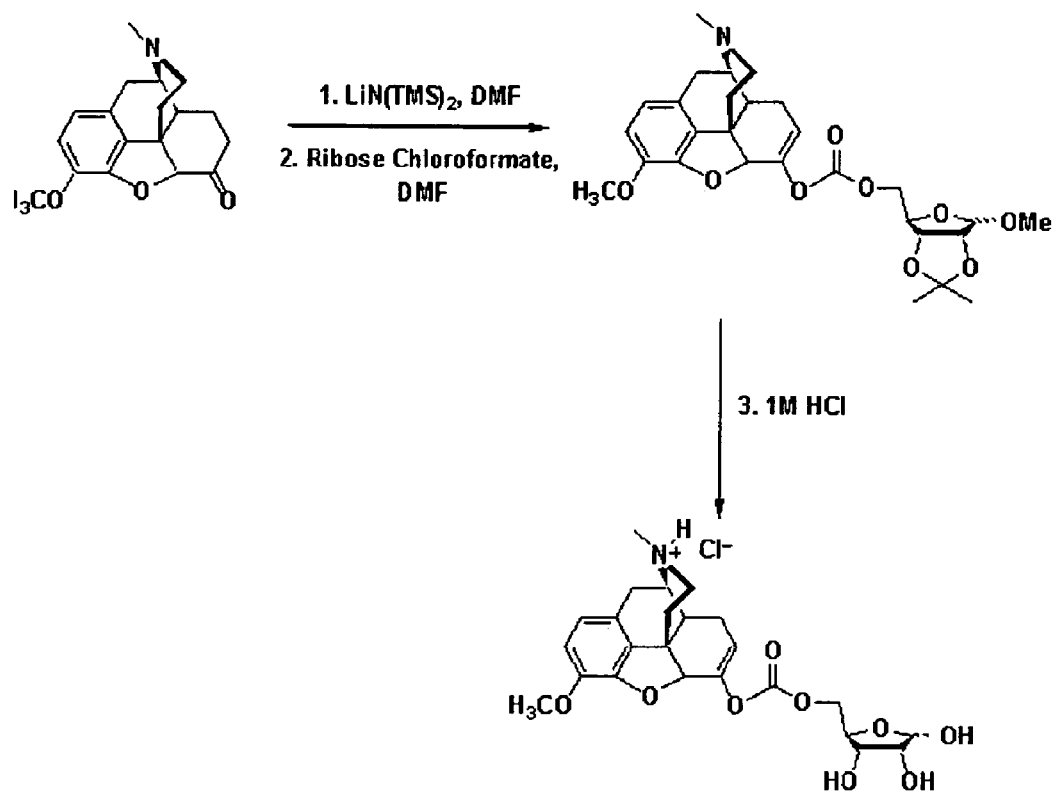
FIG. 3. illustrates preparation of Ribo-Hydrocodone.

FIG. 3 illustrates preparation of Ribo-Hydrocodone.

| Reagents | MW | Weight | mmoles | Molar Equivalents |
|---|---|---|---|---|
| 1. Hydrocodone | 299 | 0.733 g | 2.45 | 1.0 |
| 1. LiN(TMS)$_2$ in THF | 1M | 3.68 ml | 3.68 | 1.5 |
| 1. DMF | — | 8 ml | — | — |
| 2. Ribose Chloroformate | — | — | 4.90 | 2.0 |
| 2. DMF | — | 3 ml | — | — |
| 3. 1M HCl | 1M | 10 ml | — | — |

Ribo-Hydrocodone

To a solution of hydrocodone in DMF was added LiN(TMS)$_2$ in THF via syringe. The solution was stirred at ambient temperatures for 5 minutes then the chloroformate of ribose in DMF was added via syringe. The resulting solution was stirred at ambient temperatures for 2 hours. A TLC was taken (9:1 CHCl$_3$:MeOH; UV and 5% H$_2$SO$_4$ in MeOH; R$_{f(product)}$=~0.5). Reaction was neutralized to pH 7 with 1M HCl. Solvent was removed. Crude product was taken up in CHCl$_3$ (50 ml), washed with water (3×50 ml), dried over MgSO$_4$, filtered and solvent removed. Final product was purified using preparative HPLC (10 mM CH$_3$COONH$_4$/MeCN; 0-20 min: 80/20→0/100). Solid was collected as a clear, colorless glass (0.095 g, 7% yield): $^1$H NMR (DMSO-d$_6$) δ 1.26 (s, 3H), 1.39 (s, 3H), 1.50 (m, 2H), 1.89 (s, 4H), 2.08 (m, 2H), 2.29 (s, 4H), 2.40 (m, 2H), 2.88 (d, 1H), 3.08 (m, 1H), 3.25 (s, 3H), 3.73 (s, 3H), 4.12 (m, 2H), 4.28 (t, 1H), 4.58 (d, 1H), 4.72 (d, 1H), 4.97 (s, 1H), 4.98 (s, 1H), 5.70 (s, 1H), 6.66 (d, 1H), 6.75 (d, 1H). MS Calculated mass=529.2 Found=530.4 (M+H).

To the protected ribose intermediate was added 10 ml of 1M HCl. The resulting solution was stirred at ambient temperatures for 2 hours. Solvent was removed and final product dried under vacuum. Solid was collected as a waxy, slightly yellow solid (0.092 g, quant.): $^1$H NMR (DMSO-d$_6$) δ 1.51 (t, 1H), 1.83 (d, 1H), 2.41 (dt, 1H), 2.27 (t, 1H), 2.63 (dd, 1H), 2.80 (s, 3H), 2.96 (m, 2H), 3.20 (m, 1H), 3.75 (s, 3H), 3.82-4.34 (br m, 12H), 5.15 (s, 1H), 5.72 (s, 1H), 6.75 (d, 1H), 6.88 (d, 1H), 11.37 (br s, 1H).

Figure 4:
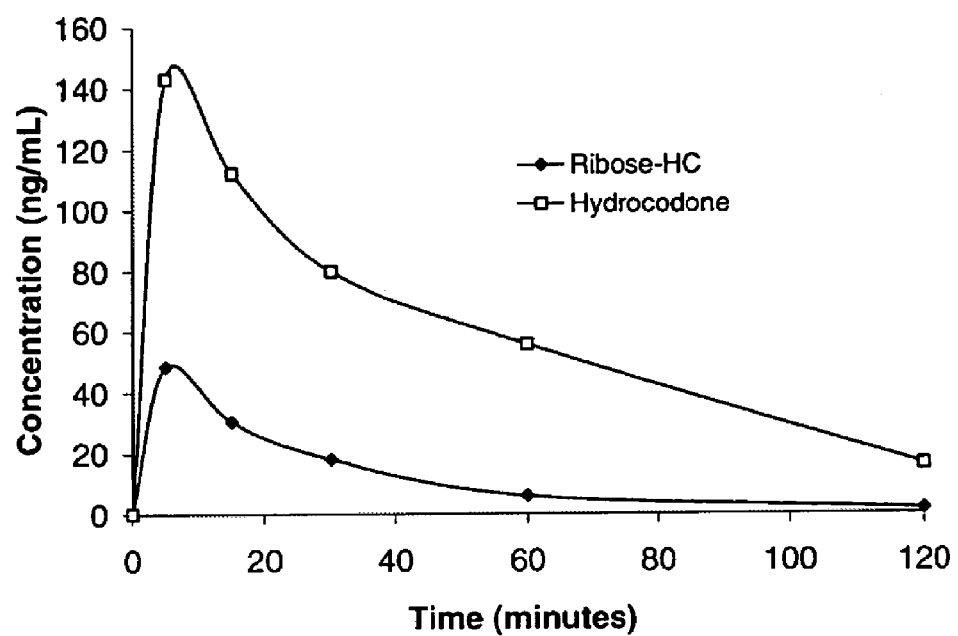
FIG. 4. Intranasal bioavailability of abuse-resistant hydrocodone carbohydrate conjugate, measured as free hydrocodone (with measured plasma levels by ELISA).

FIG. 4 illustrates intranasal bioavailability of abuse-resistant hydrocodone carbohydrate conjugate, measured as free hydrocodone (with measured plasma levels by ELISA).

Single Amino Acids

Example 35

Leu-Hydrocodone

Figure 5:
FIG. 5. illustrates preparation of Leu-Hydrocodone.

FIG. 5 illustrates preparation of Leu-Hydrocodone.

| Reagents | MW | Weight | mmoles | Molar Equivalents |
|---|---|---|---|---|
| 1. Hydrocodone | 299 | 1.00 g | 3.34 | 1.0 |
| 1. LiN(TMS)$_2$ in THF | 1M | 10.5 ml | 10.5 | 3.15 |
| 1. THF | — | 25 ml | — | — |
| 2. Boc-Leu-OSu | 328 | 3.28 g | 10.0 | 3.0 |

Leu-Hydrocodone

To a solution of hydrocodone in THF was added LiN(TMS)$_2$ in THF via syringe. The solution was stirred at ambient temperatures for 5 minutes then Boc-Leu-OSu was added. The resulting reaction mixture was stirred at ambient temperatures for 18 hours. Reaction was neutralized to pH 7 with 6M HCl. Solvent was removed. Crude material was taken up in CHCl$_3$ (100 ml), washed with sat. NaHCO$_3$ (3×100 ml), dried over MgSO$_4$, filtered, and solvent removed. Solid was collected as a yellow powder (1.98 g, 95% yield): $^1$H NMR (DMSO-d$_6$) δ 0.86 (dd, 6H), 1.31 (s, 9H), 1.46 (s, 2H), 1.55 (m, 2H), 1.69 (m, 1H), 1.87 (dt, 1H), 2.07 (dt, 2H), 2.29 (s, 3H), 2.43 (m, 2H), 2.93 (d, 1H), 3.11 (s, 1H), 3.72 (s, 3H), 3.88 (dt, 1H), 4.03 (dt, 1H), 4.87 (s, 1H), 5.51 (d, 1H), 6.65 (d, 1H), 6.73 (d, 1H), 6.90 (s, 1H).

To the Boc-Leu-Hydrocodone was added 25 ml of 4N HCl in dioxane. The resulting mixture was stirred at ambient temperatures for 18 hours. Solvent was removed and final product dried under vacuum. Solid was collected as a slightly yellow solid (1.96 g, 97% yield): $^1$H NMR (DMSO-d$_6$) δ 0.94 (d, 6H), 1.52 (m, 1H), 1.75-1.90 (m, 4H), 2.22 (dt, 1H), 2.34 (dt, 1H), 2.64 (q, 1H), 2.75 (s, 3H), 2.95-3.23 (m, 4H), 3.74 (s, 3H), 3.91 (d, 1H), 4.07 (s, 1H), 5.10 (s, 1H), 5.72 (d, 1H), 6.76 (d, 1H), 6.86 (d, 1H), 8.73 br s, 3H).

Example 36

Glu-Hydrocodone

Synthesis of Glu-Hydrocodone

Glu-Hydrocodone was prepared by a similar method to Example 35 except the amino acid starting material was Boc-Glu(OtBu)-OSu.

Example 37

Ile-Hydrocodone

Synthesis of Ile-Hydrocodone

Ile-Hydrocodone was prepared by a similar method to Example 35 except the amino acid starting material was Boc-Ile-OSu.

Dipeptides

Figure 6:
FIG. 6. illustrates preparation of Ala-Pro-Hydrocodone.
Figure 9:
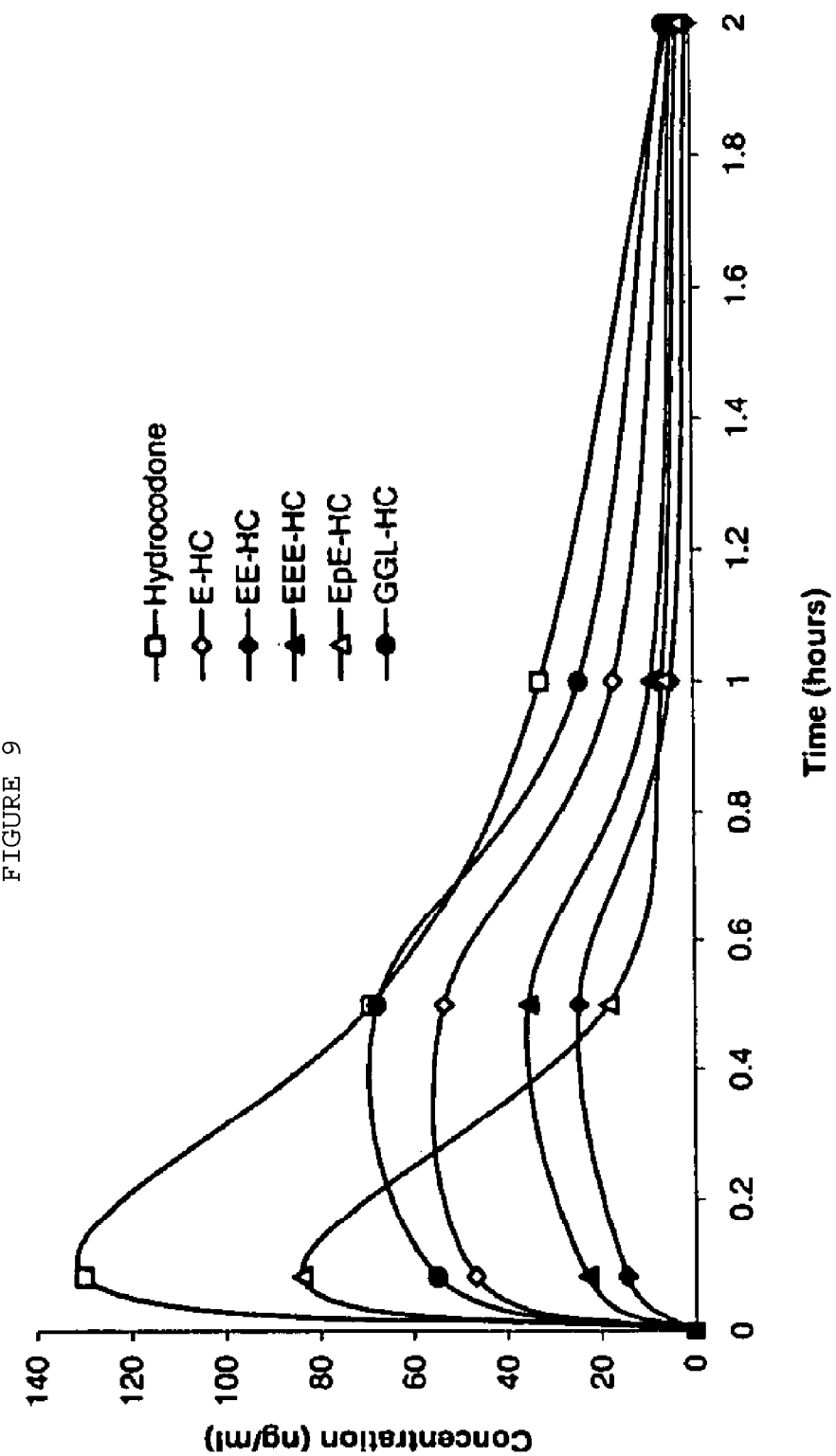
FIG. 9. Intranasal bioavailability of abuse-resistant hydrocodone amino acid, di- and tri-peptide conjugates, measured as free hydrocodone.
Figure 10:
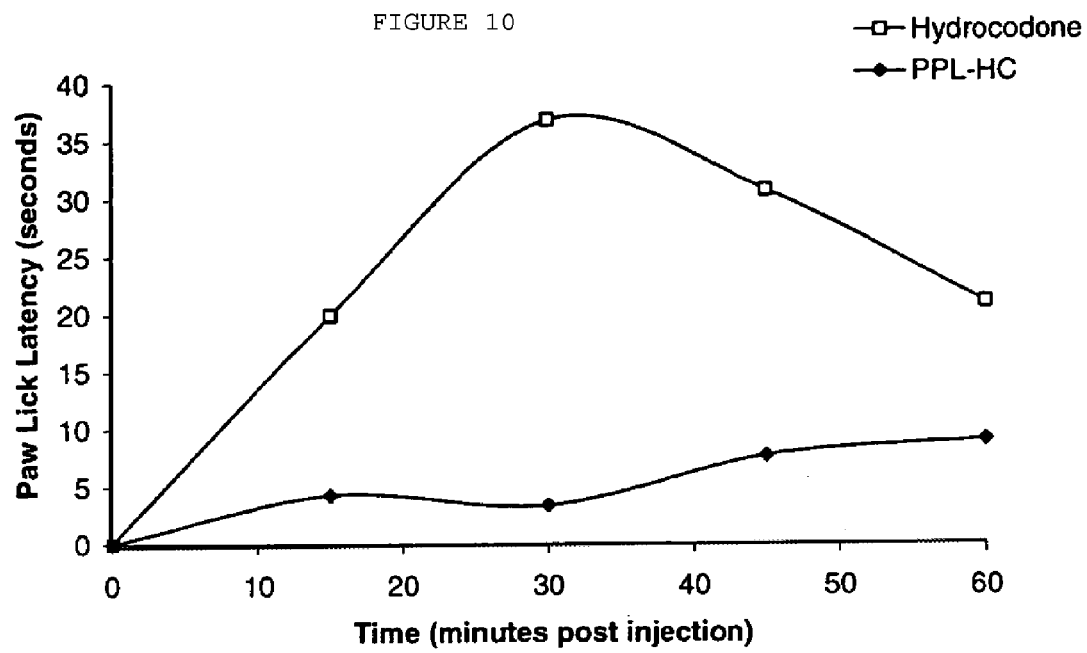
FIG. 10. Analgesic effect of abuse-resistant hydrocodone tri-peptide conjugate following intranasal administration, measured as free hydrocodone.
Figure 11:
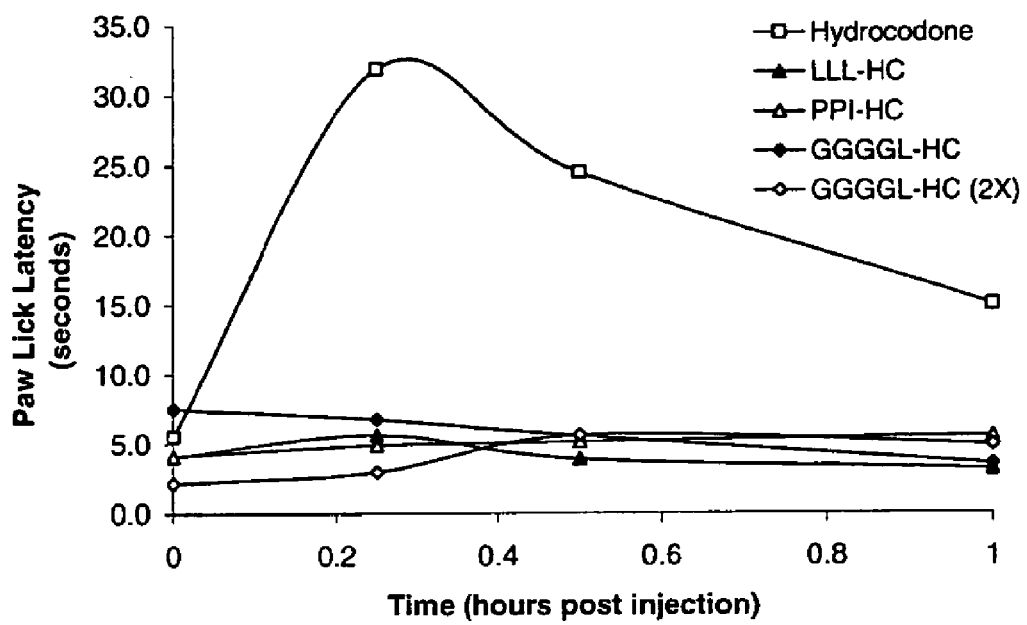
FIG. 11. Analgesic effect of abuse-resistant hydrocodone tri- and penta-peptide conjugates following subcutaneous administration, measured as free hydrocodone.
Figure 12:
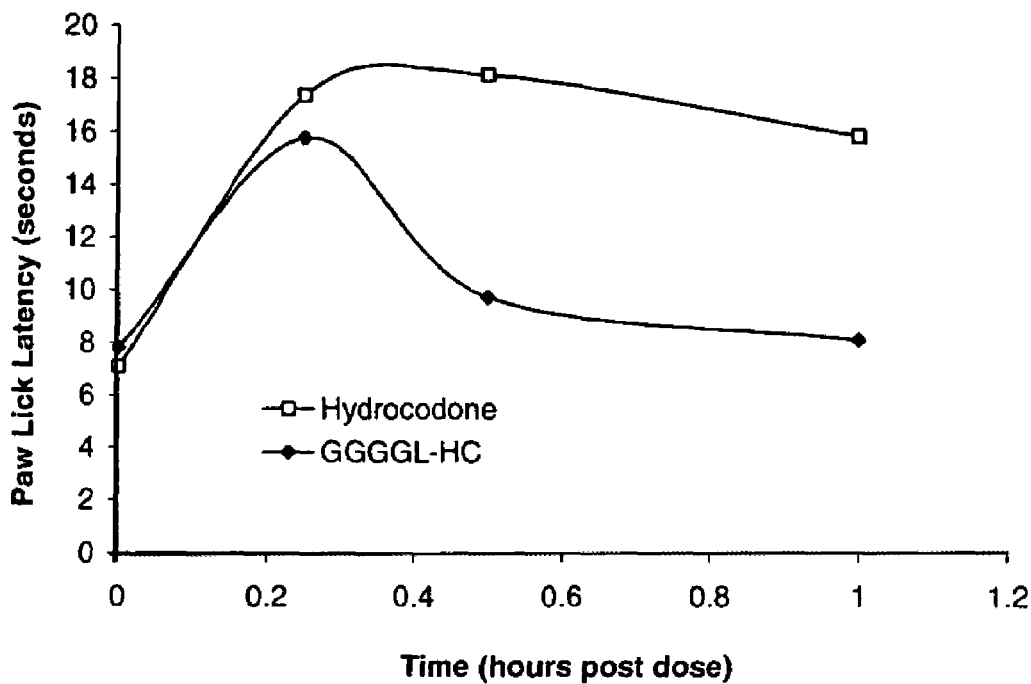
FIG. 12. Analgesic effect of abuse-resistant hydrocodone penta-peptide conjugate following intranasal administration, measured as free hydrocodone.
Figure 13:
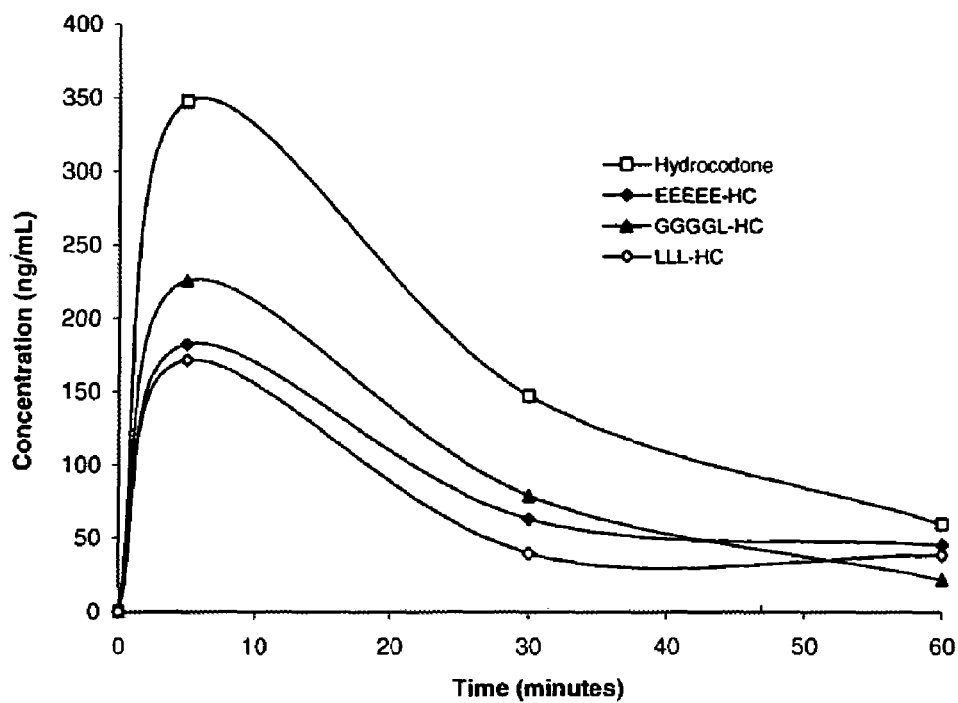
FIG. 13. Intranasal bioavailability of abuse-resistant hydrocodone tri- and penta-peptide conjugates, measured as free hydrocodone.
Figure 14:
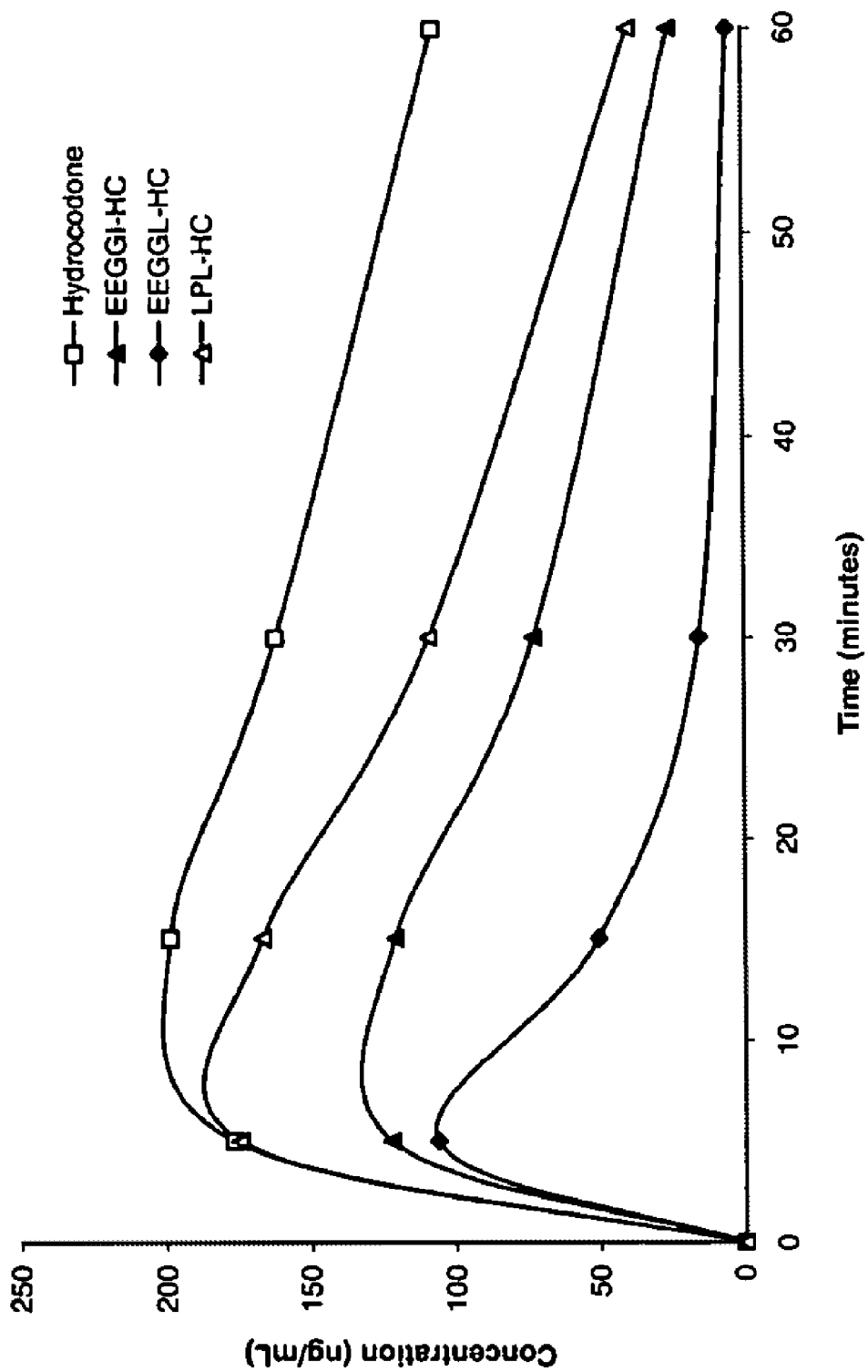
FIG. 14. Intranasal bioavailability of abuse-resistant hydrocodone tri- and penta-peptide conjugates, measured as free hydrocodone.
Figure 15:
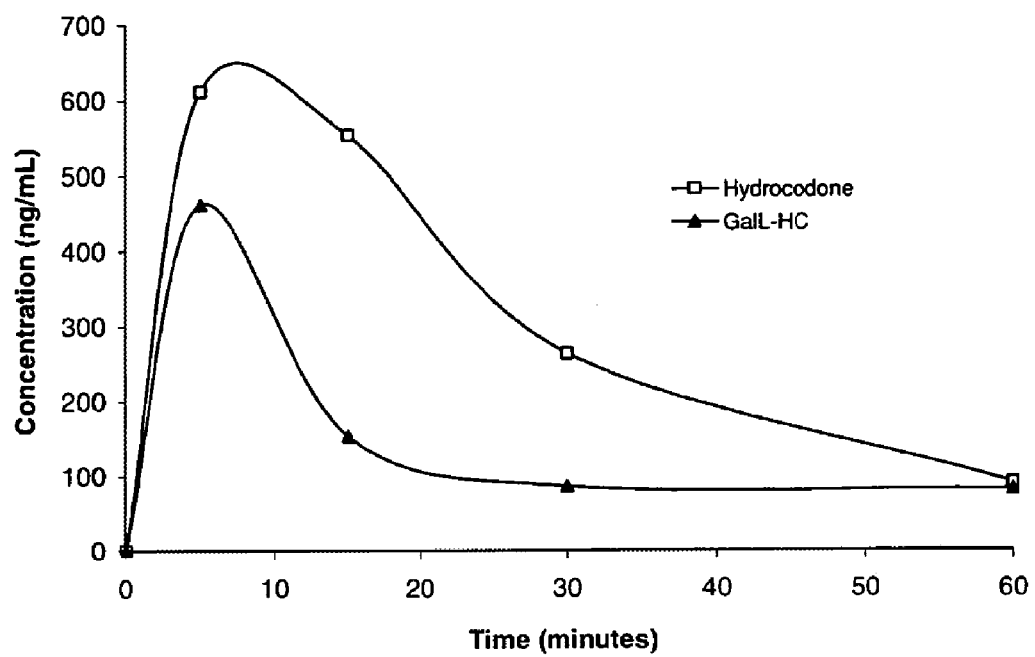
FIG. 15. Intranasal bioavailability of abuse-resistant hydrocodone an amino acid-carbohydrate peptide conjugate, measured as free hydrocodone.
Figure 16:
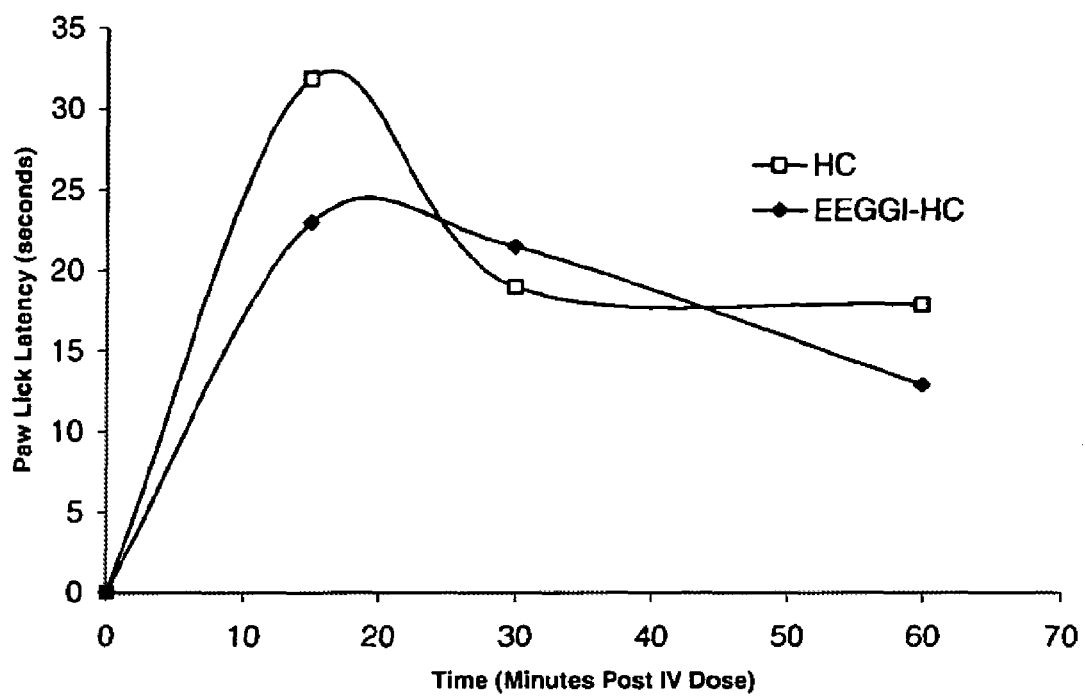
FIG. 16. Analgesic effect of abuse-resistant hydrocodone penta-peptide conjugate following intravenous administration, measured as free hydrocodone.
Figure 17:
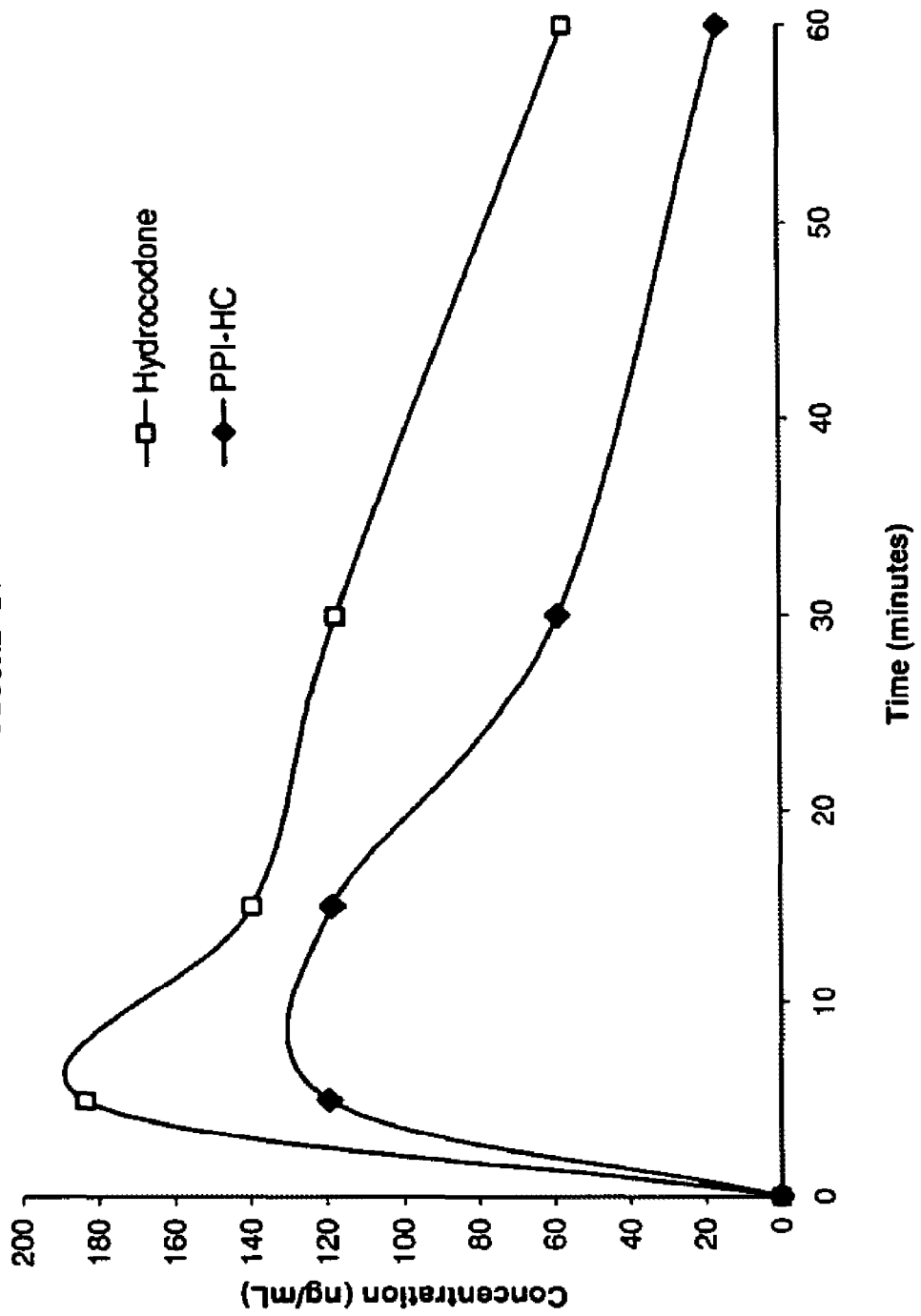
FIG. 17. Intranasal bioavailability of an abuse-resistant hydrocodone tri-peptide conjugate, measured as free hydrocodone.
Figure 18:
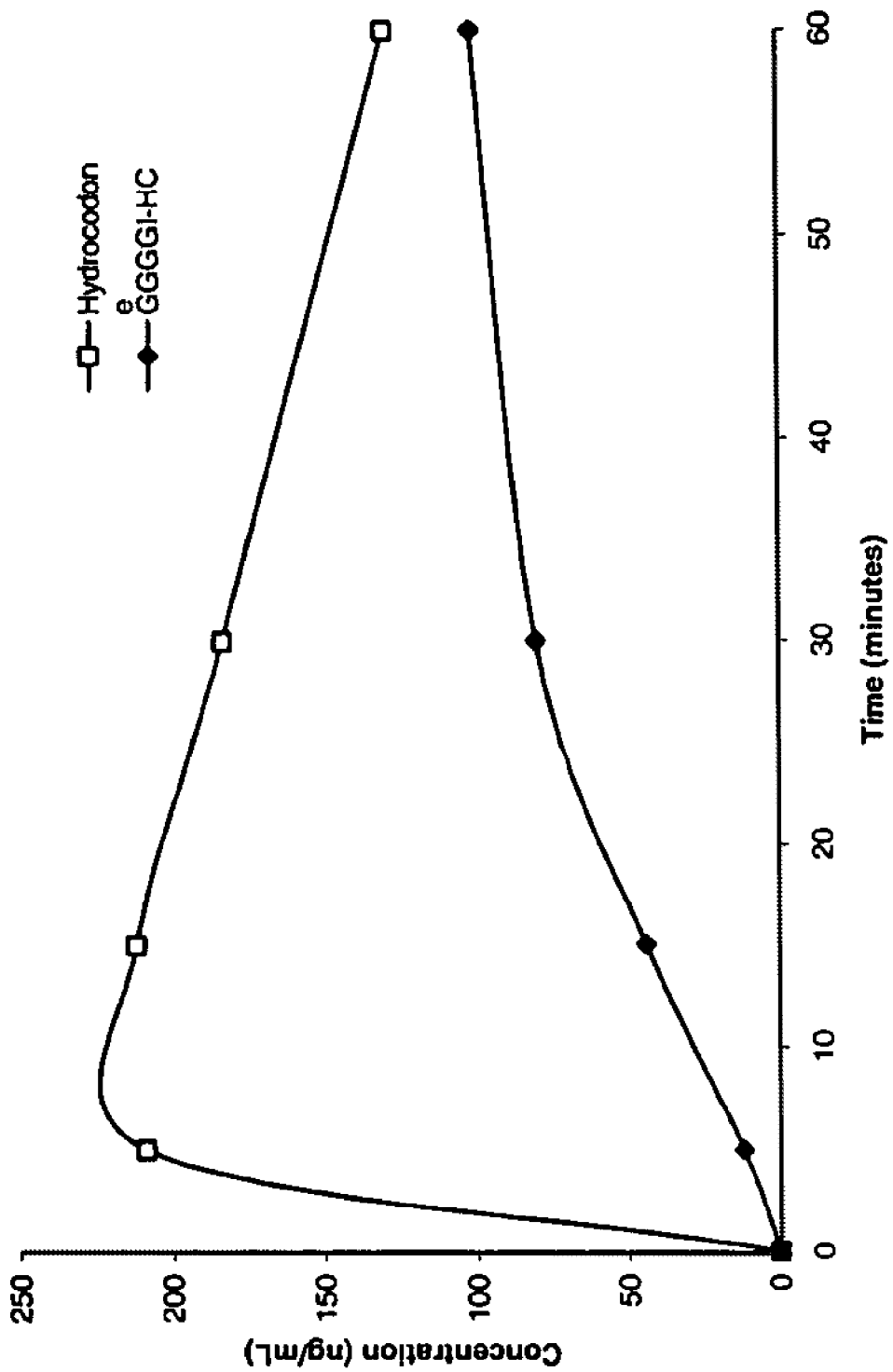
FIG. 18. Intranasal bioavailability of an abuse-resistant hydrocodone penta-peptide conjugate, measured as free hydrocodone.
Figure 19:
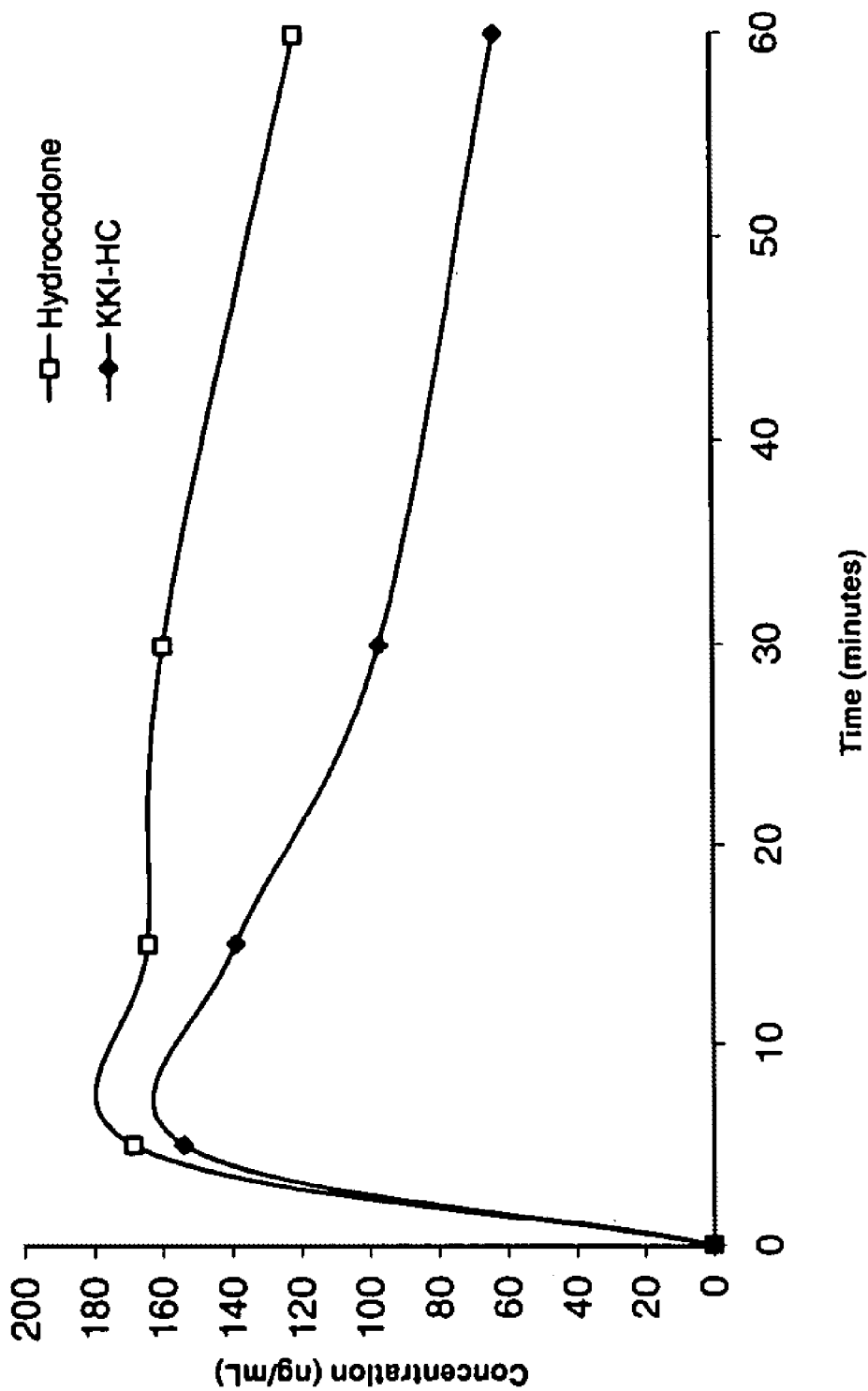
FIG. 19. Intranasal bioavailability of an abuse-resistant hydrocodone tri-peptide conjugate, measured as free hydrocodone.
Figure 20:
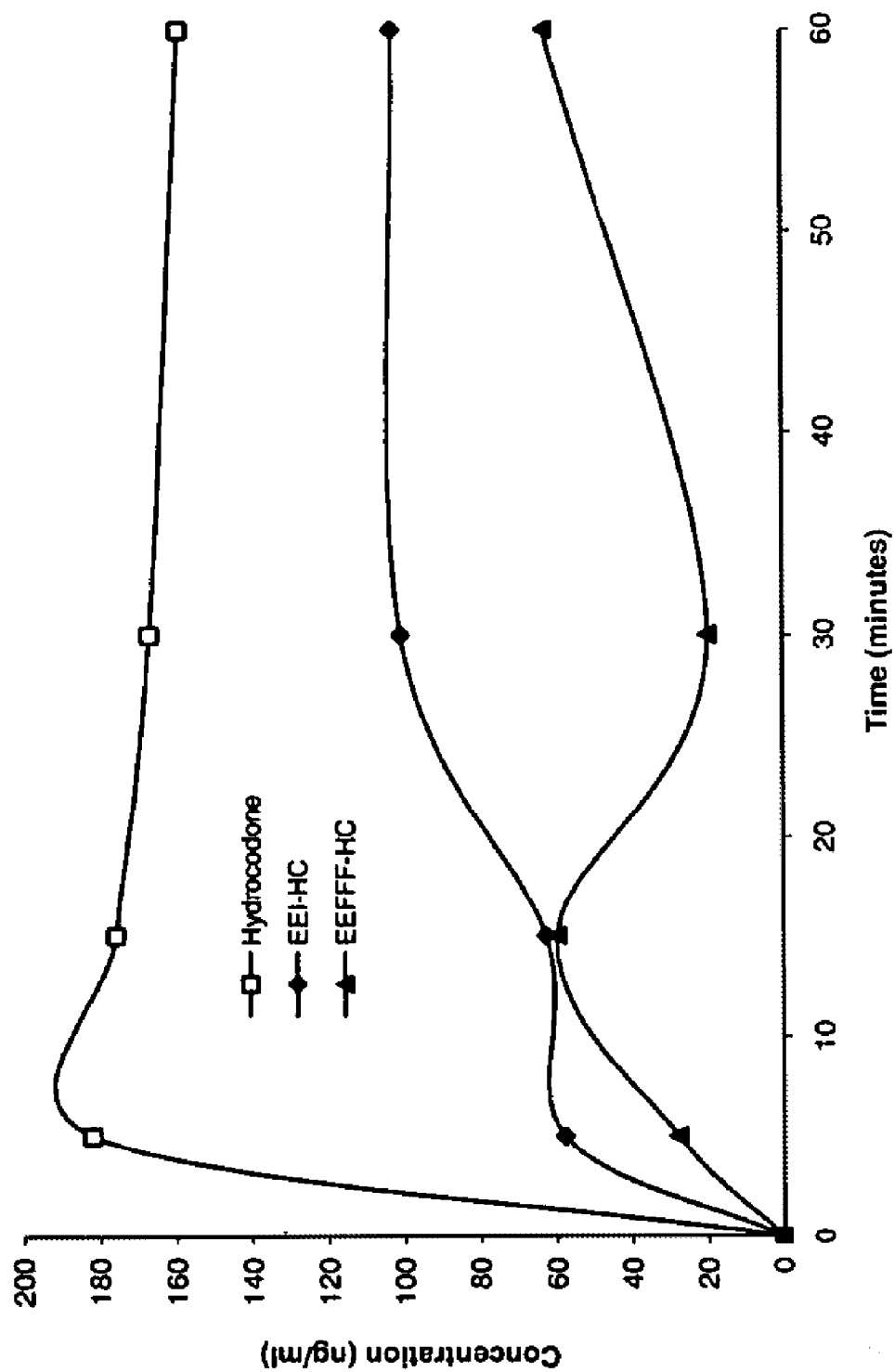
FIG. 20. Intranasal bioavailability of abuse-resistant hydrocodone tri- and penta-peptide conjugates, measured as free hydrocodone.
Figure 21:
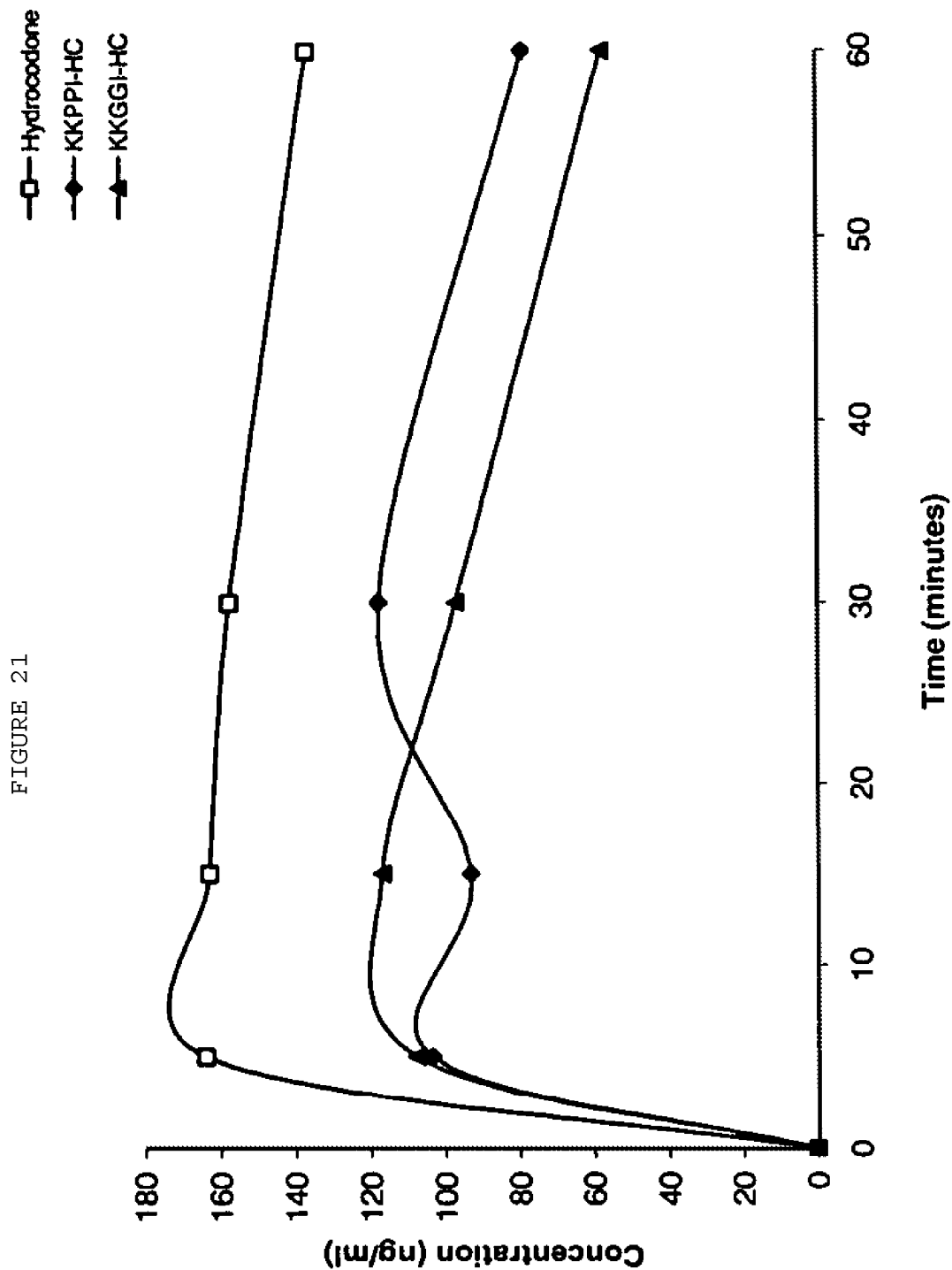
FIG. 21. Intranasal bioavailability of abuse-resistant hydrocodone penta-peptide conjugates, measured as free hydrocodone.
Figure 22:
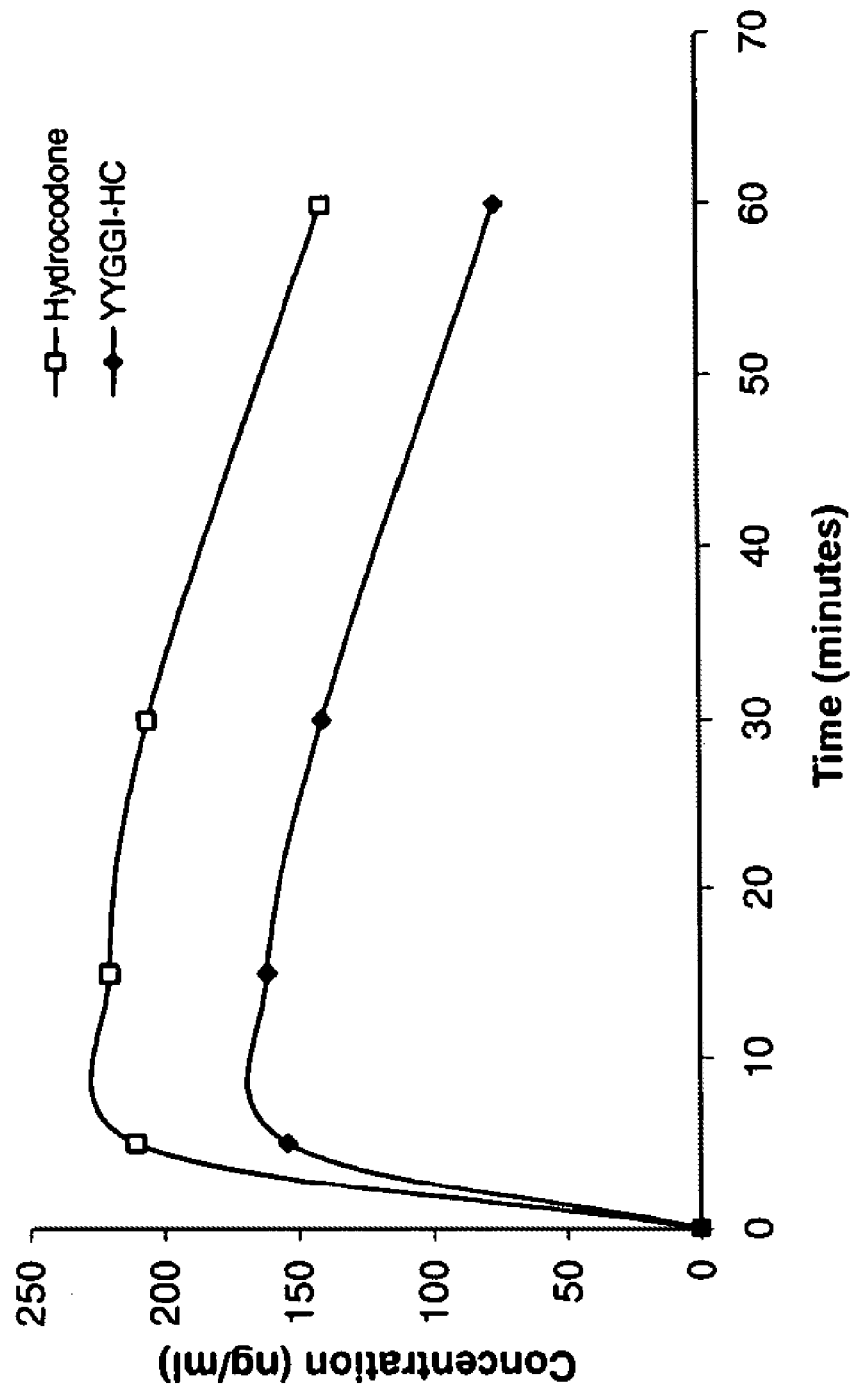
FIG. 22. Intranasal bioavailability of an abuse-resistant hydrocodone penta-peptide conjugate, measured as free hydrocodone.

FIG. 6 illustrates preparation of Ala-Pro-Hydrocodone.

Example 38

Ala-Pro-Hydrocodone

| Reagents | MW | Weight | mmoles | Molar Equivalents |
|---|---|---|---|---|
| Pro-Hydrocodone | 468 | 0.25 g | 0.53 | 1.0 |
| Boc-Ala-OSu | 286 | 0.33 g | 1.2 | 2.26 |
| NMM | 101 | 0.50 ml | 5.38 | 10.2 |
| DMF | — | 10 ml | — | — |

Ala-Pro-Hydrocodone

To a solution of Pro-Hydrocodone in DMF was added NMM followed by Boc-Ala-OSu. The solution was stirred at ambient temperatures for 18 hours. Solvent was removed. Crude material was purified using preparative HPLC (Phenomenex Luna C18, 30×250 mm, 5 μM, 100 Å; Gradient: 100 water/0 0.1% TFA-MeCN→0/100; 30 ml/min.). Solid was collected as a slightly yellow powder (0.307 g, 85% yield): $^1$H NMR (DMSO-d$_6$) δ 1.16 (d, 3H), 1.35 (s, 9H), 1.51 (m, 2H), 1.86-2.10 (m, 6H), 2.50 (m, 1H), 2.54 (m, 1H), 2.69 (m, 1H), 2.88 (s, 3H), 3.02 (dd, 1H), 3.26 (d, 1H), 3.55 (m, 1H), 3.67 (m, 1H), 3.72 (s, 3H), 3.80 (s, 1H), 4.25 (m, 1H), 4.43 (d, 1H), 5.01 (s, 1H), 5.59 (d, 1H), 6.75 (d, 1H), 6.88 (d, 1H), 6.99 (t, 1H), 9.91 (br s, 1H).

To the Boc-Ala-Pro-Hydrocodone (0.100 g) was added 10 ml of 4N HCl in dioxane. The resulting mixture was stirred at ambient temperatures for 18 hours. Solvent was removed and final product dried under vacuum. Solid was collected as a slightly yellow solid (0.56 g, 71% yield): $^1$H NMR (DMSO-$d_6$) δ 1.38 (s, 3H), 1.48 (t, 1H), 1.80-2.29 (m, 8H), 2.65 (m, 1H), 2.80 (s, 3H), 2.96 (m, 3H), 3.23 (m, 2H), 3.76 (s, 3H), 3.92 (s, 1H), 4.22 (s, 1H), 4.53 (s, 1H), 5.00 (s, 1H), 5.84 (d, 1H), 6.77 (d, 1H), 6.86 (d, 1H), 8.25 (br s, 3H).

Example 39

Glu-Glu-Hydrocodone

Synthesis of Glu-Glu-Hydrocodone
Glu-Glu-Hydrocodone was prepared by a similar method to Example 38 except the amino acid starting material was Boc-Glu(OtBu)-OSu and the conjugate starting material was Glu-Hydrocodone.

Example 40

(pyro)Glu-Glu-Hydrocodone

Synthesis of (pyro)Glu-Glu-Hydrocodone
The compound (pyro)Glu-Glu-Hydrocodone was prepared by a similar method to Example 38 except the amino acid starting material was Boc-pyroglutamic acid-OSu and the conjugate starting material was Glu-Hydrocodone.

Tripeptides
FIG. 7 illustrates the preparation of Gly-Gly-Leu-Hydrocodone.

Example 41

Gly-Gly-Leu-Hydrocodone

| Reagents | MW | Weight | mmoles | Molar Equivalents |
|---|---|---|---|---|
| Leu-Hydrocodone | 484 | 2.21 g | 4.56 | 1.0 |
| Boc-Gly-Gly-OSu | 329 | 3.00 g | 9.12 | 2.0 |
| NMM | 101 | 5.0 ml | 45.6 | 10 |
| DMF | — | 100 ml | — | — |

Gly-Gly-Leu-Hydrocodone
To a solution of Leu-Hydrocodone in DMF was added NMM followed by Boc-Gly-Gly-OSu. The solution was stirred at ambient temperatures for 18 hours. Solvent was removed. Crude material was purified using preparative HPLC (Phenomenex Luna C18, 30×250 mm, 5 μM, 100 Å; Gradient: 90 water/10 0.1% TFA-MeCN→0/100; 30 ml/min.). Solid was collected as a slightly yellow powder (2.08 g, 73% yield): $^1$H NMR (DMSO-$d_6$) δ 0.88 (dd, 6H), 1.38 (s, 9H), 1.53-1.72 (m, 5H), 1.89 (d, 1H), 2.15 (m, 1H), 2.67 (m, 2H), 2.94 (s, 3H), 3.05 (m, 2H), 3.25 (m, 2H), 3.56 (d, 3H), 3.76 (s, 6H), 3.98 (s, 1H), 4.35 (q, 1H), 5.04 (s, 1H), 5.59 (d, 1H), 6.77 (d, 1H), 6.85 (d, 1H), 7.04 (t, 1H), 8.01 (t, 1H), 8.30 (d, 1H), 9.99 (br s, 1H).

To the Boc-Gly-Gly-Leu-Hydrocodone (2.08 g) was added 50 ml of 4N HCl in dioxane. The resulting mixture was stirred at ambient temperatures for 18 hours. Solvent was removed and final product dried under vacuum. Solid was collected as a slightly yellow solid (1.72 g, 86% yield): $^1$H NMR (DMSO-$d_6$) δ 0.89 (dd, 6H), 1.50-1.87 (m, 5H), 2.26 (m, 2H), 2.66 (m, 2H), 2.82-2.97 (m, 5H), 3.21 (m, 2H), 3.60 (m, 4H), 3.88 (m, 5H), 4.37 (m, 1H), 5.04 (s, 1H), 5.60 (s, 1H), 6.79 (d, 2H), 8.07 (br s, 3H), 8.54 (br s, 1H), 8.66 (br s, 1H), 11.29 (br s, 1H).

Example 42

Glu-Glu-Glu-Hydrocodone

Synthesis of Glu-Glu-Glu-Hydrocodone
Glu-Glu-Glu-Hydrocodone was prepared by a similar method to Example 41 except the amino acid starting material was Boc-Glu(OtBu)-Glu(OtBu)-OSu and the conjugate starting material was Glu-Hydrocodone.

Example 43

Pro-Pro-Leu-Hydrocodone

Synthesis of Pro-Pro-Leu-Hydrocodone
Pro-Pro-Leu-Hydrocodone was prepared by a similar method to Example 41 except the amino acid starting material was Boc-Pro-Pro-OSu.

Example 44

Leu-Leu-Leu-Hydrocodone

Synthesis of Leu-Leu-Leu-Hydrocodone
Leu-Leu-Leu-Hydrocodone was prepared by a similar method to Example 41 except the amino acid starting material was Boc-Leu-Leu-OSu.

Example 45

Pro-Pro-Ile-Hydrocodone

Synthesis of Pro-Pro-Ile-Hydrocodone
Pro-Pro-Ile-Hydrocodone was prepared by a similar method to Example 41 except the amino acid starting material was Boc-Pro-Pro-OSu and the conjugate starting material was Ile-Hydrocodone.

Example 46

Leu-Pro-Leu-Hydrocodone

Synthesis of Leu-Pro-Leu-Hydrocodone
Leu-Pro-Leu-Hydrocodone was prepared by similar methods except the amino acid starting material was Boc-Leu-Pro-OSu.

Example 47

Lys-Lys-Ile-Hydrocodone

Synthesis of Lys-Lys-Ile-Hydrocodone
Lys-Lys-Ile-Hydrocodone was prepared by similar methods except the amino acid starting material was Boc-Lys(Boc)-Lys(Boc)-OSu and the conjugate starting material was Ile-Hydrocodone.

Example 48

Glu-Glu-Ile-Hydrocodone

Synthesis of Glu-Glu-Ile-Hydrocodone
Glu-Glu-Ile-Hydrocodone was prepared by similar methods except the amino acid starting material was Boc-Glu(OtBu)-Glu(OtBu)-OSu and the conjugate starting material was Ile-Hydrocodone.

Example 49

Tyr-Tyr-Ile-Hydrocodone !Synthesis of Tyr-Tyr-Ile-Hydrocodone

Tyr-Tyr-Ile-Hydrocodone was prepared by similar methods except the amino acid starting material was Boc-Tyr(tBu)-Tyr(tBu)-OSu and the conjugate starting material was Ile-Hydrocodone.
Pentapeptides

Example 50

Gly-Gly-Gly-Gly-Leu-Hydrocodone

FIG. 8 illustrates preparation of Gly-Gly-Gly-Gly-Leu-Hydrocodone.

| Reagents | MW | Weight | mmoles | Molar Equivalents |
|---|---|---|---|---|
| Gly-Gly-Leu-Hydrocodone | 599 | 0.580 g | 0.970 | 1.0 |
| Boc-Gly-Gly-OSu | 329 | 0.638 g | 1.94 | 2.0 |
| NMM | 101 | 1.06 ml | 9.70 | 10 |
| DMF | — | 20 ml | — | — |

Gly-Gly-Gly-Gly-Leu-Hydrocodone
To a solution of Gly-Gly-Leu-Hydrocodone in DMF was added NMM followed by Boc-Gly-Gly-OSu. The solution was stirred at ambient temperatures for 18 hours. Solvent was removed. Crude material was purified using preparative HPLC (Phenomenex Luna C18, 30×250 mm, 5 μM, 100 Å; Gradient: 85 water/15 0.1% TFA-MeCN→50/50; 30 ml/min.). Solid was collected as a slightly yellow powder (0.304 g, 37% yield).
To the Boc-Gly-Gly-Gly-Gly-Leu-Hydrocodone (0.304 g) was added 25 ml of 4N HCl in dioxane. The resulting mixture was stirred at ambient temperatures for 18 hours. Solvent was removed and final product dried under vacuum. Solid was collected as a slightly yellow solid (0.247 g, 97% yield): $^1$H NMR (DMSO-$d_6$) δ 0.87 (m, 6H), 1.23 (s, 1H), 1.51-1.86 (m, 4H), 2.18 (m, 1H), 2.71 (m, 2H), 2.77 (s, 3H), 2.96 (m, 2H), 3.17 (m, 2H), 3.61 (s, 3H), 3.81-3.84 (m, 10H), 4.22 (m, 1H), 4.36 (m, 1H), 5.09 (m, 1H), 5.59 (d, 1H), 6.74 (dd, 2H), 8.16 (br s, 4H), 8.38 (br s, 1H), 8.74 (br s, 1H), 11.42 (br s, 1H).

Example 51

Glu$_5$-Hydrocodone

Synthesis of Glu$_5$-Hydrocodone
Glu$_5$-Hydrocodone was prepared by a similar method to Example 50 except the amino acid starting material was Boc-Glu(OtBu)-Glu(OtBu)-OSu and the conjugate starting material was Glu$_3$-Hydrocodone.

Example 52

Glu$_2$-Gly$_2$-Ile-Hydrocodone

Synthesis of Glu$_2$-Gly$_2$-Ile-Hydrocodone
Glu$_2$-Gly$_2$-Ile-Hydrocodone was prepared by a similar method to Example 50 except the amino acid starting material was Boc-Glu(OtBu)-Glu(OtBu)-OSu and the conjugate starting material was Gly$_2$-Ile-Hydrocodone.

Example 53

Glu$_2$-Gly$_2$-Leu-Hydrocodone

Synthesis of Glu$_2$-Gly$_2$-Leu-Hydrocodone
Glu$_2$-Gly$_2$-Leu-Hydrocodone was prepared by a similar method to Example 50 except the amino acid starting material was Boc-Glu(OtBu)-Glu(OtBu)-OSu and the conjugate starting material was Gly$_2$-Leu-Hydrocodone.

Example 54

Gly$_4$-Ile-Hydrocodone

Synthesis of Gly$_4$-Ile-Hydrocodone
Glu$_4$-Ile-Hydrocodone was prepared by a similar method to Example 50 except the amino acid starting material was Boc-Gly-Gly-OSu and the conjugate starting material was Gly$_2$-Ile-Hydrocodone.

Example 55

Glu$_2$-Phe$_3$-Hydrocodone

Synthesis of Glu$_2$-Phe$_3$-Hydrocodone
Glu$_2$-Phe$_3$-Hydrocodone was prepared by a similar method to Example 50 except the amino acid starting material was Boc-Glu(OtBu)-Glu(OtBu)-OSu and the conjugate starting material was Phe$_3$-Hydrocodone.

Example 56

Lys$_2$-Gly$_2$-Ile-Hydrocodone

Synthesis of Lys$_2$-Gly$_2$-Ile-Hydrocodone
Lys$_2$-Gly$_2$-Ile-Hydrocodone was prepared by a similar method to Example 50 except the amino acid starting material was Boc-Lys(Boc)-Lys(Boc)-OSu and the conjugate starting material was Gly$_2$-Ile-Hydrocodone.

Example 57

Lys$_2$-Gly$_2$-Ile-Hydrocodone

Synthesis of Lys$_2$-Pro$_2$-Ile-Hydrocodone
Lys$_2$-Pro$_2$-Ile-Hydrocodone was prepared by a similar method to Example 50 except the amino acid starting material was Boc-Lys(Boc)-Lys(Boc)-OSu and the conjugate starting material was Pro$_2$-Ile-Hydrocodone.

Example 58

Tyr$_2$-Gly$_2$-Ile-Hydrocodone

Synthesis of Tyr$_2$-Gly$_2$-Ile-Hydrocodone
Tyr$_2$-Gly$_2$-Ile-Hydrocodone was prepared by a similar method to Example 50 except the amino acid starting material was Boc-Tyr(tBu)-Tyr(tBu)-OSu and the conjugate starting material was Gly$_2$-Ile-Hydrocodone.

Example 59

Gly$_2$-Pro$_2$-Ile-Hydrocodone

Synthesis of Gly$_2$-Pro$_2$-Ile-Hydrocodone
Gly$_2$-Pro$_2$-Ile-Hydrocodone was prepared by a similar method to Example 50 except the amino acid starting material was Boc-Gly$_2$-OSu and the conjugate starting material was Pro$_2$-Ile-Hydrocodone.

Example 60

Asp$_2$-Phe$_2$-Ile-Hydrocodone

Synthesis of Asp$_2$-Phe$_2$-Ile-Hydrocodone
Asp$_2$-Phe$_2$-Ile-Hydrocodone was prepared by a similar method to Example 50 except the amino acid starting material was Boc-Asp(OtBu)-Asp(OtBu)-OSu and the conjugate starting material was Phe$_2$-Ile-Hydrocodone.

Example 61

Glu$_2$-Asp$_2$-Ile-Hydrocodone

Synthesis of Glu$_2$-Asp$_2$-Ile-Hydrocodone
Glu$_2$-Asp$_2$-Ile-Hydrocodone was prepared by a similar method to Example 50 except the amino acid starting material was Boc-Glu(OtBu)-Glu(OtBu)-OSu and the conjugate starting material was Asp$_2$-Ile-Hydrocodone.

Example 62

Lys$_2$-Asp$_2$-Ile-Hydrocodone

Synthesis of Lys$_2$-Asp$_2$-Ile-Hydrocodone
Lys$_2$-Asp$_2$-Ile-Hydrocodone was prepared by a similar method to Example 50 except the amino acid starting material was Boc-Lys(Boc)-Lys(Boc)-OSu and the conjugate starting material was Asp$_2$-Ile-Hydrocodone.

Example 63

Tyr$_2$-Glu$_2$-Ile-Hydrocodone

Synthesis of Tyr$_2$-Glu$_2$-Ile-Hydrocodone
Tyr$_2$-Glu$_2$-Ile-Hydrocodone was prepared by a similar method to Example 50 except the amino acid starting material was Boc-Tyr(tBu)-Tyr(tBu)-OSu and the conjugate starting material was Glu$_2$-Ile-Hydrocodone.

Example 64

Asp$_4$-Ile-Hydrocodone

Synthesis of Asp$_4$-Ile-Hydrocodone
Asp$_4$-Ile-Hydrocodone was prepared by a similar method to Example 50 except the amino acid starting material was Boc-Asp(OtBu)-Asp(OtBu)-OSu and the conjugate starting material was Asp$_2$-Ile-Hydrocodone.

Example 65

Glu$_2$-Phe$_2$-Ile-Hydrocodone

Synthesis of Glu$_2$-Phe$_2$-Ile-Hydrocodone
Glu$_2$-Phe$_2$-Ile-Hydrocodone was prepared by a similar method to Example 50 except the amino acid starting material was Boc-Glu(OtBu)-Glu(OtBu)-OSu and the conjugate starting material was Phe$_2$-Ile-Hydrocodone.

Example 66

Lys$_2$-Glu$_2$-Ile-Hydrocodone

Synthesis of Lys$_2$-Glu$_2$-Ile-Hydrocodone
Lys$_2$-Glu$_2$-Ile-Hydrocodone was prepared by a similar method to Example 50 except the amino acid starting material was Boc-Lys(Boc)-Lys(Boc)-OSu and the conjugate starting material was Glu$_2$-Ile-Hydrocodone.

Example 67

Tyr$_2$-Phe-Pro-Ile-Hydrocodone

Synthesis of Tyr$_2$-Phe-Pro-Ile-Hydrocodone
Tyr$_2$-Phe-Pro-Ile-Hydrocodone was prepared by a similar method to Example 50 except the amino acid starting material was Boc-Tyr(tBu)-Tyr(tBu)-OSu and the conjugate starting material was Phe-Pro-Ile-Hydrocodone.
YYFFI-HC

Example 68

Tyr-Tyr-Phe-Phe-Ile-(6-O)-Hydrocodone

Preparation of Tyr-Tyr-Phe-Phe-Ile-(6-O)-hydrocodone
Hydrocodone bitartrate (48.38 g) was stirred in 500 ml 1N NaOH for 5 minutes. Suspension was split into 2 batches and extracted using CHCl$_3$ (2×250 ml), organics were dried using MgSO$_4$ and filtered. Solvent was removed and product was obtained as a white powder (29.05 g).
To a solution of hydrocodone freebase (7.12 g) in tetrahydrofuran (THF) (300 ml) was added LiN(TMS)$_2$ in THF (1M, 36.0 ml) via syringe. The solution was stirred at ambient temperatures for 10 minutes then Boc-Ile-OSu (11.7 g) was added. The resulting reaction mixture was stirred at ambient temperatures for 3 hours. Reaction was neutralized to pH 7 with 1M HCl and stirred for 10 minutes. Solvent was removed. Crude material was taken up in diethyl ether (100 ml), washed with sat. NaHCO$_3$ (3×100 ml), dried over MgSO$_4$, filtered, and solvent was removed. Solid was collected as a yellow powder (11.1 g).
To the Boc-Ile-Hydrocodone (11.1 g) was added 125 ml of 4N HCl in dioxane. The resulting mixture was stirred at ambient temperatures for 1 hour. Solvent was removed and final product dried under vacuum. Solid was collected as a slightly yellow powder (10.43 g).
To a suspension of Boc-Phe-Phe-OH (10.0 g) and N-hydroxysuccinimide (NHS) (3.06 g) in acetone (300 ml) was added dicyclohexylcarbodiimide (DCC) (4.99 g). The solution was stirred at ambient temperatures under argon for 18 hrs. Solid dicyclohexylurea (DCU) was filtered away and washed with acetone. Solvent was removed from filtrate. Crude material was recrystallized using a system of acetone and hexane. Solvent was filtered off and the solid was collected as a white powder (12.2 g).
To a solution of Ile-HC.2HCl (6.00 g) in N,N-dimethylformamide (DMF) (150 ml) was added 4-methyl morpholine (NMM) (6.79 ml) followed by Boc-Phe-Phe-OSu (6.93 g). The solution was stirred at ambient temperatures for 18 hours. Solvent was reduced to approximately ¼ total volume, added to sat. NaHCO$_3$ (~100 ml), and stirred for 30 minutes. The precipitate was filtered and washed thoroughly with water. Solid material was dried in vacuum, dissolved in a small amount of ethyl acetate, and filtered. Product was obtained as a slightly yellow powder (8.39 g).

To Boc-Phe-Phe-Ile-HC (2.99 g) was added 50 ml 4N HCl in dioxane. The resulting suspension was stirred at ambient temperatures for 1 hour. Solvent was removed and product was dried. Product was obtained as a yellow solid (2.60 g).

To a solution of Boc-Tyr(tBu)-OH (1.00 g) in 15 ml DMF was added O—(N-succinimidyl)-1,1,3,3-tetramethyluronium tetrafluoroborate (TSTU) (0.892 g) and NMM (0.65 ml). After 10 minutes of activation, H-Tyr(tBu)-OH (0.844 g) in 40 ml DMF:dioxane:water (2:2:1) was added. The resulting suspension was stirred at ambient temperature for 4 hours. After this time, water (15 ml) was added and the resulting solution was stirred at ambient temperature for 30 minutes. The solvent volume was reduced to ¼ and extracted with ethyl acetate (250 ml), washed with 5% acetic acid in water (2×150 ml), water (3×150 ml), and brine (150 ml). The organic layer was dried over $MgSO_4$, filtered, and solvent removed. Crude product was purified using recrystallization with IPAC/hexane solvent system. Final product was isolated as a white solid (1.025 g).

To a suspension of Boc-Tyr(tBu)-Tyr(OtBu)-OH (7.32 g) and NHS (1.54 g) in acetone (150 ml) was added DCC (2.51 g). The solution was stirred at ambient temperatures under argon for 18 hrs. Solid DCU was filtered away and washed with acetone. Solvent was removed from filtrate. Crude material was washed with warm hexane. Solid was collected as a white powder (6.65 g).

To a solution of Phe-Phe-Ile-HC.2HCl (2.63 g) in DMF (100 ml) was added NMM (3.70 ml) followed by Boc-Tyr (tBu)-Tyr(tBu)-OSu (4.41 g). The solution was stirred at ambient temperatures for 18 hours. Solvent was reduced to approximately ¼ total volume, added to sat. $NaHCO_3$ (~100 ml), and stirred for 30 minutes. The precipitate was filtered and washed thoroughly with water. Solid material was dried in vacuum and purified by reverse phase HPLC (2.77 g). Product was deprotected using 4N HCl in dioxane (~50 ml).

To a solution of Phe-Phe-Ile-HC.2HCl (5.00 g) in DMF (250 ml) was added NMM (3.52 ml) followed by Boc-Tyr (tBu)-Tyr(tBu)-OSu (4.61 g). The solution was stirred at ambient temperatures for 6 hours. Solvent was reduced to approximately ¼ total volume, added to sat. $NaHCO_3$ (~500 ml), and stirred for 30 minutes. The precipitate was filtered and washed thoroughly with water. Solid material was dried in vacuum overnight, dissolved in methanol, and any remaining solid material was filtered. The solvent was evaporated from the filtrate and the product was recrystallized using ethanol (~60 ml). The precipitate was filtered and dried in vacuum overnight. Product was collected as a pale brown powder (4.57 g).

Boc-Tyr(OtBu)-Tyr(OtBu)-Phe-Phe-Ile-HC (3.53 g) was deprotected using 4N HCl in dioxane (~100 ml). This material was stirred at ambient temperatures for ~1 hour. The solvent was evaporated and the product was collected as a slightly yellow powder (3.64 g).

FIGS. 9 through 34 demonstrate plasma levels measured by ELISA of various compounds described in Examples 35 through 68.

Glycopeptides

Figure 35:
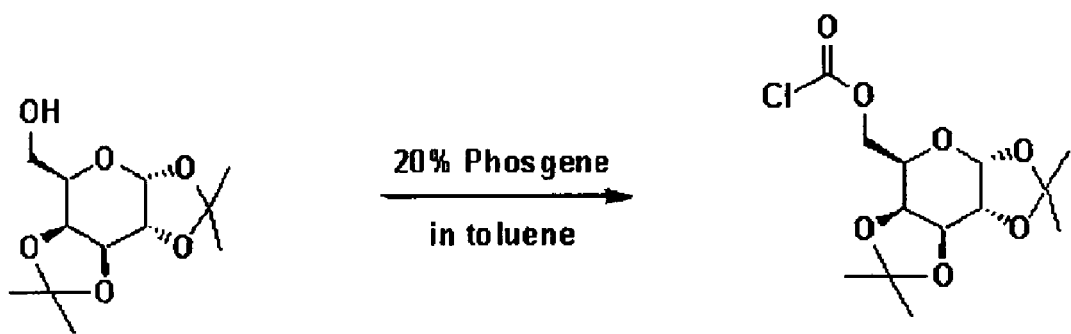
FIG. 35. illustrates preparation of 1,2:3,4-di-O-isopropylidene-D-galactopyranose.

FIG. 35 illustrates preparation of 1,2:3,4-di-O-isopropylidene-D-galactopyranose.

| Reagents | MW | Weight | mmoles | Molar Equivalents |
|---|---|---|---|---|
| 1,2:3,4-di-O-isopropylidene-D-galactopyranose | 260 | 1.00 g | 3.85 | 1 |
| 20% Phosgene in toluene | — | 20 ml | — | — |

Chloroformate of
1,2:3,4-di-O-isopropylidene-D-galactopyranose

To a stirring solution of 20% phosgene in toluene under an inert atmosphere was added 1,2:3,4-di-O-isopropylidene-D-galactopyranose via syringe. The resulting clear, colorless solution was stirred at ambient temperature for 30 minutes. After stirring, Ar(g) was bubbled through the solution for approximately 20 minutes to remove any excess phosgene. Solvent was then removed and product dried under vacuum for 18 hours. Product was used without further purification or characterization.

Example 69

Galactose-CO-Leu-Hydrocodone

Synthesis of Galactose-CO-Leu-Hydrocodone

To the chloroformate of galactose (1.5 eq) in dimethylformamide (DMF) (2 ml/mmol) was added Leu-Hydrocodone (1 eq) and 4-methylmorpholine (NMM) (6 eq). The reaction was stirred at ambient temperatures for 18 hours. Reaction was quenched by the addition of water, solvents were removed and crude product was isolated by purification with reverse-phase HPLC.

Product was deprotected using 1:1 1M HCl:THF (1 ml/0.1 mmol) in 3 hours. Product was re-purified by reverse-phase HPLC.

Example 70

Galactose-CO-Pro2-Ile-Hydrocodone

Synthesis of Galactose-CO-$Pro_2$-Ile-Hydrocodone

Galactose-CO-$Pro_2$-Ile-Hydrocodone was prepared in a manner similar to Example 69 except $Pro_2$-Ile-Hydrocodone was used as the conjugated starting material.

Example 71

Galactose-CO-Pro2-Leu-Hydrocodone

Synthesis of Galactose-CO-$Pro_2$-Leu-Hydrocodone

Galactose-CO-$Pro_2$-Leu-Hydrocodone was prepared in a manner similar to Example 69 $Pro_2$-Leu-Hydrocodone was used as the conjugated starting material.

Figure 36:
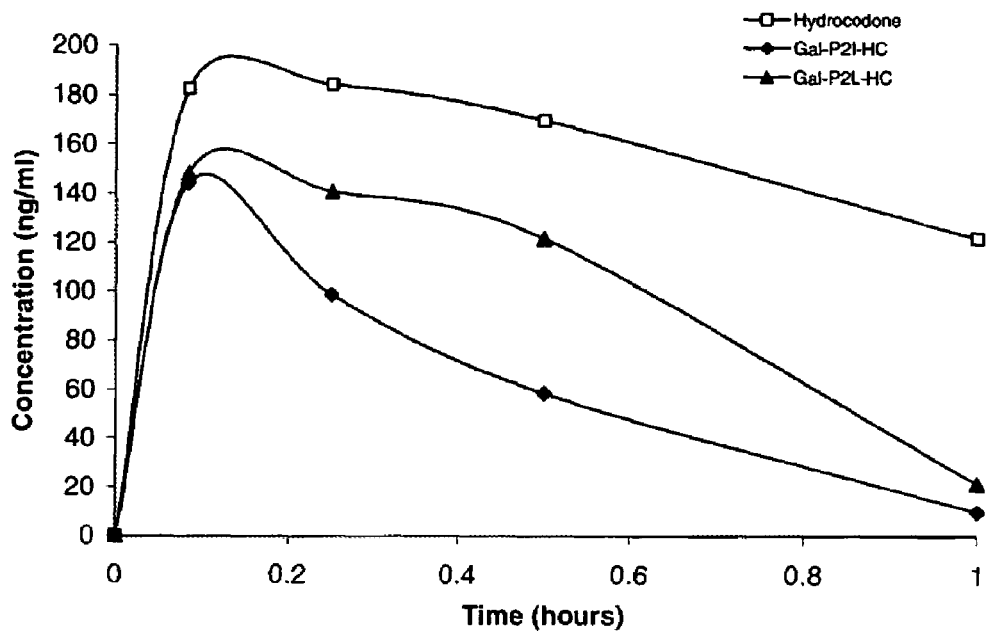
FIG. 36. Oral bioavailability of abuse-resistant hydrocodone glyco-peptide conjugates, measured as free hydrocodone.

FIG. 36 illustrates oral bioavailability of abuse-resistant hydrocodone glyco-peptide conjugates, measured as free hydrocodone.

Example 72

Gulonic Acid-Ile-Hydrocodone

Synthesis of Gulonic Acid-Ile-Hydrocodone

Gulonic acid-Ile-Hydrocodone was prepared in a manner similar to Example 69 except Ile-Hydrocodone was used as the conjugated starting material and Gulonic acid-OSu was used as the carbohydrate starting material.

Figure 37:
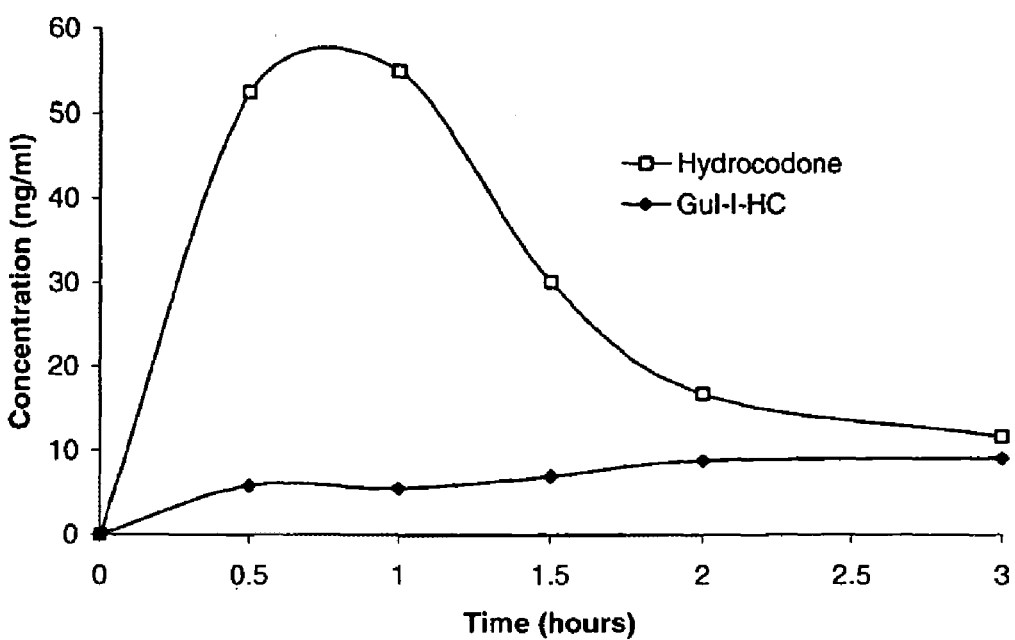
FIG. 37. Oral bioavailability of an abuse-resistant hydrocodone amino acid-carbohydrate conjugate, measured as free hydrocodone.
Figure 40:
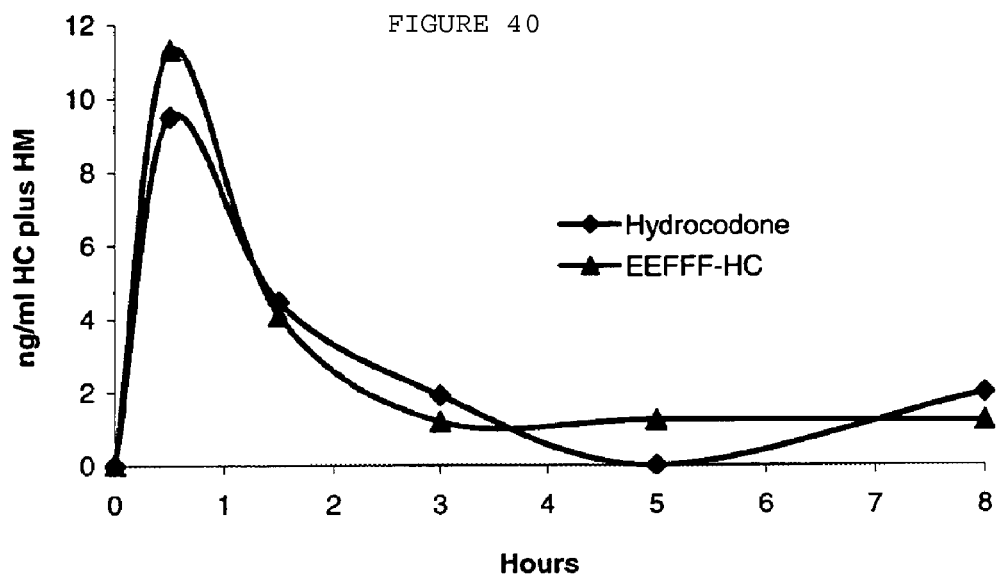
FIG. 40. Oral bioavailability in rats for hydrocodone vs. EEFFF-HC at a dose (1 mg/kg) approximating a therapeutic human dose equivalent measured as free hydrocodone.
Figure 41:
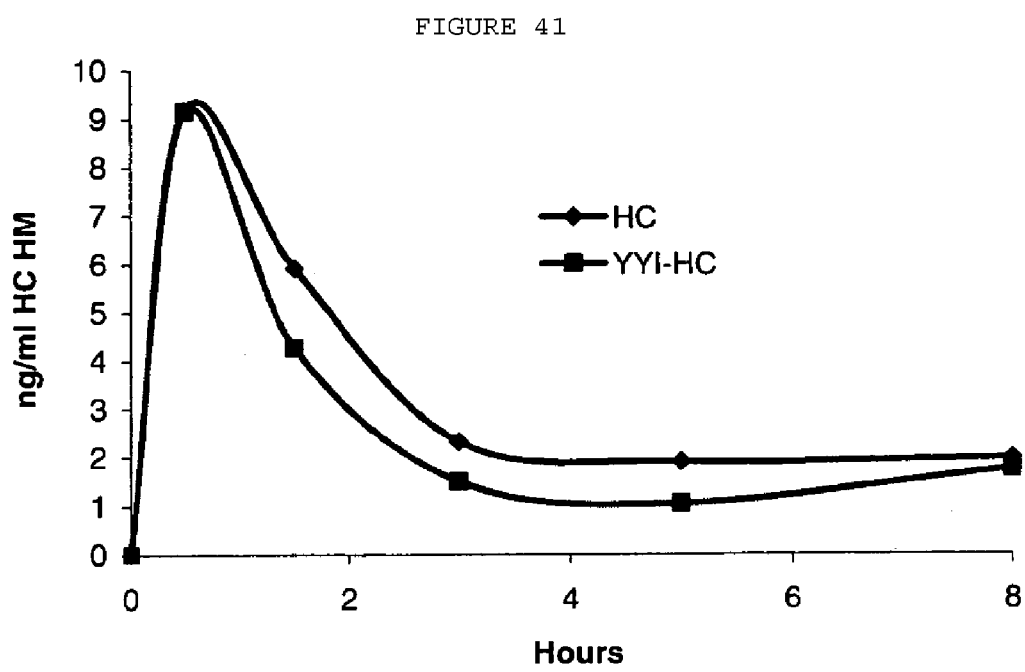
FIG. 41. Oral bioavailability in rats for hydrocodone vs. YYI-HC at a dose (1 mg/kg) approximating a therapeutic human dose equivalent measured as free hydrocodone.
Figure 42:
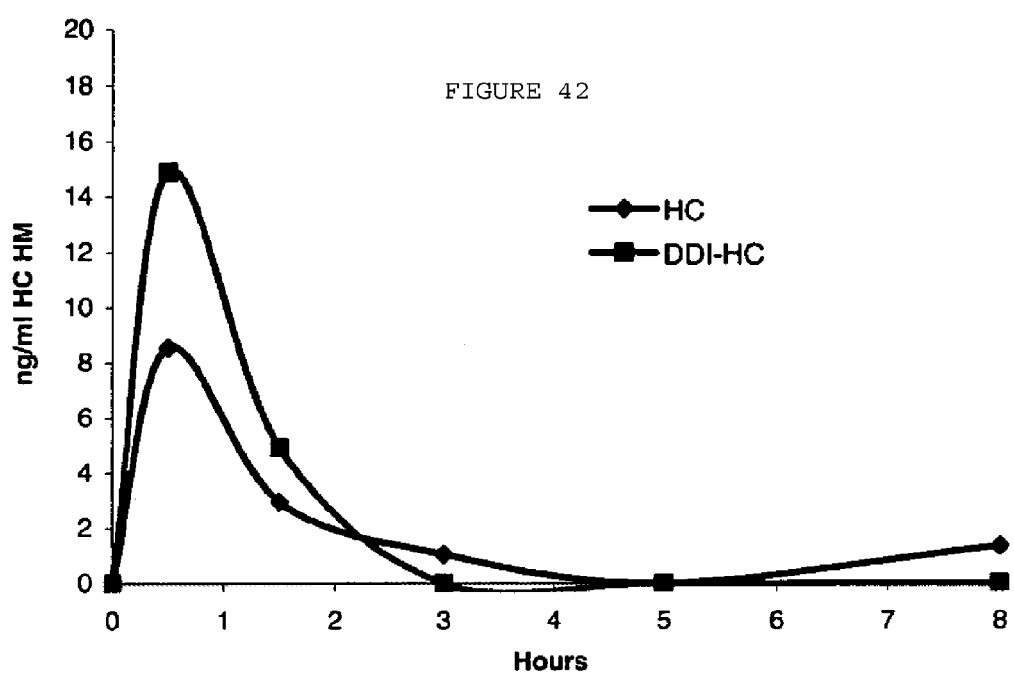
FIG. 42. Oral bioavailability in rats for hydrocodone vs. DDI-HC at a dose (1 mg/kg) approximating a therapeutic human dose equivalent measured as free hydrocodone.
Figure 43:
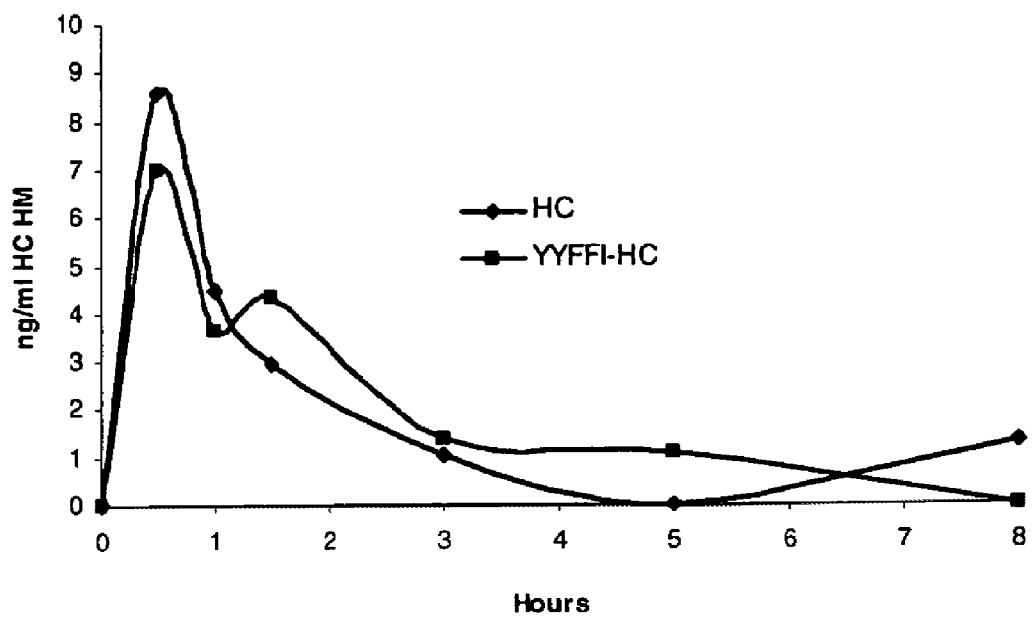
FIG. 43. Oral bioavailability in rats for hydrocodone vs. YYFFI-HC at a dose (1 mg/kg) approximating a therapeutic human dose equivalent measured as free hydrocodone.
Figure 44:
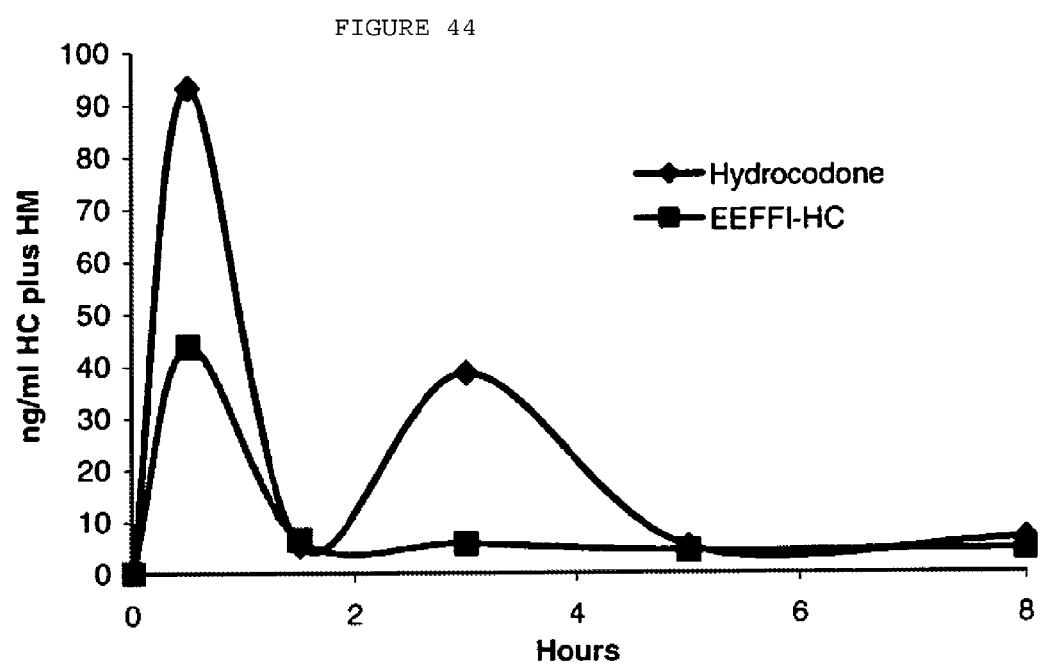
FIG. 44. Oral bioavailability in rats for hydrocodone vs. EEFFI-HC at a dose (5 mg/kg) approaching a human overdose equivalent measured as free hydrocodone.
Figure 45:
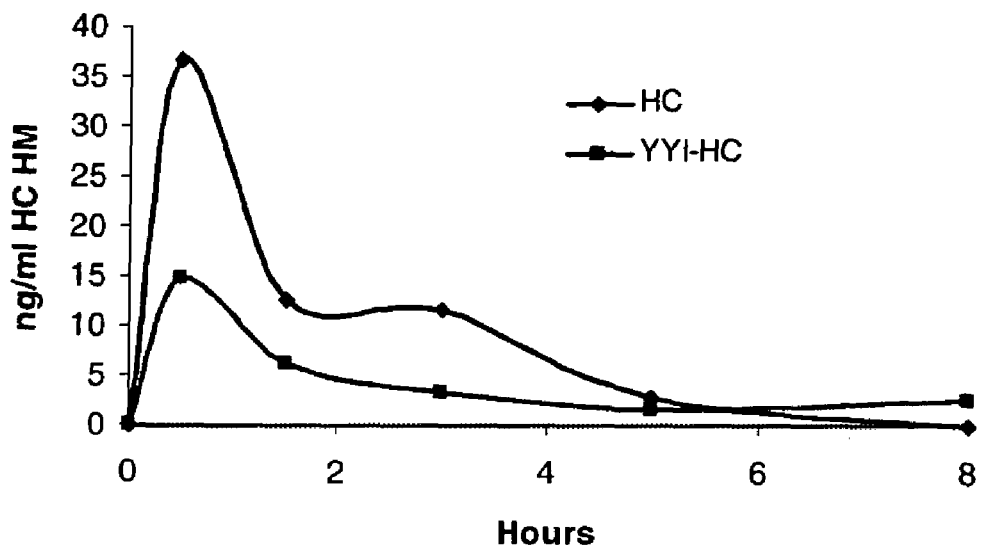
FIG. 45. Oral bioavailability in rats for hydrocodone vs. YYI-HC at a dose (5 mg/kg) approaching a human overdose equivalent measured as free hydrocodone.
Figure 46:
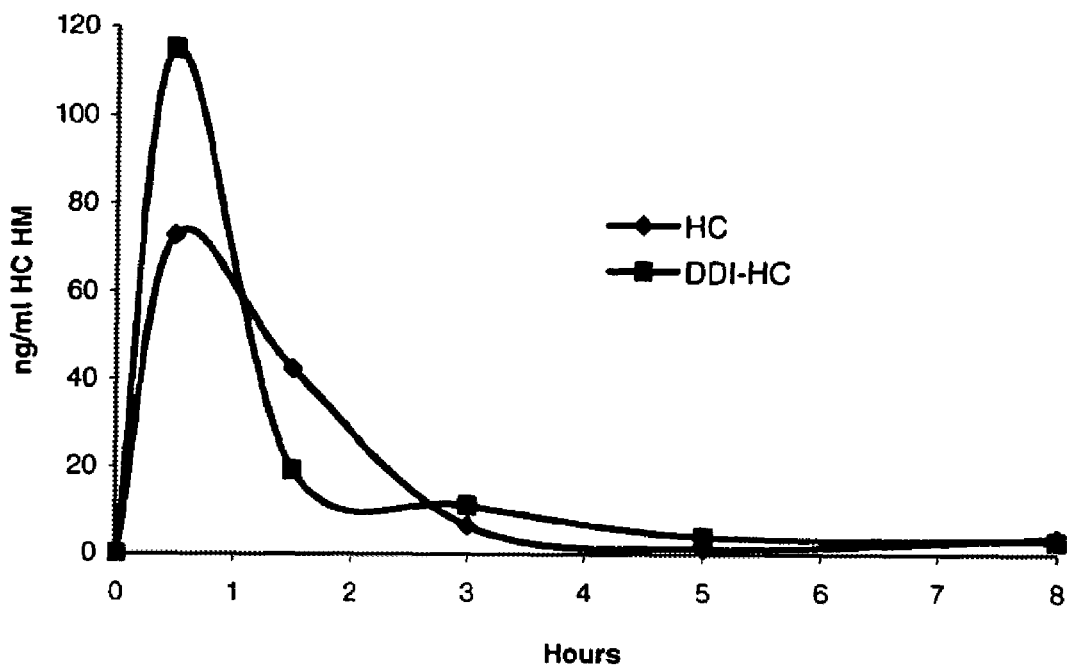
FIG. 46. Oral bioavailability in rats for hydrocodone vs. DDI-HC at a dose (5 mg/kg) approaching a human overdose equivalent measured as free hydrocodone.
Figure 47:
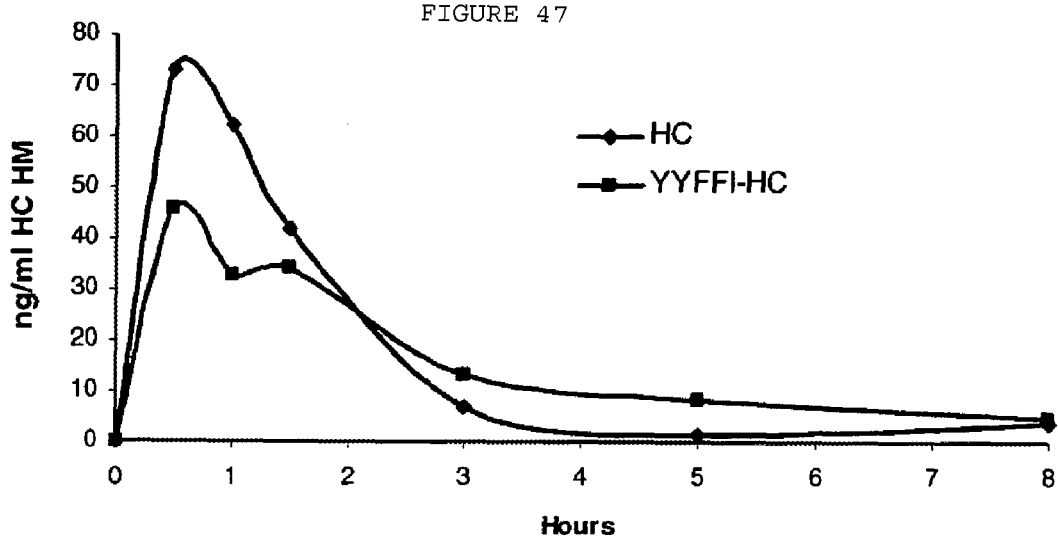
FIG. 47. Oral bioavailability in rats for hydrocodone vs. YYFFI-HC at a dose (5 mg/kg) approaching a human overdose equivalent measured as free hydrocodone.
Figure 48:
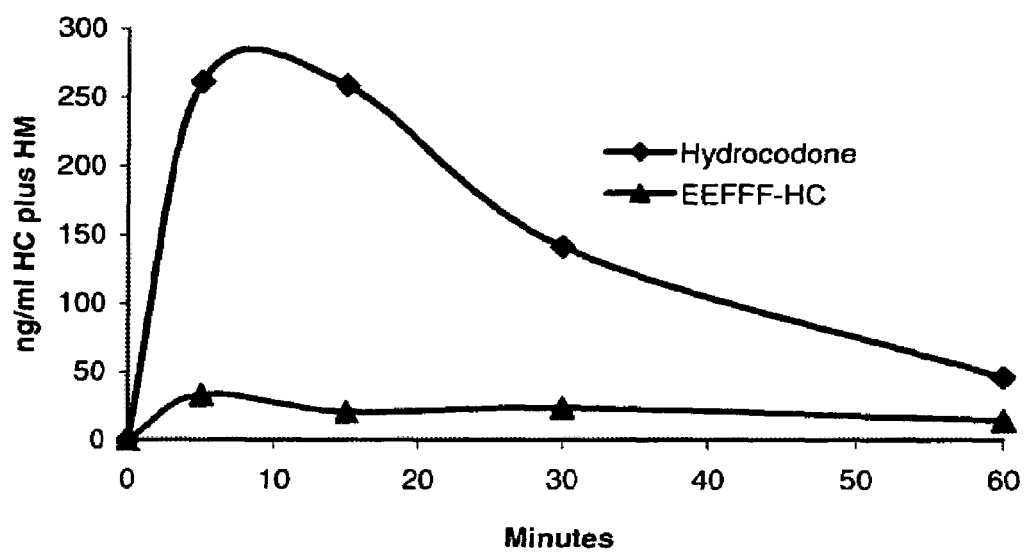
FIG. 48. Decrease in bioavailability of EEFFF-HC as compared to hydrocodone by the intranasal route of administration measured as free hydrocodone.
Figure 49:
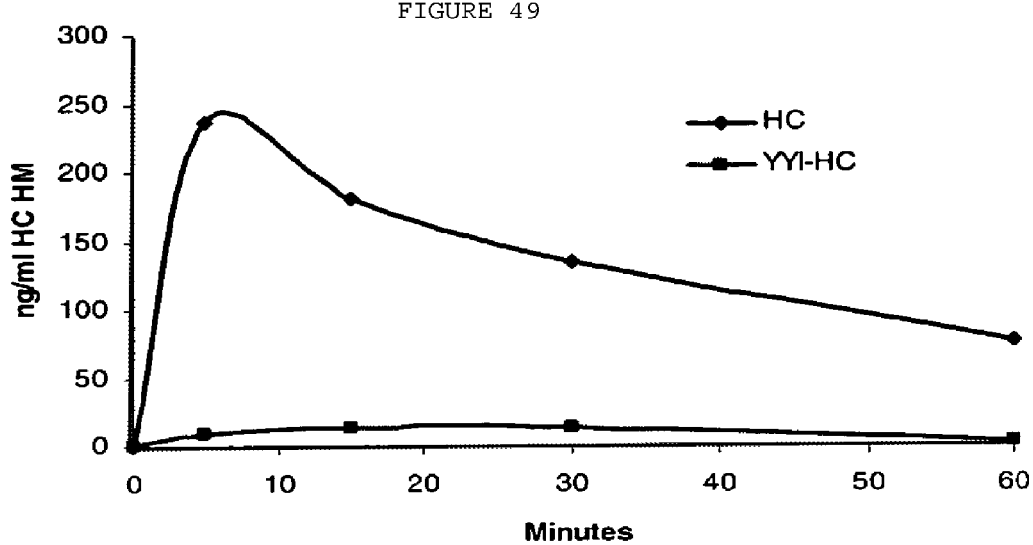
FIG. 49. Decrease in bioavailability of YYI-HC as compared to hydrocodone by the intranasal route of administration measured as free hydrocodone.
Figure 50:
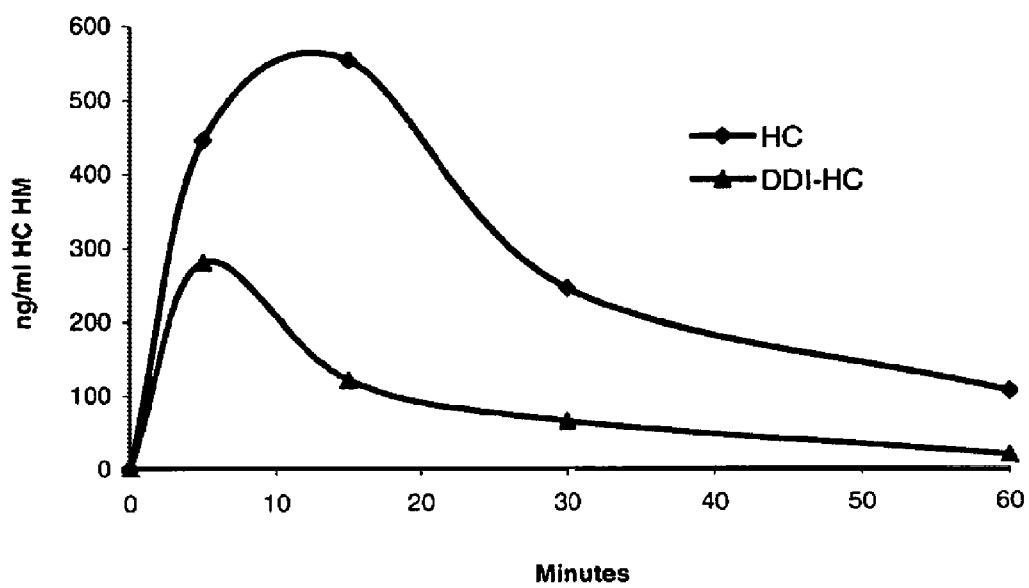
FIG. 50. Decrease in bioavailability of DDI-HC as compared to hydrocodone by the intranasal route of administration measured as free hydrocodone.
Figure 51:
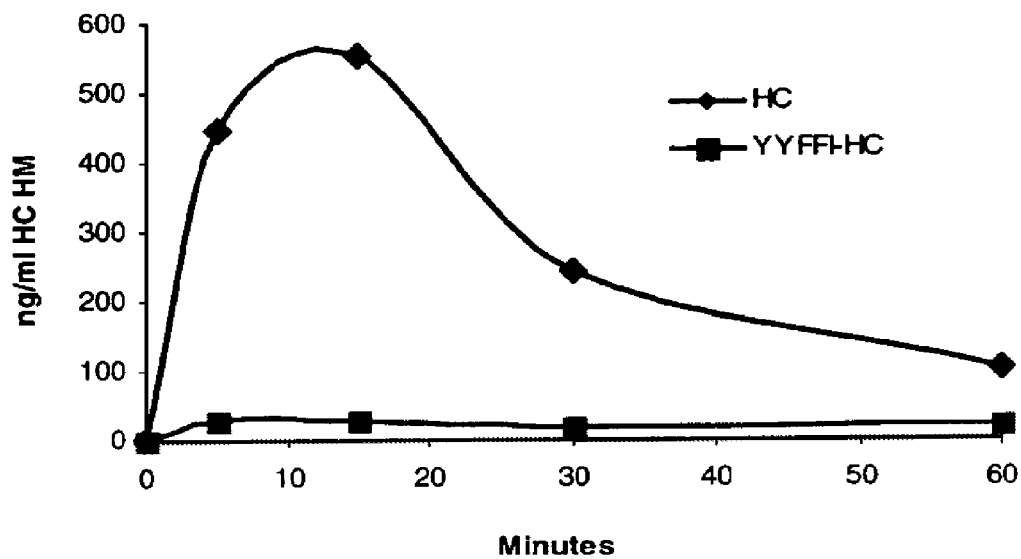
FIG. 51. Decrease in bioavailability of YYFFI-HC as compared to hydrocodone by the intranasal route of administration measured as free hydrocodone.
Figure 52:
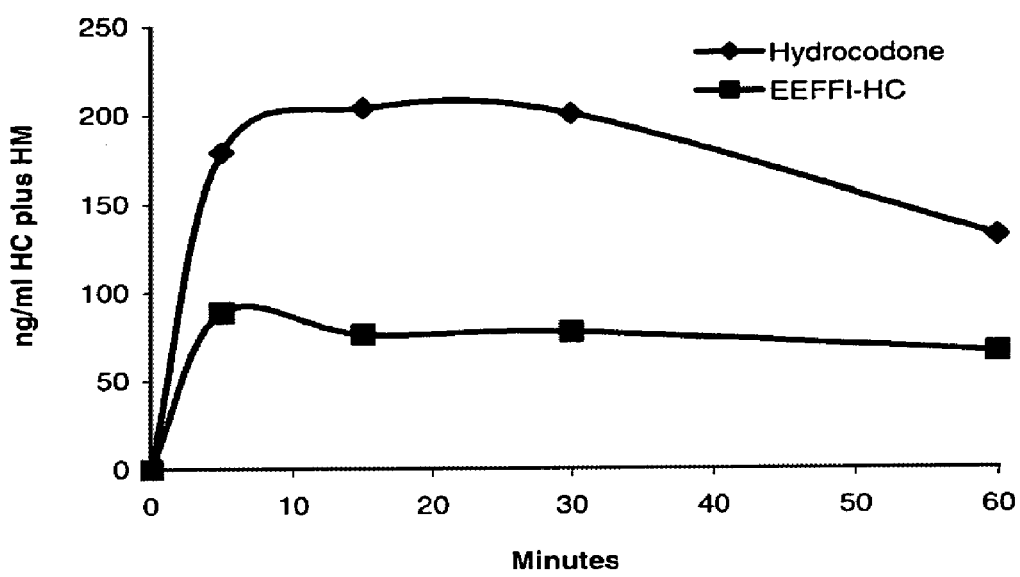
FIG. 52. Decrease in bioavailability of EEFFI-HC as compared to hydrocodone by the intravenous route of administration measured as free hydrocodone.
Figure 53:
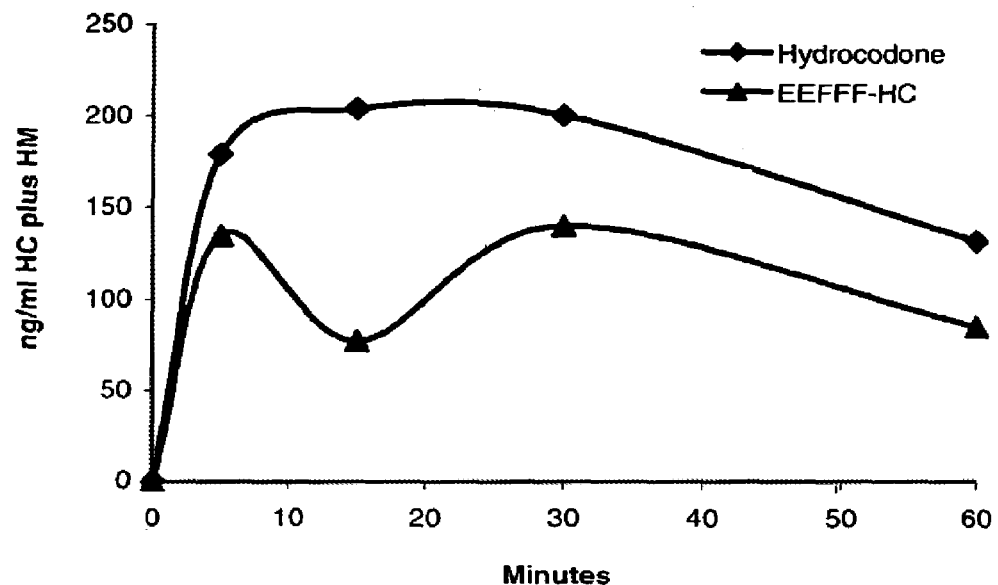
FIG. 53. Decrease in bioavailability of EEFFF-HC as compared to hydrocodone by the intravenous route of administration measured as free hydrocodone.
Figure 54:
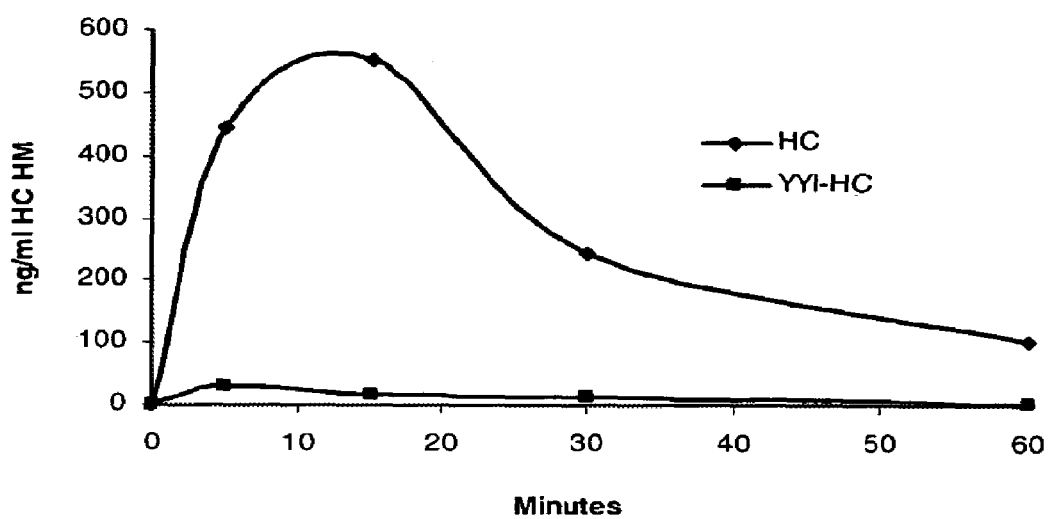
FIG. 54. Decrease in bioavailability of YYI-HC as compared to hydrocodone by the intravenous route of administration measured as free hydrocodone.
Figure 55:
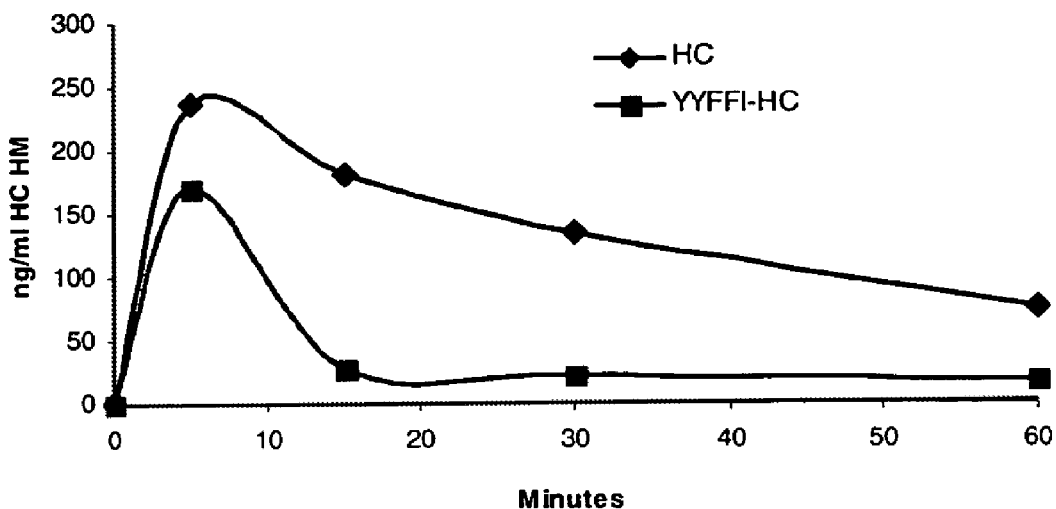
FIG. 55. Decrease in bioavailability of YYFFI-HC as compared to hydrocodone by the intravenous route of administration measured as free hydrocodone.
Figure 56:
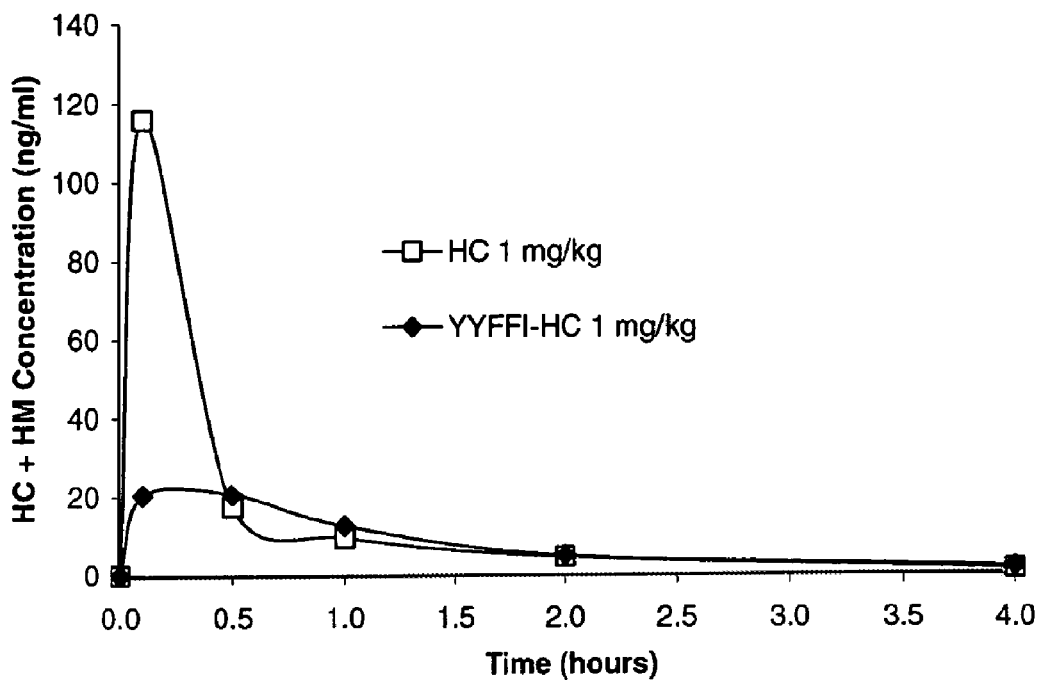
FIG. 56. Oral bioavailability of hydrocodone plus hydromorphone (concentration vs. time) following administration of hydrocodone bitratrate or YYFFI-HC at 1 mg/kg (equimolar doses with equivalent content of hydrocodone base) in rats, measured as free hydrocodone.
Figure 57:
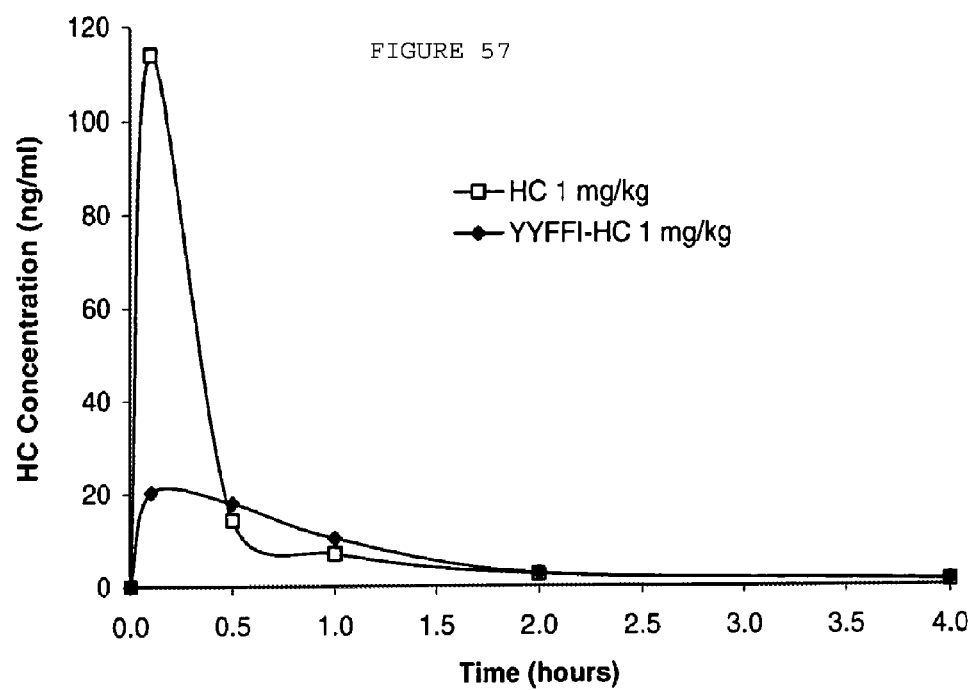
FIG. 57. Oral bioavailability of hydrocodone (concentration vs. time) following administration of hydrocodone bitratrate or YYFFI-HC at 1 mg/kg (equimolar doses with equivalent content of hydrocodone base) in rats, measured as free hydrocodone.
Figure 58:
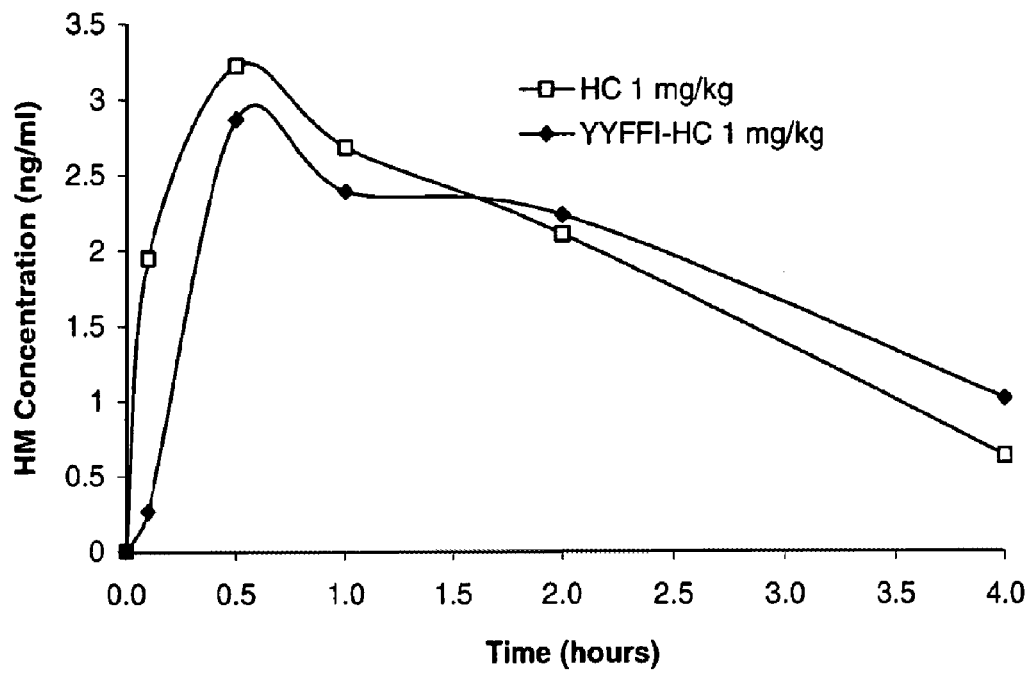
FIG. 58. Oral bioavailability of hydromorphone (concentration vs. time) following administration of hydrocodone bitratrate or YYFFI-HC at 1 mg/kg (equimolar doses with equivalent content of hydrocodone base) in rats, measured as free hydrocodone.
Figure 59:
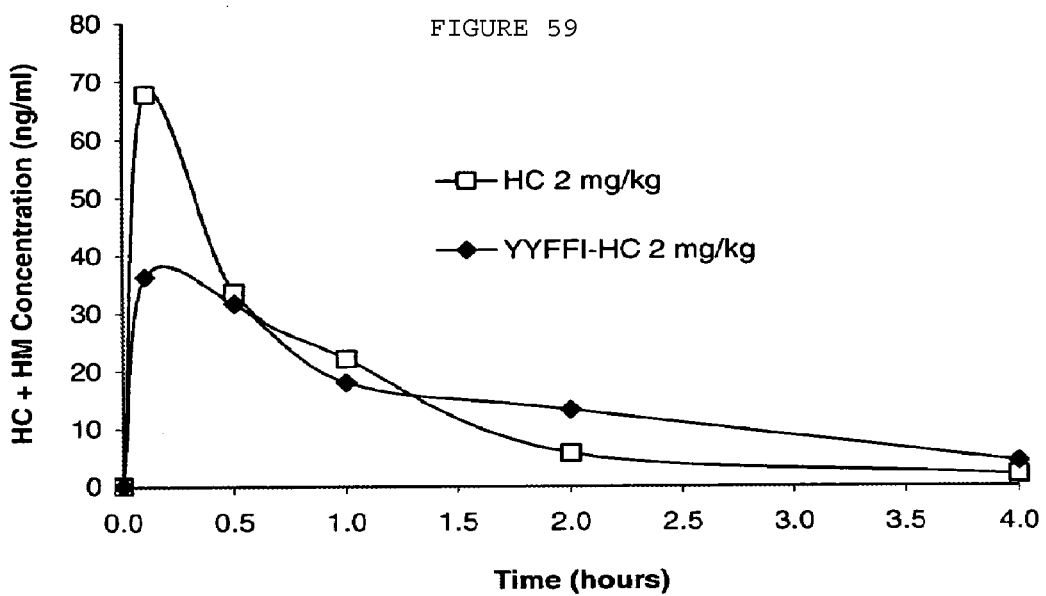
FIG. 59. Oral bioavailability of hydrocodone plus hydromorphone (concentration vs. time) following administration of hydrocodone bitratrate or YYFFI-HC at 2 mg/kg (equimolar doses with equivalent content of hydrocodone base) in rats, measured as free hydrocodone.
Figure 60:
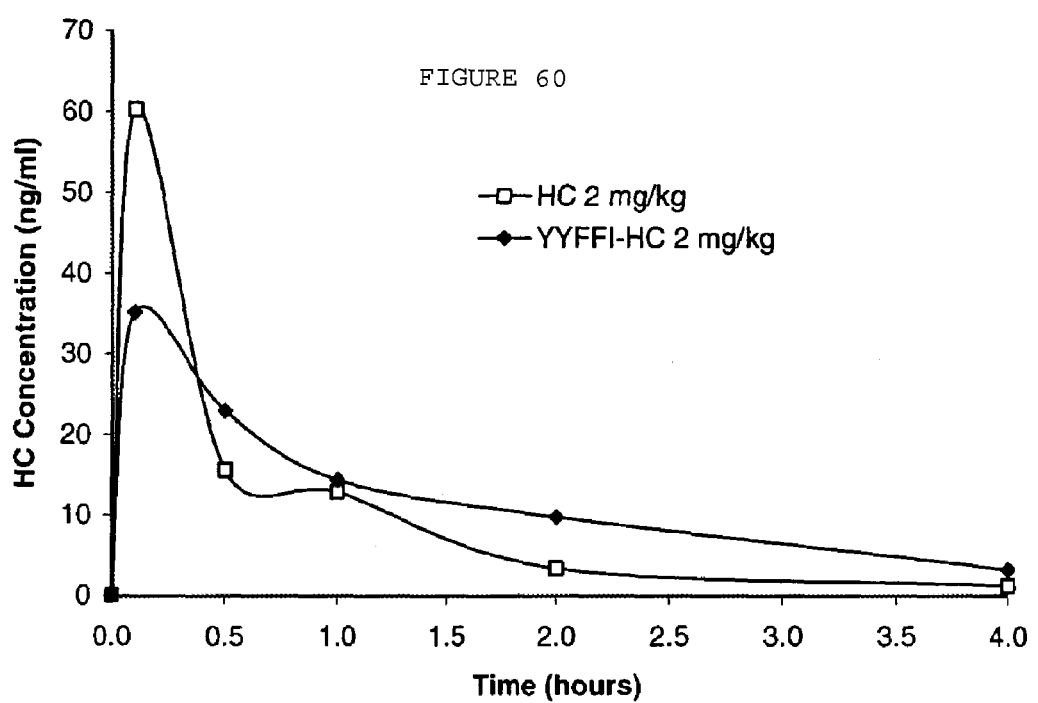
FIG. 60. Oral bioavailability of hydrocodone (concentration vs. time) following administration of hydrocodone bitratrate or YYFFI-HC at 2 mg/kg (equimolar doses with equivalent content of hydrocodone base) in rats, measured as free hydrocodone.
Figure 61:
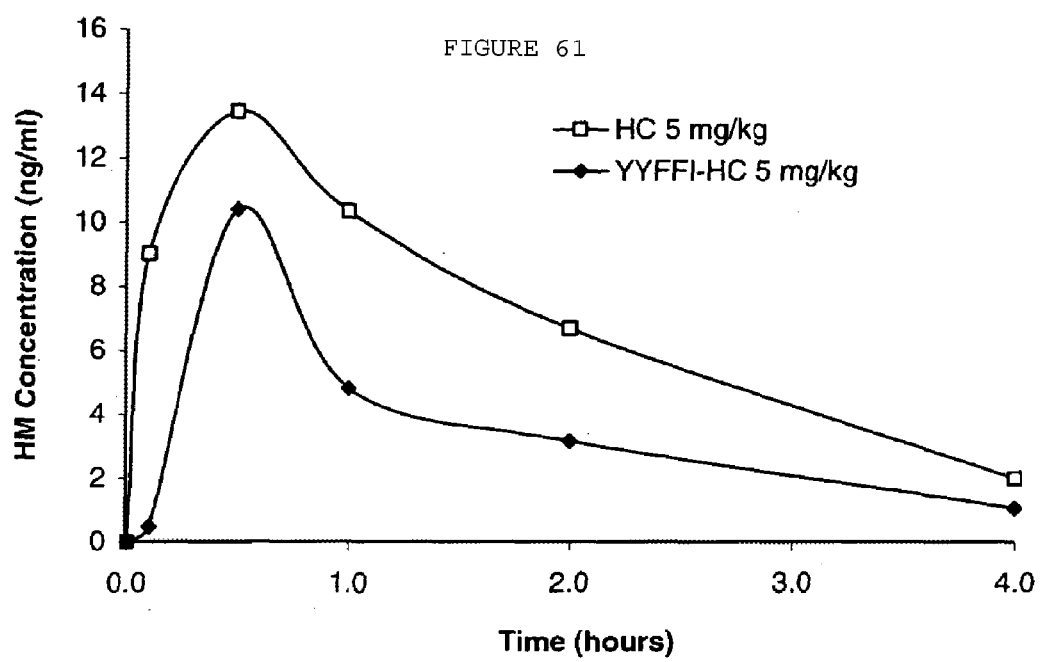
FIG. 61. Oral bioavailability of hydromorphone (concentration vs. time) following administration of hydrocodone bitratrate or YYFFI-HC at 2 mg/kg (equimolar doses with equivalent content of hydrocodone base) in rats, measured as free hydrocodone.
Figure 62:
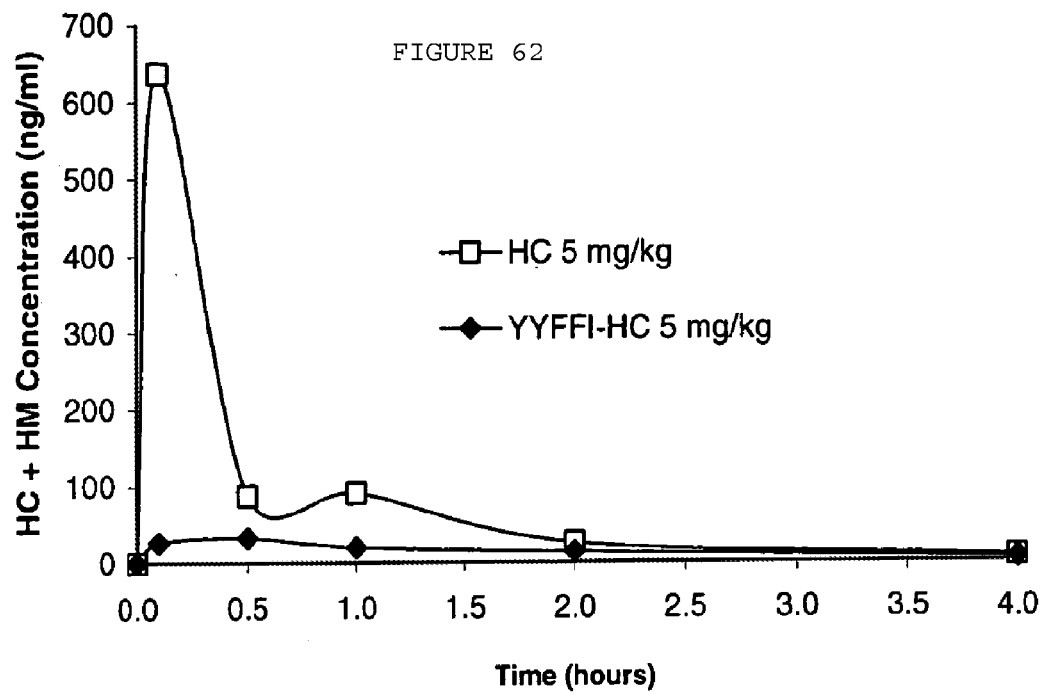
FIG. 62. Oral bioavailability of hydrocodone plus hydromorphone (concentration vs. time) following administration of hydrocodone bitratrate or YYFFI-HC at 5 mg/kg (equimolar doses with equivalent content of hydrocodone base) in rats, measured as free hydrocodone.
Figure 63:
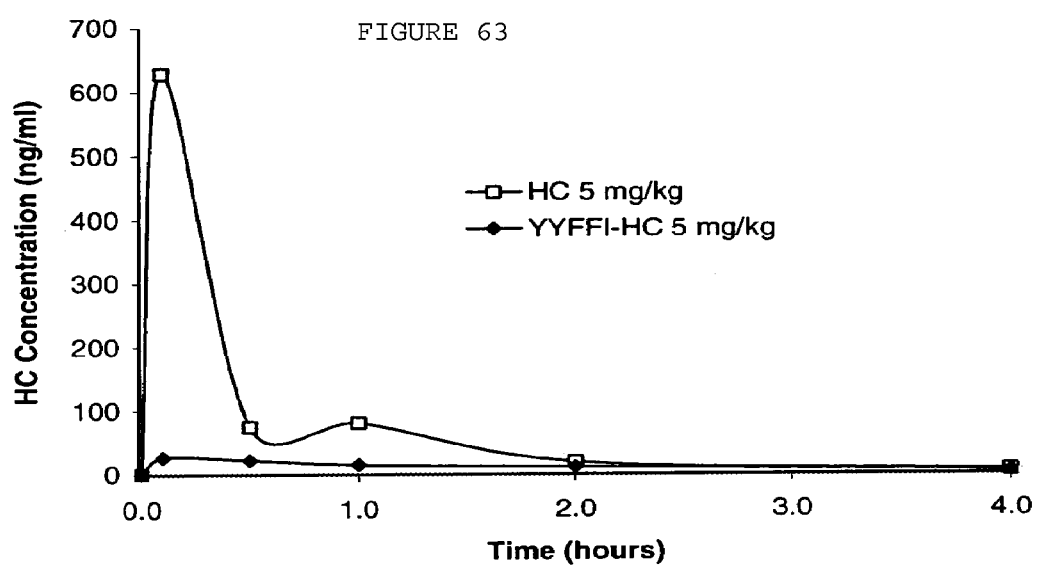
FIG. 63. Oral bioavailability of hydrocodone (concentration vs. time) following administration of hydrocodone bitratrate or YYFFI-HC at 5 mg/kg (equimolar doses with equivalent content of hydrocodone base) in rats, measured as free hydrocodone.
Figure 66:
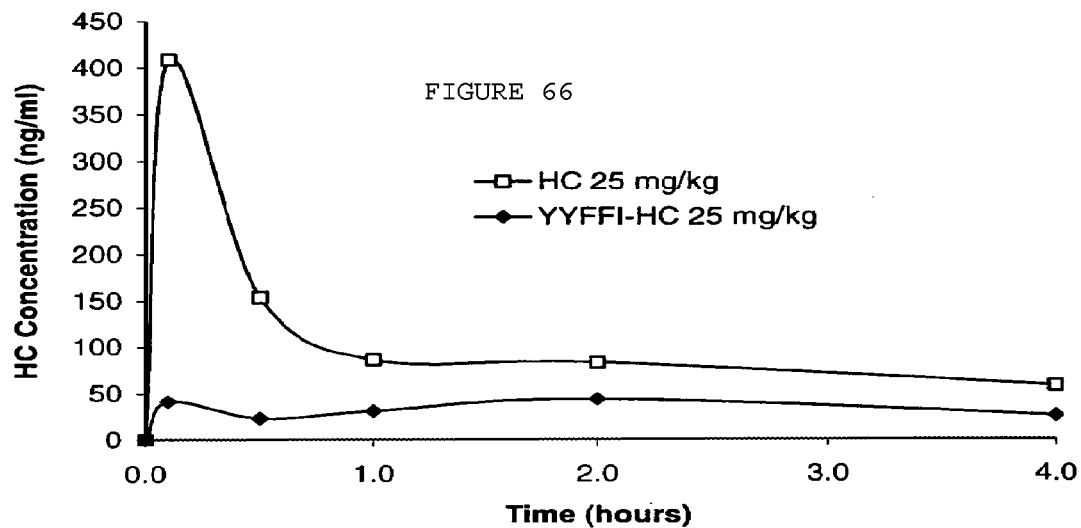
FIG. 66. Oral bioavailability of hydrocodone (concentration vs. time) following administration of hydrocodone bitratrate or YYFFI-HC at 25 mg/kg (equimolar doses with equivalent content of hydrocodone base) in rats, measured as free hydrocodone.
Figure 67:
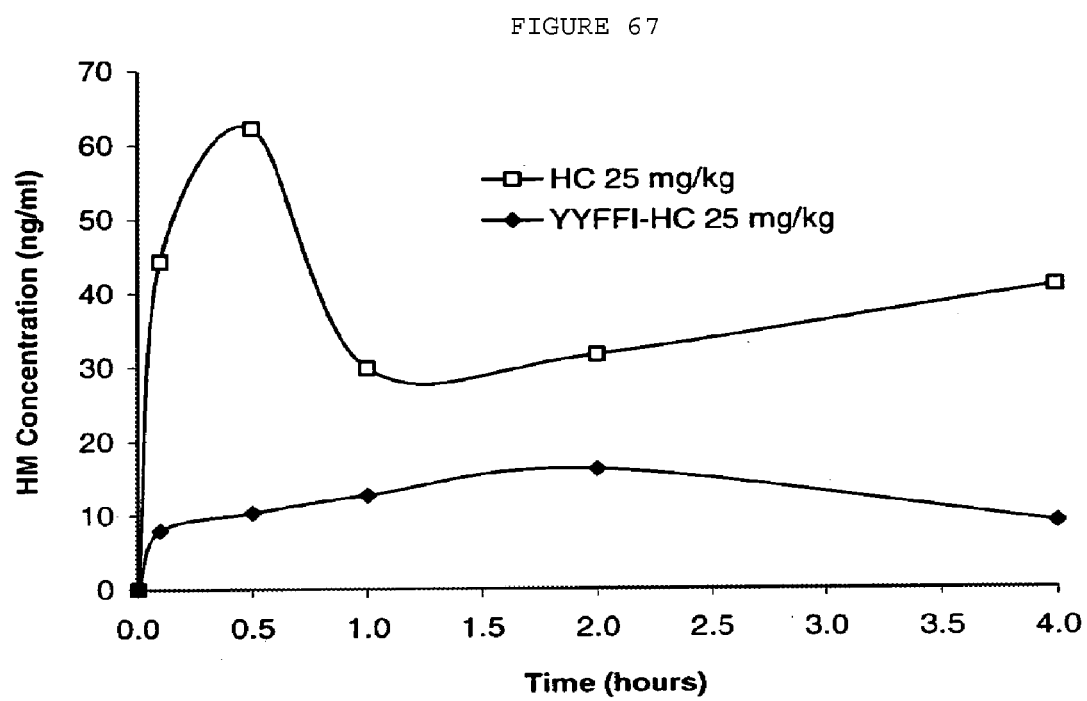
FIG. 67. Oral bioavailability of hydromorphone (concentration vs. time) following administration of hydrocodone bitratrate or YYFFI-HC at 25 mg/kg (equimolar doses with equivalent content of hydrocodone base) in rats, measured as free hydrocodone.
Figure 68:
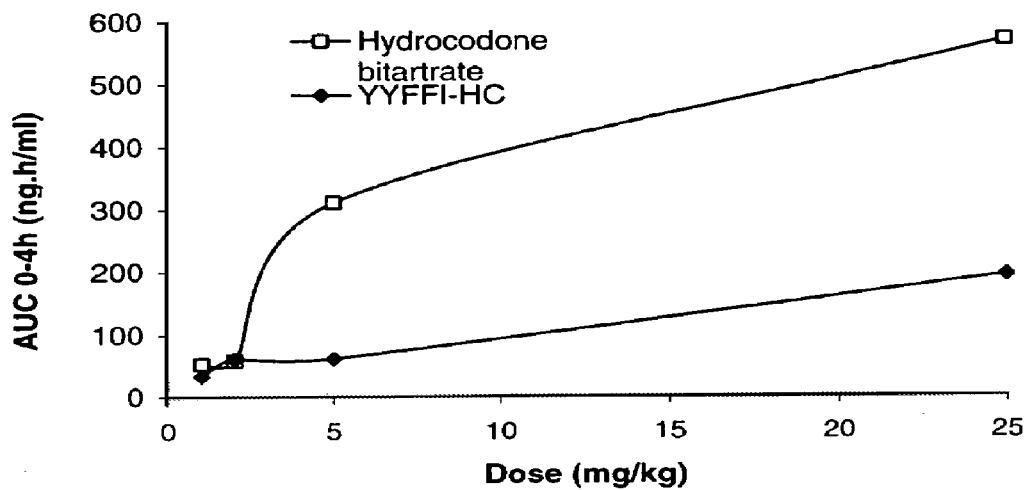
FIG. 68. Oral bioavailability ($AUC_{0-4h}$) of hydrocodone plus hydromorphone (concentration vs. dose) in proportion to dose following administration of hydrocodone bitratrate or YYFFI-HC at escalating doses (1, 2, 5, and 25 mg/kg—equimolar doses with equivalent content of hydrocodone base) in rats, measured as free hydrocodone.
Figure 69:
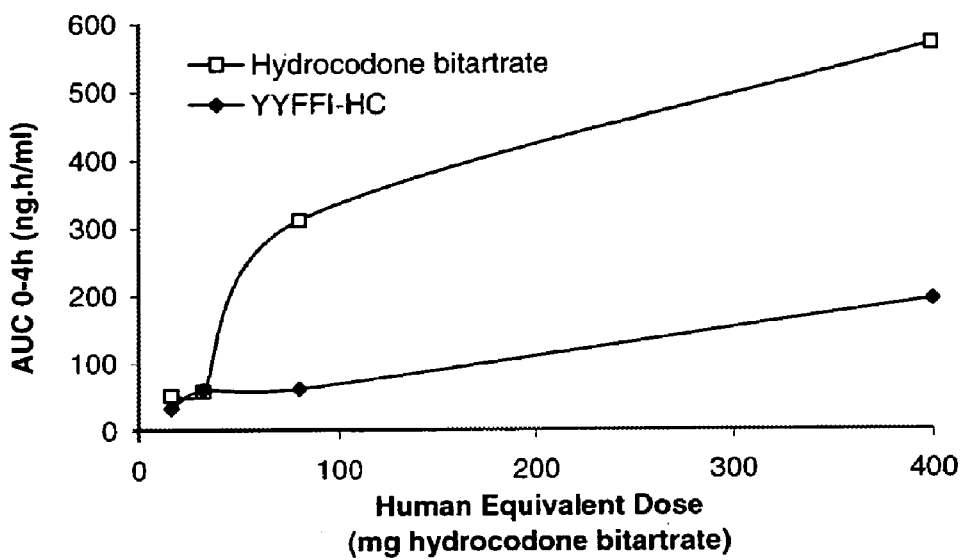
FIG. 69. Oral bioavailability ($AUC_{0-4h}$) of hydrocodone plus hydromorphone in proportion to human equivalent doses (HED) following administration of hydrocodone bitratrate or YYFFI-HC at escalating doses (1, 2, 5, and 25 mg/kg—equimolar doses with equivalent content of hydrocodone base) in rats, measured as free hydrocodone.
Figure 70:
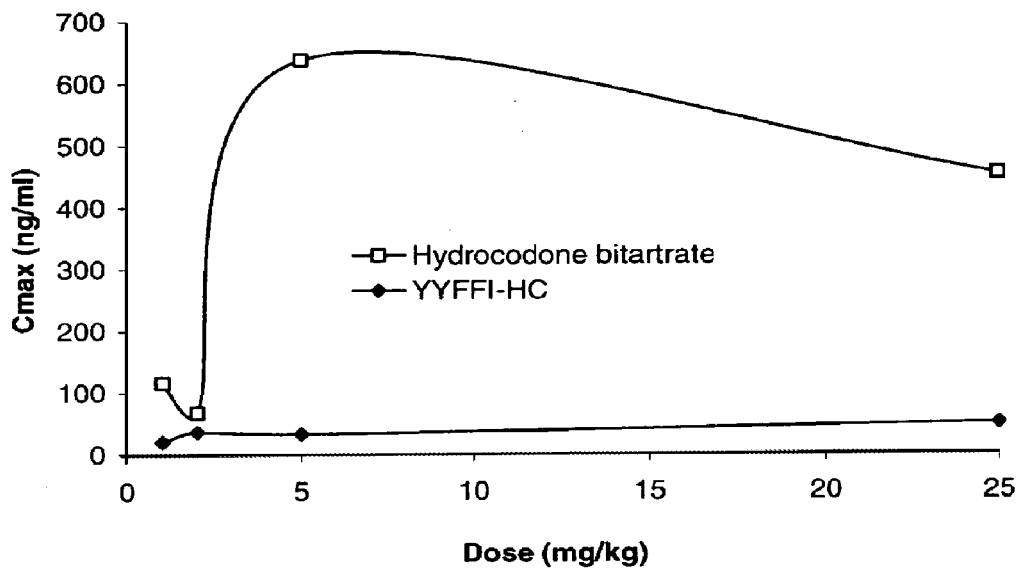
FIG. 70. Oral bioavailability ($C_{max}$) of hydrocodone plus hydromorphone (concentration vs. dose) in proportion to dose following administration of hydrocodone bitratrate or YYFFI-HC at escalating doses (1, 2, 5, and 25 mg/kg—equimolar doses with equivalent content of hydrocodone base) in rats, measured as free hydrocodone.
Figure 71:
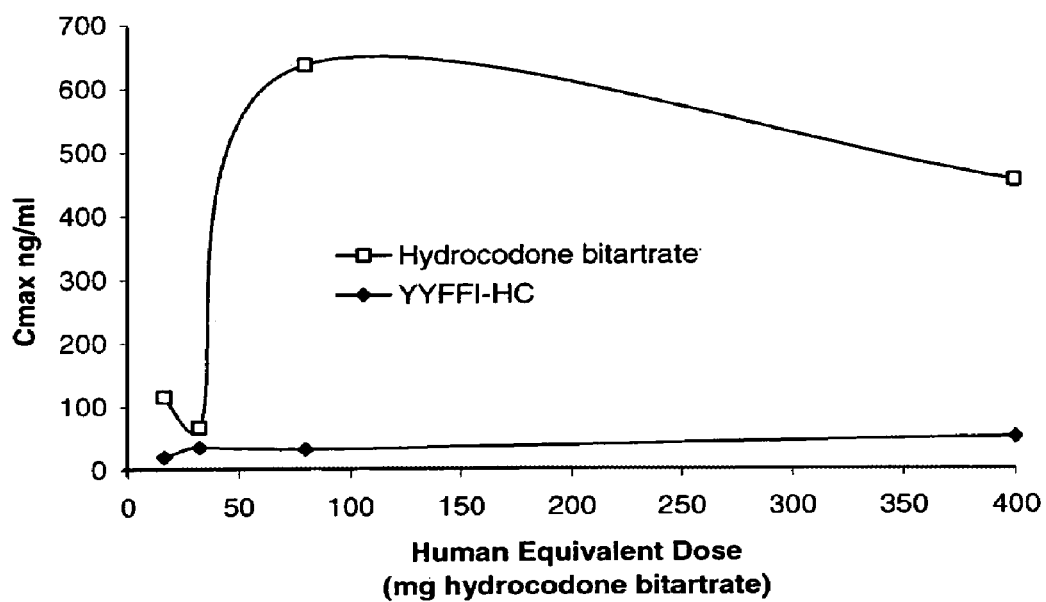
FIG. 71. Oral bioavailability ($C_{max}$) of hydrocodone plus hydromorphone in proportion to human equivalent doses (HED) following administration of hydrocodone bitratrate or YYFFI-HC at escalating doses (1, 2, 5, and 25 mg/kg—equimolar doses with equivalent content of hydrocodone base) in rats, measured as free hydrocodone.
Figure 72:
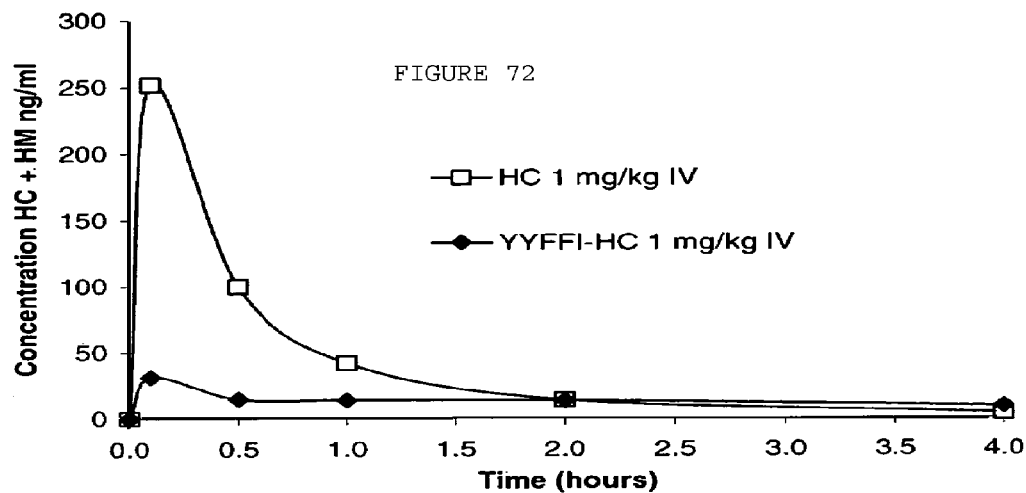
FIG. 72. Intravenous bioavailability of hydrocodone plus hydromorphone and YYFFI-HC (concentration vs. time) following administration of hydrocodone bitratrate or YYFFI-HC at 1 mg/kg (equimolar doses with equivalent content of hydrocodone base) in rats, measured as free hydrocodone.
Figure 73:
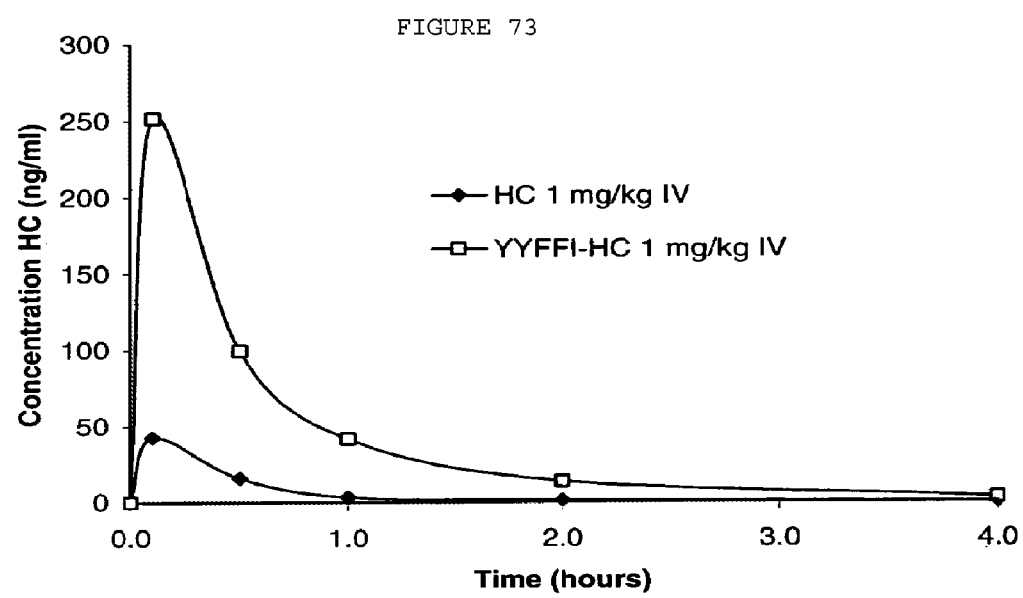
FIG. 73. Intravenous bioavailability of hydrocodone (concentration vs. time) following administration of hydrocodone bitratrate or YYFFI-HC at 1 mg/kg (equimolar doses with equivalent content of hydrocodone base) in rats, measured as free hydrocodone.
Figure 74:
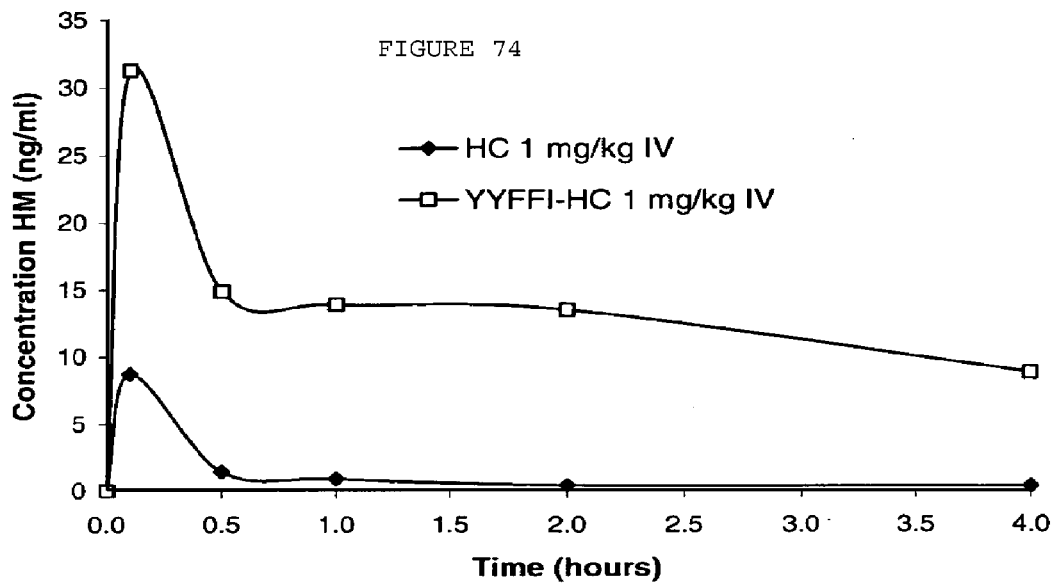
FIG. 74. Intravenous bioavailability of hydromorphone (concentration vs. time) following administration of hydrocodone bitratrate or YYFFI-HC at 1 mg/kg (equimolar doses with equivalent content of hydrocodone base) in rats, measured as free hydrocodone.
Figure 75:
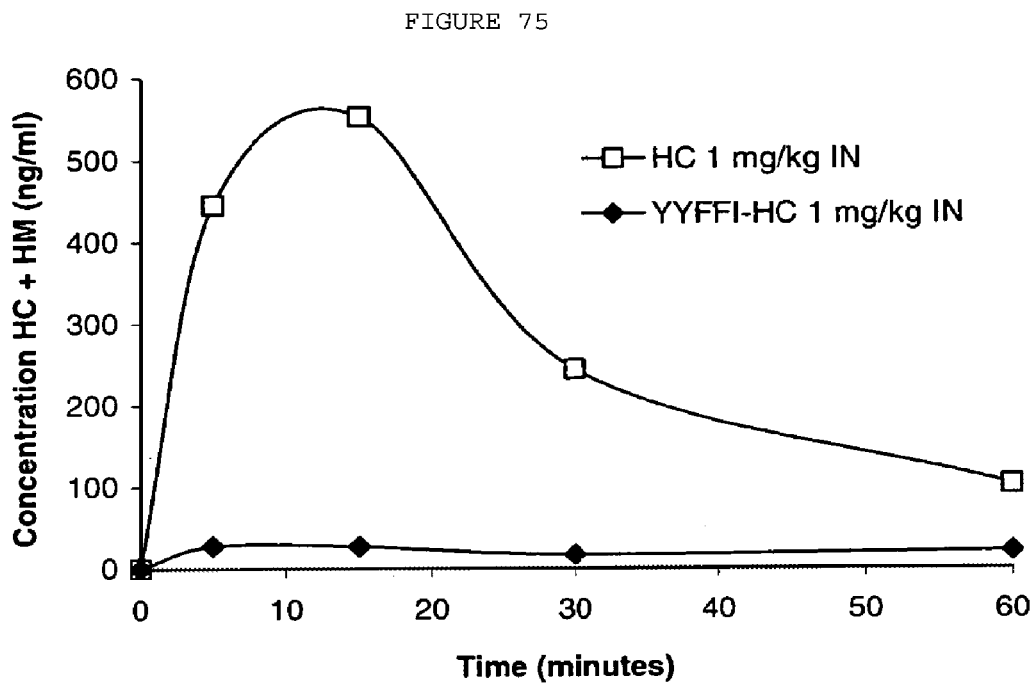
FIG. 75. Intranasal bioavailability of hydrocodone plus hydromorphone (concentration vs. time) following administration of hydrocodone bitratrate or YYFFI-HC at 1 mg/kg (equimolar doses with equivalent content of hydrocodone base) in rats, measured as free hydrocodone.
Figure 76:
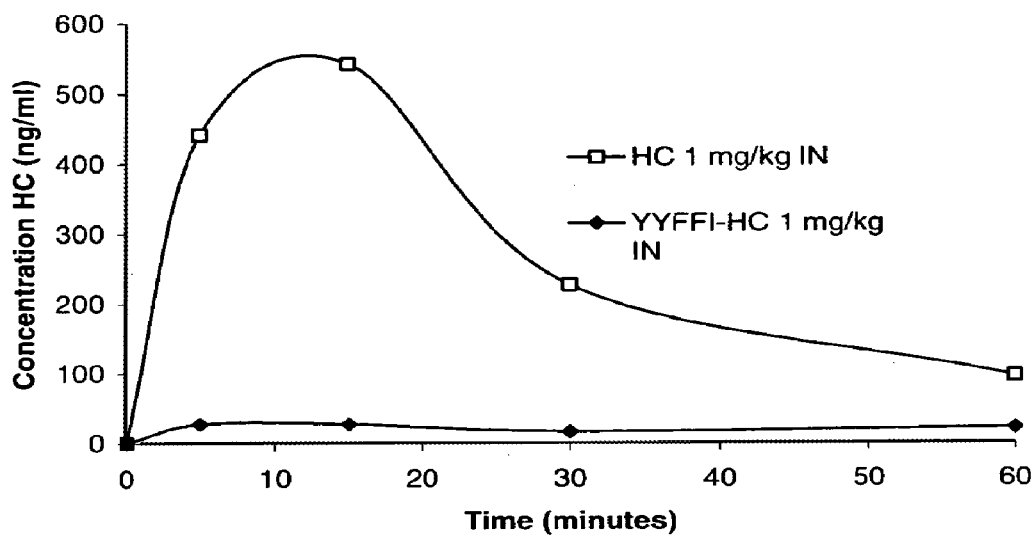
FIG. 76. Intranasal bioavailability of hydrocodone (concentration vs. time) following administration of hydrocodone bitratrate or YYFFI-HC at 1 mg/kg (equimolar doses with equivalent content of hydrocodone base) in rats, measured as free hydrocodone.
Figure 77:
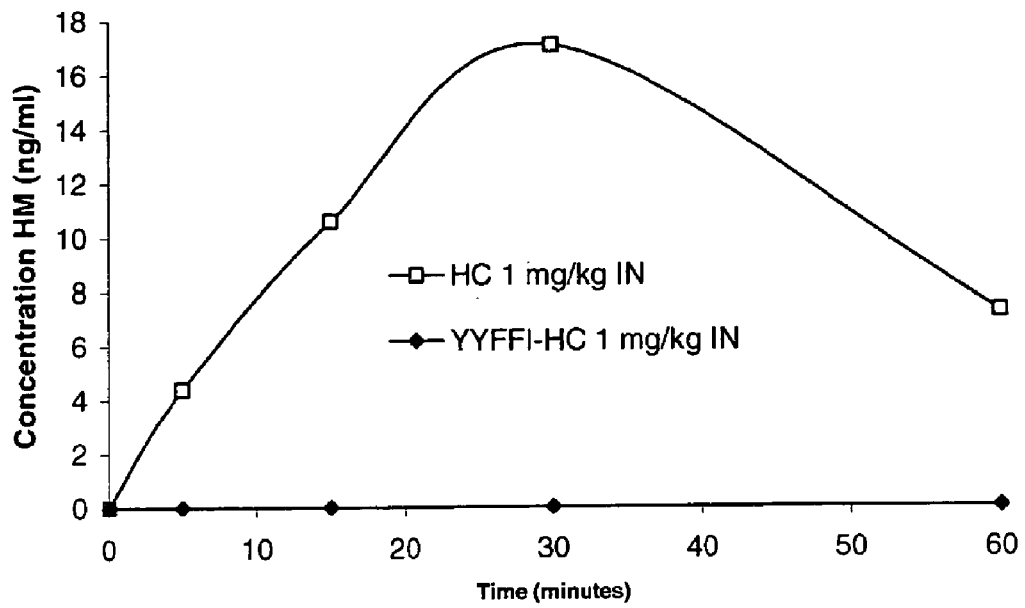
FIG. 77. Intranasal bioavailability of hydromorphone (concentration vs. time) following administration of hydrocodone bitratrate or YYFFI-HC at 1 mg/kg (equimolar doses with equivalent content of hydrocodone base) in rats, measured as free hydrocodone.
Figure 78:
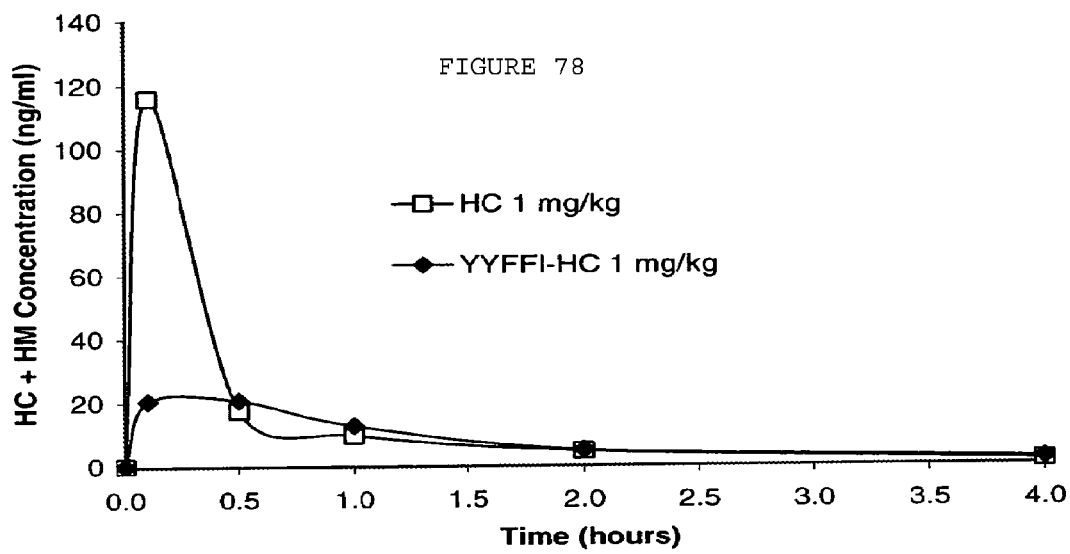
FIG. 78. Oral bioavailability of hydrocodone plus hydromorphone (concentration vs. time) following administration of hydrocodone bitratrate or YYFFI-HC at 1 mg/kg (equimolar doses with equivalent content of hydrocodone base) in rats, measured as free hydrocodone.
Figure 79:
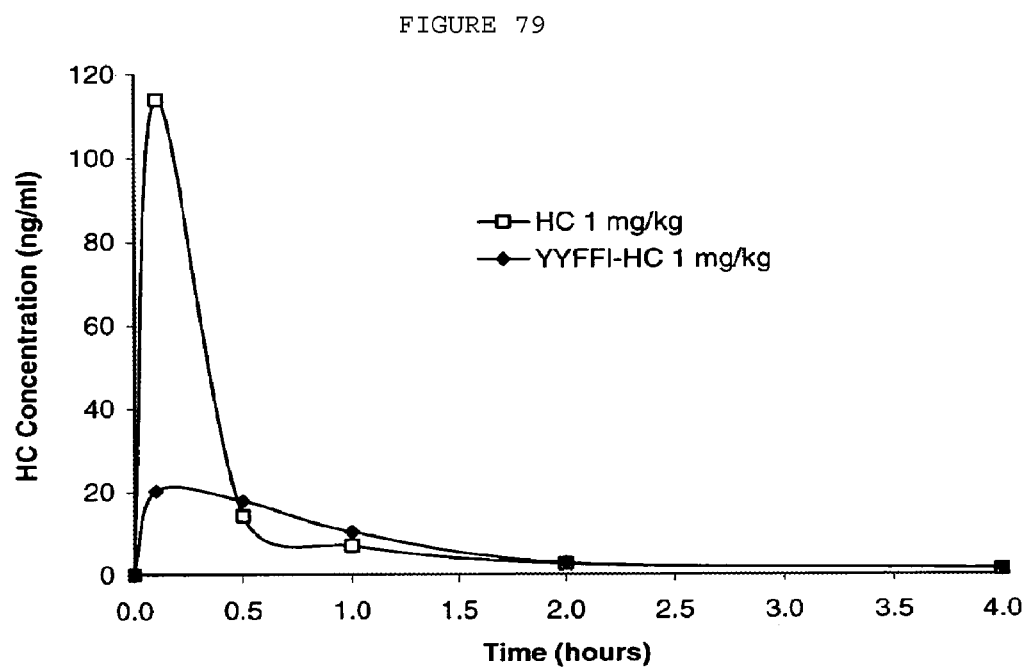
FIG. 79. Oral bioavailability of hydrocodone (concentration vs. time) following administration of hydrocodone bitratrate or YYFFI-HC at 1 mg/kg (equimolar doses with equivalent content of hydrocodone base) in rats, measured as free hydrocodone.
Figure 80:
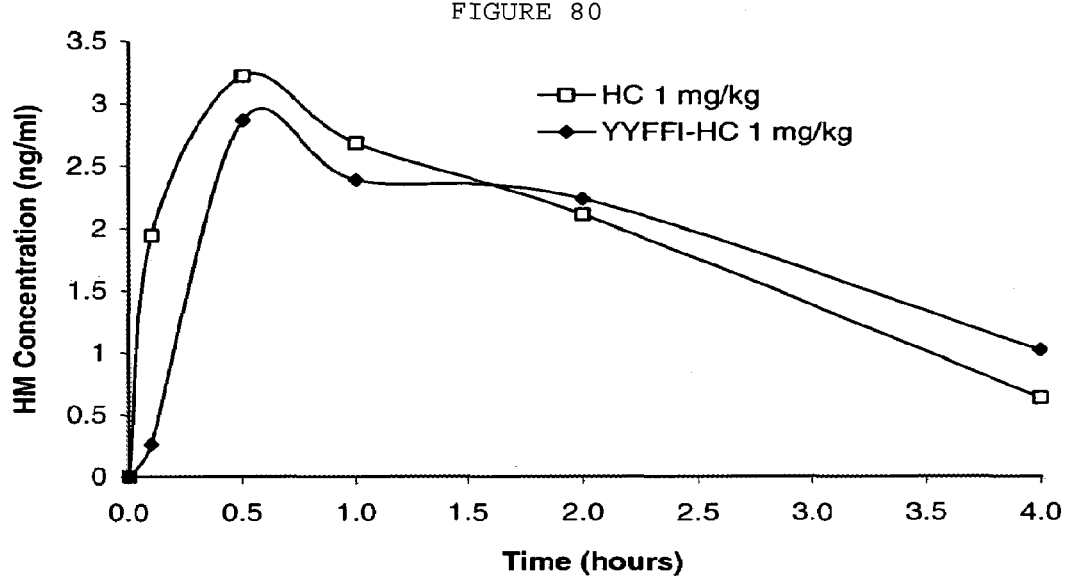
FIG. 80. Oral bioavailability of hydromorphone (concentration vs. time) following administration of hydrocodone bitratrate or YYFFI-HC at 1 mg/kg (equimolar doses with equivalent content of hydrocodone base) in rats, measured as free hydrocodone.
Figure 81:
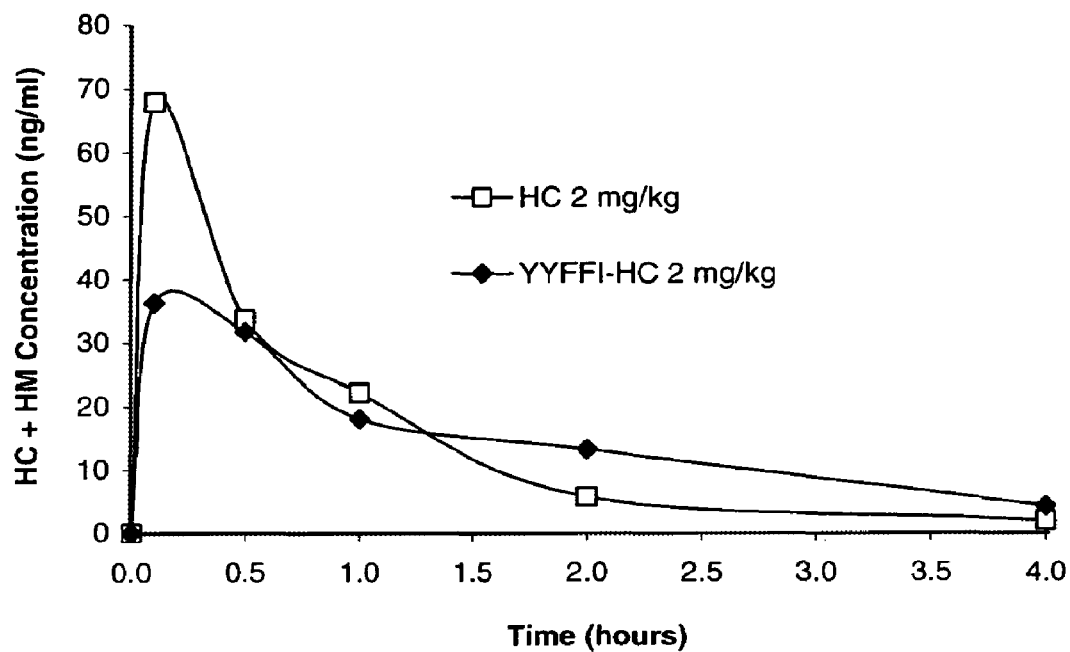
FIG. 81. Oral bioavailability of hydrocodone plus hydromorphone (concentration vs. time) following administration of hydrocodone bitratrate or YYFFI-HC at 2 mg/kg (equimolar doses with equivalent content of hydrocodone base) in rats, measured as free hydrocodone.
Figure 82:
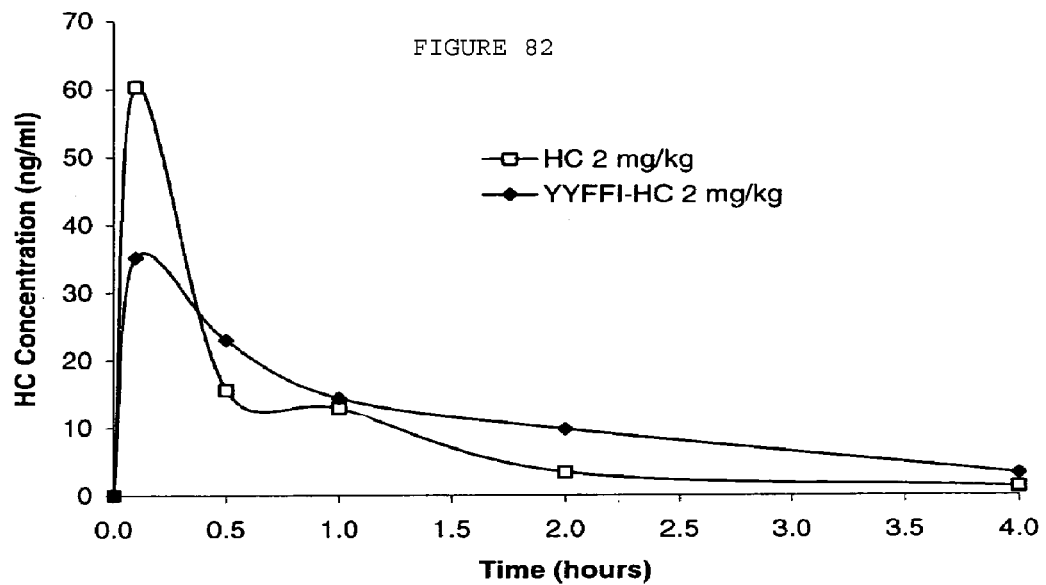
FIG. 82. Oral bioavailability of hydrocodone (concentration vs. time) following administration of hydrocodone bitratrate or YYFFI-HC at 2 mg/kg (equimolar doses with equivalent content of hydrocodone base) in rats, measured as free hydrocodone.
Figure 83:
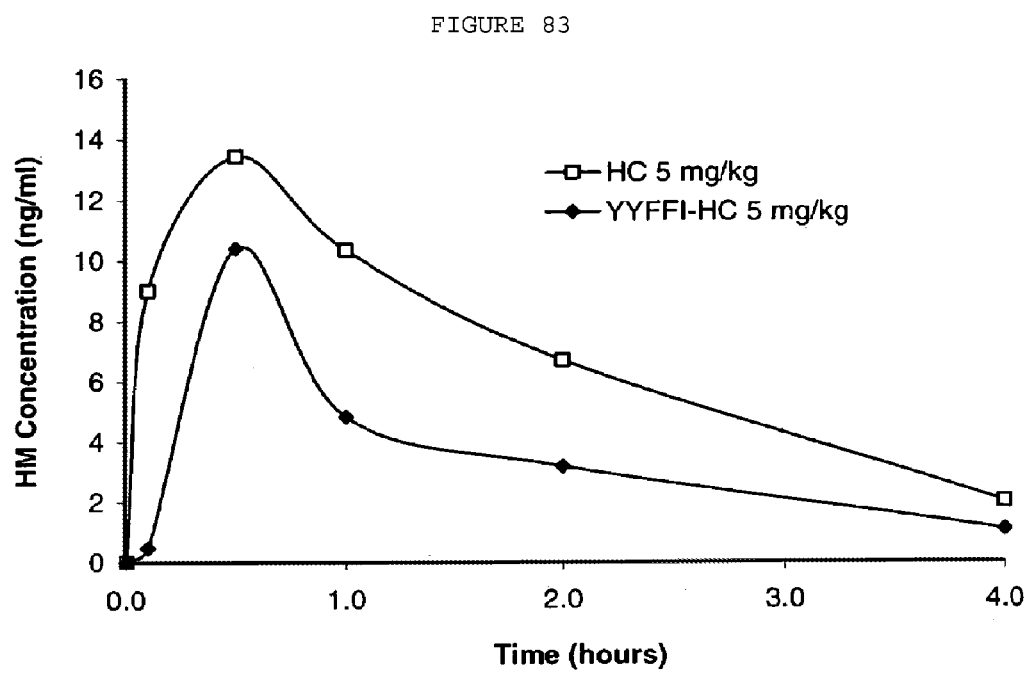
FIG. 83. Oral bioavailability of hydromorphone (concentration vs. time) following administration of hydrocodone bitratrate or YYFFI-HC at 2 mg/kg (equimolar doses with equivalent content of hydrocodone base) in rats, measured as free hydrocodone.
Figure 84:
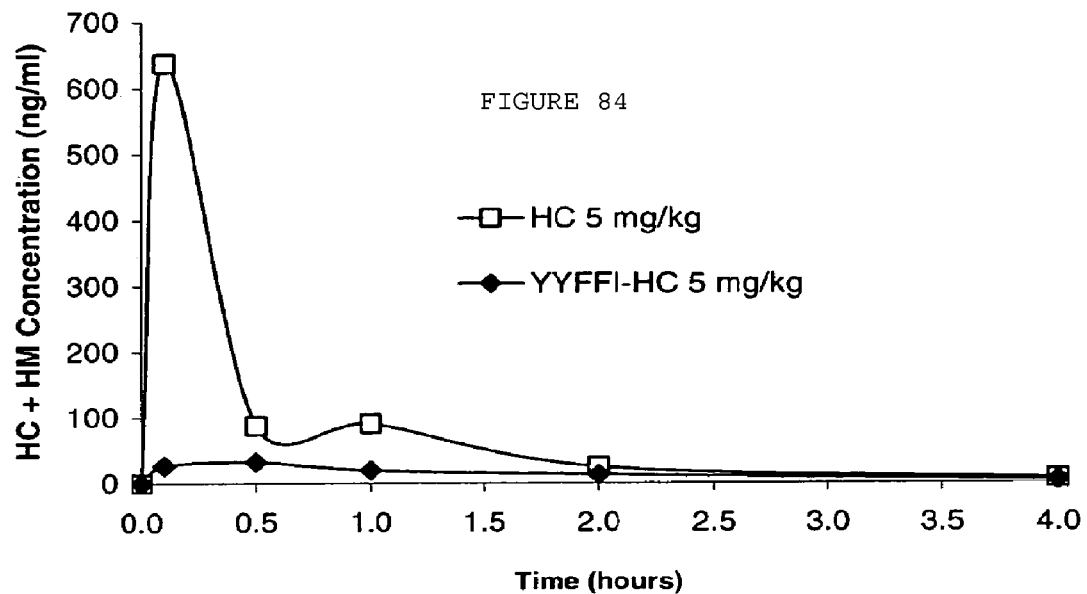
FIG. 84. Oral bioavailability of hydrocodone plus hydromorphone (concentration vs. time) following administration of hydrocodone bitratrate or YYFFI-HC at 5 mg/kg (equimolar doses with equivalent content of hydrocodone base) in rats, measured as free hydrocodone.
Figure 85:
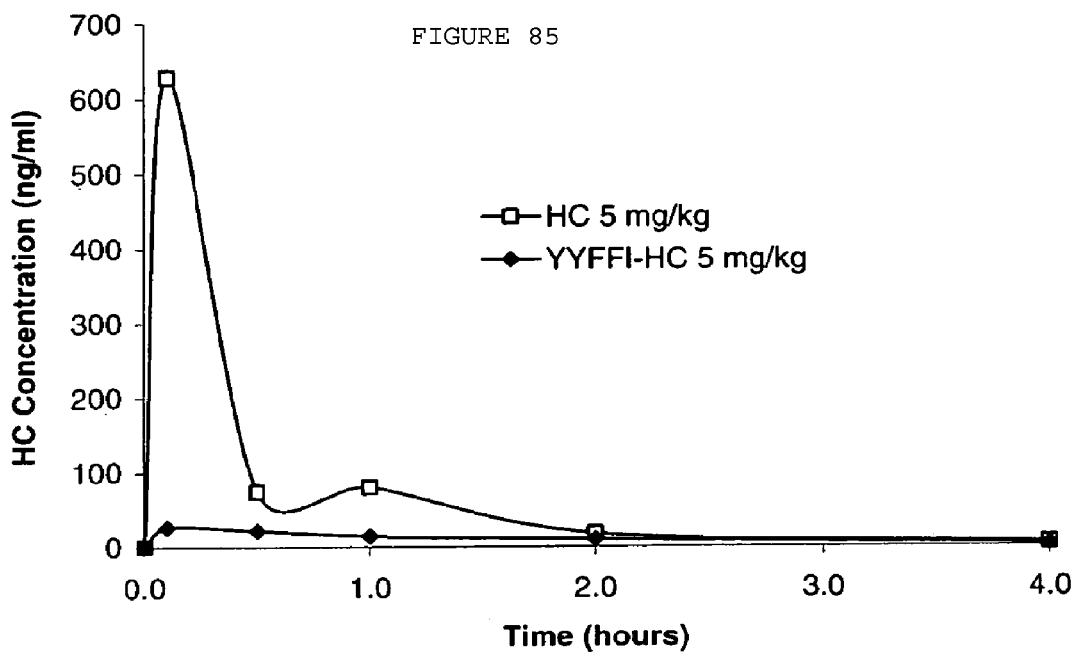
FIG. 85. Oral bioavailability of hydrocodone (concentration vs. time) following administration of hydrocodone bitratrate or YYFFI-HC at 5 mg/kg (equimolar doses with equivalent content of hydrocodone base) in rats, measured as free hydrocodone.
Figure 86:
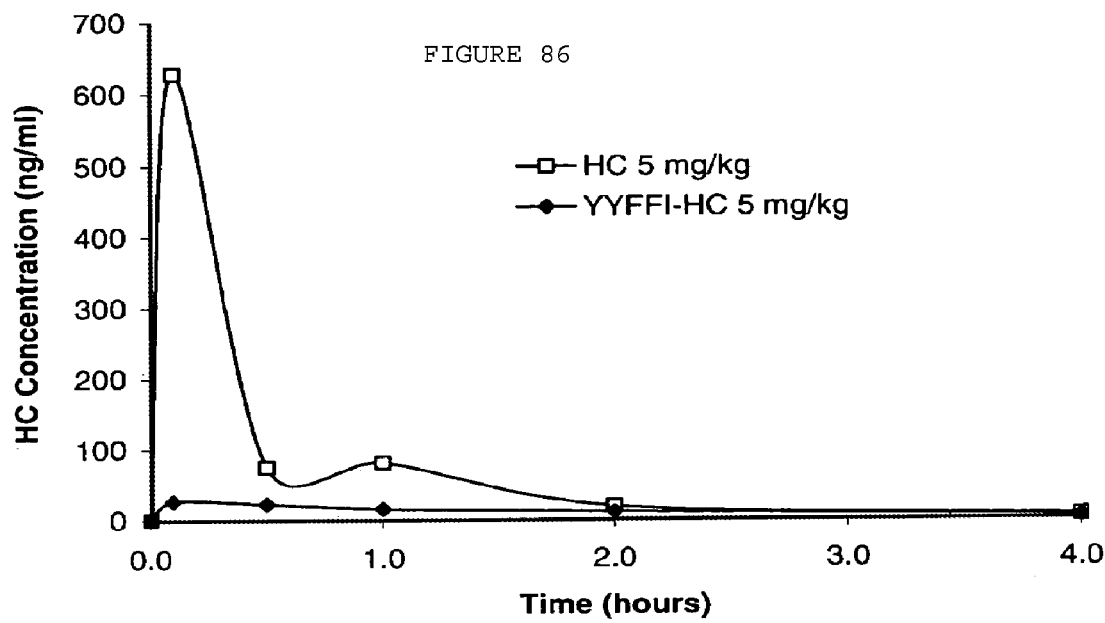
FIG. 86. Oral bioavailability of hydromorphone (concentration vs. time) following administration of hydrocodone bitratrate or YYFFI-HC at 5 mg/kg (equimolar doses with equivalent content of hydrocodone base) in rats, measured as free hydrocodone.
Figure 87:
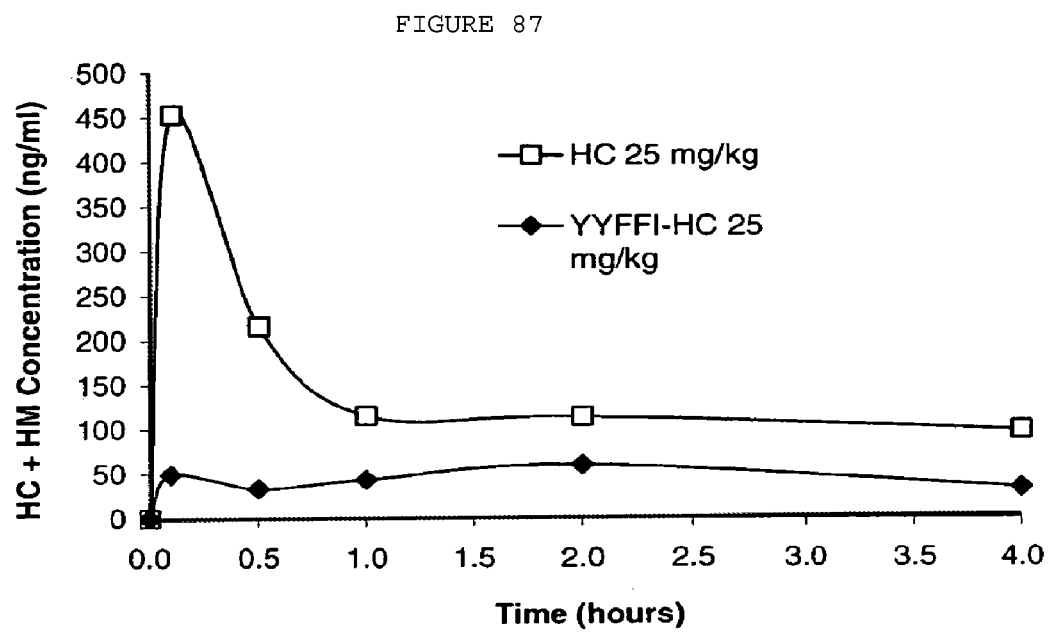
FIG. 87. Oral bioavailability of hydrocodone plus hydromorphone (concentration vs. time) following administration of hydrocodone bitratrate or YYFFI-HC at 25 mg/kg (equimolar doses with equivalent content of hydrocodone base) in rats, measured as free hydrocodone.
Figure 88:
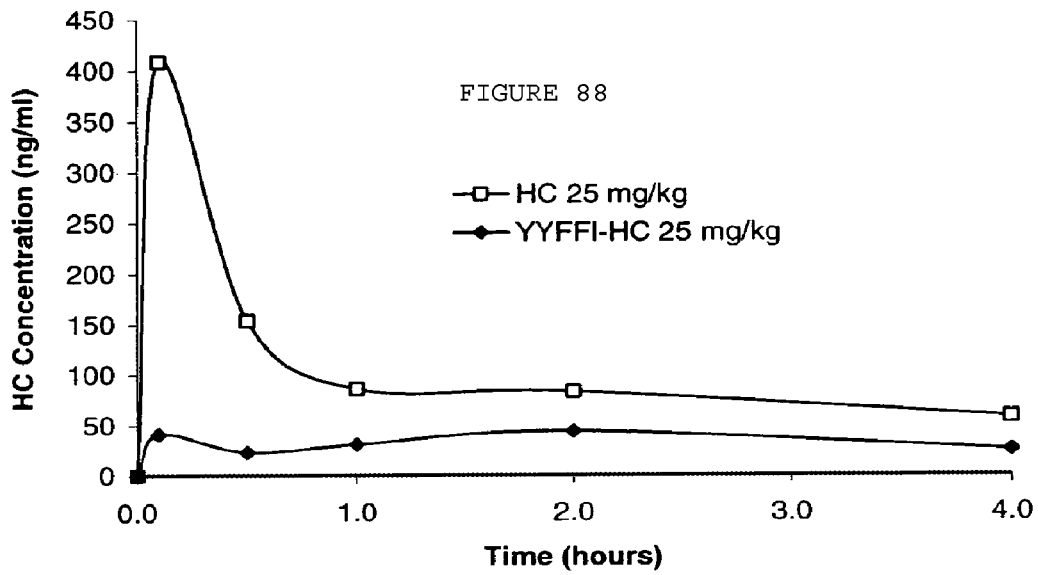
FIG. 88. Oral bioavailability of hydrocodone (concentration vs. time) following administration of hydrocodone bitratrate or YYFFI-HC at 25 mg/kg (equimolar doses with equivalent content of hydrocodone base) in rats, measured as free hydrocodone.
Figure 89:
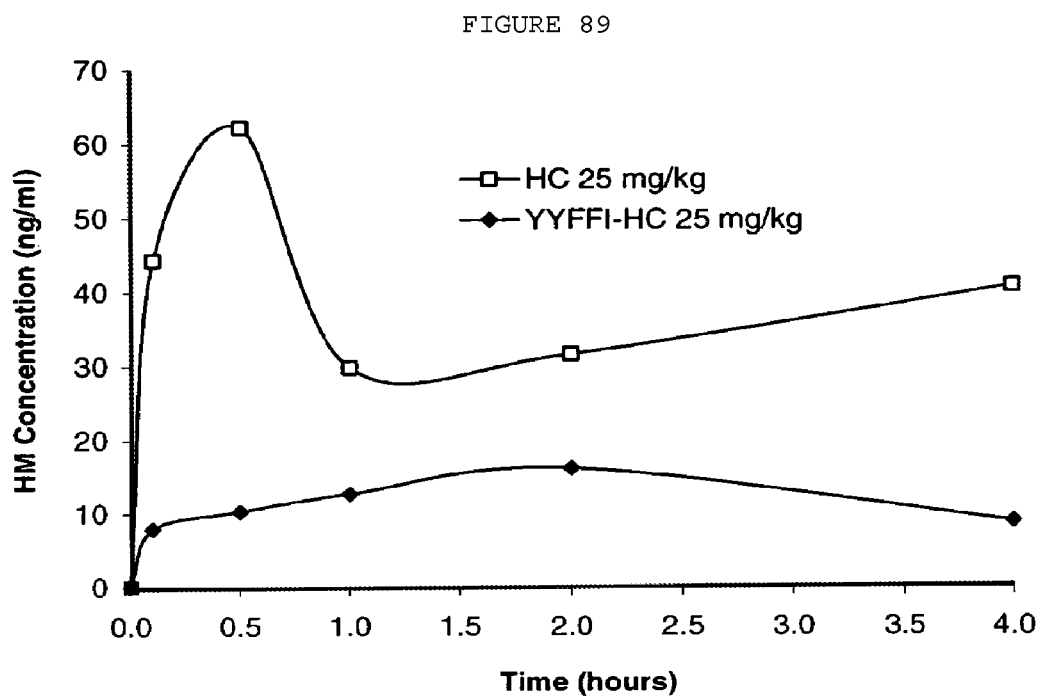
FIG. 89. Oral bioavailability of hydromorphone (concentration vs. time) following administration of hydrocodone bitratrate or YYFFI-HC at 25 mg/kg (equimolar doses with equivalent content of hydrocodone base) in rats, measured as free hydrocodone.
Figure 90:
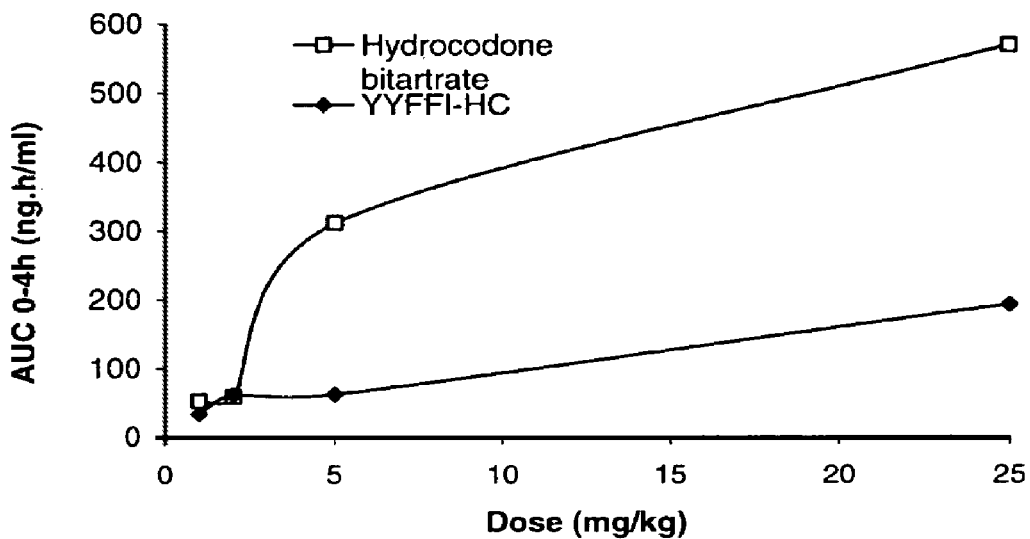
FIG. 90. Oral bioavailability ($AUC_{0-4}$) of hydrocodone plus hydromorphone (concentration vs. dose) in proportion to dose following administration of hydrocodone bitratrate or YYFFI-HC at escalating doses (1, 2, 5, and 25 mg/kg—equimolar doses with equivalent content of hydrocodone base) in rats, measured as free hydrocodone.
Figure 91:
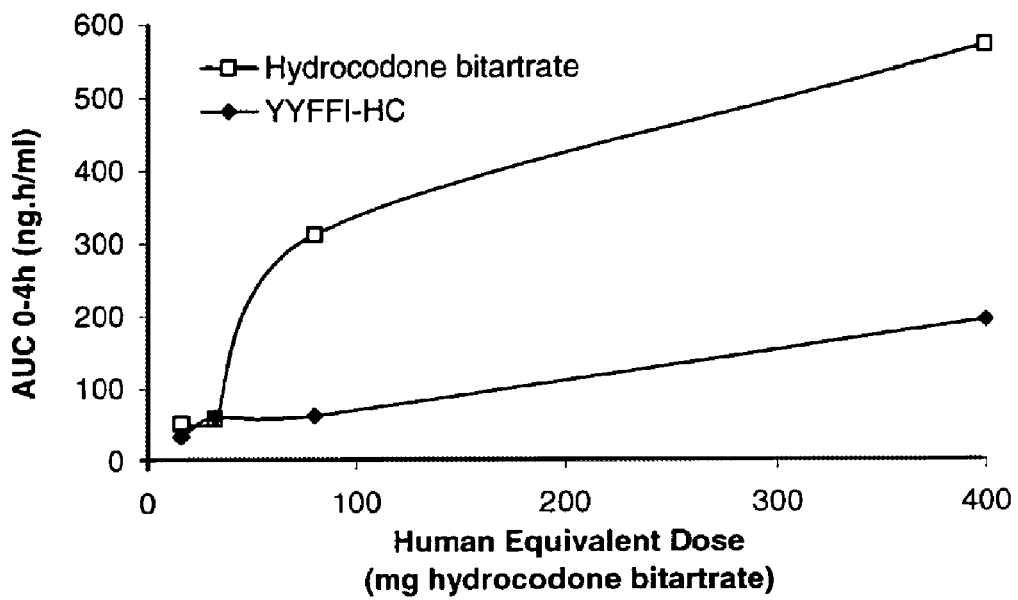
FIG. 91. Oral bioavailability ($AUC_{0-4}$) of hydrocodone plus hydromorphone in proportion to human equivalent doses (HED) following administration of hydrocodone bitratrate or YYFFI-HC at escalating doses (1, 2, 5, and 25 mg/kg—equimolar doses with equivalent content of hydrocodone base) in rats, measured as free hydrocodone.
Figure 92:
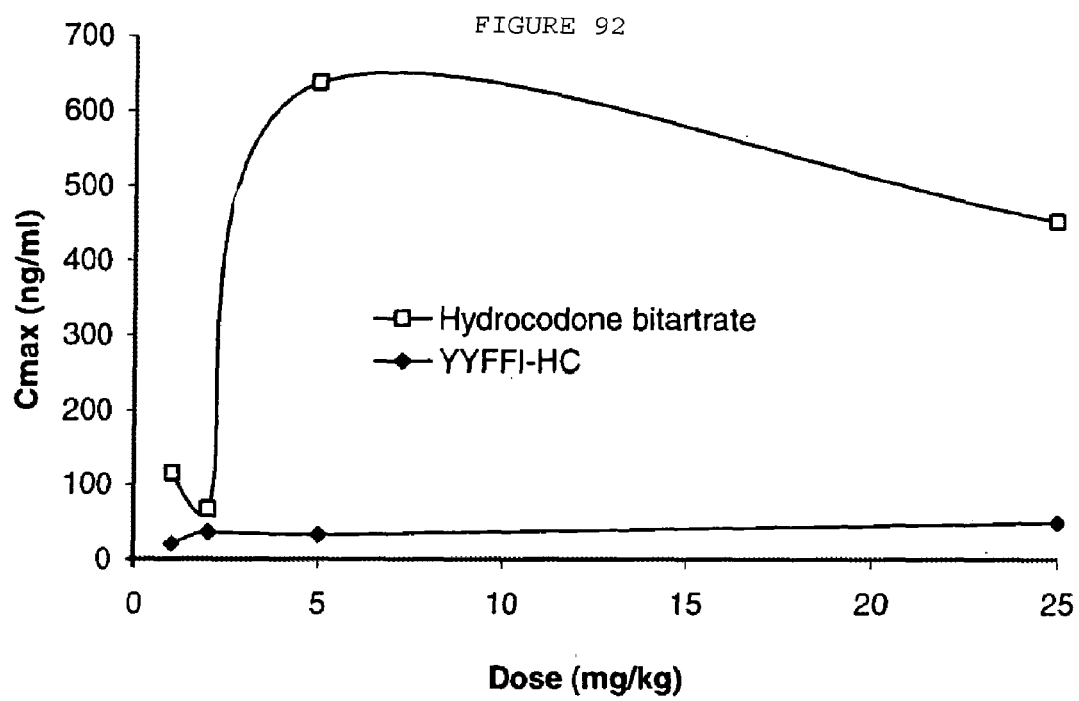
FIG. 92. Oral bioavailability ($C_{max}$) of hydrocodone plus hydromorphone (concentration vs. dose) in proportion to dose following administration of hydrocodone bitratrate or YYFFI-HC at escalating doses (1, 2, 5, and 25 mg/kg—equimolar doses with equivalent content of hydrocodone base) in rats, measured as free hydrocodone.
Figure 93:
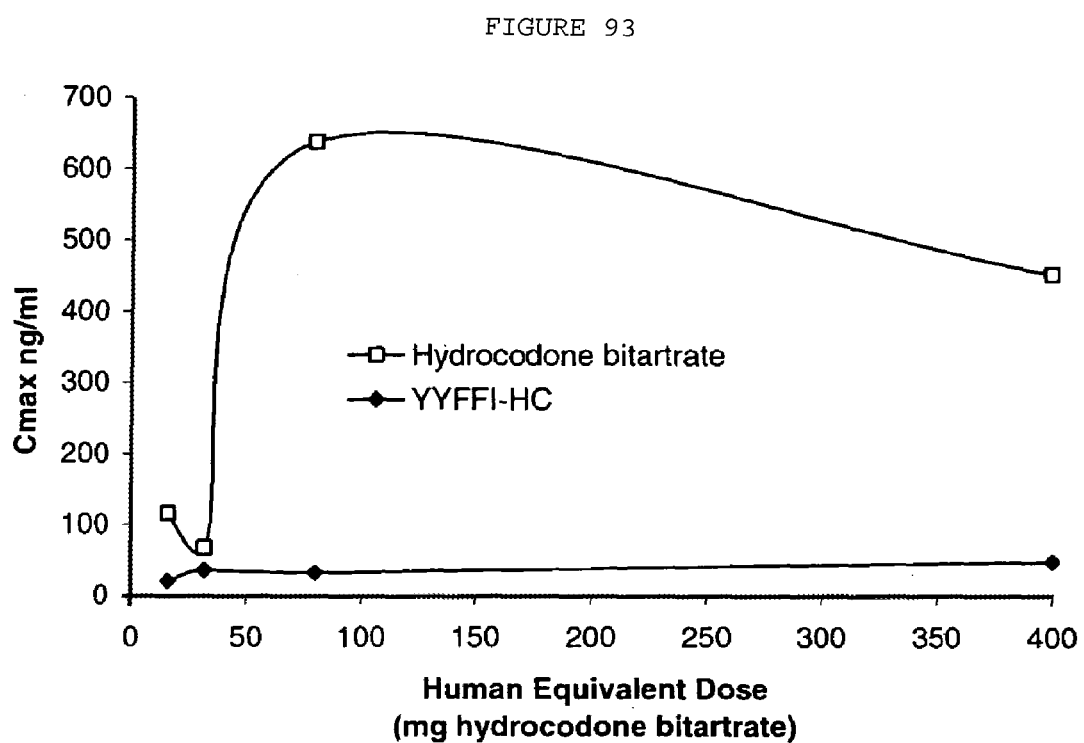
FIG. 93. Oral bioavailability ($C_{max}$) of hydrocodone plus hydromorphone in proportion to human equivalent doses (HED) following administration of hydrocodone bitratrate or YYFFI-HC at escalating doses (1, 2, 5, and 25 mg/kg—equimolar doses with equivalent content of hydrocodone base) in rats, measured as free hydrocodone.
Figure 94:
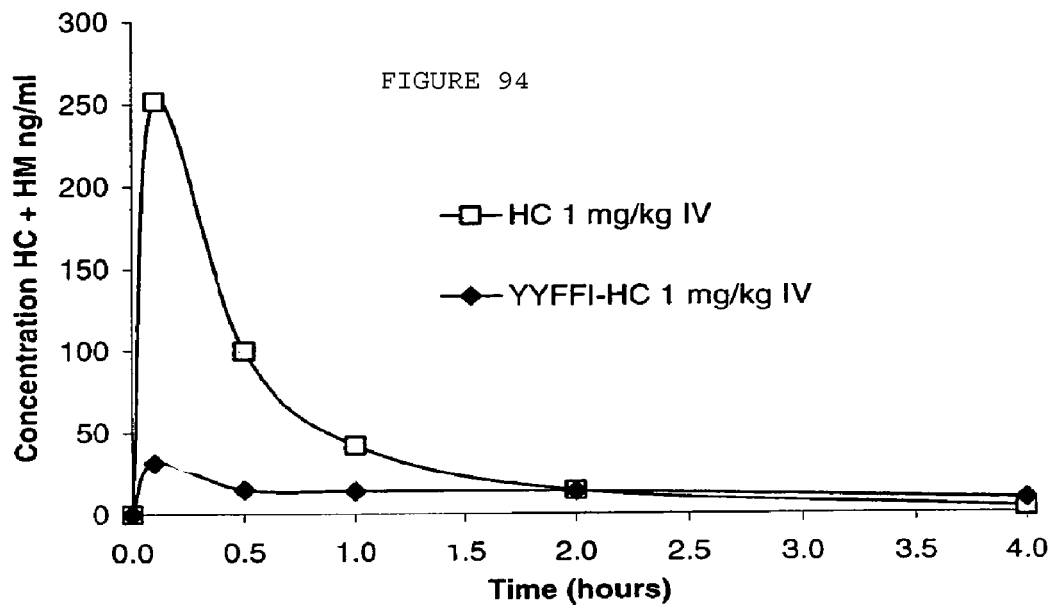
FIG. 94. Intravenous bioavailability of hydrocodone plus hydromorphone and YYFFI-HC (concentration vs. time) following administration of hydrocodone bitratrate or YYFFI-HC at 1 mg/kg (equimolar doses with equivalent content of hydrocodone base) in rats, measured as free hydrocodone.
Figure 95:
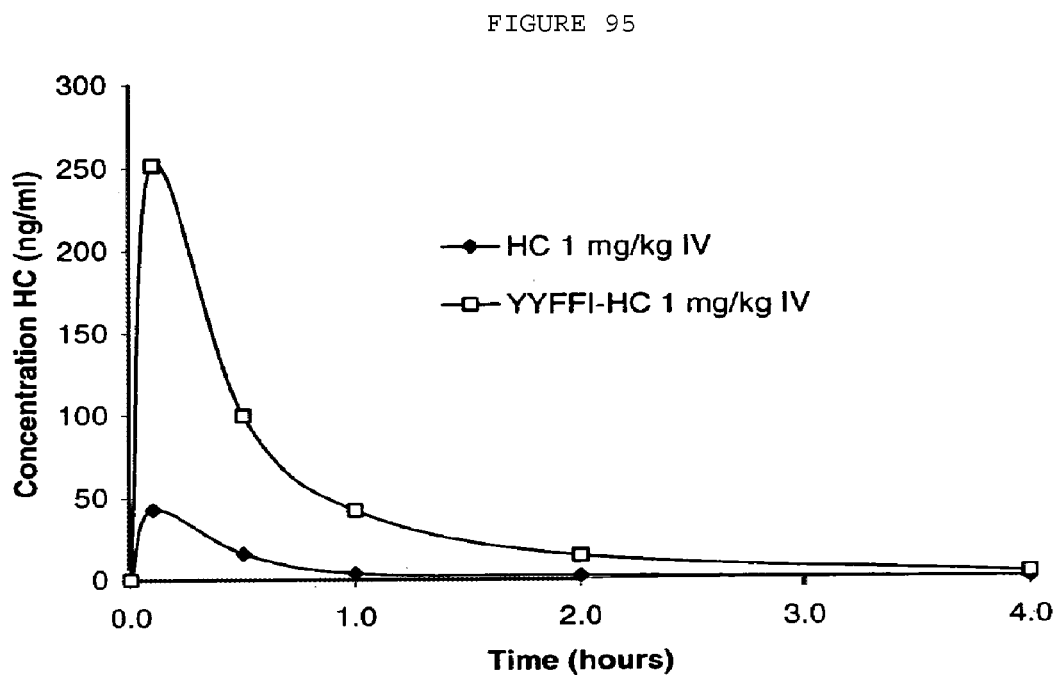
FIG. 95. Intravenous bioavailability of hydrocodone (concentration vs. time) following administration of hydrocodone bitratrate or YYFFI-HC at 1 mg/kg (equimolar doses with equivalent content of hydrocodone base) in rats, measured as free hydrocodone.
Figure 96:
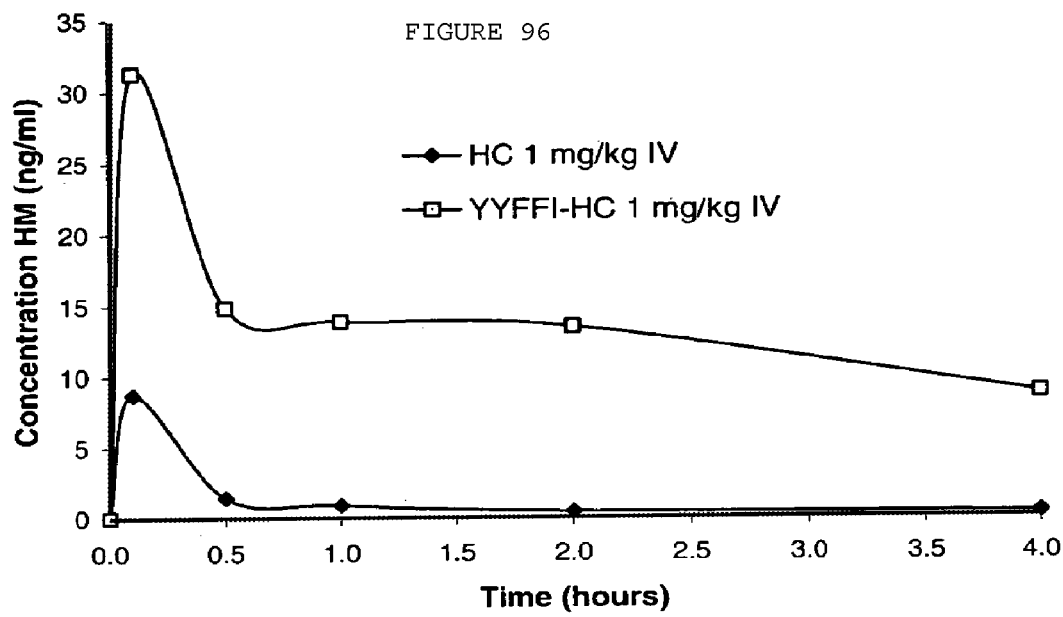
FIG. 96. Intravenous bioavailability of hydromorphone (concentration vs. time) following administration of hydrocodone bitratrate or YYFFI-HC at 1 mg/kg (equimolar doses with equivalent content of hydrocodone base) in rats, measured as free hydrocodone.
Figure 97:
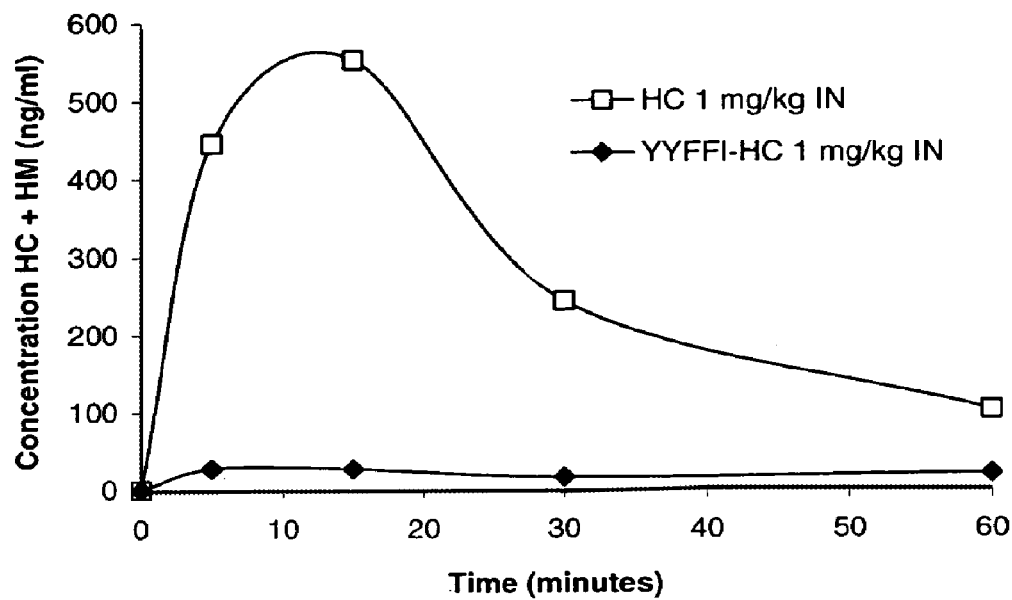
FIG. 97. Intranasal bioavailability of hydrocodone plus hydromorphone (concentration vs. time) following administration of hydrocodone bitratrate or YYFFI-HC at 1 mg/kg (equimolar doses with equivalent content of hydrocodone base) in rats, measured as free hydrocodone.
Figure 98:
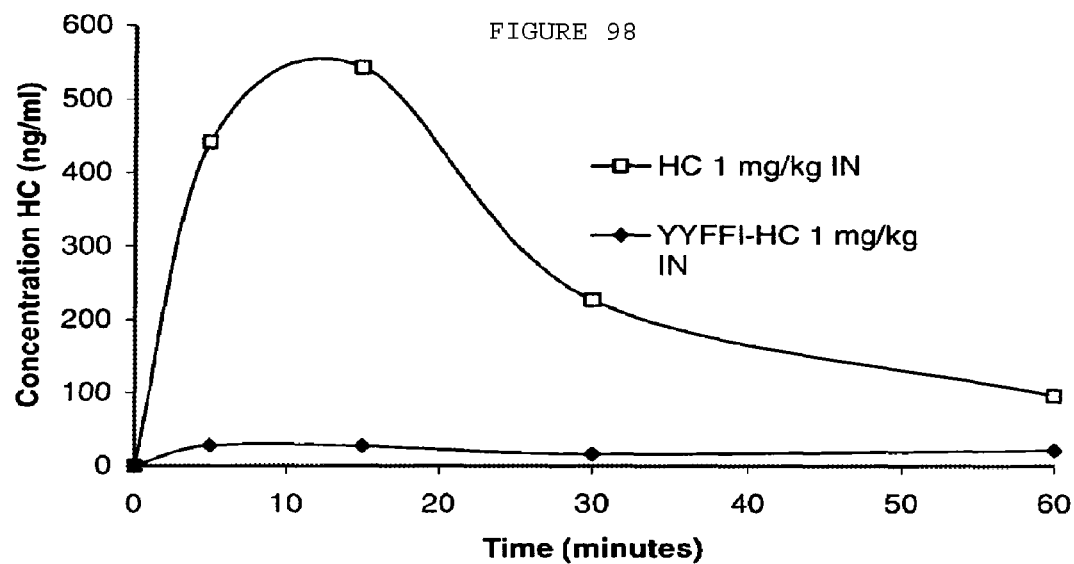
FIG. 98. Intranasal bioavailability of hydrocodone (concentration vs. time) following administration of hydrocodone bitratrate or YYFFI-HC at 1 mg/kg (equimolar doses with equivalent content of hydrocodone base) in rats, measured as free hydrocodone.
Figure 99:
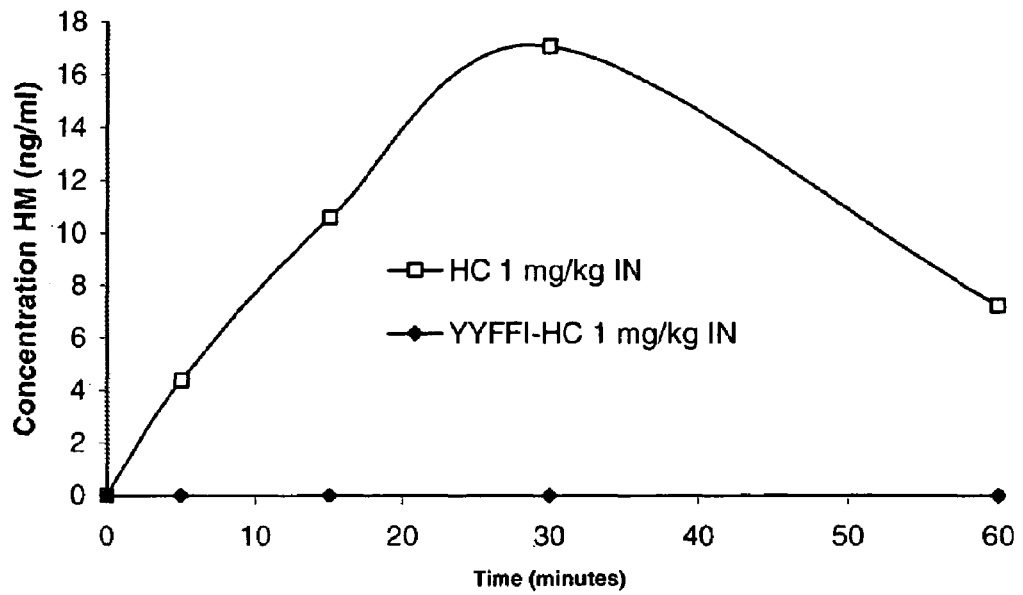
FIG. 99. Intranasal bioavailability of hydromorphone (concentration vs. time) following administration of hydrocodone bitratrate or YYFFI-HC at 1 mg/kg (equimolar doses with equivalent content of hydrocodone base) in rats, measured as free hydrocodone.

FIG. 37 illustrates Oral bioavailability of an abuse-resistant hydrocodone amino acid-carbohydrate conjugate, measured as free hydrocodone.
D-Amino Acids Example 73

(d)-Lys-(1)-Lys-Ile-Hydrocodone

Preparation of (d)-Lys-(1)-Lys-Ile-Hydrocodone

To a solution of Ile-Hydrocodone in DMF was added NMM followed by Boc-(d)-Lys(Boc)-(1)-Lys(Boc)-OSu. The solution was stirred at ambient temperatures for 18 hours. Solvent was removed. Crude material was purified using preparative HPLC (Phenomenex Luna C18, 30×250 mm, 5 µM, 100 Å; Gradient: 90 water/10 0.1% TFA-MeCN→0/100; 30 ml/min.). Solid was collected as a slightly yellow powder. To the Boc-(d)-Lys(Boc)-(1)-Lys(Boc)-Hydrocodone was added 4N HCl in dioxane. The resulting mixture was stirred at ambient temperatures for 18 hours. Solvent was removed and final product dried under vacuum. Solid was collected as a slightly yellow solid.

Nucleosides

FIG. 38 illustrates nucleosides and conjugation sites. Examples 74 through 83 are also described through FIGS. 39 through 77 (with plasma levels measured by LC/MS/MS).

Example 74

Oral Bioavailability of Peptide-Hydrocodone Conjugates at a Dose (1 mg/kg) Approximating a Therapeutic Human Dose and at an Elevated Dose Example 74 illustrates that when the peptides EEFFI (Table 46, FIG. 39), EEFFF (Table 47, FIG. 40), YYI (Table 48, FIG. 41), DDI (Table 49, FIG. 42), and YYFFI (Table 50, FIG. 43) are conjugated to the active agent hydrocodone oral bioavailability is maintained or increased over an equivalent hydrocodone dose when the dose is administered as 1 mg/kg. This dose is the equivalent of a human dose of 10 to 14 mg for an individual weighing 70 kg (148 lbs) according to Chou et al. However, when administered orally at 5 mg/kg peak levels and bioavailability of EEFFI-HC (Table 51, FIG. 44), YYI-HC (Table 52, FIG. 45), DDI-HC (Table 53, FIG. 46) and YYFFI-HC (Table 54, FIG. 47) are substantially decreased. A 5 mg/kg dose in rats approximates an 80 mg human equivalent dose (HED) of hydrocodone bitartrate; a dose that would be likely to be harmful to a naïve patient in immediate release form with the potential for fatal overdose. Human equivalent doses are defined as the equivalent dose for a 60 kg person adjusted for the body surface area of the animal model. The adjustment factor for rats is 6.2. The HED for a rat dose of 5 mg/kg of hydrocodone base, for example, is equivalent to 48.39 mg (5/6.2×60) hydrocodone base; which is equivalent to 79.98 (48.39/0.605) mg hydrocodone bitartrate, when adjusted for the salt content.

Thus the peptide-hydrocodone conjugates maintain their therapeutic value at the lower dose (1 mg/kg), whereas when given at a dose above a safe level (5 mg/kg) bioavailability is decreased as compared to hydrocodone, thus diminishing the potential for overdose by oral ingestion. The decrease in bioavailability of hydrocodone from peptide hydrocodone conjugates relative to hydrocodone ranged from 9 to 70 percent (Table 55).

TABLE 46

Oral Pharmacokinetics of Hydrocodone vs. EEFFI-HC (1 mg/kg dose).

| Drug | Hours | | | | | AUC (ng/ml h) 0-8 h | Percent HC | Cmax ng/ml | Percent HC |
| --- | --- | --- | --- | --- | --- | --- | --- | --- | --- |
| | 0.5 | 1.5 | 3 | 5 | 8 | | | | |
| Hydrocodone Bitartrate | 9.5 | 4.5 | 1.9 | 0 | 2 | 19.1 | 100 | 9.5 | 100 |
| EEFFI-HC | 12.9 | 5.2 | 4.2 | 0 | 1.6 | 25.8 | 135 | 12.9 | 136 | hydrocodone plus hydromorphone (ng/ml)

TABLE 47

Oral Pharmacokinetics of Hydrocodone vs. EEFFF-HC (1 mg/kg dose).

| Drug | Hours | | | | | AUC (ng/ml h) 0-8 h | Percent HC | Cmax ng/ml | Percent HC |
| --- | --- | --- | --- | --- | --- | --- | --- | --- | --- |
| | 0.5 | 1.5 | 3 | 5 | 8 | | | | |
| Hydrocodone Bitartrate | 9.5 | 4.5 | 1.9 | 0 | 2 | 19.1 | 100 | 9.5 | 100 |
| EEFFF-HC | 11.3 | 4.1 | 1.2 | 1.2 | 1.2 | 20.7 | 108 | 11.3 | 119 | hydrocodone plus hydromorphone (ng/ml)

TABLE 48

Oral Pharmacokinetics of Hydrocodone vs. YYI-HC (1 mg/kg dose).

| Drug | Hours | | | | | AUC (ng/ml h) 0-8 h | Percent HC | Cmax ng/ml | Percent HC |
| --- | --- | --- | --- | --- | --- | --- | --- | --- | --- |
| | 0.5 | 1.5 | 3 | 5 | 8 | | | | |
| Hydrocodone Bitartrate | 9.2 | 5.9 | 2.3 | 1.9 | 2 | 26.1 | 100 | 9.2 | 100 |
| YYI-HC | 9.2 | 4.3 | 1.5 | 1.1 | 1.8 | 20.4 | 78 | 9.2 | 100 | hydrocodone plus hydromorphone (ng/ml)

TABLE 49

Oral Pharmacokinetics of Hydrocodone vs. DDI-HC (1 mg/kg dose).

| Drug | Hours | | | | | AUC (ng/ml h) 0-8 h | Percent HC | Cmax ng/ml | Percent HC |
| --- | --- | --- | --- | --- | --- | --- | --- | --- | --- |
| | 0.5 | 1.5 | 3 | 5 | 8 | | | | |
| Hydrocodone Bitartrate | 8.6 | 3 | 1.1 | 0 | 1.4 | 14 | 100 | 8.6 | 100 |
| DDI-HC | 14.9 | 5 | 0 | 0 | 0 | 17.4 | 124 | 14.9 | 173 | hydrocodone plus hydromorphone (ng/ml)

TABLE 50

Oral Pharmacokinetics of Hydrocodone vs. YYFFI-HC (1 mg/kg dose).

| Drug | Hours | | | | | | AUC (ng/ml h) 0-8 h | Percent HC | Cmax ng/ml | Percent HC |
| --- | --- | --- | --- | --- | --- | --- | --- | --- | --- | --- |
| | 0.5 | 1.0 | 1.5 | 3 | 5 | 8 | | | | |
| Hydrocodone Bitartrate | 8.6 | 4.5 | 3 | 1.1 | 0 | 1.4 | 13.6 | 100 | 8.6 | 100 |
| YYFFI-HC | 7 | 3.7 | 4.3 | 1.4 | 1.1 | 0 | 14.9 | 110 | 7 | 81 | hydrocodone plus hydromorphone (ng/ml)

TABLE 51

Oral Pharmacokinetics of Hydrocodone vs. EEFFI-HC (5 mg/kg dose).

| Drug | Hours | | | | | AUC (ng/ml h) 0-8 h | Percent HC | Cmax ng/ml | Percent HC |
| --- | --- | --- | --- | --- | --- | --- | --- | --- | --- |
| | 0.5 | 1.5 | 3 | 5 | 8 | | | | |
| Hydrocodone Bitartrate | 93 | 5.3 | 39 | 5 | 6.5 | 167 | 100 | 93 | 100 |
| EEFFI-HC | 44 | 6.5 | 5.7 | 4.2 | 4.5 | 68 | 41 | 44 | 47 | hydrocodone plus hydromorphone (ng/ml)

TABLE 52

Oral Pharmacokinetics of Hydrocodone vs. YYI-HC (5 mg/kg dose).

| Drug | Hours | | | | | AUC (ng/ml h) 0-8 h | Percent HC | Cmax ng/ml | Percent HC |
| --- | --- | --- | --- | --- | --- | --- | --- | --- | --- |
| | 0.5 | 1.5 | 3 | 5 | 8 | | | | |
| Hydrocodone Bitartrate | 37 | 13 | 12 | 3 | 0 | 71 | 100 | 37 | 100 |
| YYI-HC | 15 | 6.3 | 3.3 | 1.6 | 2.7 | 33 | 46 | 15 | 41 | hydrocodone plus hydromorphone (ng/ml)

TABLE 53

Oral Pharmacokinetics of Hydrocodone vs. DDI-HC (5 mg/kg dose).

| Drug | Hours | | | | | AUC (ng/ml h) 0-8 h | Percent HC | Cmax ng/ml | Percent HC |
|---|---|---|---|---|---|---|---|---|---|
| | 0.5 | 1.5 | 3 | 5 | 8 | | | | |
| Hydrocodone Bitartrate | 73 | 42 | 6.7 | 1.2 | 3.8 | 128 | 100 | 73 | 100 |
| DDI-HC | 115 | 19 | 11 | 4 | 3.1 | 145 | 113 | 115 | 158 | hydrocodone plus hydromorphone (ng/ml)

TABLE 54

Oral Pharmacokinetics of Hydrocodone vs. YYFFI-HC (5 mg/kg dose).

| Drug | Hours | | | | | | AUC (ng/ml h) 0-8 h | Percent HC | Cmax ng/ml | Percent HC |
|---|---|---|---|---|---|---|---|---|---|---|
| | 0.5 | 1.0 | 1.5 | 3 | 5 | 8 | | | | |
| Hydrocodone Bitartrate | 73 | 62 | 42 | 6.7 | 1.2 | 3.8 | 123 | 100 | 73 | 100 |
| YYFFI-HC | 46 | 33 | 34 | 13 | 8.3 | 4.5 | 105 | 86 | 46 | 63 | hydrocodone plus hydromorphone (ng/ml)

TABLE 55

Decrease in Oral Bioavailability at 5 mg/kg vs. Therapeutic Dose of 1 mg/kg.

| Drug | Bioavailability 1 mg/kg | | Bioavailability 5 mg/kg | | Percent Decrease 1 mg/kg vs. 5 mg/kg | |
|---|---|---|---|---|---|---|
| | AUC | Cmax | AUC | Cmax | AUC | Cmax |
| YYI-HC | 78 | 100 | 46 | 40 | 41 | 60 |
| DDI-HC | 124 | 174 | 113 | 158 | 9 | 9 |
| YYFFI-HC | 109 | 81 | 86 | 62 | 15 | 23 |
| EEFFI-HC | 135 | 136 | 41 | 47 | 70 | 65 |

Example 75

Bioavailability of Peptide-HC Conjugates by the Intranasal Route

Example 75 illustrates that when the peptides EEFFF (Table 56, FIG. 48), YYI (Table 57, FIG. 49), DDI (Table 58, FIG. 50) and YYFFI (Table 59, FIG. 51) are conjugated to the active agent hydrocodone the bioavailability by the intravenous route is substantially decreased thereby diminishing the possibility of overdose when the drug is administered by snorting.

TABLE 56

Intranasal Pharmacokinetics of Hydrocodone vs. EEFFF-HC (1 mg/kg dose).

| Drug | Minutes | | | | AUC (ng/ml h) 0-1 h | Percent HC | Cmax ng/ml | Percent HC |
|---|---|---|---|---|---|---|---|---|
| | 5 | 15 | 30 | 60 | | | | |
| Hydrocodone Bitartrate | 262 | 259 | 142 | 47 | 152 | 100 | 262 | 100 |
| EEFFF-HC | 34 | 21 | 24 | 15 | 21 | 14 | 34 | 13 | hydrocodone plus hydromorphone (ng/ml)

TABLE 57

Intranasal Pharmacokinetics of Hydrocodone vs. YYI-HC (1 mg/kg dose).

| Drug | Minutes | | | | AUC (ng/ml h) 0-1 h | Percent HC | Cmax ng/ml | Percent HC |
|---|---|---|---|---|---|---|---|---|
| | 5 | 15 | 30 | 60 | | | | |
| Hydrocodone Bitartrate | 446 | 553 | 244 | 103 | 288 | 100 | 553 | 100 |
| YYI-HC | 31 | 17 | 12 | 2 | 12 | 4 | 31 | 6 | hydrocodone plus hydromorphone (ng/ml)

TABLE 58

Intranasal Pharmacokinetics of Hydrocodone vs. DDI-HC (1 mg/kg dose).

| Drug | Minutes | | | | AUC (ng/ml h) | Percent | Cmax | Percent |
|---|---|---|---|---|---|---|---|---|
| | 5 | 15 | 30 | 60 | 0-1 h | HC | ng/ml | HC |
| Hydrocodone Bitartrate | 446 | 553 | 244 | 103 | 288 | 100 | 553 | 100 |
| DDI-HC | 281 | 121 | 64 | 16 | 88 | 31 | 281 | 51 | hydrocodone plus hydromorphone (ng/ml)

TABLE 59

Intranasal Pharmacokinetics of Hydrocodone vs. YYFFI-HC (1 mg/kg dose).

| Drug | Minutes | | | | AUC (ng/ml h) | Percent | Cmax | Percent |
|---|---|---|---|---|---|---|---|---|
| | 5 | 15 | 30 | 60 | 0-1 h | HC | ng/ml | HC |
| Hydrocodone Bitartrate | 446 | 553 | 244 | 103 | 288 | 100 | 553 | 100 |
| YYFFI-HC | 28 | 27 | 16 | 21 | 20 | 100 | 28 | 5 | hydrocodone plus hydromorphone (ng/ml)

Example 76

Bioavailability of Peptide-HC Conjugates by the Intravenous Route

Example 76 illustrates that when the peptides EEFFI (Table 60, FIG. 52), EEFFF (Table 61, FIG. 53), YYI (Table 62, FIG. 54) and YYFFI (Table 63, FIG. 55) are conjugated to the active agent hydrocodone the bioavailability by the intravenous route is substantially decreased thereby diminishing the possibility of overdose when the drug is administered by this unintended route.

TABLE 60

Intravenous Pharmacokinetics of Hydrocodone vs. EEFFI-HC (1 mg/kg dose).

| Drug | Minutes | | | | AUC (ng/ml h) | Percent | Cmax | Percent |
|---|---|---|---|---|---|---|---|---|
| | 5 | 15 | 30 | 60 | 0-1 h | HC | ng/ml | HC |
| Hydrocodone Bitartrate | 179 | 204 | 201 | 132 | 173 | 100 | 179 | 100 |
| EEFFI-HC | 89 | 76 | 78 | 66 | 66 | 38 | 89 | 44 | hydrocodone plus hydromorphone (ng/ml)

TABLE 61

Intravenous Pharmacokinetics of Hydrocodone vs. EEFFF-HC (1 mg/kg dose).

| Drug | Minutes | | | | AUC (ng/ml h) | Percent | Cmax | Percent |
|---|---|---|---|---|---|---|---|---|
| | 5 | 15 | 30 | 60 | 0-1 h | HC | ng/ml | HC |
| Hydrocodone Bitartrate | 179 | 204 | 201 | 132 | 173 | 100 | 179 | 100 |
| EEFFF-HC | 135 | 77 | 140 | 85 | 107 | 62 | 135 | 75 | hydrocodone plus hydromorphone (ng/ml)

TABLE 62

Intravenous Pharmacokinetics of Hydrocodone vs. YYI-HC (1 mg/kg dose).

| Drug | Minutes | | | | AUC (ng/ml h) 0-1 h | Percent HC | Cmax ng/ml | Percent HC |
| --- | --- | --- | --- | --- | --- | --- | --- | --- |
| | 5 | 15 | 30 | 60 | | | | |
| Hydrocodone Bitartrate | 238 | 182 | 136 | 77 | 138 | 100 | 238 | 100 |
| YYI-HC | 9 | 13 | 13 | 3 | 10 | 7 | 13 | 6 | hydrocodone plus hydromorphone (ng/ml)

TABLE 63

Intravenous Pharmacokinetics of Hydrocodone vs. YYFFI-HC (1 mg/kg dose).

| Drug | Minutes | | | | AUC (ng/ml h) 0-1 h | Percent HC | Cmax ng/ml | Percent HC |
| --- | --- | --- | --- | --- | --- | --- | --- | --- |
| | 5 | 15 | 30 | 60 | | | | |
| Hydrocodone Bitartrate | 238 | 182 | 136 | 77 | 138 | 100 | 238 | 100 |
| YYFFI-HC | 171 | 28 | 22 | 18 | 40 | 29 | 171 | 72 | hydrocodone plus hydromorphone (ng/ml)

Example 77

Hydrocodone Conjugates

Bioavailability (AUC and $C_{max}$) of various peptide-hydrocodone conjugates relative to that of hydrocodone bitartrate are shown in Table 64. The invention is well illustrated by the in vivo performance of YYFFI-HC (FIGS. 56 through 77). At the relatively low doses of 1 and 2 mg/kg (human equivalent doses (HEDs) of 16 and 32 mg hydrocodone bitartrate) YYFFI-HC showed comparable bioavailability to that of hydrocodone bitartrate (Table 65, FIGS. 78 through 83). At the elevated doses of 5 and 25 mg/kg bioavailability of hydrocodone and hydromorphone were substantially decreased as compared to that of hydrocodone (Table 66, FIGS. 84 through 99). These doses (HED of 80 and 400 mg hydrocodone bitartrate) are equivalent to amounts well above the available prescription doses of hydrocodone bitartrate which range from 2.5 to 10 mg. When delivered by the parenteral routes of intravenous and intranasal administration a substantial decrease in bioavailability of hydrocodone and hydromorphone from YYFFI-HC as compared to hydrocodone bitratrate was observed. These examples establish that covalent modification of an opioid via attachment of a peptide provides a method of delivering bioequivalent doses when given at doses approximating a normal prescribed dose. When administered by parenteral routes or at oral doses in excess of the intended prescription the bioavailability is substantially decreased. Collectively, the examples clearly illustrate the utility of the invention for decreasing the abuse potential of opioids.

TABLE 64

Mean hydrocodone concentrations following oral administration of hydrocodone bitartrate or YYFFI-HC at escalating doses.

| | Dose[1]/Concentration (ng/ml) | | | | | | | |
| --- | --- | --- | --- | --- | --- | --- | --- | --- |
| | 1 mg/kg | | 2 mg/kg | | 5 mg/kg | | 25 mg/kg | |
| Hours | HC[2] | YYFFI-HC[3] | HC[2] | YYFFI-HC[3] | HC[2] | YYFFI-HC[3] | HC[2] | YYFFI-HC[3] |
| 0 | 0 | 0 | 0 | 0 | 0 | 0 | 0 | 0 |
| 0.1 | 114.0 | 20.3 | 60.3 | 35.2 | 628.7 | 26.6 | 408.9 | 41.4 |
| 0.5 | 14.3 | 17.9 | 15.6 | 23 | 74.3 | 22.5 | 153.9 | 23.3 |
| 1.0 | 7.0 | 10.4 | 12.9 | 14.4 | 80.8 | 15.1 | 86.2 | 31.0 |
| 2.0 | 2.6 | 2.8 | 3.4 | 9.8 | 18.4 | 10.3 | 83.3 | 43.9 |
| 4.0 | 1.0 | 1.2 | 1.3 | 3.3 | 4.9 | 3.6 | 57.8 | 25.0 |

[1]hydrocodone base content
[2]hydrocodone bitartrate
[3]YYFFI-HC HCl

TABLE 65

Hydrocodone pharmacokinetic parameters following oral administration of hydrocodone bitartrate or YYFFI-HC at escalating doses.

| | Dose[1]/Concentration (ng/ml) | | | | | | | |
|---|---|---|---|---|---|---|---|---|
| | 1 mg/kg | | 2 mg/kg | | 5 mg/kg | | 25 mg/kg | |
| Parameter | HC[2] | YYFFI-HC[3] | HC[2] | YYFFI-HC[3] | HC[2] | YYFFI-HC[3] | HC[2] | YYFFI-HC[3] |
| AUC | 45.1 | 26.3 | 38.2 | 48 | 234 | 47 | 419.0 | 135.0 |
| Percent HC + HM[4] | 100 | 58 | 100 | 126 | 100 | 20 | 100 | 32 |
| Cmax | 114.0 | 20.3 | 60.3 | 35.2 | 628.7 | 26.6 | 408.9 | 41.4 |
| Percent HC + HM[4] | 100 | 18 | 100 | 58 | 100 | 4 | 100 | 10 |

[1]hydrocodone base content
[2]hydrocodone bitartrate
[3]YYFFI-HC HCl
[4]percent relative to parameter following administration of hydrocodone bitartrate

TABLE 66

Mean hydromorphone concentrations following oral administration of hydrocodone bitartrate or YYFFI-HC at escalating doses.

| | Dose[1]/Concentration (ng/ml) | | | | | | | |
|---|---|---|---|---|---|---|---|---|
| | 1 mg/kg | | 2 mg/kg | | 5 mg/kg | | 25 mg/kg | |
| Hours | HC[2] | YYFFI-HC[3] | HC[2] | YYFFI-HC[3] | HC[2] | YYFFI-HC[3] | HC[2] | YYFFI-HC[3] |
| 0 | 0 | 0 | 0 | 0 | 0 | 0 | 0 | 0 |
| 0.1 | 1.95 | 0.27 | 7.61 | 1.13 | 9.03 | 0.49 | 44.36 | 8.00 |
| 0.5 | 3.22 | 2.87 | 18.10 | 8.74 | 13.46 | 10.41 | 62.24 | 10.35 |
| 1.0 | 2.69 | 2.39 | 9.23 | 3.63 | 10.36 | 4.82 | 29.89 | 12.70 |
| 2.0 | 2.11 | 2.24 | 2.31 | 3.41 | 6.68 | 3.17 | 31.62 | 16.22 |
| 4.0 | 0.64 | 1.02 | 0.59 | 0.88 | 2.00 | 1.07 | 40.86 | 8.98 |

[1]hydrocodone base content
[2]hydrocodone bitartrate
[3]YYFFI-HC HCl

TABLE 67

Hydromorphone pharmacokinetic parameters following oral administration of hydrocodone bitartrate or YYFFI-HC at escalating doses.

| | Dose[1]/Concentration (ng/ml) | | | | | | | |
|---|---|---|---|---|---|---|---|---|
| | 1 mg/kg | | 2 mg/kg | | 5 mg/kg | | 25 mg/kg | |
| Parameter | HC[2] | YYFFI-HC[3] | HC[2] | YYFFI-HC[3] | HC[2] | YYFFI-HC[3] | HC[2] | YYFFI-HC[3] |
| AUC | 7.8 | 7.5 | 21.0 | 12.9 | 28.1 | 14.3 | 149 | 49 |
| Percent HM[4] | 100 | 97 | 100 | 61 | 100 | 51 | 100 | 33 |
| Cmax | 3.2 | 2.9 | 18.1 | 8.7 | 13.5 | 10.4 | 44.4 | 16.2 |
| Percent HM[4] | 100 | 89 | 100 | 48 | 100 | 77 | 100 | 37 |

[1]hydrocodone base content
[2]hydrocodone bitartrate
[3]YYFFI-HC HCl
[4]percent relative to parameter following administration of hydrocodone bitartrate

TABLE 68

Mean hydrocodone plus hydromorphone concentrations following oral administration of hydrocodone bitartrate or YYFFI-HC at escalating doses.

| | Dose[1]/Concentration (ng/ml) | | | | | | | |
|---|---|---|---|---|---|---|---|---|
| | 1 mg/kg | | 2 mg/kg | | 5 mg/kg | | 25 mg/kg | |
| Hours | HC[2] | YYFFI-HC[3] | HC[2] | YYFFI-HC[3] | HC[2] | YYFFI-HC[3] | HC[2] | YYFFI-HC[3] |
| 0 | 0 | 0 | 0 | 0 | 0 | 0 | 0 | 0 |
| 0.1 | 116 | 20.6 | 67.9 | 36.3 | 637.7 | 27.1 | 453.3 | 49.4 |
| 0.5 | 17.5 | 20.;8 | 33.7 | 31.7 | 87.8 | 32.9 | 216.1 | 33.7 |

TABLE 68-continued

Mean hydrocodone plus hydromorphone concentrations following oral administration of hydrocodone bitartrate or YYFFI-HC at escalating doses.

| | Dose[1]/Concentration (ng/ml) | | | | | | | |
|---|---|---|---|---|---|---|---|---|
| | 1 mg/kg | | 2 mg/kg | | 5 mg/kg | | 25 mg/kg | |
| Hours | HC[2] | YYFFI-HC[3] | HC[2] | YYFFI-HC[3] | HC[2] | YYFFI-HC[3] | HC[2] | YYFFI-HC[3] |
| 1.0 | 9.7 | 12.8 | 22.1 | 18.0 | 91.2 | 19.9 | 116.1 | 43.7 |
| 2.0 | 4.7 | 5.0 | 5.7 | 13.2 | 25.1 | 13.5 | 114.9 | 60.1 |
| 4.0 | 1.6 | 2.2 | 1.9 | 4.2 | 6.9 | 4.7 | 98.7 | 34.0 |

[1] hydrocodone base content
[2] hydrocodone bitartrate
[3] YYFFI-HC HCl

TABLE 69

Hydrocodone plus hydromorphone pharmacokinetic parameters following oral administration of hydrocodone bitartrate or YYFFI-HC at escalating doses.

| | Dose[1]/Concentration (ng/ml) | | | | | | | |
|---|---|---|---|---|---|---|---|---|
| | 1 mg/kg | | 2 mg/kg | | 5 mg/kg | | 25 mg/kg | |
| Parameter | HC[2] | YYFFI-HC[3] | HC[2] | YYFFI-HC[3] | HC[2] | YYFFI-HC[3] | HC[2] | YYFFI-HC[3] |
| AUC | 53 | 34 | 59 | 61 | 312 | 62 | 569 | 193 |
| Percent HC[4] | 100 | 64 | 100 | 103 | 100 | 20 | 100 | 34 |
| Cmax | 116 | 20.8 | 67.9 | 36.3 | 638 | 32.9 | 453 | 49.4 |
| Percent HC[4] | 100 | 18 | 100 | 53 | 100 | 5 | 100 | 11 |

[1] hydrocodone base content
[2] hydrocodone bitartrate
[3] YYFFI-HC HCl
[4] percent relative to parameter following administration of hydrocodone bitartrate

TABLE 70

Mean hydrocodone plus hydromorphone, hydrocodone, and hydromorphone, concentrations following intravenous administration of hydrocodone bitartrate or YYFFI-HC at 1 mg/kg (hydrocodone base content).

| | Concentration (ng/ml) | | | | | |
|---|---|---|---|---|---|---|
| | HC + HM | | HC | | HM | |
| Hours | HC[1] | YYFFI-HC[2] | HC[1] | YYFFI-HC[2] | HC[1] | YYFFI-HC[2] |
| 0 | 0 | 0 | 0 | 0 | 0 | 0 |
| 0.1 | 208.9 | 22.6 | 42.97 | 8.75 | 251.9 | 31.3 |
| 0.5 | 83.7 | 13.5 | 16.09 | 1.44 | 99.8 | 14.9 |
| 1.0 | 38.4 | 13.0 | 3.65 | 0.92 | 42.1 | 13.9 |
| 2.0 | 12.4 | 13.1 | 1.77 | 0.41 | 14.2 | 13.5 |
| 4.0 | 2.9 | 8.5 | 0.70 | 0.33 | 3.6 | 8.8 |

[1] hydrocodone bitartrate
[2] YYFFI-HC HCl

TABLE 71

Hydrocodone plus hydromorphone, hydrocodone, and hydromorphone pharmacokinetic parameters following intravenous administration of hydrocodone bitartrate or YFFI-HC at 1 mg/kg (hydrocodone base content).

| | Concentration (ng/ml) | | | | | |
|---|---|---|---|---|---|---|
| | HC + HM | | HC | | HM | |
| Parameter | HC[1] | YYFFI-HC[2] | HC[1] | YYFFI-HC[2] | HC[1] | YYFFI-HC[2] |
| AUC | 140.0 | 50.0 | 24.10 | 4.50 | 164 | 54 |
| Percent[1] | 100 | 36 | 100 | 19 | 100 | 33 |

TABLE 71-continued

Hydrocodone plus hydromorphone, hydrocodone, and hydromorphone pharmacokinetic parameters following intravenous administration of hydrocodone bitartrate or YFFI-HC at 1 mg/kg (hydrocodone base content).

| | Concentration (ng/ml) | | | | | |
|---|---|---|---|---|---|---|
| | HC + HM | | HC | | HM | |
| Parameter | HC[1] | YYFFI-HC[2] | HC[1] | YYFFI-HC[2] | HC[1] | YYFFI-HC[2] |
| Cmax | 208.9 | 22.6 | 43.0 | 8.7 | 252 | 31.3 |
| Percent[1] | 100 | 10.8 | 100 | 20.2 | 100 | 12.4 |

[1]hydrocodone bitartrate
[2]YYFFI-HC HCl
[3]percent relative to parameter following administration of hydrocodone bitartrate

TABLE 72

Mean hydrocodone plus hydromorphone, hydrocodone, and hydromorphone, concentrations following intranasal administration of hydrocodone bitartrate or YYFFI-HC at 1 mg/kg.

| | Concentration (ng/ml) | | | | | |
|---|---|---|---|---|---|---|
| | HC + HM | | HC | | HM | |
| Minutes | HC[1] | YYFFI-HC[2] | HC[1] | YYFFI-HC[2] | HC[1] | YYFFI-HC[2] |
| 0 | 0 | 0 | 0 | 0 | 0 | 0 |
| 5 | 446 | 28 | 441 | 28 | 4.4 | bql[3] |
| 15 | 553 | 27 | 543 | 27 | 10.6 | bql[4] |
| 30 | 244 | 16 | 227 | 16 | 17.1 | bql[5] |
| 60 | 103 | 21 | 96 | 21 | 7.2 | bql[6] |

[1]hydrocodone bitartrate
[2]YYFFI-HC HCl

TABLE 73

Hydrocodone plus hydromorphone, hydrocodone, and hydromorphone pharmacokinetic parameters following intravenous administration of hydrocodone bitartrate or YYFFI-HC at 1 mg/kg (hydrocodone base content).

| | Concentration (ng/ml) | | | | | |
|---|---|---|---|---|---|---|
| | HC + HM | | HC | | HM | |
| Parameter | HC[1] | YYFFI-HC[2] | HC[1] | YYFFI-HC[2] | HC[1] | YYFFI-HC[2] |
| AUC | 288.0 | 20.0 | 74.70 | 10.30 | 7.0 | NA |
| Percent[3] | 100 | 6.9 | 100 | 13.8 | 100 | NA |
| Cmax | 553.0 | 28.0 | 543.0 | 28.0 | 17 | NA |
| Percent[3] | 100 | 5.1 | 100 | 5.2 | 100 | NA |

[1]hydrocodone bitartrate
[2]YYFFI-HC HCl
[3]percent relative to parameter following administration of hydrocodone bitartrate Summary of in vivo testing of abuse resistant hydrocodone conjugates. In vivo testing of hydrocodone conjugates demonstrates for instance decreased intranasal analgesic response, decreased intravenous analgesic response, decreased subcutaneous analgesic response, decreased oral $C_{max}$, decreased intranasal bioavailability (AUC and $C_{max}$), and decreased intravenous bioavailability (AUC and $C_{max}$) of hydrocodone conjugates and is described in further detail below.

Example 78

Decreased Intranasal Analgesic Response to Hydrocodone Conjugates

Male Sprague-Dawley rats were dosed by placing 0.02 ml of water containing hydrocodone conjugate or hydrocodone bitartrate into the nasal flares. All doses contained equivalent amounts of hydrocodone base. The time (seconds) until paw lick latency was used a measure of the analgesic effect. Rats were habituated to determine baseline response. Hot plate tests were conducted at 55° C. A limit of 45 seconds was used in all testing to avoid tissue damage. All animals were humanely sacrificed following the end of testing. The paw lick latency (analgesic effect)-time curves shown in FIGS. 61 and 63 indicate the decrease in analgesia produced by the hydrocodone conjugates as compared to an equimolar (hydrocodone base) dose of hydrocodone bitartrate. The analgesic response as determined by the hot plate test is a pharmacodynamic measurement of the pharmacological effect of hydrocodone. These examples illustrate that hydrocodone conjugates decrease the analgesic effect by the intranasal route of administration as compared to hydrocodone bitartrate.

Example 79

Decreased Intravenous Analgesic Response to Hydrocodone Conjugates

Male Sprague-Dawley rats were dosed by tail vein injection of 0.1 ml of water containing hydrocodone conjugates or hydrocodone bitartrate. All doses contained equivalent amounts of hydrocodone base. The time (seconds) until paw lick latency was used a measure of the analgesic effect. Rats were habituated to determine baseline response. Hot plate tests were conducted at 55° C. A limit of 45 seconds was used in all testing to avoid tissue damage. All animals were humanely sacrificed following the end of testing. The paw lick latency (analgesic effect)-time curve shown in FIG. 16 indicates the decrease in analgesia produced by a hydrocodone conjugate as compared to an equimolar (hydrocodone base) dose of hydrocodone bitartrate. The analgesic response as determined by the hot plate test is a pharmacodynamic measurement of the pharmacological effect of hydrocodone. This example illustrates that a hydrocodone conjugate decreased the analgesic effect by the intravenous route of administration as compared to hydrocodone bitartrate.

Example 80

Decreased Subcutaneous Analgesic Response to Hydrocodone Conjugates

Male Sprague-Dawley rats were dosed by subcutaneous injection of 0.1 ml of water containing hydrocodone conjugates or hydrocodone bitartrate. All doses contained equivalent amounts of hydrocodone base. The time (seconds) until paw lick latency was used a measure of the analgesic effect. Rats were habituated to determine baseline response. Hot plate tests were conducted at 55° C. A limit of 45 seconds was used in all testing to avoid tissue damage. All animals were humanely sacrificed following the end of testing. The paw lick latency (analgesic effect)-time curve shown in FIG. 11 indicates the decrease in analgesia produced by a hydrocodone conjugate as compared to an equimolar (hydrocodone base) dose of hydrocodone bitartrate. The analgesic response as determined by the hot plate test is a pharmacodynamic measurement of the pharmacological effect of hydrocodone. This example illustrates that a hydrocodone conjugate decreased the analgesic effect by the subcutaneous route of administration as compared to hydrocodone bitartrate.

Example 81

Decreased Oral $C_{max}$ of Hydrocodone Conjugates

Male Sprague-Dawley rats were provided water ad libitum, fasted overnight and dosed by oral gavage with hydrocodone conjugates or hydrocodone bitartrate. All doses contained equivalent amounts of hydrocodone base. Plasma hydrocodone concentrations were measured by ELISA (Hydromorphone, 106619-1, Neogen, Corporation, Lexington, Ky.). The assay is specific for hydromorphone (the major hydrocodone metabolite, 100% reactive) and hydrocodone (62.5% reactive). The plasma concentration-time curves of various hydrocodone conjugates vs. hydrocodone bitartrate are shown in FIGS. 2, 25, 33, and 34. These examples illustrate that hydrocodone conjugates decrease the peak level ($C_{max}$) of hydrocodone plus hydromorphone as compared to that produced by equimolar (hydrocodone base) doses of hydrocodone bitartrate when given by the oral route of administration.

Example 82

Decreased Intranasal Bioavailability (AVC and $C_{max}$) Hydrocodone Conjugates Male Sprague-Dawley rats were provided water ad libitum and doses were administered by placing 0.02 ml of water containing hydrocodone conjugates or hydrocodone bitartrate into the nasal flares. All doses contained equivalent amounts of hydrocodone base. Plasma hydrocodone concentrations were measured by ELISA (Hydromorphone, 106619-1, Neogen, Corporation, Lexington, Ky.). The assay is specific for hydromorphone (the major hydrocodone metabolite, 100% reactive) and hydrocodone (62.5% reactive). The plasma concentration-time curves of various hydrocodone conjugates vs. hydrocodone bitartrate are shown in FIGS. 4, 9, 13-15, 18-22, 24, 26-34. These examples illustrate that hydrocodone conjugates decrease the peak level ($C_{max}$) and total absorption (AVC) of hydrocodone plus hydromorphone as compared to those produced by equimolar (hydrocodone base) doses of hydrocodone bitartrate when given by the intranasal route of administration.

Example 83

Figure 23:
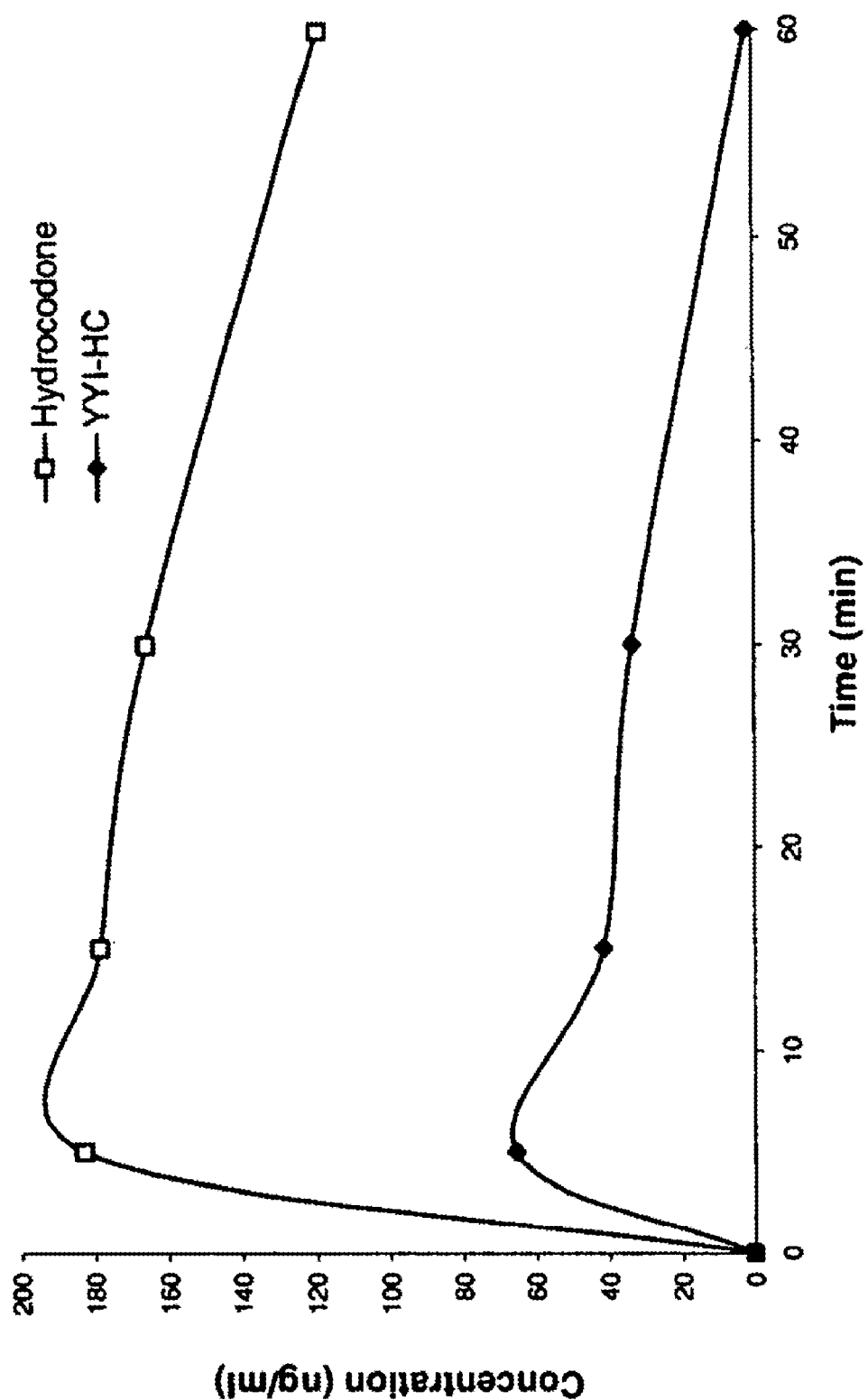
FIG. 23. Intravenous bioavailability of an abuse-resistant hydrocodone tri-peptide conjugate, measured as free hydrocodone.
Figure 24:
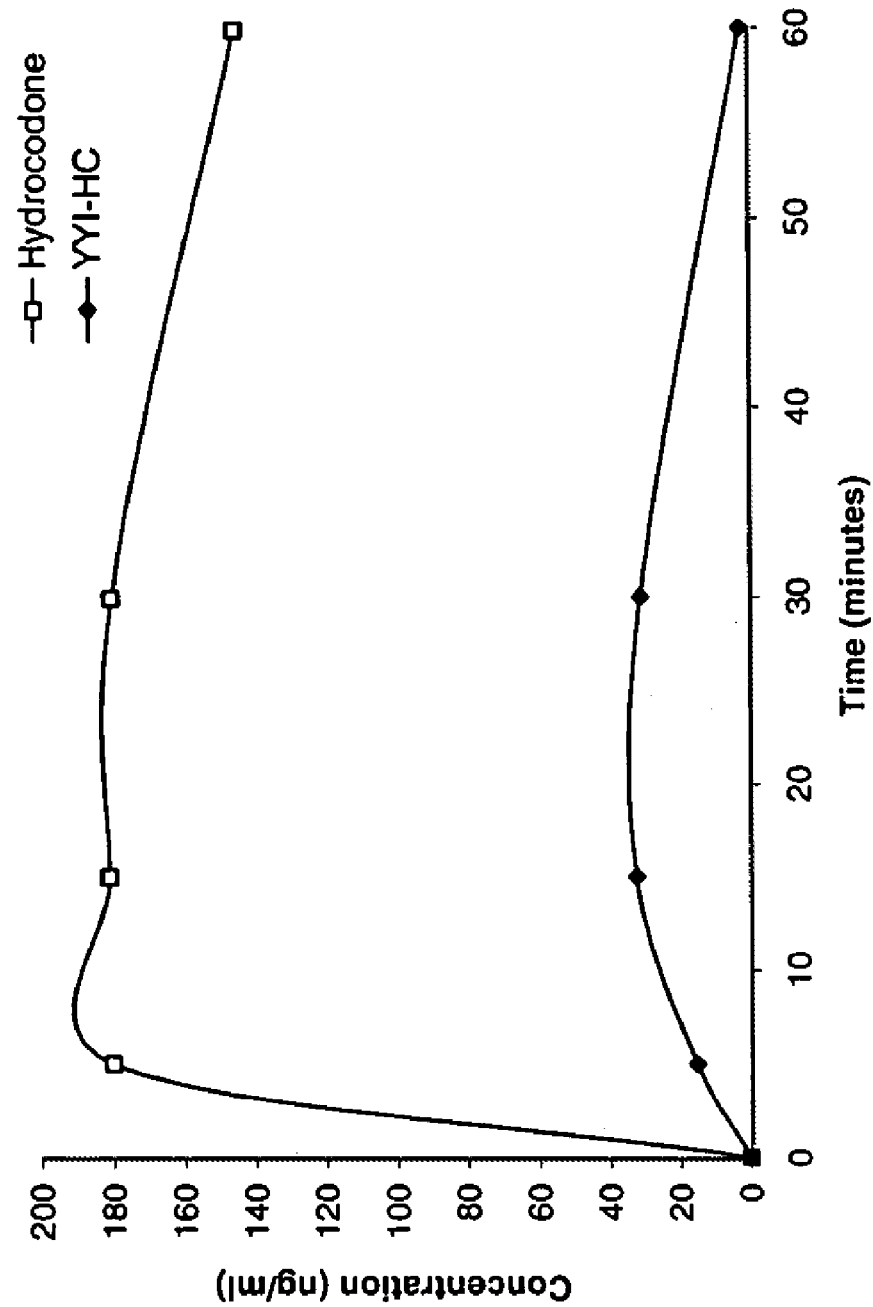
FIG. 24. Intranasal bioavailability of an abuse-resistant hydrocodone tri-peptide conjugate, measured as free hydrocodone.
Figure 25:
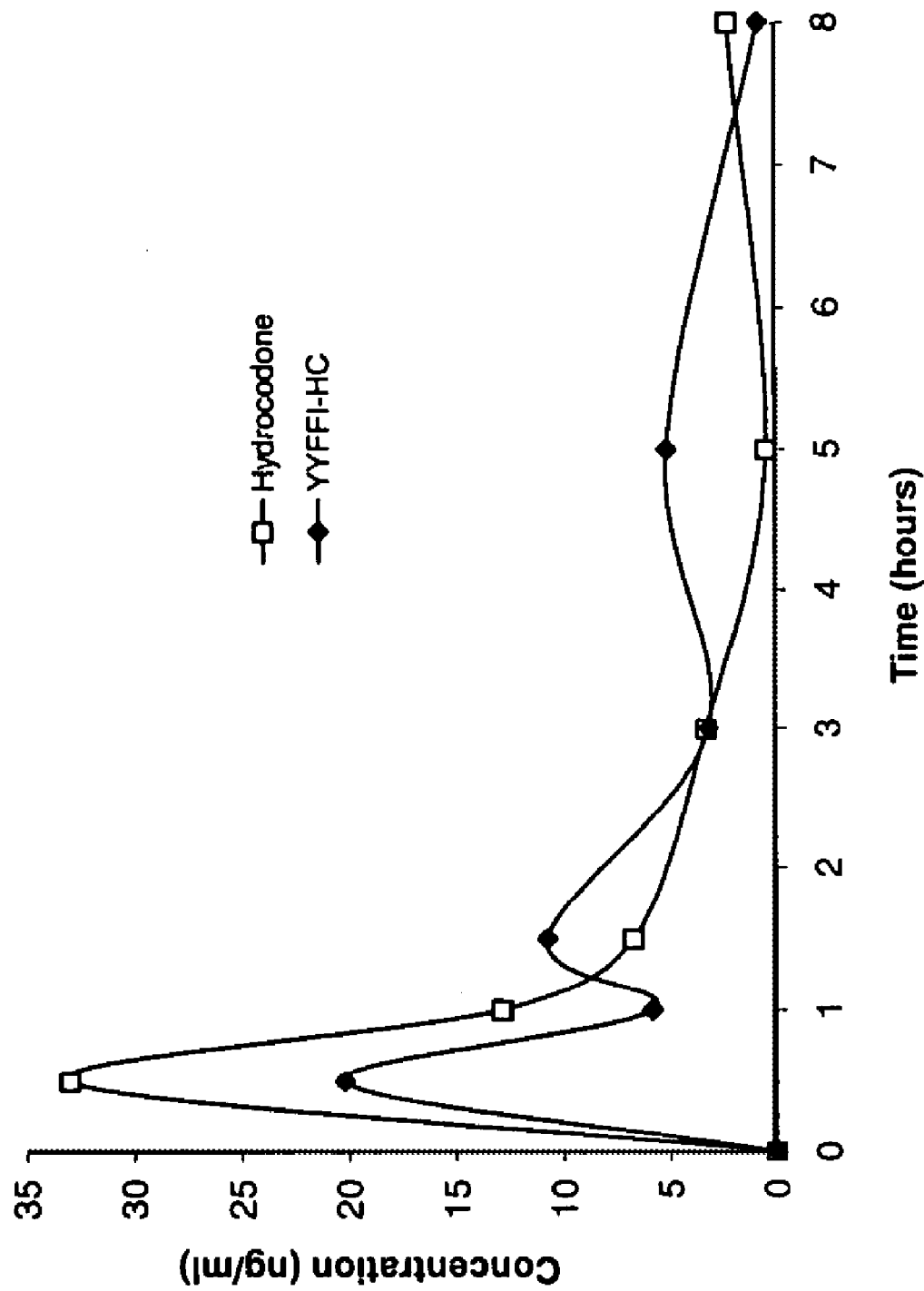
FIG. 25. Oral bioavailability of an abuse-resistant hydrocodone penta-peptide conjugate, measured as free hydrocodone.
Figure 26:
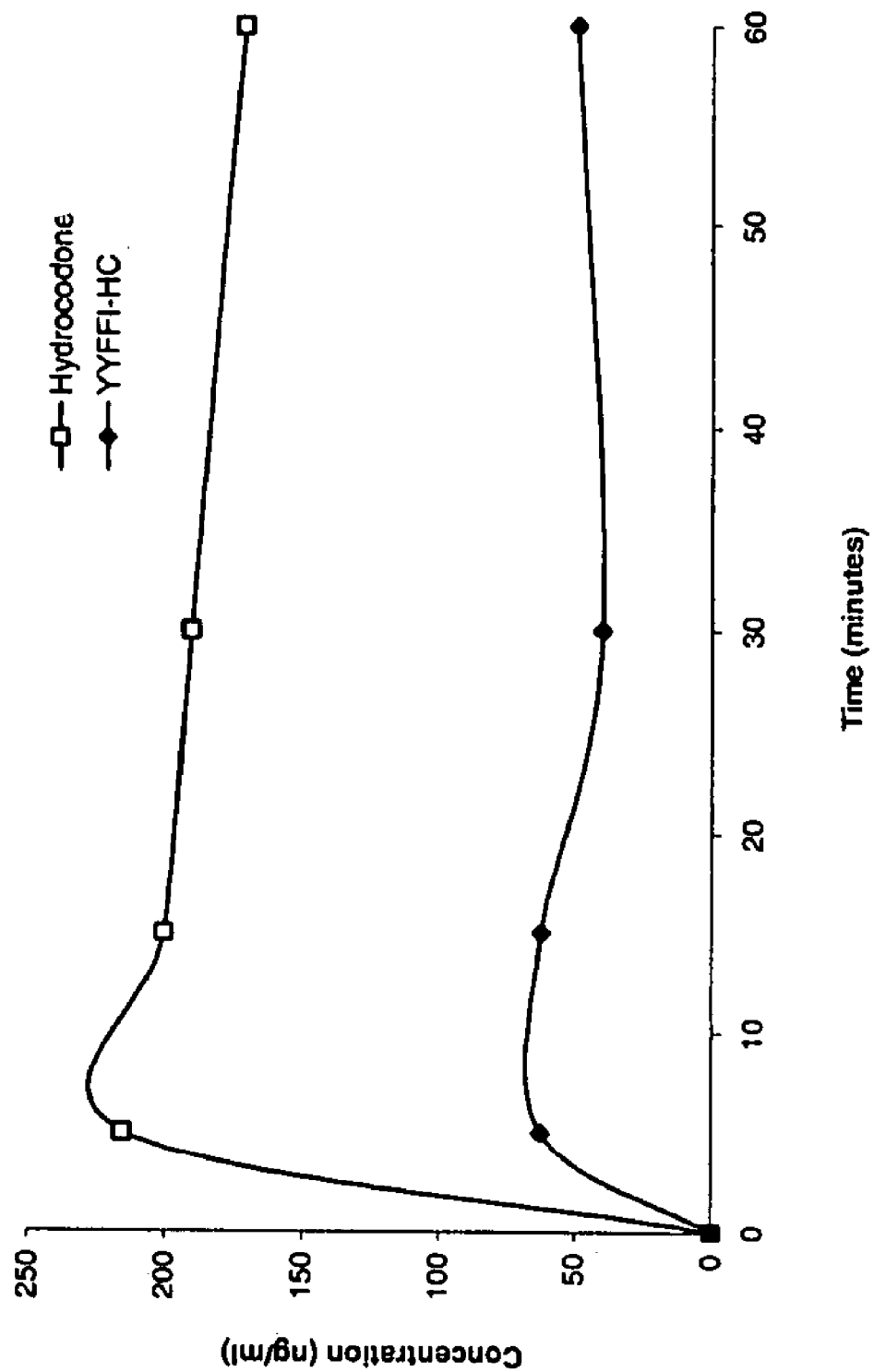
FIG. 26. Intranasal bioavailability of an abuse-resistant hydrocodone tri-penta-peptide conjugate, measured as free hydrocodone.
Figure 27:
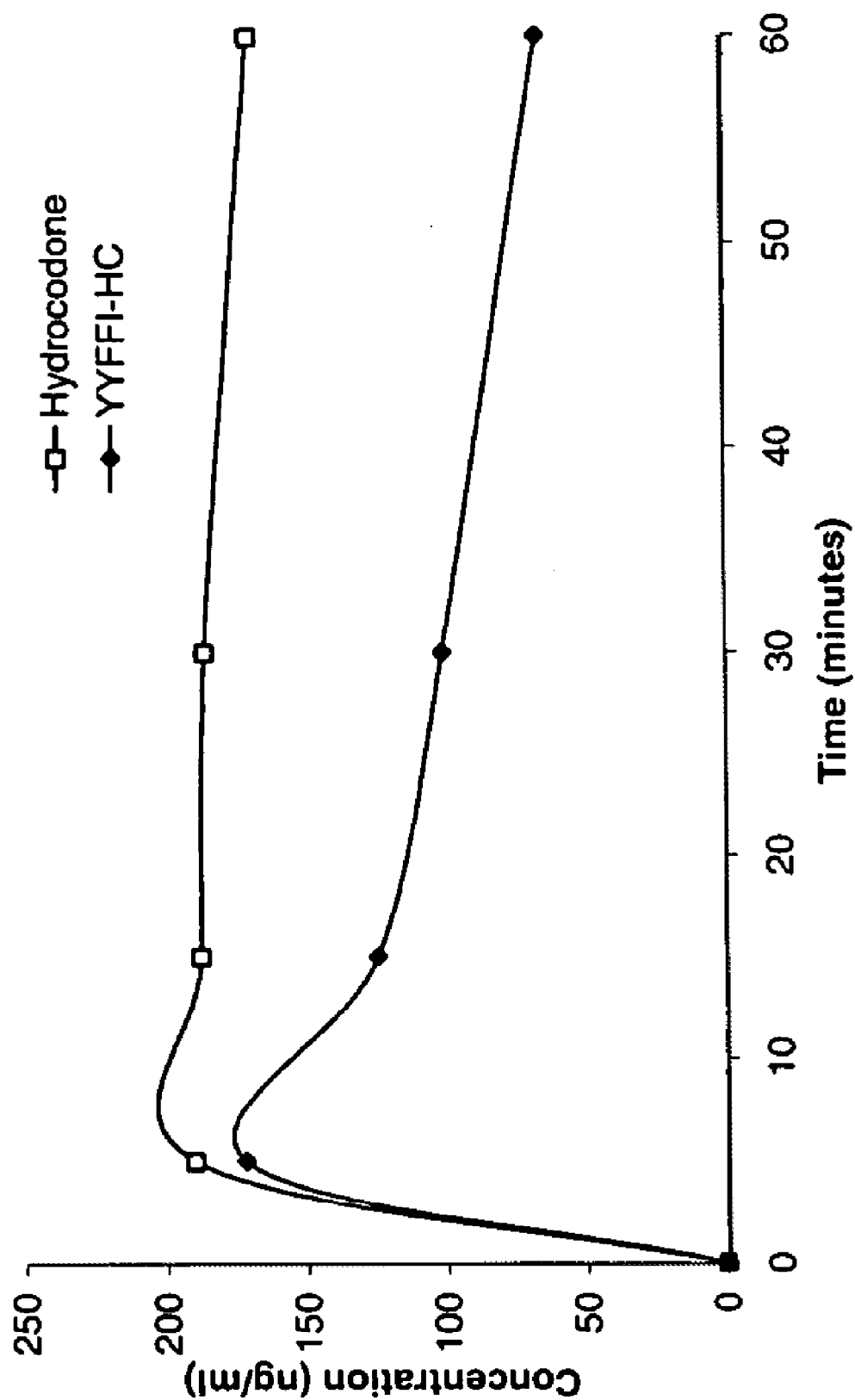
FIG. 27. Intranasal bioavailability of an abuse-resistant hydrocodone penta-peptide conjugate, measured as free hydrocodone.
Figure 28:
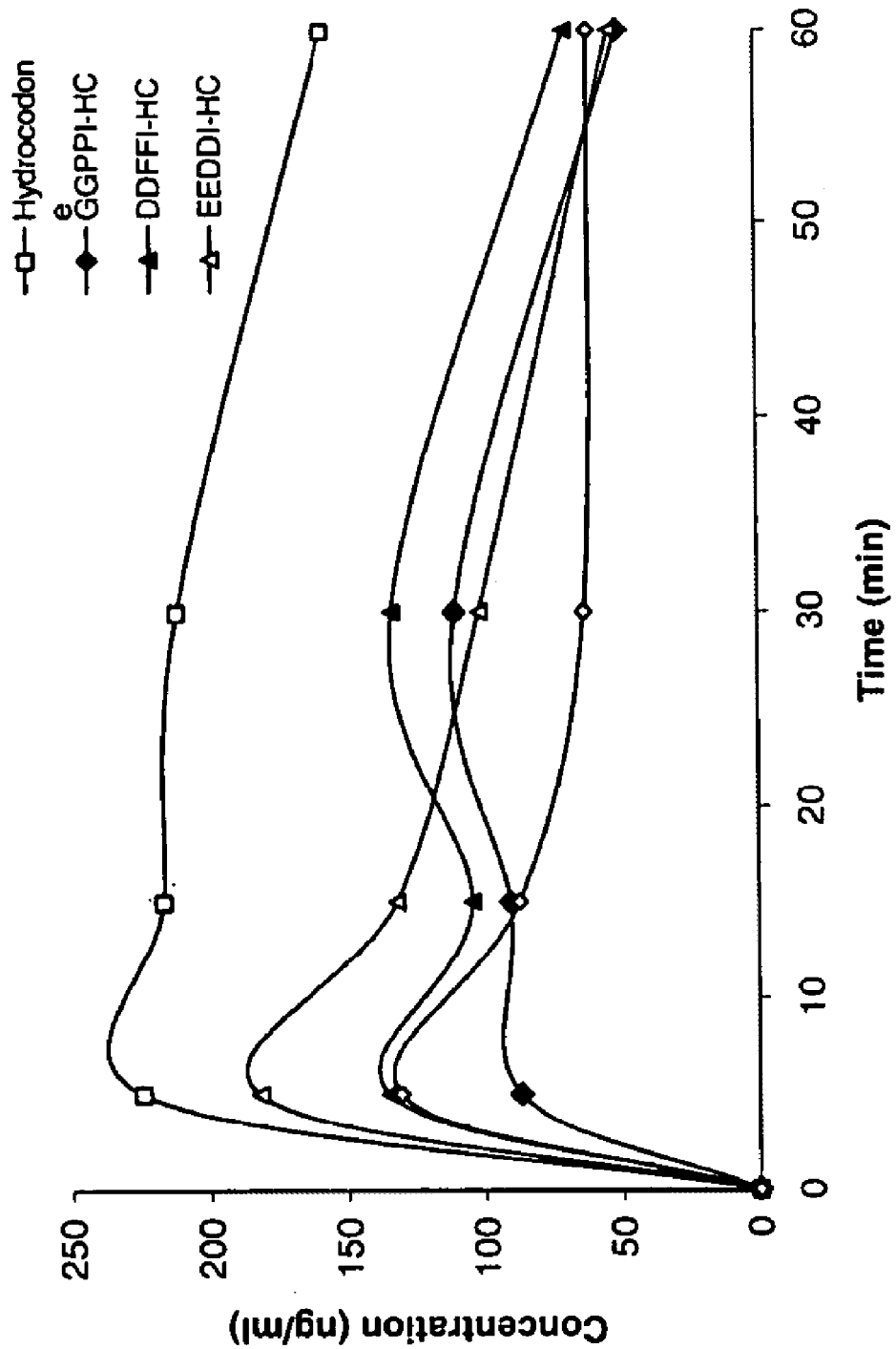
FIG. 28. Intranasal bioavailability of abuse-resistant hydrocodone penta-peptide conjugates, measured as free hydrocodone.
Figure 29:
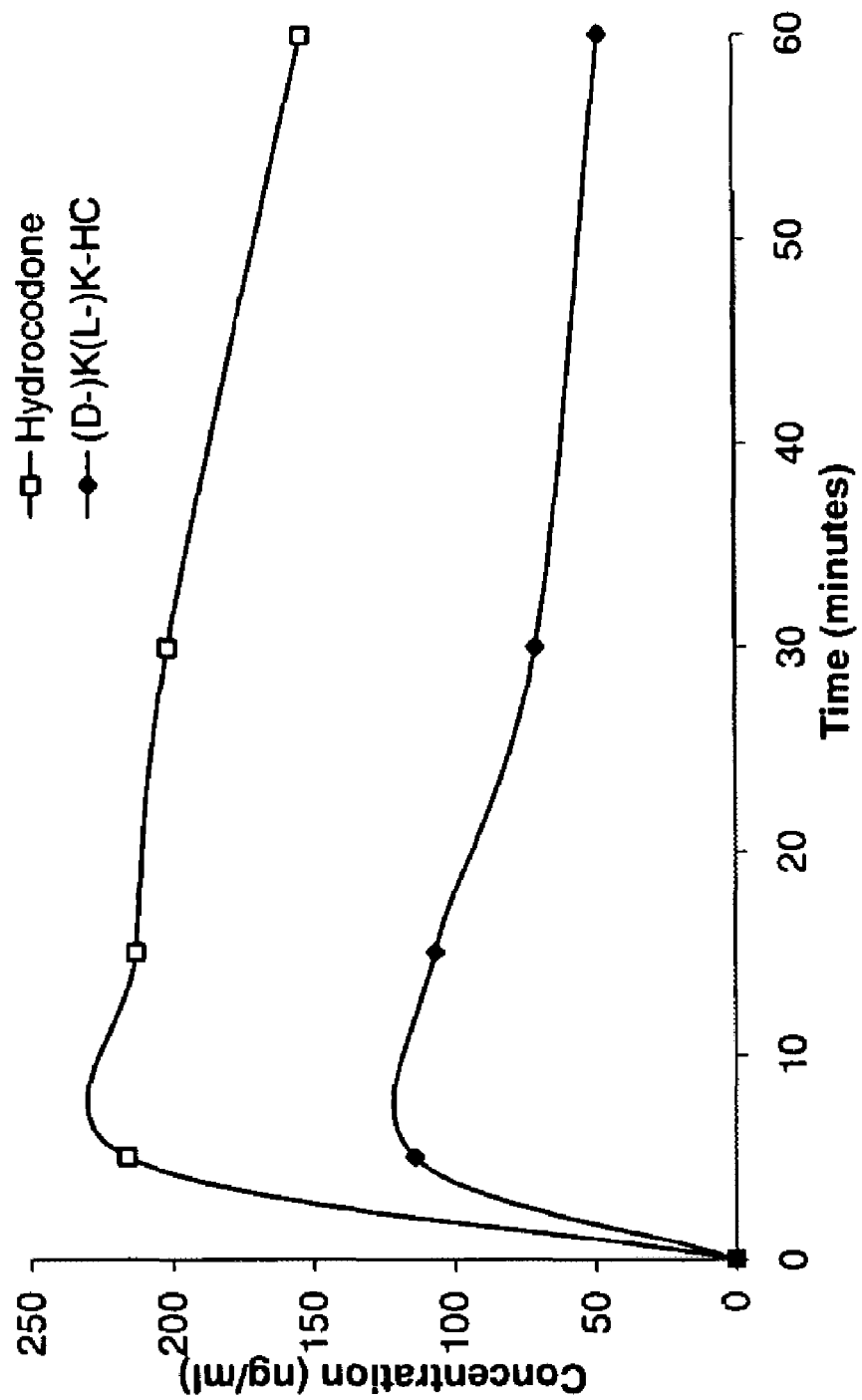
FIG. 29. Intranasal bioavailability of an abuse-resistant hydrocodone tri-peptide conjugate containing D- and L-isomers, measured as free hydrocodone.
Figure 30:
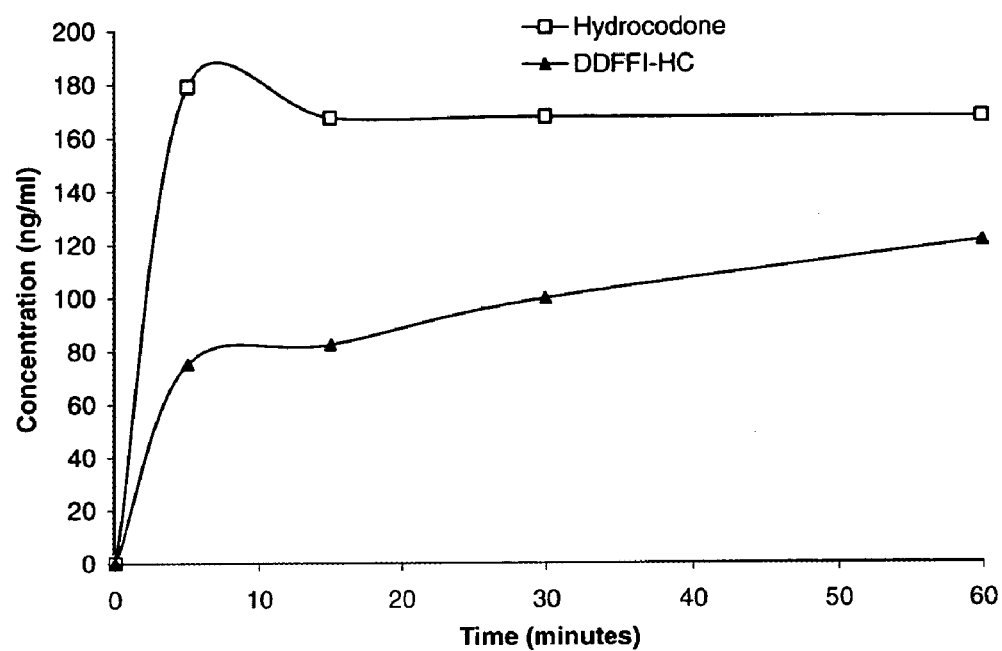
FIG. 30. Intranasal bioavailability of an abuse-resistant hydrocodone penta-peptide conjugate, measured as free hydrocodone.
Figure 31:
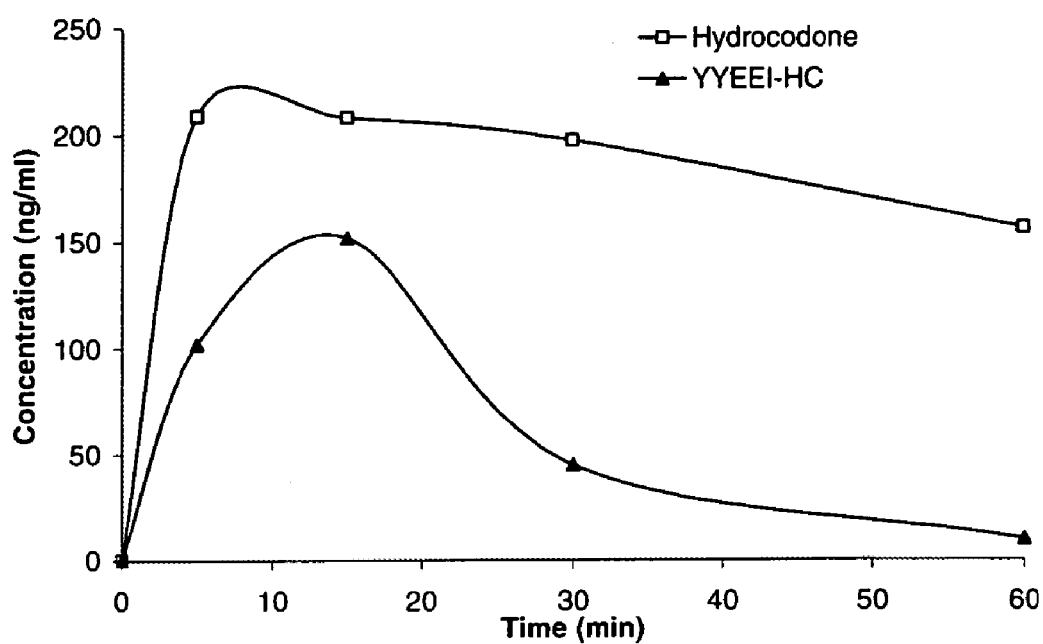
FIG. 31. Intranasal bioavailability of an abuse-resistant hydrocodone penta-peptide conjugate, measured as free hydrocodone.
Figure 32:
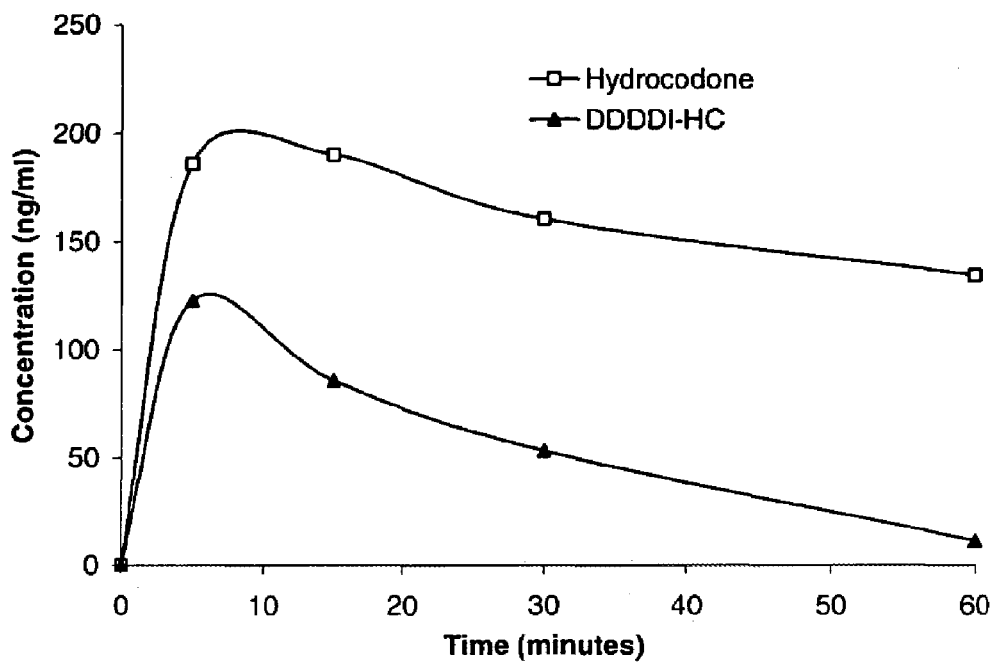
FIG. 32. Intranasal bioavailability of an abuse-resistant hydrocodone penta-peptide conjugate, measured as free hydrocodone.
Figure 33:
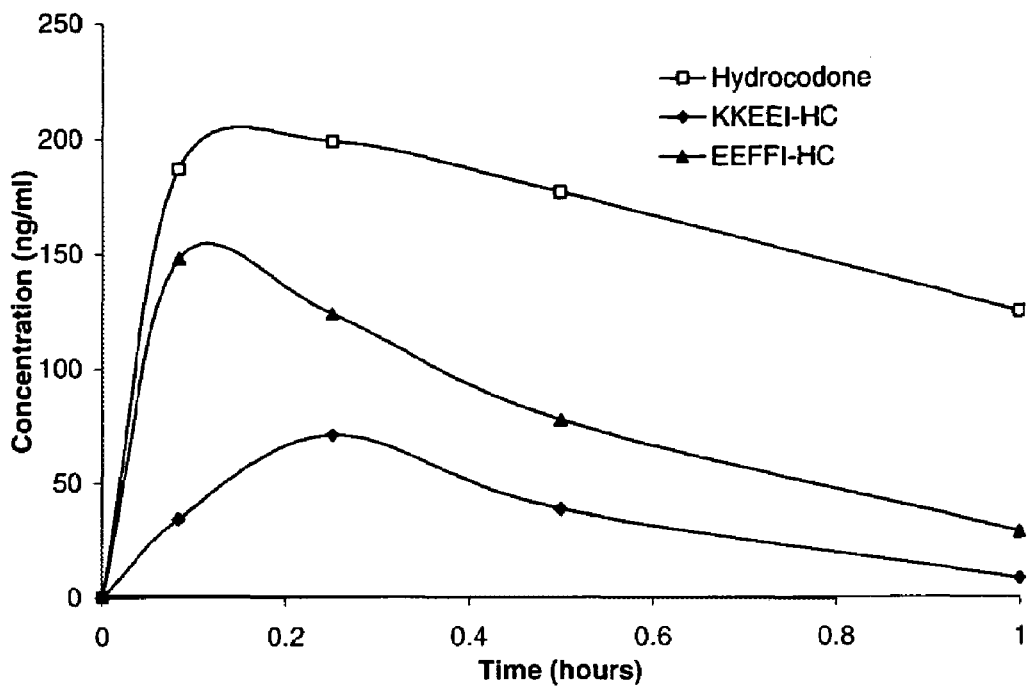
FIG. 33. Intranasal bioavailability of abuse-resistant hydrocodone penta-peptide conjugates, measured as free hydrocodone.
Figure 34:
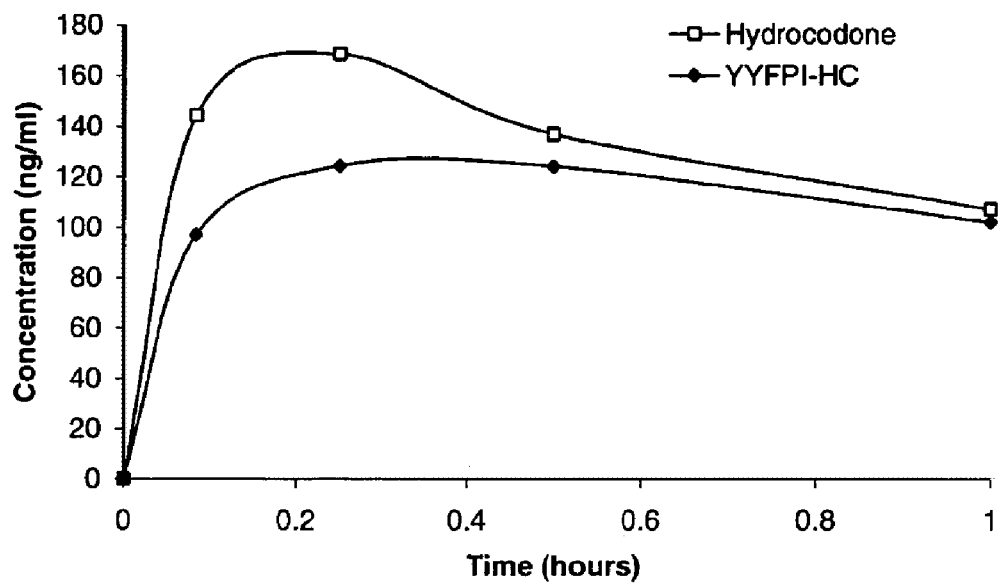
FIG. 34. Intranasal bioavailability of an abuse-resistant hydrocodone penta-peptide conjugate, measured as free hydrocodone.

Decreased Intravenous Bioavailability (AVUC and $C_{max}$) Hydrocodone Conjugates Male Sprague-Dawley rats were provided water ad libitum and doses were administered by intravenous tail vein injection of 0.1 ml of water containing hydrocodone conjugates or hydrocodone bitartrate. All doses contained equivalent amounts of d-amphetamine base. Plasma hydrocodone concentrations were measured by ELISA (Hydromorphone, 106619-1, Neogen, Corporation, Lexington, Ky.). The assay is specific for hydromorphone (the major hydrocodone metabolite, 100% reactive) and hydrocodone (62.5% reactive). The plasma concentration-time curves of a hydrocodone conjugate vs. hydrocodone bitartrate is shown in FIG. 23. This example illustrates that a dose of hydrocodone conjugate decreases the peak level ($C_{max}$) and total absorption (AVC) of hydrocodone plus hydromorphone as compared to those produced by an equimolar (hydrocodone base) dose of hydrocodone bitartrate when given by the intranasal route of administration.

Examples 84 through 118 Oxycodone

Examples 84 through 118 illustrate the compounds and compositions for reducing the potential for overdose and abuse while maintaining therapeutic value wherein the active agent oxycodone (OC) is covalently attached to a chemical moiety. The compound which is di-substituted at the 6 and 14 position of oxycodone is termed PPL(2)-OC.

Oral, intranasal, and intravenous bioavailability studies of oxycodone and oxycodone conjugates were conducted in male Sprague-Dawley rats. Doses of oxycodone hydrochloride and oxycodone conjugates containing equivalent amounts of oxycodone were administered in deionized water. Oral administration was in 0.5 ml by gavage needle. Intranasal doses were administered by placing 20 microliters into the nasal flares of rats anesthetized with isoflurane. Intravenous administration was in 0.1 ml by tail vein injection. Plasma was collected by retroorbital sinus puncture under isoflurane anesthesia. Oxycodone and oxymorphone (major active metabolite) concentrations were determined by LC/MS/MS.

The below examples are illustrative only and PPL(2)-OC is not meant to be limiting. As such, synthesis and attachment of oxycodone may be accomplished for instance view the following exemplary methods. Additionally, Examples 84 through 96 describe methods for attaching amino acid or various length peptides to oxycodone.

Oxycodone Synthetic Examples

Example 84

Synthesis of [Boc-X]$_2$-Oxycodone

To a solution of oxycodone free base (2.04 g, 6.47 mmol) in THF (~35 ml) was added LiN(TMS)$_2$ (19.41 ml, 19.41 mmol) and stirred for ~30 mins. To this was added solid Boc-X-OSu (X=amino acid, 21 mmol) at one time and the reaction mixture was stirred at room temperature overnight. The solution was neutralized with 1N HCl and the THF was removed under reduced pressure. The residue was diluted with EtOAc (200 mL), satd. NaHCO$_3$ (150 mL) was added and stirred for 1 h. EtOAc part was washed with NaHCO3 and brine. Dried over Na$_2$SO$_4$ and evaporated to dryness. Compound was obtained by purification over silica gel column (30% EtOAc/Hexane).

Deprotection of [Boc-X]$_2$-Oxycodone:

General method of deprotection: The above compound was reacted with 4N HCl/dioxane (25 mL/gm) at room temperature for 4 h. Solvent was evaporated and dried over vacuum to give X$_2$-Oxycodone.3HCl.

Examples:
1. (Val)$_2$-Oxycodone
2. (Ile)$_2$-Oxycodone
3. (Leu)$_2$-Oxycodone
4. (Lys)$_2$-Oxycodone
5. (Phe)$_2$-Oxycodone
6. (Glu)$_2$-Oxycodone

Example 85

Synthesis of [Boc-Z—Y—X]$_2$-Oxycodone [X, Y and Z are Amino Acids]

To a solution of X$_2$-Oxycodone.3HCl (1 mmol) in DMF (15-20 mL) were added NMM (10-12 eqv) and Boc-Z—Y-OSu (2.6 eqv). The reaction mixture was stirred at RT overnight. Solvent was evaporated under reduced pressure. To the residue was added satd. NaHCO$_3$ (~30 mL) and stir for 1-2 h. The white/pale yellow residue was filtered, thoroughly washed with water and dried in the vacuum oven at room temperature.

Deprotection of [Boc-X—Y—Z]$_2$-Oxycodone:

Deprotection is same as general method mentioned above. For 100-200 mg of tripeptide derivative 10-15 ml 4N HCl/dioxane is used. Deprotection is done overnight to give [X—Y—Z]$_2$-Oxycodone.3HCl.

Deprotection of Tripeptide Derivatives Containing Threonine and Serine:

First the tripeptide derivatives are dissolved 95% TFA (5% water) and stirred for 4 h at room temperature. Solvent is evaporated, the residue is co-evaporated with toluene twice and dried over vacuum. 4N HCl/dioxane is added and stirred overnight. Residue was evaporated to dryness and dried over vacuum.

Examples:
1. (Glu-Asp-Val)$_2$-Oxycodone
2. (Ile-Tyr-Val)$_2$-Oxycodone
3. (Tyr-Pro-Val)$_2$-Oxycodone
4. (Gly-Leu-Val)$_2$-Oxycodone
5. (Phe-Val-Val)$_2$-Oxycodone
6. (Ser-Thr-Val)$_2$-Oxycodone
7. (Lys-Ser-Val)$_2$-Oxycodone

Example 86

Synthesis of [Boc-X]-O$^6$-Oxycodone

To a solution of oxycodone (10 mmol) in THF (50 mL) was added LiN(TMS)$_2$ (10.5 mmol) at 0oC. After 20 mins was added Boc-X-OSu (11 mmol) and then the reaction mixture was stirred at room temperature overnight. The solution was cooled down to 0oC and neutralized with 1N HCl. The organic solvent was evaporated and to the residue were added EtOAc (200 mL) and saturated aq. NaHCO$_3$ (150 mL) and stirred for 1 h. The EtOAc portion was washed with water, brine, dried over Na$_2$SO$_4$ and evaporated to dryness. The residue was purified over silica gel (70% EtOAc-Hexane) to give the title compound.

Deprotection of Boc-X—O$^6$-Oxycodone:

A solution of [Boc-X]-Oxycodone in 4N HCl/dioxane (10 ml/mmol) was stirred at room temperature 4 h. Solvent was evaporated under reduced pressure and the residue was dried under vacuum to give X—O$^6$-Oxycodone.2HCl.

Examples:
1. Val-Oxycodone
2. Ile-Oxycodone
3. Leu-Oxycodone

Example 87

Synthesis of Boc-Z—Y—X—O$^6$-Oxycodone

To a solution of X—O$^6$-Oxycodone.2HCl (1 mmol) in DMF were added NMM (10 mmol) and Boc-Z—Y-OSu (1.2 mmol). The reaction mixture was stirred at room temperature overnight. Solvent was evaporated to the residue was added saturated NaHCO$_3$ solution and stirred for 1 h. The precipitate was filtered, thoroughly washed with water and dried to give the title compound.

Deprotection of Boc-Z—Y—X—O$^6$-Oxycodone:

Deprotection is same as general method mentioned above to give Z—Y—X—O$^6$-Oxycodone.2HCl.

Examples:
1. Pro-Glu-Val-Oxycodone
2. Glu-Leu-Val-Oxycodone
3. Glu-Tyr-Val-Oxycodone

Example 88

Synthesis of Boc-X—O$^6$-Oxycodone-O$^{14}$—Ac

To a solution of [Boc-X]-O$^6$-Oxycodone (1 mmol) in pyridine (15 mL) were added DMAP (75 mg), triethyl amine (1.5 mmol) and Ac$_2$O (8 mmol). The reaction mixture was heated at 65° C. for 3 days. The dark brown solution was cooled down to room temperature and MeOH (5 mL) was added and stirred for 1 h. The solvent was evaporated, co-evaporated with toluene. The residue was taken in EtOAc (50 mL), washed with satd. NaHCO$_3$, brine, dried over Na$_2$SO$_4$ and evaporated to dryness. The residue was purified over silica gel to give the title compound.

Example 89

Synthesis of Boc-X—O$^6$-Oxycodone-O$^{14}$—CO$_2$Et

To a solution of [Boc-X]-O$^6$-Oxycodone (1 mmol) in THF (10 mL) was added LiN(TMS)$_2$ (1.05 mmol) at 0° C. After 20 mins, ethyl chloroformate (1.1 mmol) was added and reaction mixture was slowly brought to room temperature and stirred at room temperature for 1 h. The solution was poured into 2% aqueous acetic acid (ice cold) and extracted with EtOAc. The EtOAc part was washed with water, aq. NaHCO$_3$, brine, dried over Na$_2$SO$_4$ and evaporated to dryness. The residue was purified over silica gel to give the title compound.

Deprotection of Boc-X—O$^6$-Oxycodone-O$^{14}$—R(R=Ac, CO$_2$Et):

Deprotection is same as general method mentioned above to give X—O$^6$-Oxycodone-O$^{14}$—R.2HCl (R=Ac, CO$_2$Et).

Examples:
1. (Val)-Oxycodone-(CO$_2$Et)
2. (Val)-Oxycodone-(OAc)

Example 90

Synthesis of Boc-Z—Y—X—O$^6$-Oxycodone-O$^{14}$—R(R=Ac, CO$_2$Et)

To a solution of X—O$^6$-Oxycodone-O$^{14}$—R.2HCl (1 mmol, R=Ac, CO$_2$Et) in DMF were added NMM (10 mmol) and Boc-Z—Y-OSu (1.2 mmol). The reaction mixture was stirred at room temperature overnight. Solvent was evaporated to the residue was added saturated NaHCO$_3$ solution and stirred for 1 h. The precipitate was filtered, thoroughly washed with water and dried to give the title compound.

Deprotection of Boc-Z—Y—X—O$^6$-Oxycodone-O$^{14}$—R (R=Ac, CO$_2$Et):

Deprotection is same as general method mentioned above. Deprotection is done overnight to give Z—Y—X—O$^6$-Oxycodone-O$^{14}$—R.2HCl.

Examples:
1. (Ile-Tyr-Val)-Oxycodone-(CO$_2$Et)
2. (Ile-Tyr-Val)-Oxycodone-(OAc)

Example 91

Synthesis of Boc-X—O$^6$-Oxycodone-O$^{14}$—Y—Boc

To a solution of Boc-X—Oxycodone (1 mmol) in THF (10 mL) was added LiN(TMS)$_2$ (1.1 mmol) at 0° C. and the solution was stirred for 30 mins then Boc-Y-OSu (1.25 mmol) was added. The reaction mixture was stirred at room temperature overnight. The solution was cooled down to 0° C., neutralized with 1N HCl and the organic part was evaporated. To the residue were added EtOAc (50 mL) and satd. NaHCO$_3$ (50 ml), stirred for 1 h. The organic part was washed with water, brine, dried over Na$_2$SO$_4$ and evaporated to dryness. The residue was purified over silica gel to give the title compound.

Deprotection of Boc-X—O$^6$-Oxycodone-O$^{14}$—Y—Boc:

Boc-X—O$^6$-Oxycodone-O$^{14}$—Y—Boc was deprotected following the general method for deprotection mentioned above to give X—O$^6$-Oxycodone-O$^{14}$—Y.3HCl.

Example:
Val-Oxycodone-Gly

Example 92

Synthesis of Boc-A-B—X—O$^6$-Oxycodone-O$^{14}$—Y—B-A-Boc (A,B,X,Y=amino acids)

To a solution of X—O$^6$-Oxycodone-O$^{14}$—Y.3HCl (1 mmol) and NMM (10 mmol) in DMF (10 mL) was added Boc-A-B-OSu (2.5 mmol) and the reaction mixture was stirred at room temperature overnight. Solvent was evaporated under reduced pressure and to the residue satd. NaHCO$_3$ (15 mL) was added and stirred for 1 h. The precipitate was filtered off and the residue was washed thoroughly with water and dried.

Deprotection of Boc-A-B—X—O$^6$-Oxycodone-O$^{14}$—Y—B-A-Boc:

Deprotection is same as general method mentioned above. Deprotection is done overnight to give A-B—X—O$^6$-Oxycodone-O$^{14}$—Y—B-A.3HCl.

Examples:
1. (Ile-Tyr-Val)-Oxycodone-(Gly-Tyr-Ile)
2. (Leu-Tyr-Val)-Oxycodone-(Gly-Tyr-Leu)

Example 93

Synthesis of Boc-X—O$^6$-Oxycodone-O$^{14}$—Y-Cbz

To a solution of Boc-X-Oxycodone (1 mmol) in THF (10 mL) was added LiN(TMS)$_2$ (1.1 mmol) at 0° C. and the solution was stirred for 30 mins then Cbz-Y-OSu (1.25 mmol) was added. The reaction mixture was stirred at room temperature overnight. The solution was cooled down to 0° C., neutralized with 1N HCl and the organic part was evaporated. To the residue were added EtOAc (50 mL) and satd. NaHCO$_3$ (50 ml), stirred for 1 h. The organic part was washed with water, brine, dried over Na$_2$SO$_4$ and evaporated to dryness. The residue was purified over silica gel to give the title compound.

Deprotection of Boc-X—O$^6$-Oxycodone-O$^{14}$—Y-Cbz.2HCl:

Boc-X—O$^6$-Oxycodone-O$^{14}$—Y-Cbz was deprotected following the general method for deprotection mentioned above to give X—O$^6$-Oxycodone-O$^{14}$—Y-Cbz.2HCl.

Example 94

Synthesis of Boc-A-B—X—O$^6$-Oxycodone-O$^{14}$—Y-Cbz

To a solution of X—O$^6$-Oxycodone-O$^{14}$—Y-Cbz.2HCl (1 mmol) and NMM (10 mmol) in DMF (10 mL) was added Boc-A-B-OSu (1.1 mmol) and the reaction mixture was stirred at room temperature overnight. Solvent was evaporated under reduced pressure and to the residue satd. NaHCO$_3$ (20 mL) was added and stirred vigorously for 2-3 h. The precipitate was filtered off and the residue was washed thoroughly with water and dried.

Example 95

Synthesis of Boc-A-B—X—O$^6$-Oxycodone-O$^{14}$—Y—NH2

To a suspension of Boc-A-B—X—O$^6$-Oxycodone-O$^{14}$—Y-Cbz and Pd/C (25 Wt %) in EtOH (20 ml/gm) and cyclohexene (10 ml/gm) was heated under reflux for 30 mins. The reaction mixture was cooled down to room temperature and filtered. The filtrate was evaporated to dryness to give the title compound.

Example 96

Synthesis of Boc-A-B—X—$O^6$-Oxycodone-$O^{14}$—Y—C-D-Boc (A,B,C,D,X,Y=Amino Acids)

Figure 100:
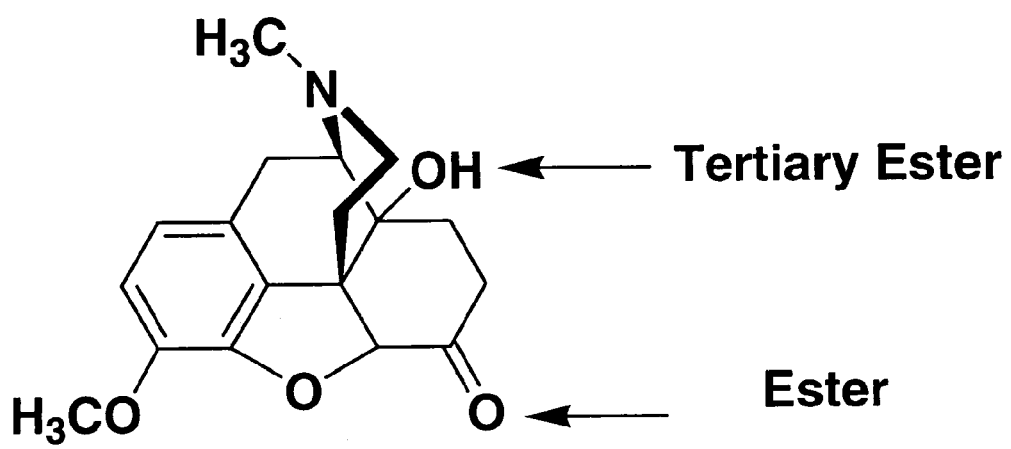
FIG. 100. depicts oxycodone.

To a solution of Boc-A-B—X—$O^6$-Oxycodone-$O^{14}$—Y—$NH_2$ (1 mmol) in DMF (10 mL) were added NMM (5 mmol) and Boc-D-C-OSu (1.1 mmol) and the reaction mixture was stirred at room temperature overnight. Solvent was evaporated under reduced pressure and to the residue satd. $NaHCO_3$ was added and stirred for 1 h. The white precipitate was filtered, washed with water and dried.
Deprotection of Boc-A-B—X—$O^6$-Oxycodone-$O^{14}$—Y—C-D-Boc:

Deprotection is same as general method mentioned above. Deprotection is done overnight to give A-B—X—$O^6$-Oxycodone-$O^{14}$—Y—C-D.3HCl.
Examples:
  1. (Ile-Tyr-Val)-Oxycodone-(Val-Glu-Gly)
  2. (Leu-Tyr-Val)-Oxycodone-(Val-Glu-Gly)
Mono-Substituted Single Amino Acids (Enol Ester)
FIG. 100 depicts oxycodone.

Example 97

Phe-Oxycodone

To a solution of oxycodone-freebase (1.0 eq) in tetrahydrofuran (THF) (10 ml/mmol) was added $LiN(TMS)_2$ (3.5 eq). After 5 minutes, Boc-Phe-OSu (3.5 eq) was added. The reaction was stirred at ambient temperatures for 18 hours, quenched with water and solvents removed. Crude protected product was purified using reverse-phase HPLC. Deprotection occurred with 4N HCl in dioxane (20 ml/mmol) to obtain Phe-Oxycodone.

Example 98

Synthesis of Ile-Oxycodone

Ile-Oxycodone was prepared in a similar manner to Example 97 except Boc-Ile-OSu was used as the amino acid starting material.
Mono-Substituted Tripeptides (Enol Ester)

Example 99

$Pro_2$-Leu-Oxycodone

To a solution of Leu-Oxycodone (1.0 eq) in dimethylformamide (10 ml/0.1 mmol) was added 4-methylmorpholine (10 eq) and Boc-Pro-Pro-OSu (2 eq). The reaction was stirred at ambient temperatures for 18 hours, quenched with water, and solvents removed. Crude protected product was purified using reverse phase HPLC. Deprotection occurred using 4N HCl in dioxane (20 ml/mmol) to obtain $Pro_2$-Leu-Oxycodone.

Example 100

Synthesis of $Pro_2$-Ile-Oxycodone $Pro_2$-Ile-Oxycodone was prepared in a similar manner to Example 99 except Ile-Oxycodone was used as the conjugated starting material.

Example 101

Oxycodone Disubstituted Tripeptides

General Synthetic Procedure
Synthesis of [Boc-Val]$_2$-OC
To a solution of OC (2.04 g, 6.47 mmol) in tetrahydrofuran (THF) (~35 ml) was added $LiN(TMS)_2$ (19.41 ml, 19.41 mmol) and stirred for ~30 mins. To this was added solid Boc-Val-OSu (6.72 g, 21 mmol) at one time and the reaction mixture was stirred at room temperature overnight. The solution was neutralized with 1N HCl and the THF was removed under reduced pressure. The residue was diluted with ethyl acetate (EtOAc) (200 mL), satd. $NaHCO_3$ (150 mL) was added and stirred for 1 h. EtOAc part was washed with $NaHCO_3$ and brine. Dried over $Na_2SO_4$ and evaporated to dryness. Crude product was purified with either silica gel column. (30% EtOAc/Hexane).

Deprotection: For the deprotection of 2.5 g of [Boc-Val]$_2$-OC, 75-80 mL of 4N HCl/dioxane was used. Reaction was complete within 3-4 hours. Evaporate dioxane and dry over vacuum at lease for 24 h.

Coupling: To a solution of Val$_2$-OC.3HCl (250 mg, 0.4 mmol) in DMF (10-12 ml) were added NMM (10-12 eqv) and Boc-X—Y-OSu (2.6 eqv). The reaction mixture was stirred at RT overnight. Solvents were evaporated under reduced pressure. To the residue was added satd. $NaHCO_3$ (~30 mL) and stirred for 1 h. The white/pale yellow residue was filtered, thoroughly washed with water and dried in the vacuum oven at RT.

Deprotection: Deprotection was same as above method. For 100-200 mg of tripeptide derivative 10-15 ml 4N HCl/dioxane was used. Deprotection lasts 18 hours.

Deprotection of tripeptide derivatives containing Threonine and Serine: Tripeptide derivatives were dissolved in 95% TFA (5% water) and stirred for 4 h at room temperature. Solvent was evaporated and the residue was co-evaporated with toluene twice and dried over vacuum. 4N HCl/dioxane was added and stirred overnight. Product was evaporated to dryness and dried over vacuum.

Example 102

Oxycodone Branched Amino Acid Chains

Figure 101:
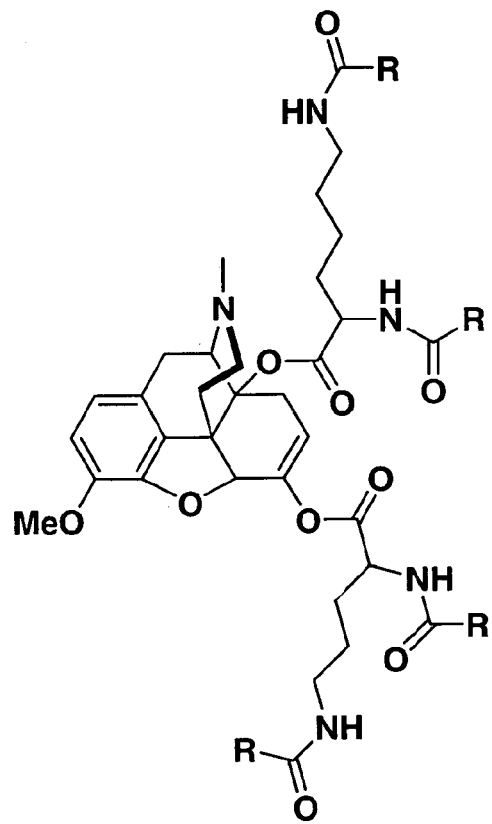
FIG. 101. depicts oxycodone with lysine branched peptides.

General Synthesis
FIG. 101 depicts oxycodone with lysine branched peptides.

Example 103

(Lys)$_2$-Oxycodone

Method was similar to other single amino acid derivatives except Boc-Lys(Boc)-OSu was used as the amino acid starting material.

Example 104

XX-Lys(XX)-Oxycodone

To a solution of (Lys)$_2$-Oxycodone (1.0 eq) in dimethylformamide (1 ml/mmol) was added 4-methylmorpholine (5.5 eq) followed by Boc-XX$_2$-OSu (4.1). Reaction was stirred at ambient temperature for 24 hours. Solvents were removed and crude product was purified by reverse phase HPLC.

Example 105

Synthesis of [Gly$_2$-Lys(-Gly$_2$)]$_2$-Oxycodone

[Gly$_2$-Lys(-Gly$_2$)]$_2$-Oxycodone was prepared in a manner similar to Example 104 except Boc-Gly$_2$-OSu was used as the amino acid starting material.

Example 106

Oxycodone D-Amino Acids

General Synthesis
Disubstituted D-amino acid tripeptides were prepared in a manner similar to disubstituted tripeptide conjugates except the amino acid starting material used the unnatural D-amino acids.
[(1)-Lys-(d)-Lys-Leu]$_2$-Oxycodone
To a solution of (Leu)$_2$-Oxycodone (1.0 eq) in dimethylformamide (1 ml/mmol) was added 4-methylmorpholine (10 eq) followed by Boc-(1)-Lys(Boc)-(d)-Lys(Boc)-OSu (3 eq). Reaction was stirred at ambient temperature for 24 hours. Solvents were removed and crude product was purified by reverse phase HPLC.

Example 107

Synthetic Amino Acids

Synthesis of [Boc-Z]$_2$-OC [where Z can Equal Cyclohexylalanine (Cha), Dipropylglycine (Dpg), Tert-Leucine (Tle) or any Other Synthetic Amino Acid]
To a solution of OC (6.47 mmol) in THF was added LiN(TMS)$_2$ (19.41 mmol) and stirred for ~30 mins. To this was added solid Boc-Z-OSu (21 mmol) at one time and the reaction mixture was stirred at room temperature overnight. The solution was neutralized with 1N HCl and the THF was removed under reduced pressure. The residue was diluted with ethyl acetate (EtOAc), satd. NaHCO$_3$ was added and stirred for 1 h. EtOAc part was washed with NaHCO$_3$ and brine. Dried over Na$_2$SO$_4$ and evaporated to dryness. Crude product was purified with either silica gel column. (30% EtOAc/Hexane).

Example 108

Non-Standard Amino Acids (Naturally Occurring, not the Standard 20)

Synthesis of [Boc-N]$_2$-OC [where N can Equal Norleucine (Nle), Homophenylalanine (hPhe) or Any Other Non-Standard Amino Acid]
To a solution of OC (6.47 mmol) in THF was added LiN(TMS)$_2$ (19.41 mmol) and stirred for ~30 mins. To this was added solid Boc-N-OSu (21 mmol) at one time and the reaction mixture was stirred at room temperature overnight. The solution was neutralized with 1N HCl and the THF was removed under reduced pressure. The residue was diluted with ethyl acetate (EtOAc), satd. NaHCO$_3$ was added and stirred for 1 h. EtOAc part was washed with NaHCO$_3$ and brine. Dried over Na$_2$SO$_4$ and evaporated to dryness. Crude product was purified with either silica gel column. (30% EtOAc/Hexane).

Other Oxycodone Conjugates

Example 109

Glycopeptides

Using galactose and a number of tripeptides, glycopeptides will be produced.
Initial Glycopeptides to be Produced
1. (Gal-Gly$_2$-Ile)$_2$-OC
2. (Gal-Pro$_2$-Ile)$_2$-OC
3. (Gal-Gly$_2$-Leu)$_2$-OC
4. (Gal-Pro$_2$-Leu)$_2$-OC

Example 110

Glycosylation of Oxycodone

Figure 102:
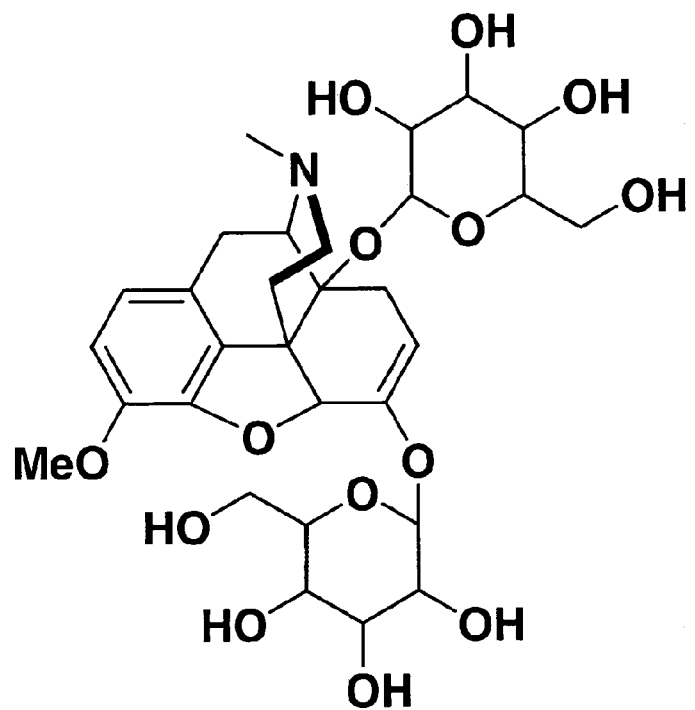
FIG. 102. depicts a glycosylated oxycodone.

FIG. 102 depicts a glycosylated oxycodone.
A glycosylation reaction of Oxycodone with a carbohydrate will be attempted. The linkage produced would essentially be an enol ether which are difficult to cleave chemically yet glycosidic bonds are commonly broken down in vivo. Either site or both may be conjugated.

Example 111

Formation of an Enol Ether with Serine

Figure 103:
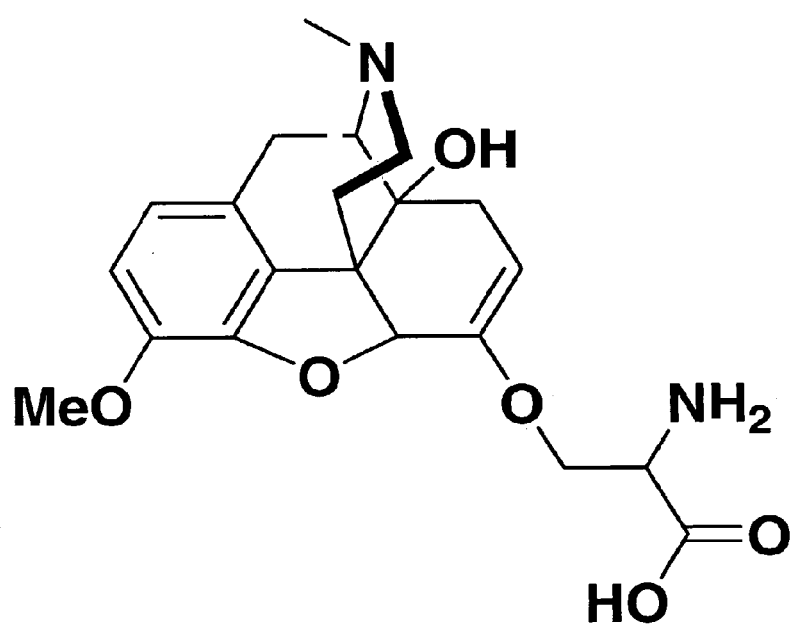
FIG. 103. depicts formation of an enol ether with serine.

FIG. 103 depicts formation of an enol ether with serine.
Using serine and OC, an enol ether conjugate will be produced. This conjugate would be stable to most hydrolysis conditions. Only the enol ether would be formed in this reaction.

Example 112

Vitamins

Figure 104:
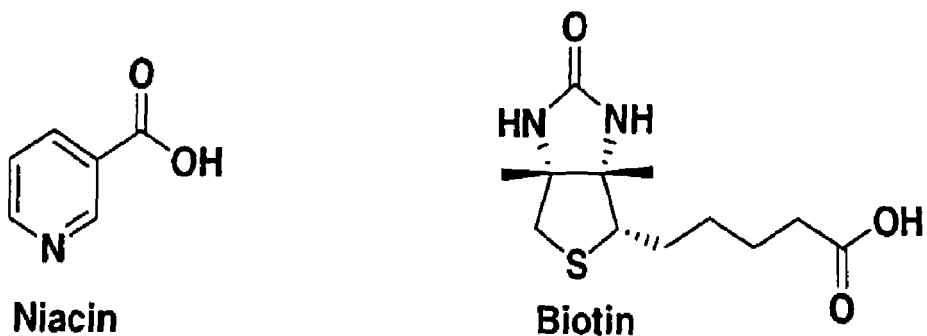
FIG. 104. depicts niacin and biotin.
Figure 105:
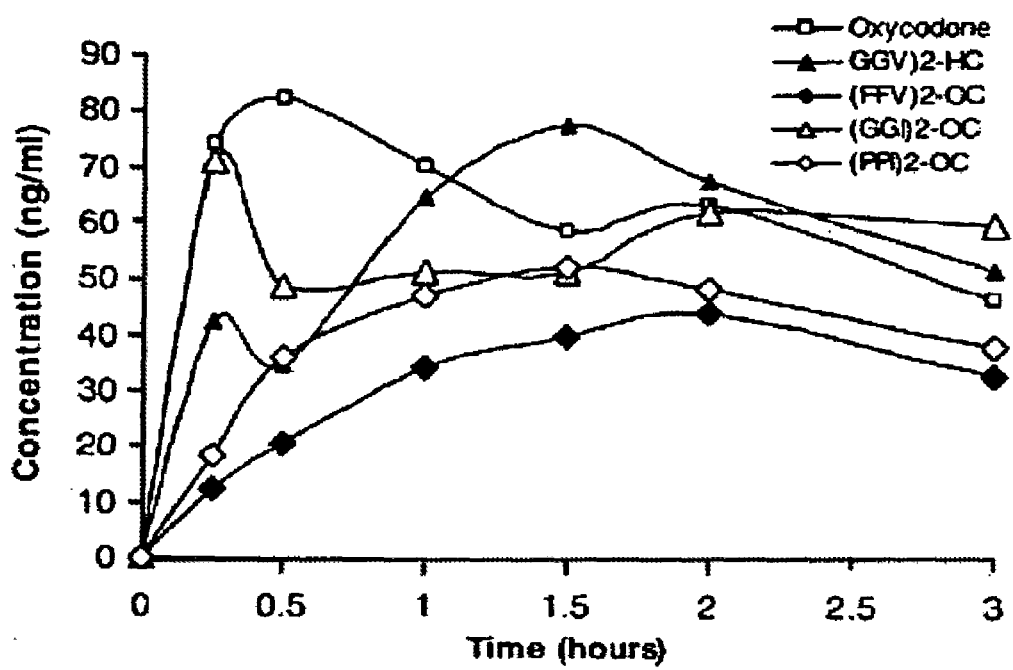
FIG. 105. Oral bioavailability of abuse-resistant oxycodone disubstituted tripeptide conjugates, measured as free oxycodone.
Figure 106:
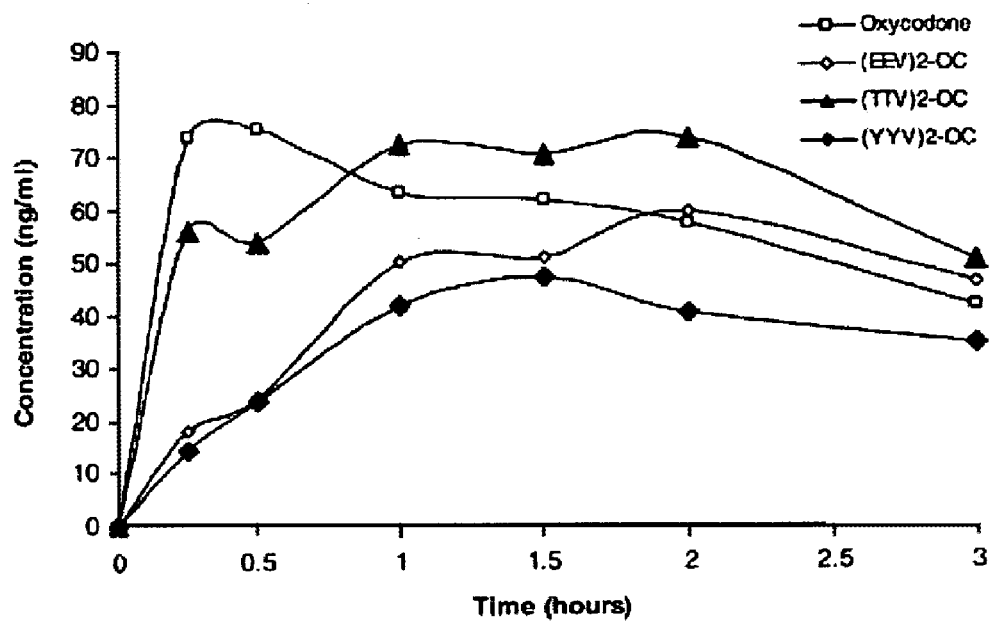
FIG. 106. Oral bioavailability of abuse-resistant oxycodone disubstituted tripeptide conjugates, measured as free oxycodone.
Figure 107:
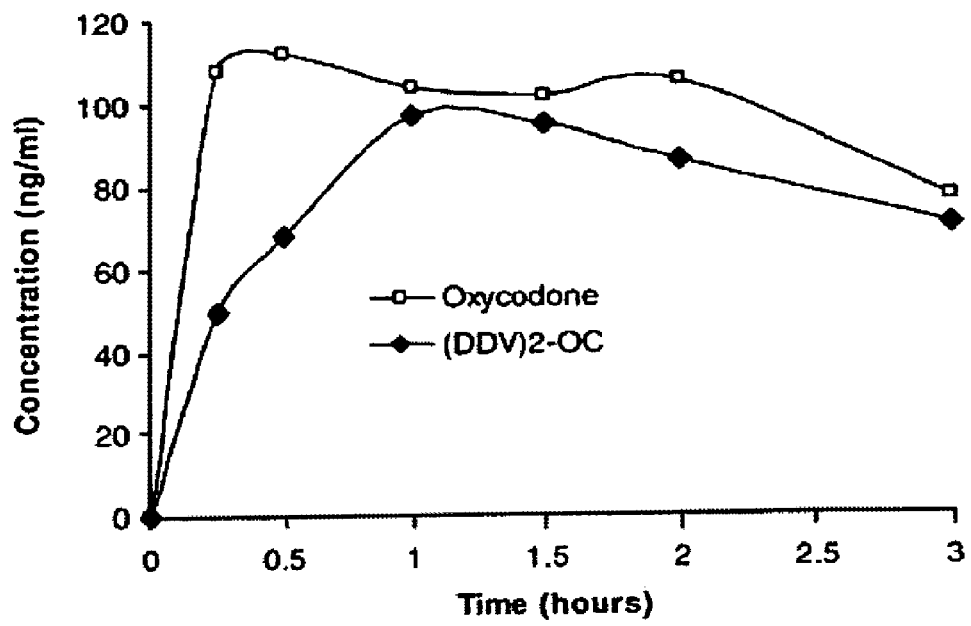
FIG. 107. Oral bioavailability of abuse-resistant oxycodone disubstituted tripeptide conjugates, measured as free oxycodone.
Figure 108:
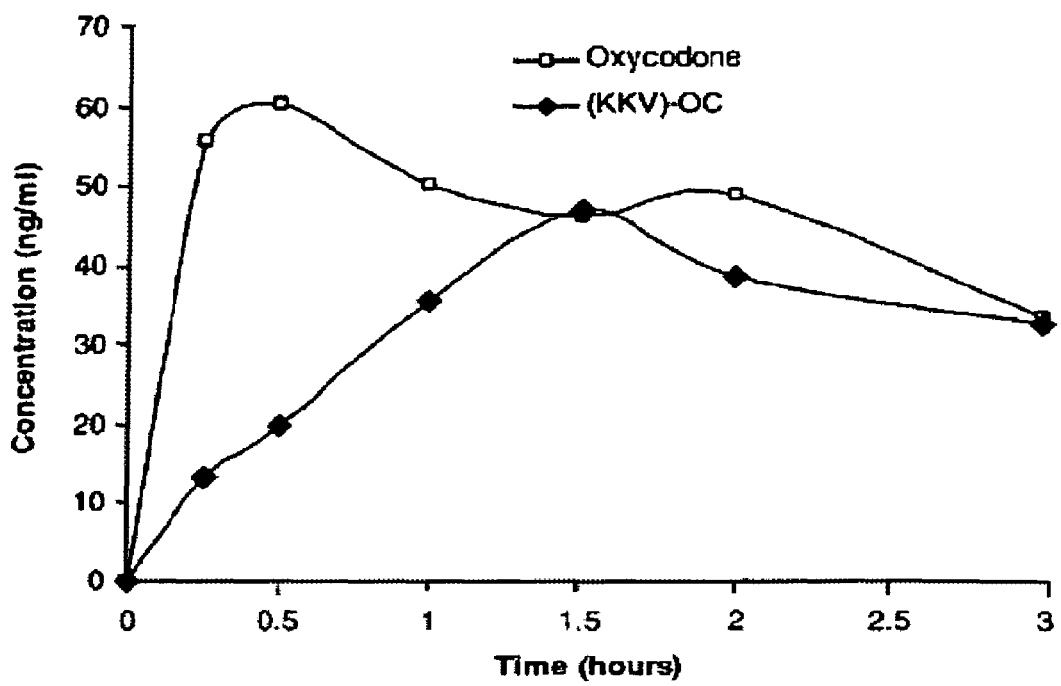
FIG. 108. Oral bioavailability of abuse-resistant oxycodone disubstituted tripeptide conjugates, measured as free oxycodone.
Figure 109:
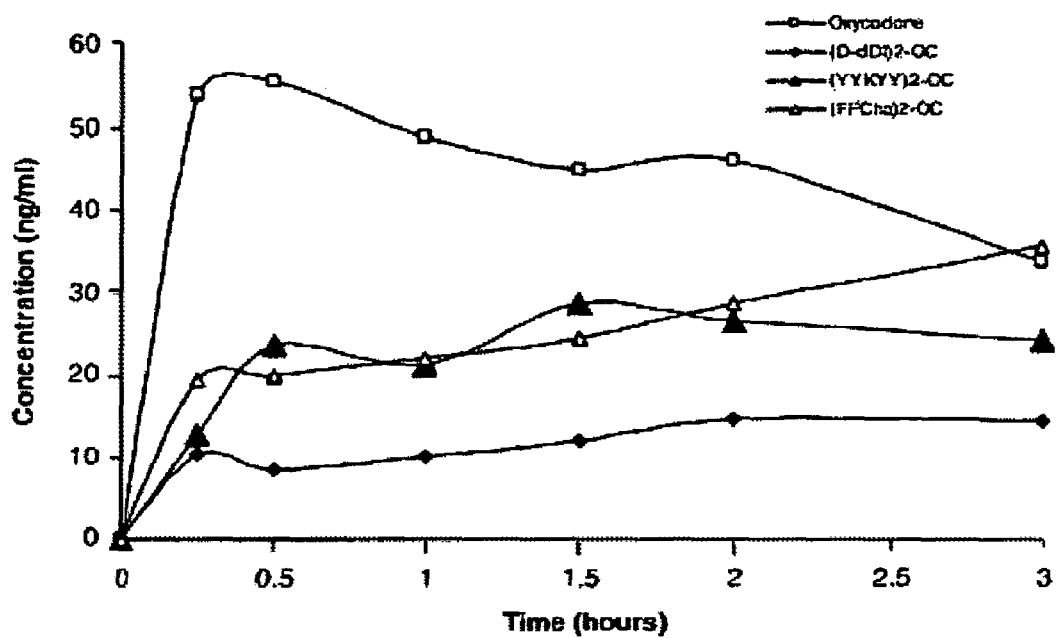
FIG. 109. Oral bioavailability of abuse-resistant oxycodone disubstituted tripeptide conjugates, measured as free oxycodone.
Figure 110:
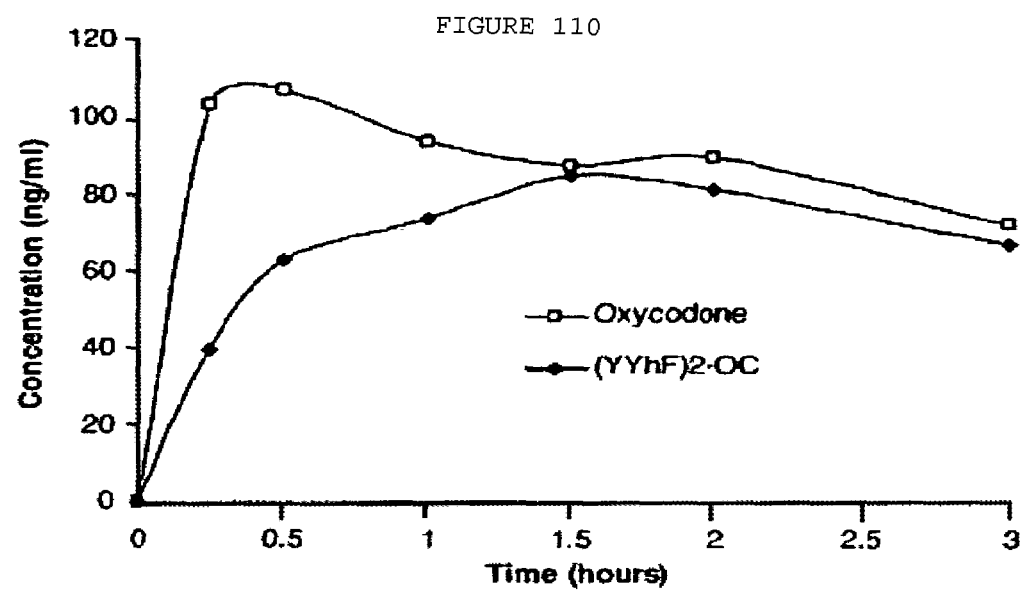
FIG. 110. Oral bioavailability of abuse-resistant oxycodone disubstituted tripeptide conjugates, measured as free oxycodone.
Figure 111:
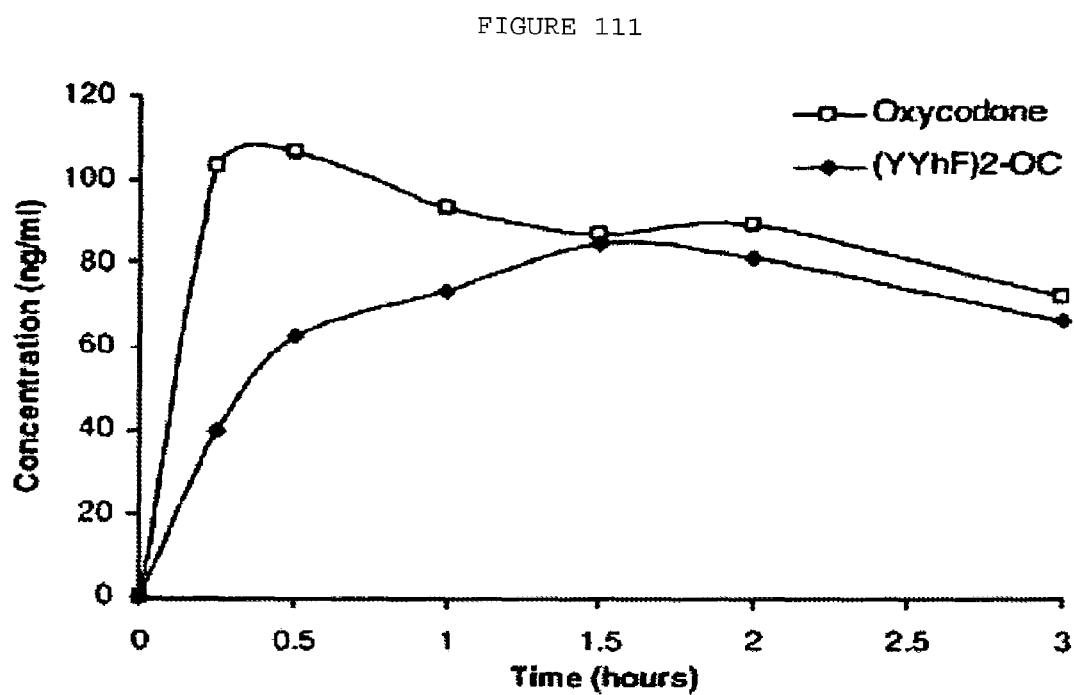
FIG. 111. Oral bioavailability of abuse-resistant oxycodone disubstituted tripeptide conjugates, measured as free oxycodone.
Figure 112:
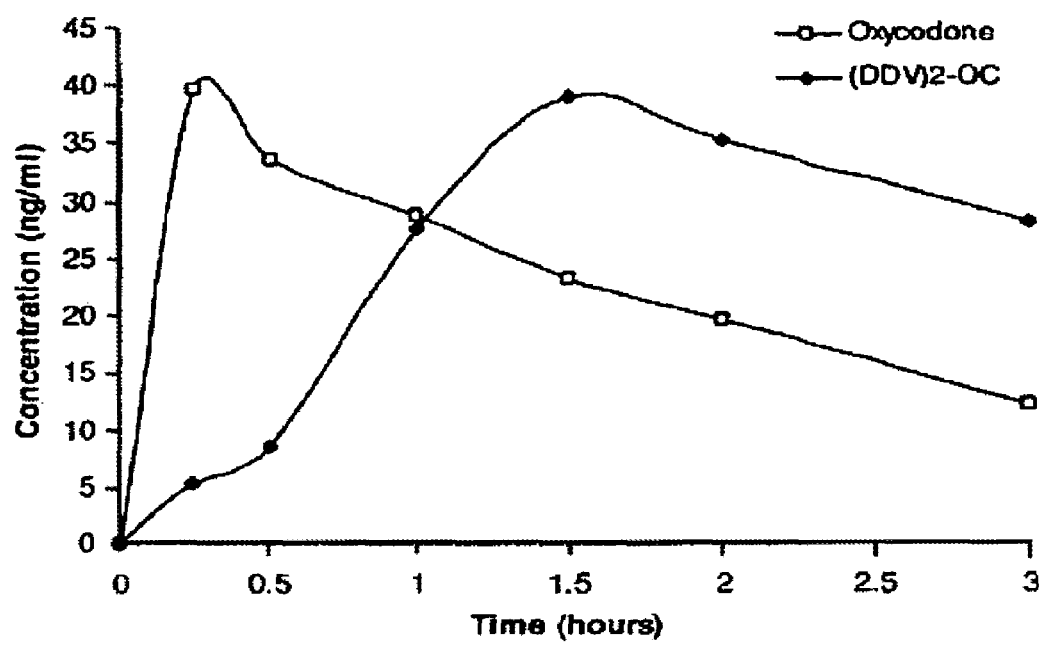
FIG. 112. Oral bioavailability of abuse-resistant oxycodone disubstituted tripeptide conjugates, measured as free oxycodone.
Figure 113:
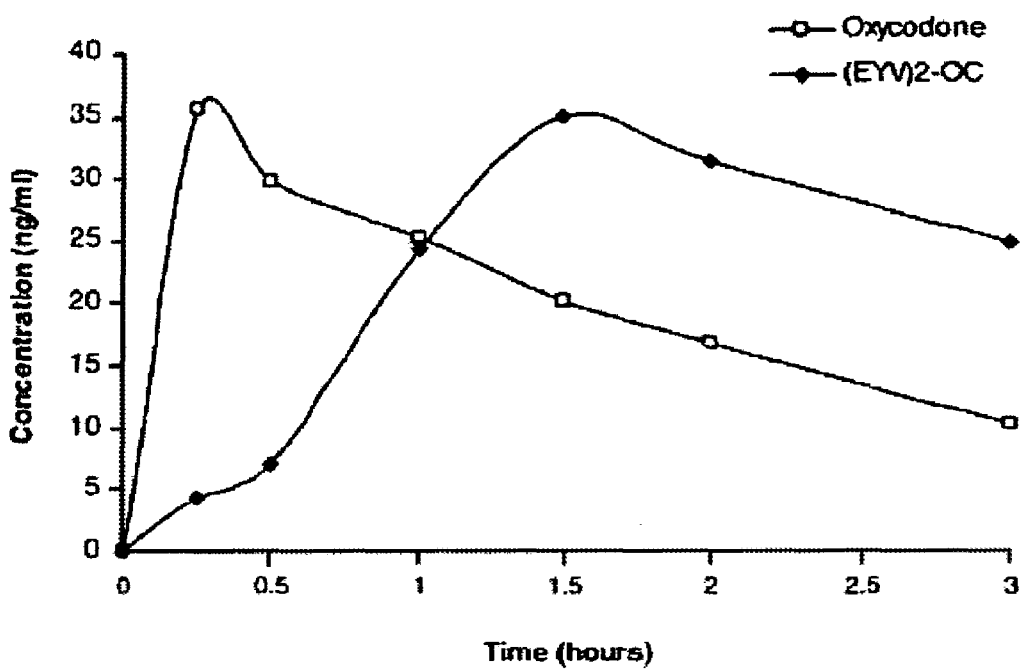
FIG. 113. Oral bioavailability of abuse-resistant oxycodone disubstituted tripeptide conjugates, measured as free oxycodone.
Figure 114:
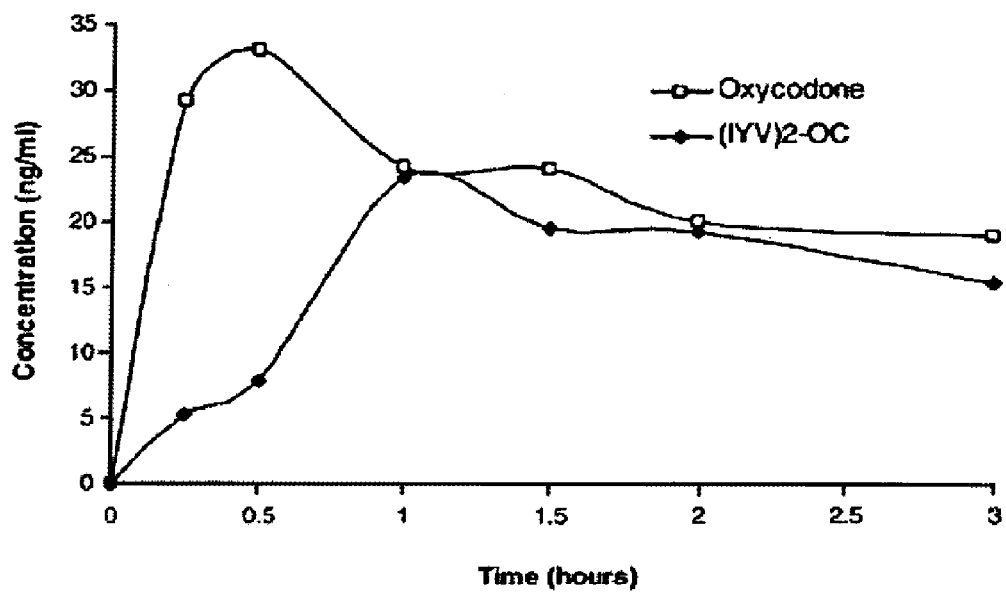
FIG. 114. Oral bioavailability of abuse-resistant oxycodone disubstituted tripeptide conjugates, measured as free oxycodone.
Figure 115:
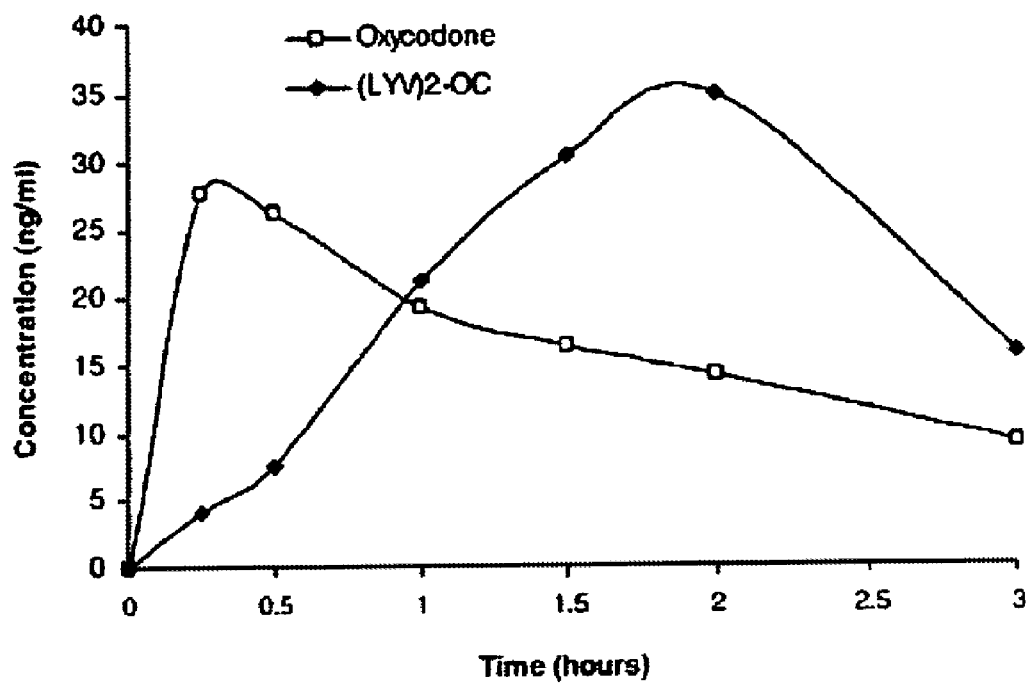
FIG. 115. Oral bioavailability of abuse-resistant oxycodone disubstituted tripeptide conjugates, measured as free oxycodone.
Figure 116:
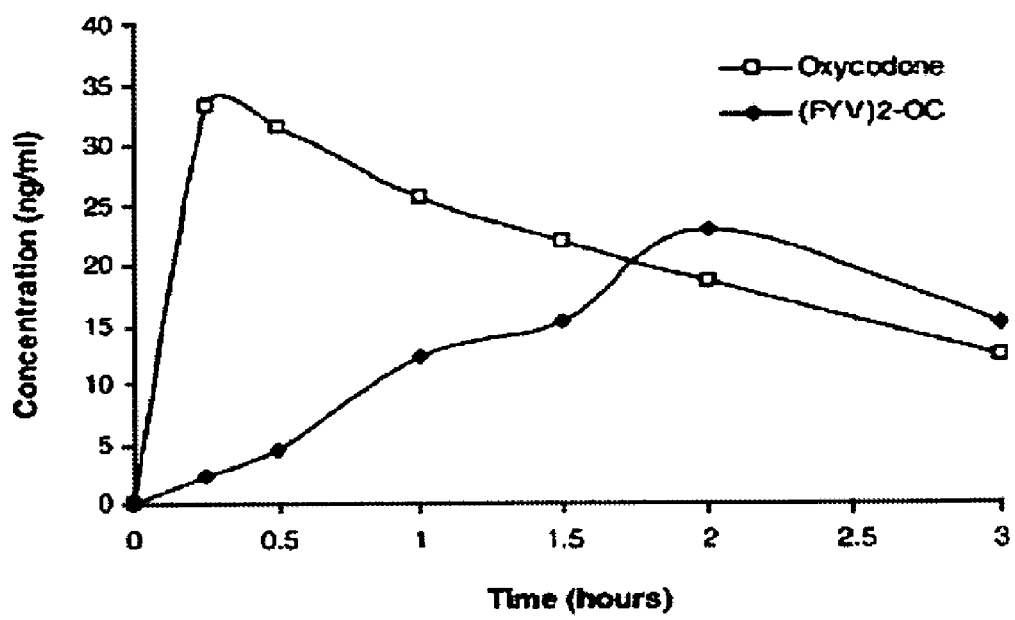
FIG. 116. Oral bioavailability of abuse-resistant oxycodone disubstituted tripeptide conjugates, measured as free oxycodone.
Figure 117:
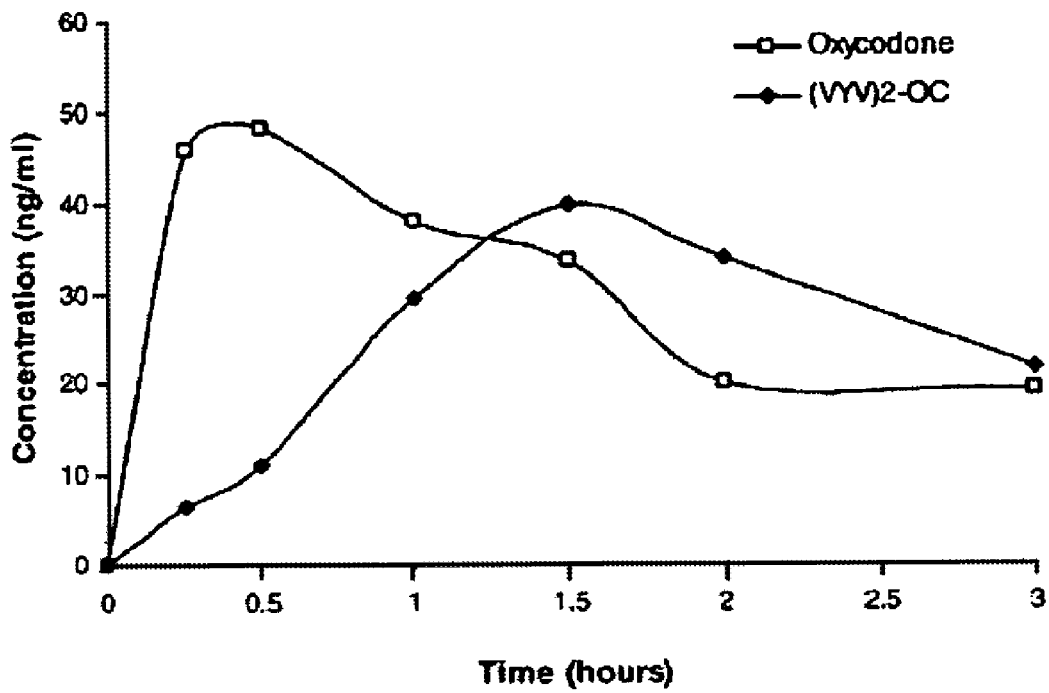
FIG. 117. Oral bioavailability of abuse-resistant oxycodone disubstituted tripeptide conjugates, measured as free oxycodone.
Figure 118:
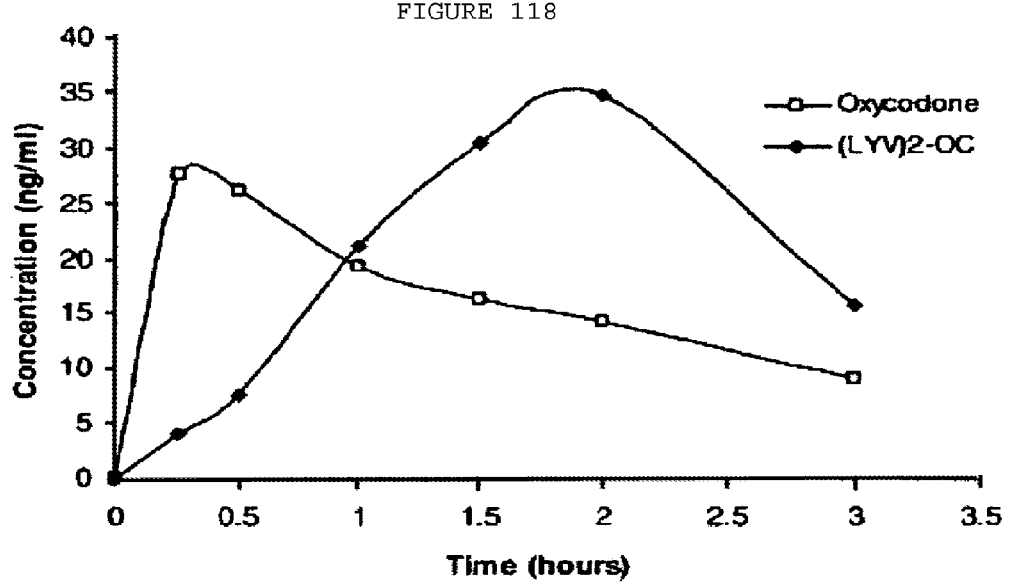
FIG. 118. Oral bioavailability of abuse-resistant oxycodone disubstituted tripeptide conjugates, measured as free oxycodone.
Figure 119:
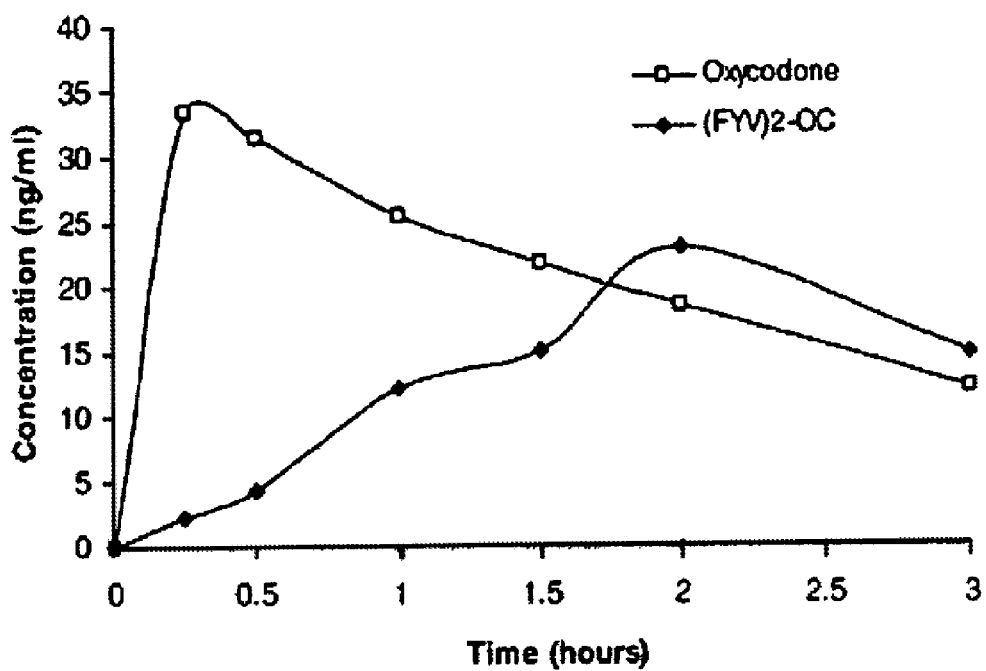
FIG. 119. Oral bioavailability of abuse-resistant oxycodone disubstituted tripeptide conjugates, measured as free oxycodone.

FIG. 104 depicts niacin and biotin.
Vitamins can be used to cap or further functionalize the peptide chain. Niacin and biotin will be conjugated to four different dipeptides.
Conjugates to Prepare
1. (Nia-Gly$_2$-Ile)$_2$-OC
2. (Nia-Gly$_2$-Leu)$_2$-OC
3. (Bio-Gly$_2$-Ile)$_2$-OC
4. (Bio-Gly$_2$-Leu)$_2$-OC FIGS. 105-141 demonstrate plasma levels of oxycodone measured by ELISA.

Example 113

Decreased oral $C_{max}$ of Oxycodone Conjugates

Male Sprague-Dawley rats were provided water ad libitum, fasted overnight and dosed by oral gavage with oxycodone conjugates or oxycodone HCl. All doses contained equivalent amounts of oxycodone base. Plasma oxycodone concentrations were measured by ELISA (Oxymorphone, 102919, Neogen, Corporation, Lexington, Ky.). The assay is specific for oxymorphone (the major oxycodone metabolite) and oxycodone. Plasma concentration-time curves are shown in FIGS. 105-123. These examples illustrate that doses of oxycodone conjugates decrease the peak level ($C_{max}$) of oxycodone plus oxymorphone as compared to that produced by equimolar (oxycodone base) doses of oxycodone HCl when given by the oral route of administration.

Example 114

Oral Bioavailability of a Peptide-Oxycodone Conjugates at a Dose (2.5 mg/kg) Approximating a Therapeutic Human Dose This example illustrates that when the peptide PPL (Table 74, FIG. 142) is conjugated (disubstituted at the 6 and 14 positions) to the active agent oxycodone oral bioavailability is maintained as compared to an equimolar oxycodone dose when the dose administered is 1 mg/kg. This dose is the equivalent of a human dose of 25 to 35 mg for an individual weighing 70 kg (148 lbs) according to Chou et al.

TABLE 74

Oral Pharmacokinetics of Oxycodone vs. P2L$_{(2)}$-OC (2.5 mg/kg dose).

| Drug | Hours | | | | | AUC (ng/ml h) 0-8 h | Percent OC | Cmax ng/ml | Percent OC |
| --- | --- | --- | --- | --- | --- | --- | --- | --- | --- |
| | 0.5 | 1.5 | 3 | 5 | 8 | | | | |
| Oxycodone Bitartrate | 145 | 27 | 11 | 2 | 1 | 168 | 100 | 145 | 100 |
| PPL(2)-OC | 124 | 78 | 46 | 1 | 3 | 278 | 165 | 124 | 86 | oxycodone plus oxymorphone

Example 115

Bioavailability of P2L$_{(2)}$-Oxycodone by the Intranasal Route

This example illustrates that when PPL(2) is conjugated to the active agent oxycodone the bioavailability by the intranasal route is substantially decreased thereby diminishing the possibility of overdose (Table 75, FIG. 143).

TABLE 75

Intranasal Pharmacokinetics of Oxycodone vs. P2L$_{(2)}$-OC (1 mg/kg dose).

| Drug | Minutes | | | | AUC (ng/ml h) 0-1 h | Percent OC | Cmax ng/ml | Percent OC |
| --- | --- | --- | --- | --- | --- | --- | --- | --- |
| | 5 | 15 | 30 | 60 | | | | |
| Oxycodone Bitartrate | 2128 | 1003 | 688 | 278 | 428 | 100 | 2128 | 100 |
| PPL(2)-OC | 1380 | 499 | 390 | 98 | 261 | 61 | 1380 | 65 | oxycodone plus oxymorphone

Example 116

Bioavailability of P2L$_{(2)}$oxycodone by the intravenous route

This example illustrates that when P2L$_{(2)}$ is conjugated to the active agent oxycodone the bioavailability by the intravenous route is substantially decreased thereby diminishing the possibility of overdose (Table 76, FIG. 144).

TABLE 76

Intravenous Pharmacokinetics of Oxyocodone vs. P2L$_{(2)}$-OC (1 mg/kg dose).

| Drug | Minutes | | | | AUC (ng/ml h) 0-1 h | Percent OC | Cmax ng/ml | Percent OC |
| --- | --- | --- | --- | --- | --- | --- | --- | --- |
| | 5 | 15 | 30 | 60 | | | | |
| Oxycodone Bitartrate | 99 | 104 | 94 | 51 | 82 | 100 | 99 | 100 |
| PPL(2)-OC | 22 | 19 | 19 | 43 | 24 | 29 | 43 | 43 | oxycodone plus oxymorphone

Summary of in vivo Testing of Abuse Resistant Oxycodone Conjugates.

In vivo testing of oxycodone conjugates demonstrates for instance decreased oral $C_{max}$, decreased intranasal bioavailability (AUC and $C_{max}$), and decreased intravenous bioavailability (AUC and $C_{max}$) and is described in further detail below.

Example 117

Decreased Intranasal Bioavailability (AUC and $C_{max}$) of Oxycodone Conjugates Male Sprague-Dawley rats were provided water ad libitum and doses were administered by placing 0.02 ml of water containing oxycodone conjugates or oxycodone bitartrate into the nasal flares. All doses contained equivalent amounts of oxycodone base. Plasma oxycodone concentrations were measured by ELISA (Oxymorphone, 102919, Neogen, Corporation, Lexington, Ky.). The assay is specific for oxymorphone (the major oxycodone metabolite) and oxycodone. Plasma concentration-time curves of various oxycodone conjugates vs. oxycodone HCl are shown in FIGS. 124-141. These examples illustrate that oxycodone conjugates decrease the peak level ($C_{max}$) and total absorption (AVC) of oxycodone plus oxymorphone as compared to those produced by equimolar (oxycodone base) doses of oxycodone HCl when given by the intranasal route of administration.

Example 118

Decreased Intravenous Bioavailability (AUC and $C_{max}$) of Oxycodone Conjugates Male Sprague-Dawley rats were provided water ad libitum and doses were administered by intravenous tail vein injection of 0.1 ml of water containing oxycodone conjugates or oxycodone HCl. All doses contained equivalent amounts of oxycodone base. Plasma oxycodone concentrations were measured by ELISA (Oxymorphone, 102919, Neogen, Corporation, Lexington, Ky.). The assay is specific for oxymorphone (the major oxycodone metabolite) and oxycodone. Plasma concentration-time curves of an oxycodone conjugate vs. oxycodone HCl is shown in FIG. 144. This example illustrates that an oxycodone conjugate decreases the peak level ($C_{max}$) and total absorption (AUC) of oxycodone plus oxymorphone as compared to those produced by an equimolar (oxycodone base) dose of oxycodone HCl when given by the intravenous route of administration.

|  | oral 2 mg/kg | | intranasal 2 mg/kg | |
|---|---|---|---|---|
|  | % AUC | % Cmax | % AUC | % Cmax |
| [Gly-Glu-Val]$_2$-OC | 93 | 61 | 29 | 48 |
| [Pro-Glu-Val]$_2$-OC | 90 | 82 | 34 | 46 |
| [Glu-Pro-Val]$_2$-OC | 142 | 134 | 56 | 65 |
| [Ser-Gly-Val]$_2$-OC | 90 | 92 | 64 | 73 |
| [Glu-Tyr-Val]$_2$-OC | 115 | 103 | 18 | 20 |
| [Gly-Tyr-Val]$_2$-OC | 92 | 99 | 56 | 54 |
| [Ile-Tyr-Val]$_2$-OC | 71 | 82 | 3 | 4 |
| [Leu-Tyr-Val]$_2$-OC | 131 | 120 | 4 | 5 |

OC = Oxycodone

Collectively, examples 33 through 118 illustrate the application of the invention for reducing the overdose potential of narcotic analgesics. These examples establish that an active agent can be covalently modified by attachment of a chemical moiety in a manner that maintains therapeutic value over a normal dosing range, while substantially decreasing if not eliminating the possibility of overdose by oral, intranasal, or intravenous routes of administration with the active agent.

What is claimed is:

1. A method of treating attention deficit hyperactivity disorder in a patient in need thereof, comprising orally administering an effective amount of an amphetamine (1-phenyl-propan-2-amine) covalently bound to a chemical moiety, wherein the chemical moiety is a naturally occurring, non-standard amino acid, the amino acid is bound through its C-terminus to the amino group of the amphetamine, and the bound amphetamine maintains a steady-state serum release curve which provides a therapeutically effective bioavailability of the amphetamine.

2. The method of claim 1, wherein the naturally occurring, non-standard amino acid is homoserine.

3. The method of claim 1, wherein the naturally occurring, non-standard amino acid is ornithine.

4. The method of claim 1, wherein the naturally occurring, non-standard amino acid is sarcosine.

5. The method of claim 1, wherein the amphetamine is dextroamphetamine.

6. A method of treating attention deficit hyperactivity disorder in a patient in need thereof, comprising orally administering an effective amount of an amphetamine (1-phenyl-propan-2-amine) covalently bound to a chemical moiety, wherein the chemical moiety is a naturally occurring, non-standard amino acid and the amino acid is bound through its C-terminus to the amino group of the amphetamine, wherein the bound amphetamine is administered in an oral dosage form.

7. The method of claim 6, wherein the amphetamine is dextroamphetamine.

8. The method of claim 6, wherein the oral dosage form comprises from 5 to 500 mg of the bound amphetamine.

9. The method of claim 6, wherein the patient is administered an oral dosage form of the bound amphetamine once daily.

10. The method of claim 7, wherein the oral dosage form comprises from 5 to 500 mg of the bound amphetamine.

11. The method of claim 7, wherein the patient is administered an oral dosage form of the bound amphetamine once daily.

* * * * *